US006858616B2

(12) United States Patent
Fevig et al.

(10) Patent No.: US 6,858,616 B2
(45) Date of Patent: Feb. 22, 2005

(54) NITROGEN CONTAINING HETEROBICYCLES AS FACTOR XA INHIBITORS

(75) Inventors: John M. Fevig, Lincoln University, PA (US); Joseph Cacciola, Newark, DE (US); Charles G. Clark, Cherry Hill, NJ (US); Qi Han, Hockessin, DE (US); Patrick Yuk Sun Lam, Chadds Ford, PA (US); Donald J. P. Pinto, Kennett Square, PA (US); James R. Pruitt, Landenberg, PA (US); Mimi L. Quan, Newark, DE (US); Karen A. Rossi, Boothwyn, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 125 days.

(21) Appl. No.: 10/133,998

(22) Filed: Apr. 26, 2002

(65) Prior Publication Data

US 2003/0069237 A1 Apr. 10, 2003

Related U.S. Application Data

(62) Division of application No. 09/898,279, filed on Jul. 3, 2001, now Pat. No. 6,673,810, which is a division of application No. 09/470,326, filed on Dec. 22, 1999, now Pat. No. 6,413,980.
(60) Provisional application No. 60/127,633, filed on Apr. 2, 1999, and provisional application No. 60/113,628, filed on Dec. 23, 1998.

(51) Int. Cl.[7] .................... A61K 31/519; C07D 487/04
(52) U.S. Cl. ................. 514/262.1; 514/261.1; 544/254; 544/262
(58) Field of Search ................. 544/262, 254, 544/261.1; 514/262.1

(56) References Cited

U.S. PATENT DOCUMENTS

| 3,340,269 A | 9/1967 | Blatter |
| 3,365,459 A | 1/1968 | Blatter |
| 3,423,414 A | 1/1969 | Blatter |
| 3,939,161 A | 2/1976 | Ratajczyk |

FOREIGN PATENT DOCUMENTS

| EP | 807633 A | 11/1997 |
| JP | 57021388 A | 2/1982 |
| JP | 63145282 A | 6/1988 |
| WO | WO 9420460 A | 9/1994 |
| WO | WO 9501980 A | 1/1995 |
| WO | WO 9612720 A | 5/1996 |
| WO | WO 9852948 A | 11/1998 |
| WO | WO 9950255 A | 10/1999 |
| WO | WO 0020416 A | 4/2000 |

*Primary Examiner*—Richard L. Raymond
(74) *Attorney, Agent, or Firm*—David H. Vance; Jing S. Belfield

(57) ABSTRACT

The present application describes nitrogen containing heterobicyclics and derivatives thereof, or pharmaceutically acceptable salt forms thereof, which are useful as inhibitors of factor Xa.

21 Claims, No Drawings

NITROGEN CONTAINING HETEROBICYCLES AS FACTOR XA INHIBITORS

This application is a divisional application of U.S. application Ser. No. 09/898,279, filed Jul. 3, 2001, now U.S. Pat. No. 6,673,810, which is a divisional application of U.S. application Ser. No. 09/470,326, filed Dec. 22, 1999, now U.S. Pat. No. 6,413,980, which claims benefit of U.S. Provisional Application No. 60/113,628, filed on Dec. 23, 1998 and U.S. Provisional Application No. 60/127,633, filed on Apr. 02, 1999, the contents of which are hereby incorporated by reference.

FIELD OF THE INVENTION

This invention relates generally to nitrogen containing heterobicycles, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO94/20460 describes angiotensin II compounds of the following formula:

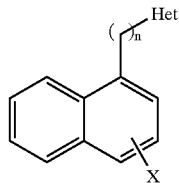

wherein X can be a number of substituents and Het can be a nitrogen-containing heterobicycle. However, WO94/20460 does not suggest Factor Xa inhibition or exemplify compounds like those of the present invention.

WO96/12720 describes phosphodiesterase type IV and TNF production inhibitors of the following formula:

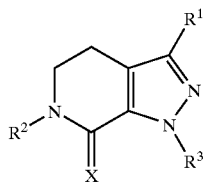

wherein X can be oxygen and $R^2$ and $R^3$ can a number of substituents including heterocycle, heterocycloalkyl, and phenyl. However, the presently claimed compounds do not correspond to the compounds of WO96/12720. Furthermore, WO96/12720 does not suggest Factor Xa inhibition.

WO98/52948 describes inhibitors of ceramide-mediated signal transduction. One of the types of inhibitors described is of the following formula:

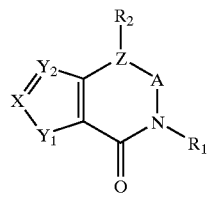

wherein $Y_1$ can be N—$R_6$, $R_6$ can be unsubstituted arylalkyl or unsubstituted heterocyclic-alkyl and $R_1$ can be a substituted aryl group. WO98/52948 does not mention factor Xa inhibition or show compounds like those of the present invention.

U.S. Pat. Nos. 3,365,459 and 3,340,269 illustrates anti-inflammatory inhibitors of the following formula:

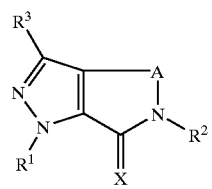

wherein A is 2–3 carbon atoms, X can be 0, and $R^1$ and $R^3$ can be substituted or unsubstituted aromatic groups. Neither of these patents, however, exemplify compounds of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. Thromb. Res. 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel nitrogen containing heterobicycles that are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide novel bicyclic compounds for use in therapy.

It is another object of the present invention to provide the use of novel bicyclic compounds for the manufacture of a medicament for the treatment of a thromboembolic disorder.

These and other objects, which will become apparent during the following detailed description, have been achieved by the inventors' discovery that the presently claimed bicyclic compounds, or pharmaceutically acceptable salt or prodrug forms thereof, are effective factor Xa inhibitors.

DETAILED DESCRIPTION OF PREFERRED EMBODIMENTS

[1] Thus, in a first embodiment, the present invention provides a novel compound selected from the group:

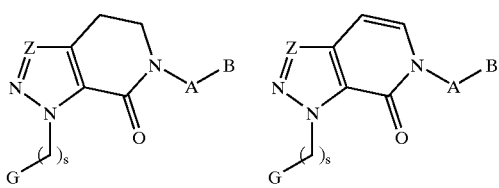

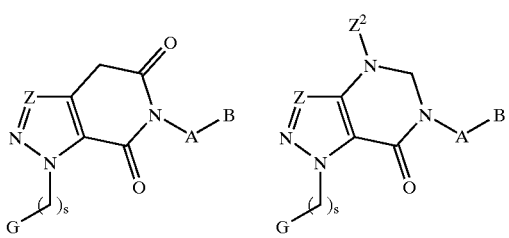

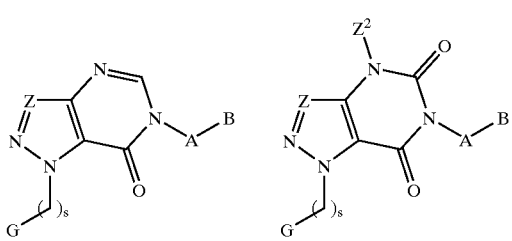

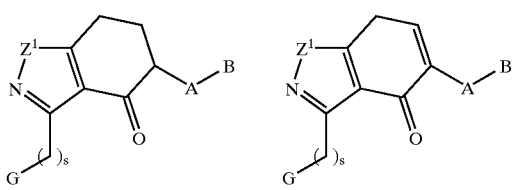

-continued

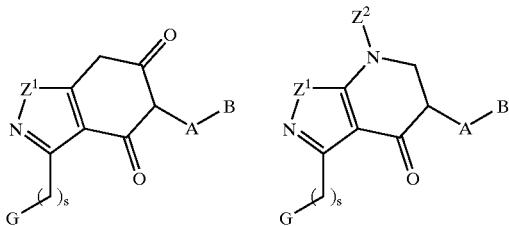

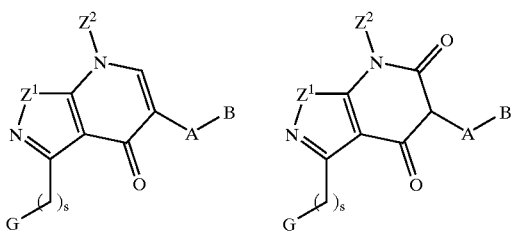

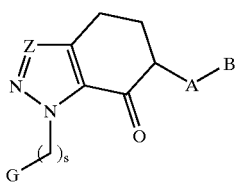

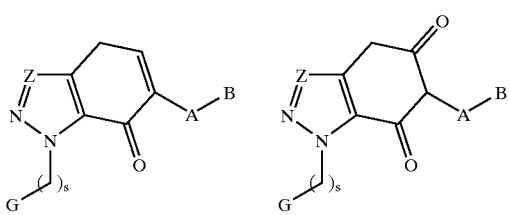

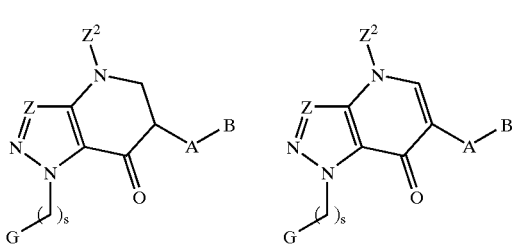

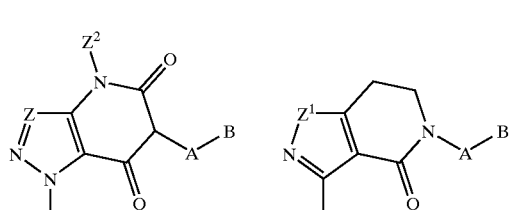

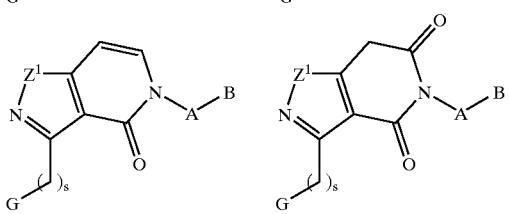

-continued
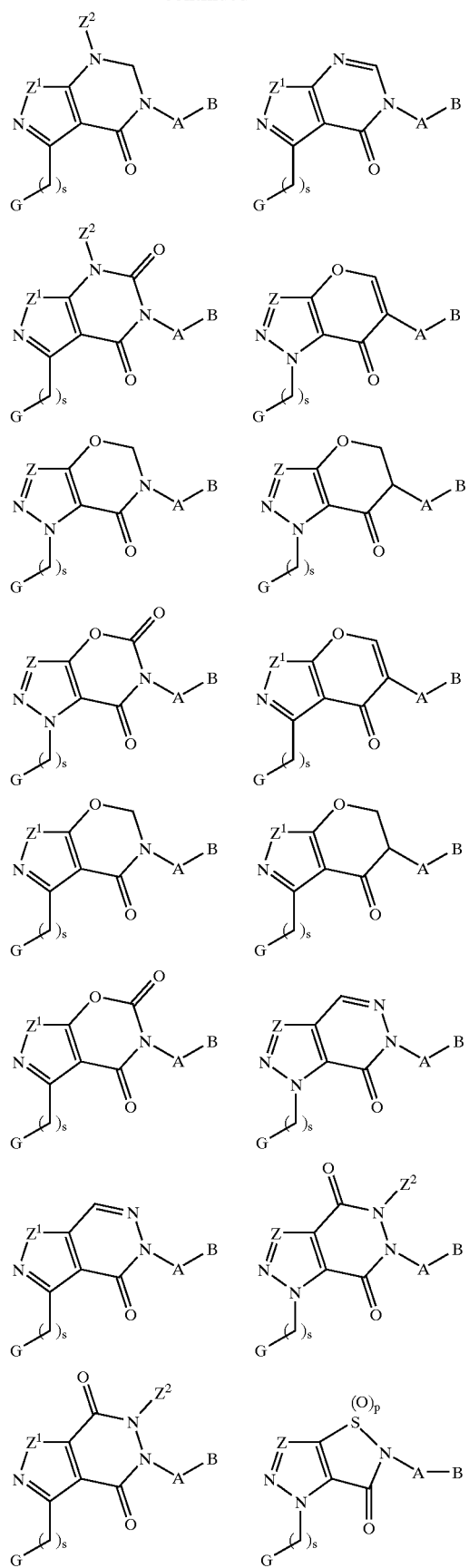
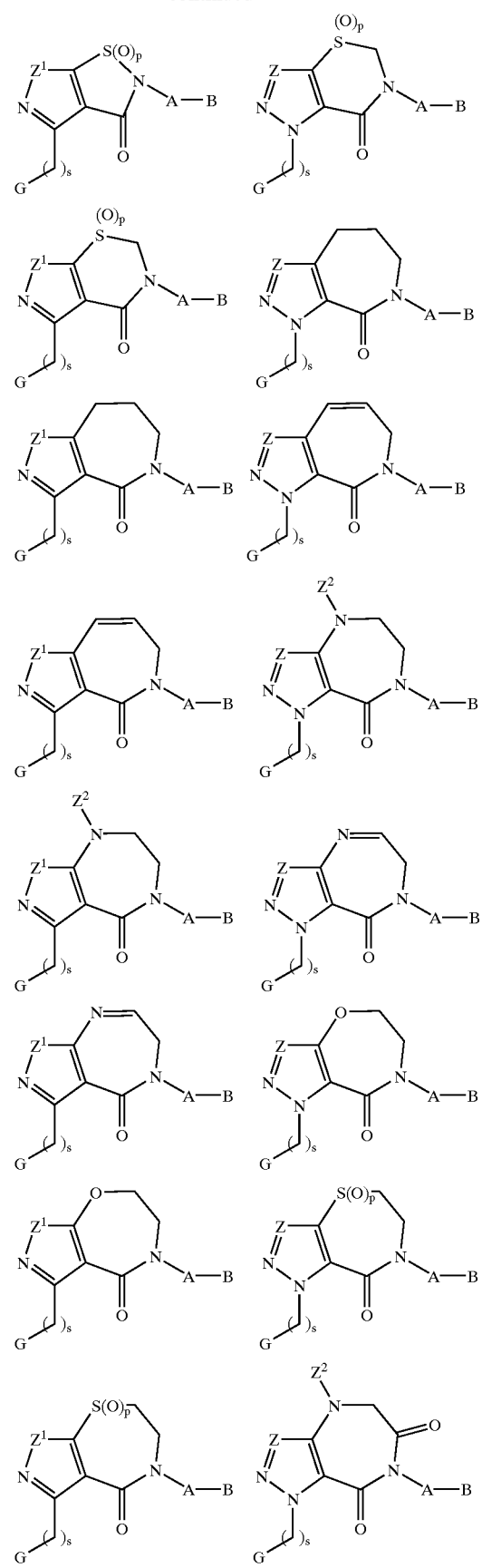

-continued

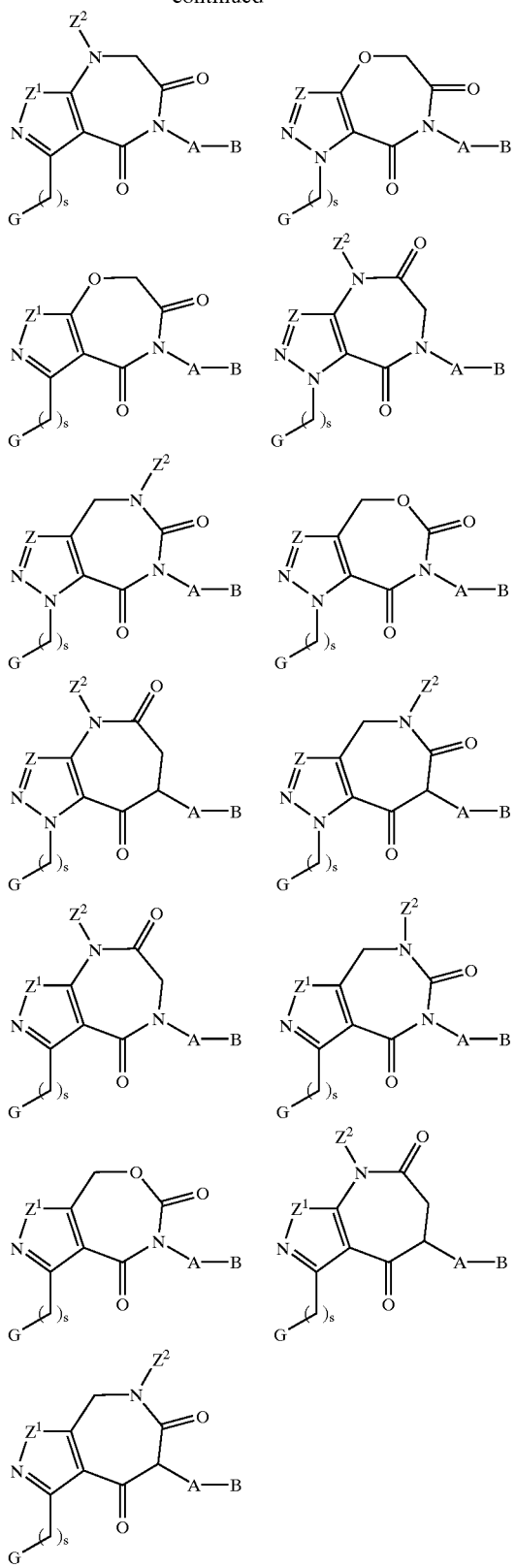

or a stereoisomer or pharmaceutically acceptable salt thereof, wherein compounds of the above formulas are substituted with 0–2 $R^3$;

G is a group of formula I or II:

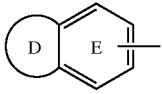

I

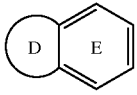

II ring D is selected from —$(CH_2)_3$—, —$(CH_2)_4$—, —$CH_2N=CH$—, —$CH_2CH_2N=CH$—, and a 5–6 membered aromatic system containing from 0–2 heteroatoms selected from the group N, O, and S, provided that from 0–1 O and S atoms are present;

ring D, when present, is substituted with 0–2 R;

E is selected from phenyl, pyridyl, pyrimidyl, pyrazinyl, and pyridazinyl, substituted with 0–1 R;

R is selected from Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

alternatively, ring D is absent;

when ring D is absent, ring E is selected from phenyl, pyridyl, pyrimidyl, pyrazinyl, and pyridazinyl, and ring E is substituted with R" and R';

R" is selected from F, Cl, Br, I, OH, $C_{1-3}$ alkoxy, CN, $C(=NR^8)NR^7R^9$, $NHC(=NR^8)NR^7R^9$, $NR^8CH(=NR^7)$, $C(O)NR^7R^8$, $(CR^8R^9)_rNR^7R^8$, SH, $C_{1-3}$ alkyl-S, $S(O)R^{3b}$, $S(O)_2R^{3a}$, $S(O)_2NR^2R^{2a}$, and $OCF_3$;

R' is selected from H, F, Cl, Br, I, $SR^3$, $CO_2R^3$, $NO_2$, $(CH_2)_rOR^3$, $C_{1-4}$ alkyl, $OCF_3$, $CF_3$, $C(O)NR^7R^8$, and $(CR^8R^9)_rNR^7R^8$;

alternatively, R" and R' combine to form methylenedioxy or ethylenedioxy;

Z is N or $CR^{1a}$;

$Z^1$ is S, O, or $NR^3$;

$Z^2$ is selected from H, $C_{1-4}$ alkyl, phenyl, benzyl, $C(O)R^3$, and $S(O)_pR^{3c}$;

$R^{1a}$ is selected from H, —$(CH_2)_r$—$R^{1'}$, —$CH=CH$—$R^{1'}$, $NHCH_2R^{1''}$, $OCH_2R^{1''}$, $SCH_2R^{1''}$, $NH(CH_2)_2(CH_2)_rR^{1'}$, $O(CH_2)_2(CH_2)_rR^{1'}$, and $S(CH_2)_2(CH_2)_rR^{1'}$;

$R^{1'}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^2C$, $S(O)_pR^{2b}$, $NR^2(CH_2)_rOR^2$, $C(=NR^{2c})NR^2R^{2a}$, $NR^2C(O)R^{2b}$, $NR^2C(O)R^3$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

$R^{1''}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, a $C_{3-6}$ carbocyclic-$CH_2$— residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is selected from:
  $C_{3-10}$ carbocyclic residue substituted with 0–2 $R^4$, and
  5–10 membered heterocyclic system containing from 1–4 heteroatoms selected from the group consisting of N, O, and S substituted with 0–2 $R^4$;

B is selected from:
  Y, X-Y, $C(=NR^2)NR^2R^{2a}$, $NR^2C(=NR^2)NR^2R^{2a}$,
  $C_{3-10}$ carbocyclic residue substituted with 0–2 $R^{4a}$, and
  5–10 membered heterocyclic system containing from 1–4 heteroatoms selected from the group consisting of N, O, and S substituted with 0–2 $R^{4a}$;

X is selected from $C_{1-4}$ alkylene, $-CR^2(CR^2R^{2b})(CH_2)_t-$, $-C(O)-$, $-C(=NR^{1''})-$, $-CR^2(NR^{11}R^2)-$, $-CR^2(OR^2)-$, $-CR^2(SR^2)-$, $-C(O)CR^2R^{2a}-$, $-CR^2R^{2a}C(O)-$, $-S(O)_p-$, $-S(O)$, $CR^2R^{2a}-$, $-CR^2R^{2a}S(O)_p-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2-$, $NR^2CR^2R^{2a}-$, $-CR^2R^{2a}NR^2$, 0, $-CR^2R^{2a}O-$, and $-OCR^2R^{2a}-$;

Y is selected from:
  $CH_2NR^2R^{2a}$;
  $CH_2CH_2NR^2R^{2a}$;
  $C_{3-10}$ carbocyclic residue substituted with 0–2 $R^{4a}$, and
  5–10 membered heterocyclic system containing from 1–4 heteroatoms selected from the group consisting of N, O, and S substituted with 0–2 $R^{4a}$;

$R^4$, at each occurrence, is selected from H, =O, $(CH_2)_rOR^2$, F, Cl, Br, I, $C_{1-4}$ alkyl, $-CN$, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2-C_{1-4}$ alkyl, $NR^2SO_2R^5$, $S(O)_pR^5$, $(CF_2)_rCF_3$, $NCH_2R^{1'}$, $OCH_2R^{1'}$, $SCH_2R^{1'}$, $N(CH_2)_2(CH_2)_tR^{1'}$, $O(CH_2)_2(CH_2)_tR^{1'}$, and $S(CH_2)2(CH_2)_tR^{1'}$;

alternatively, one $R^4$ is a 5–6 membered aromatic heterocycle containing from 1–4 heteroatoms selected from the group consisting of N, O, and S;

$R^{4a}$, at each occurrence, is selected from H, =O, $(CH_2)_rOR^2$, $(CH_2)_r-F$, $(CH_2)_r-Br$, $(CH_2)_r-Cl$, Cl, Br, F, I, $C_{1-4}$ alkyl, $-CN$, $NO_2$, $(CH_2)_rNR^2R^{2a}\&$, $(CH_2)_rC(O)R^{2c}$, $NR^2C(O)R^{2b}$, $C(O)NR^2R^{2a}$, $(CH_2)$, $N=CHOR^3$, $C(O)NH(CH_2)_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2-C_{1-4}$ alkyl, $C(O)NHSO_2-C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from H, =O, $(CH_2)_rOR^3$, F, Cl, Br, I, $C_{1-4}$ alkyl, $-CN$, $NO_2$, $(CH_2)_rNR^3R^{3a}$, $(CH_2)_rC(O)R^3$, $(CH_2)_rC(O)OR^3C$, $NR^3C(O)R^{3a}$, $C(O)NR^3R^{3a}$, $NR^3C(O)NR^3R^{3a}$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-14}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;
m, at each occurrence, is selected from 0, 1, and 2;
p, at each occurrence, is selected from 0, 1, and 2;
r, at each occurrence, is selected from 0, 1, 2, and 3;
s, at each occurrence, is selected from 0, 1, and 2; and,
t, at each occurrence, is selected from 0, 1, 2, and 3.

[2] In a preferred embodiment, the present invention provides a novel compound, wherein the compound is selected from the group:

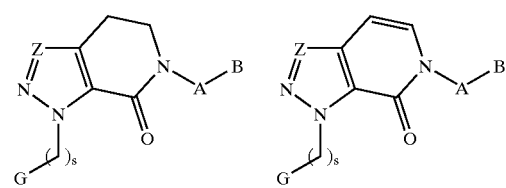

-continued

-continued wherein compounds of the above formulas are substituted with 0–2 R³;

G is selected from the group:

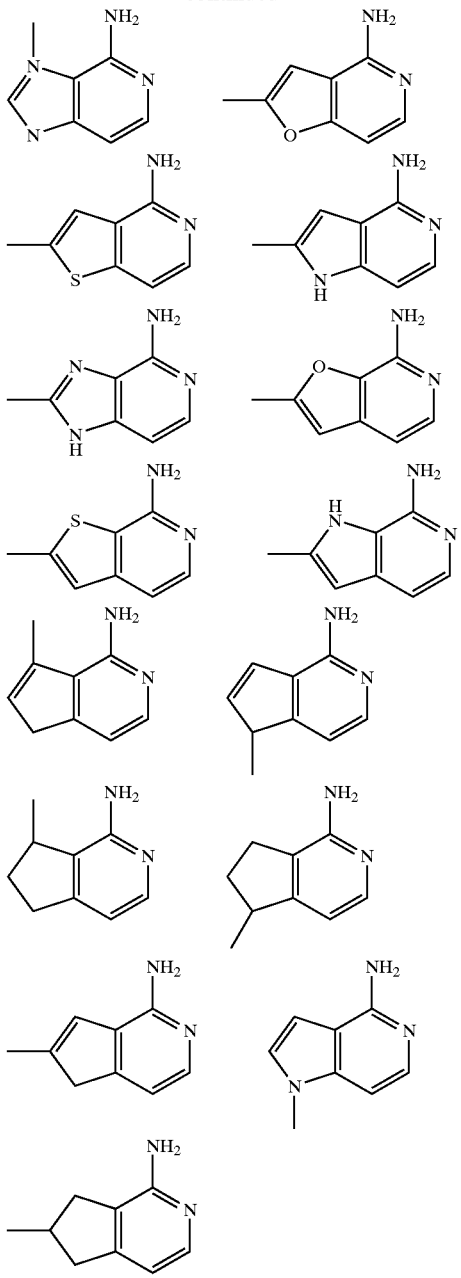

A is selected from one of the following carbocyclic and heterocyclic systems which are substituted with 0–2 $R^4$;
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: Y, X-Y, C(=NR²)NR²R²ᵃ, and NR²C(=NR²)NR²R²ᵃ;

X is selected from $C_{1-4}$ alkylene, —C(O)—, —C(=NR)—, —CR²(NR²R²ᵃ)-, —C(O)CR²R²ᵃ—, —CR²R²ᵃC(O)—, —C(O)NR²—, —NR²C(O)—, —C(O)NR²CR²R²ᵃ—, —NR²C(O)CR²R²ᵃ—, —CR²R²ᵃC(O)NR²—, —CR²R²ᵃNR²C(O)—, —NR²C(O)NR²—, —NR²—, —NR²CR²R²ᵃ—, —CR²R²ᵃNR²—, O, —CR²R²ᵃO—, and —OCR²R²ᵃ—;

Y is $CH_2NR^2R^{2a}$ or $CH_2CH_2NR^2R^{2a}$;

alternatively, Y is selected from one of the following carbocyclic and heterocyclic systems that are substituted with 0–2 $R^{4a}$;
  cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

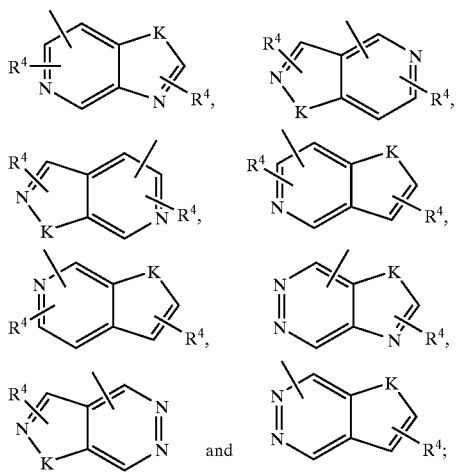

K is selected from O, S, and N; and,
s is 0.

[3] In a more preferred embodiment, the present invention provides a novel compound, wherein the compound is selected from the group:

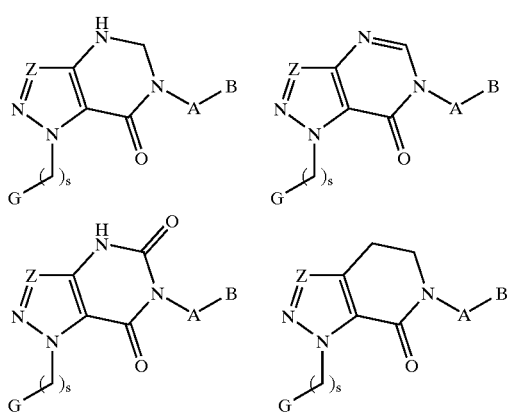

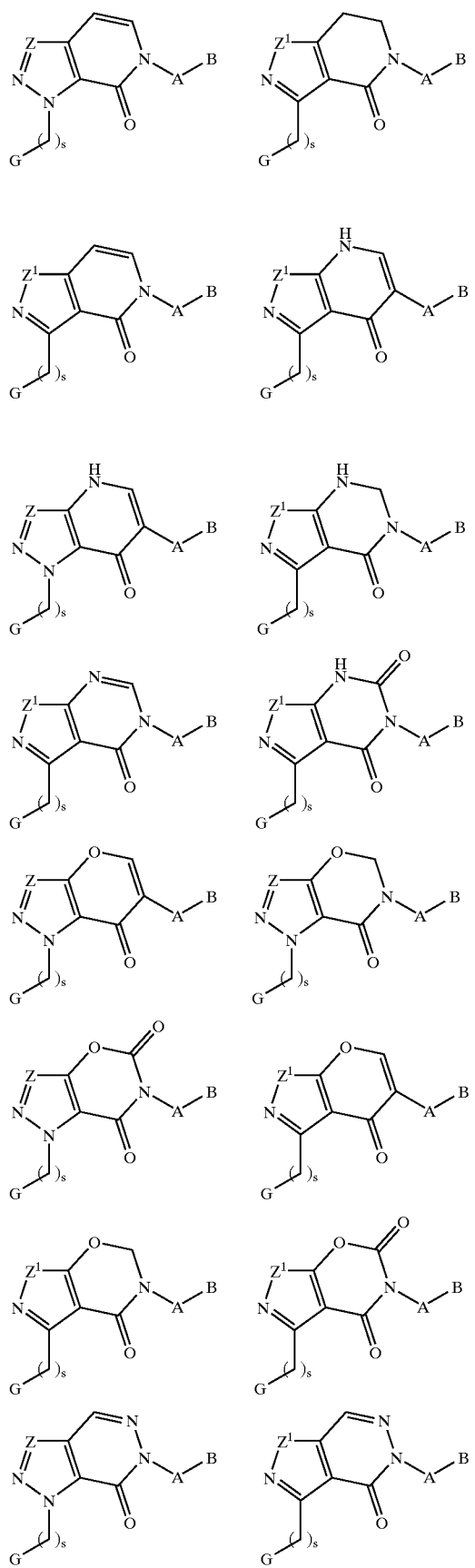
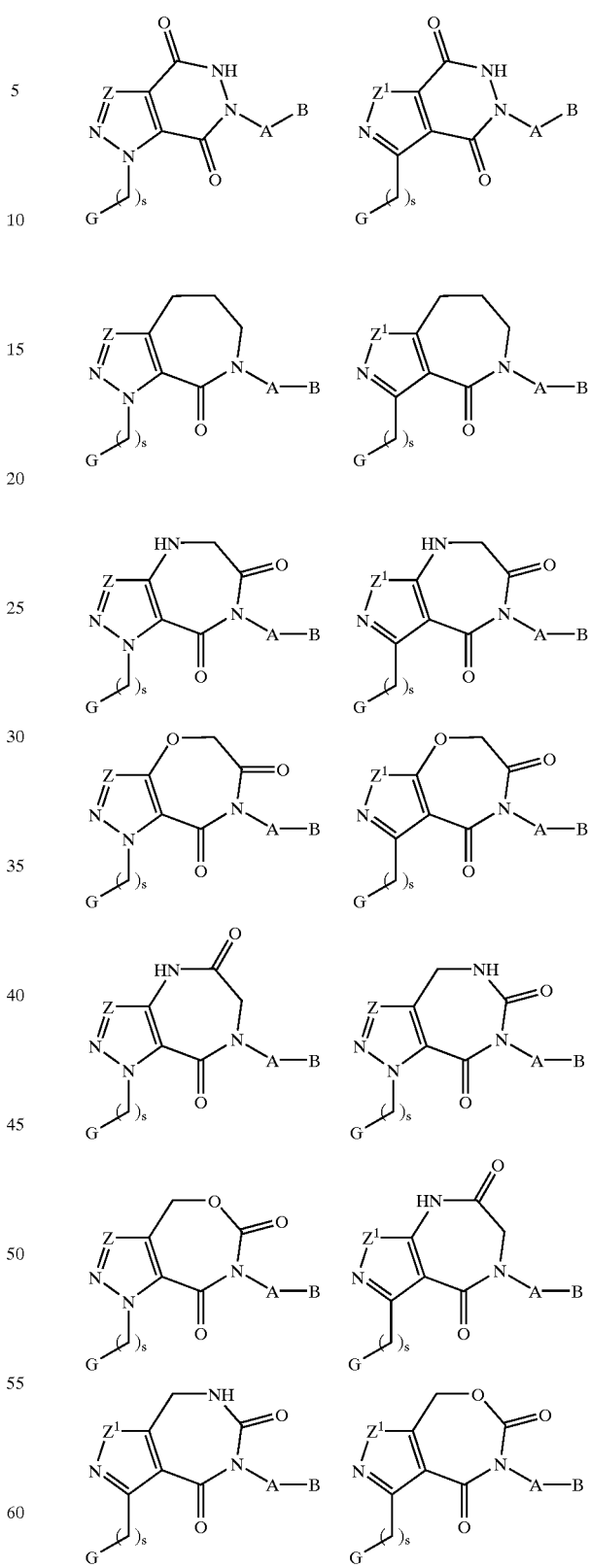
wherein compounds of the above formulas are substituted with 0–2 $R^3$;

G is selected from the group:
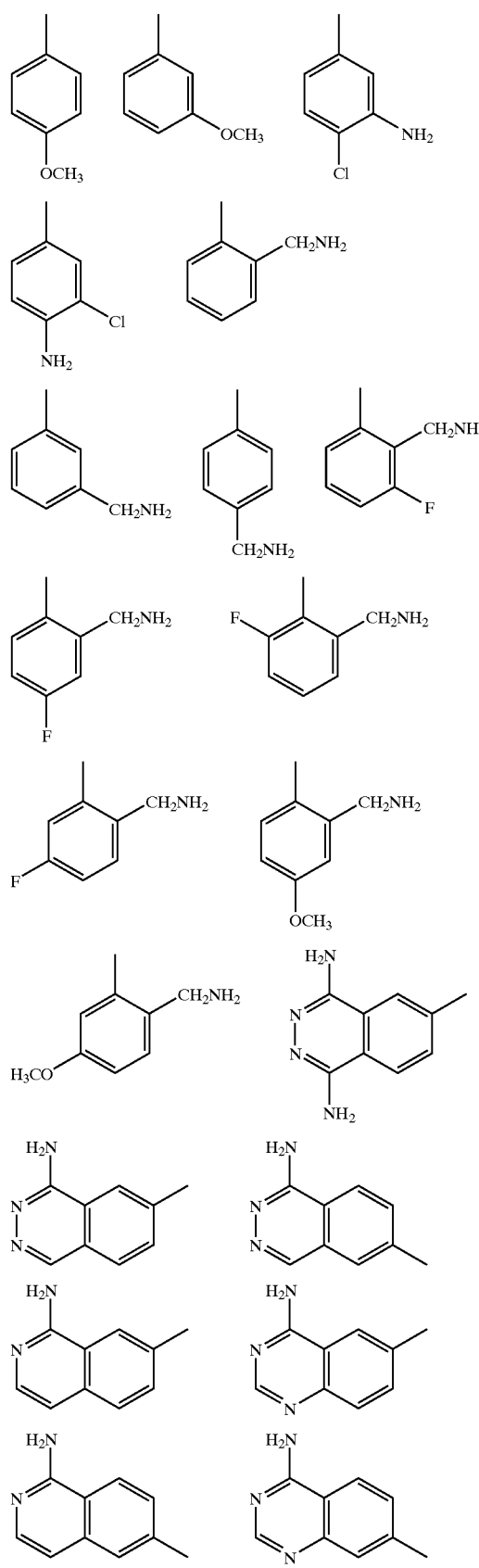
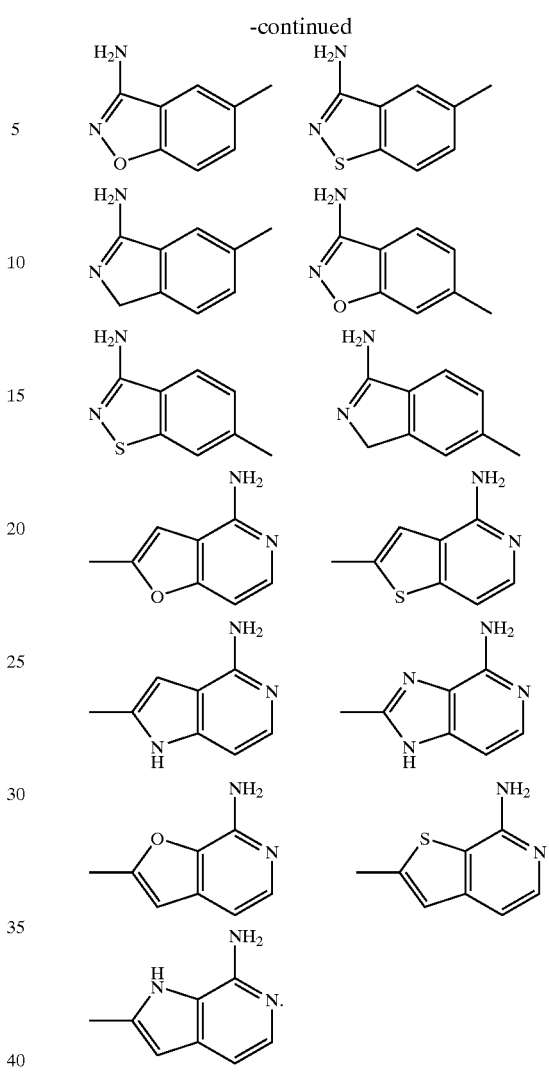
[4] In an even more preferred embodiment, the present invention provides a novel compound, wherein:
G is selected from:
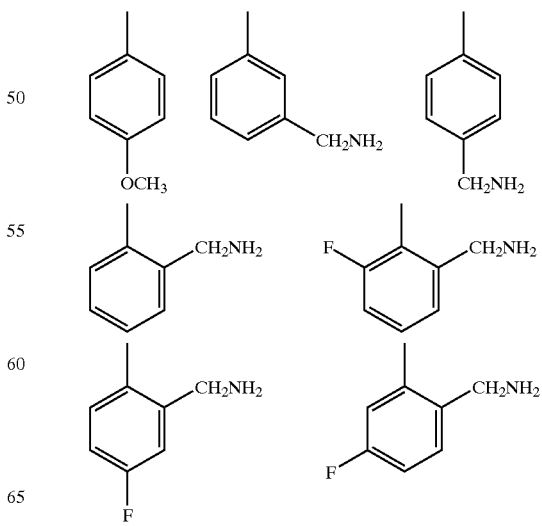

-continued

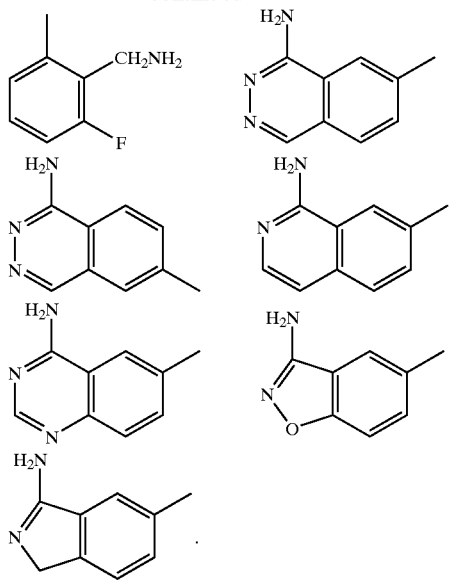

[5] In a still more preferred embodiment, the present invention provides a novel compound, wherein;
A is selected from phenyl, pyridyl, and pyrimidyl, and is substituted with 0–2 $R^4$; and,
B is selected from X-Y, phenyl, pyrrolidino, morpholino, 1,2,3-triazolyl, and imidazolyl, and is substituted with 0–1 $R^{4a}$;
$R^2$, at each occurrence, is selected from H, $CH_3$, $CH_2CH_3$, cyclopropylmethyl, cyclobutyl, and cyclopentyl;
$R^{2a}$, at each occurrence, is H or $CH_3$;
alternatively, $R^2$ and $R^{2a}$, together with the atom to which they are attached, combine to form pyrrolidine substituted with 0–2 $R^{4b}$;
$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;
$R^{4a}$ is selected from $C_{1-4}$ alkyl, $CF_3$, $(CH_2)_rOR^2$, $(CH_2)_rNR^2R^{2a}$, $S(O)_pR^5$, $SO_2NR^2R^{2a}$, and 1-$CF_3$-tetrazol-2-yl;
$R^{4b}$, at each occurrence, is selected from H, $CH_3$, and OH;
$R^5$, at each occurrence, is selected from $CF_3$, $C_{1-6}$ alkyl, phenyl, and benzyl;
X is $CH_2$ or C(O);
Y is selected from pyrrolidino and morpholino; and,
r, at each occurrence, is selected from 0, 1, and 2.
[6] In a further preferred embodiment, the present invention provides a novel compound, wherein;
A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and,
B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, and 2-(N-(3-hydroxypyrrdlidinyl)methyl)phenyl.
[7] In an even further preferred embodiment, the present invention provides a novel compound selected from:
1-[4-Methoxyphenyl]-3-cyano-6-[2'-methylsulfonyl-3-fluoro-[1,1']-biphen-4-yl]-1,4-dihydropyrazolo-[4,3-d]-pyrimidine-5,7-dione;
1-[4-Methoxyphenyl]-3-(methoxycarbonyl)-6-[12-aminosulfonyl-3-fluoro-[1,1']-biphen-4-yl]-1,6-dihydropyrazolo-[4,3-d]-pyrimidin-7-one;
1-[4-Methoxyphenyl]-3-(aminocarbonyl)-6-[2-aminosulfonyl-3-fluoro-[1,1']-biphen-4-yl]-1,6-dihydropyrazolo-[4,3-d]-pyrimidin-7-one;
1-[4-Methoxyphenyl]-3-(methoxycarbonyl)-6-[2'-aminosulfonyl-[1,1']-biphen-4-yl]-1,6-dihydropyrazolo-[4,3-d]-pyrimidin-7-one;
1-[4-Methoxyphenyl]-6-(2'-aminosulfonyl-[1,1'-biphen-4-yl]-1,6-dihydropyrazolo-[4,3-d]-pyrimidin-7-one-3-carboxylic acid;
1-[4-Methoxyphenyl]-3-(aminocarbonyl)-6-(2'-aminosulfonyl-[1,1']-biphen-4-yl]-1,6-dihydropyrazolo-[4,3-d]-pyrimidin-7-one;
1-[4-Methoxyphenyl]-3-cyano-6-[2'-aminosulfonyl-[1,1']-biphen-4-yl]-1,6-dihydropyrazolo-[4,3-d]-pyrimidin-7-one;
1-[4-Methoxyphenyl]-3-(aminomethyl)-6-[2'-aminosulfonyl-[1,1']-biphen-4-yl]-1,6-dihydropyrazolo-[4,3-d]-pyrimidin-7-one;
1-[4-Methoxyphenyl]-3-(ethoxycarbonyl)-6-[4-(2-methylimidazol-1'-yl)phenyl]-1,6-dihydropyrazolo-[4,3-d]-pyrimidin-7-one;
1-[4-Methoxyphenyl)-3-(aminocarbonyl)-6-[4-(2-methylimidazol-1'-yl)phenyl]-1,6-dihydropyrazolo-[4,3-d]-pyrimidin-7-one;
1-[4-Methoxyphenyl]-3-(ethoxycarbonyl)-6-[2'-N-pyrrolidinylmethyl-[1,1']-biphen-4-yl]-1,6-dihydropyrazolo-[4,3-d]-pyrimidin-7-one;
1-[4-Methoxyphenyl]-3-(ethoxycarbonyl)-6-[2'-N-pyrrolidinylmethyl-[1,1']-biphen-4-yl]-1,4,5,6-tetrahydropyrazolo-[4,3-d]-pyrimidin-7-one;
1-[4-Methoxyphenyl]-3-(aminocarbonyl)-6-[2'-N-pyrrolidinylmethyl-[1,1']-biphen-4-yl]-1,6-dihydropyrazolo-[4,3-d]-pyrimidin-7-one;
1-[4-Methoxyphenyl]-3-cyano-6-[2'-N-pyrrolidinylmethyl-[1,1']-biphen-4-yl]-1,6-dihydropyrazolo-[4,3-d]-pyrimidin-7-one;
1-[4-Methoxyphenyl]-3-(ethoxycarbonyl)-6-[2-fluoro-4-(2-dimethylaminomethylimidazol-1'-yl)phenyl]-1,6-dihydropyrazolo-[4,3-d]-pyrimidin-7-one;
1-[2-Aminomethylphenyl]-3-(ethoxycarbonyl)-6-[2'-methylsulfonyl-[1,1']-biphen-4-yl]-1,6-dihydropyrazolo-[4,3-d]-pyrimidin-7-one;
1-[3-Aminoiminomethylphenyl]-3-methyl-6-[2'-aminosulfonyl-[1,1']-biphen-4-yl]-1,4,5,6-tetrahydropyrazolo-[3,4-c]-pyridin-7-one;
1-[2-Aminomethylphenyl]-3-methyl-6-(2'-aminosulfonyl-[1,1']-biphen-4-yl]-1,4,5,6-tetrahydropyrazolo-[3,4-c]-pyridin-7-one;
1-[3-Aminobenzisoxazol-5'-yl]-3-methyl-6-[2'-aminosulfonyl-[1,1']-biphen-4-yl]-1,4,5,6-tetrahydropyrazolo-[3,4-c]-pyridin-7-one;
1-[4-Methoxyphenyl]-3-cyano-6-[2'-N,N-dimethylaminomethyl-[1,1']-biphen-4-yl]-1,6-dihydropyrazolo-[4,3-d]-pyrimidin-7-one;
1-[4-Methoxyphenyl]-3-cyano-5-methyl-6-[2'-N,N-dimethylaminomethyl-[1,1']-biphen-4-yl]-1,6-dihydropyrazolo-[4,3-d]-pyrimidin-7-one;
1-[2-Aminomethylphenyl]-3-cyano-6-[2'-methylsulfonyl-3-fluoro-[1,1']-biphen-4-yl]-1,6-dihydropyrazolo-[4,3-d]-pyrimidin-7-one;
1-[4-Methoxyphenyl]-3-trifluoromethyl-4-methyl-6-[2'-aminosulfonyl-(1,1']-biphen-4-yl]-1,6-dihydropyrazolo-[3,4-d]-pyridazin-7-one;
1-[4-Methoxyphenyl]-3-trifluoromethyl-4-methyl-6-[2'-N-pyrrolidinylmethyl-[1,1']-biphen-4-yl]-1,6-dihydropyrazolo-[3,4-d]-pyridazin-7-one, 1-[3-Aminobenzisoxazol-5'-yl]-3-trifluoromethyl-6-[4-(1-methylimidazol-2'-yl)phenyl]-1,6-dihydropyrazolo-[4,3-d]-pyrimidin-7-one;

1-[4-Methoxyphenyl]-3-(ethoxycarbonyl)-6-[2'-hydroxymethyl-3-fluoro-[1,1']-biphen-4-yl]-1,6-dihydropyrazolo-[4,3-d]-pyrimidin-7-one;

1-[4-Methoxyphenyl]-3-(ethoxycarbonyl) 6-[2'-N-pyrrolidinylmethyl-3-fluoro-[1,1']-biphen-4-yl]-1,6-dihydropyrazolo-[4,3-d]-pyrimidin-7-one;

1-[4-Methoxyphenyl]-3-(aminocarbonyl)-6-[2'-N-pyrrolidinylmethyl-3-fluoro-[1,1']-biphen-4-yl]-1,6-dihydropyrazolo-[4,3-d]-pyrimidin-7-one;

1-[4-Methoxyphenyl]-3-(aminocarbonyl)-6-[2'-(3-(R)-hydroxy-N-pyrrolidinylmethyl)-3-fluoro-[1,1']-biphen-4-yl]-1,6-dihydropyrazolo-[4,3-d]-pyrimidin-7-one;

1-[4-Methoxyphenyl]-3-(N-formylaminomethyl)-6-[2'-methylsulfonyl-3-fluoro-[1,1']-biphen-4-yl]-1,6-dihydropyrazolo-[4,3-d]-pyrimidin-7-one;

1-[3-Aminobenzisoxazol-5'-yl]-3-(ethoxycarbonyl)-6-[2'-hydroxymethyl-[1,1')-biphen-4-yl]-1,6-dihydropyrazolo-(4,3-d]-pyrimidin-7-one;

1-[3-Aminobenzisoxazol-5'-yl]-3-(ethoxycarbonyl)-6-[2'-N-pyrrolidinylmethyl-[(1,1]-biphen-4-yl]-1,6-dihydropyrazolo-[4,3-d]-pyrimidin-7-one;

1-[4-Methoxyphenyl)-3-trifluoromethyl-7-[2'-methylsulfonyl-[1,1']-biphen-4-yl]-4,5,6,7-tetrahydropyrazolo-[3,4-c]-azepin-8-one;

1-[4-Methoxyphenyl]-3-trifluoromethyl-7-[2'-aminosulfonyl-3-fluoro-[1,1']-biphen-4-yl]-4,5,6,7-tetrahydropyrazolo-[3,4-c]-azepin-8-one;

1-[4-Methoxyphenyl]-3-trifluoromethyl-7-[2'-N-pyrrolidinylmethyl-[1,1']-biphen-4-yl]-4,5,6,7-tetrahydropyrazolo-[3,4-c]-azepin-8-one;

1-[3-Aminobenzisoxazol-5'-yl]-3-trifluoromethyl-7-[2'-N-pyrrolidinylmethyl-[1,1']-biphen-4-yl]-4,5,6,7-tetrahydropyrazolo-(3,4-c]-azepin-8-one;

1-[3-Aminobenzisoxazol-5'-yl]-3-trifluoromethyl-7-[2'-N-dimethylaminomethyl-[1,1']-biphen-4-yl]-4,5,6,7-tetrahydropyrazolo-[3,4-c]-azepin-8-one;

1-[3-Aminobenzisoxazol-5'-yl]-3-trifluoromethyl-7-[2'-N-isopropylaminomethyl-[1,1']-biphen-4-yl]-4,5,6,7-tetrahydropyrazolo-[3,4-c]-azepin-8-one;

1-[3-Aminobenzisoxazol-5'-yl]-3-trifluoromethyl-7-[2'-(3-(R)-hydroxy-N-pyrrolidinyl)methyl-(1,1']-biphen-4-yl]-4,5,6,7-tetrahydropyrazolo-[3,4-c]-azepin-8-one;

1-[3-Aminobenzisoxazol-5'-yl]-3-trifluoromethyl-7-[2'-(3-(R)-hydroxy-N-pyrrolidinyl)methyl-3-fluoro-[1,1']-biphen-4-yl]-4,5,6,7-tetrahydropyrazolo-[3,4-c]-azepin-8-one;

1-[3-Aminobenzisoxazol-5l-yl]-3-trifluoromethyl-7-[2'-N-pyrrolidinylmethyl-3-fluoro-[1,1']-biphen-4-yl]-4,5,6,7-tetrahydropyrazolo-[3,4-c]-azepin-8-one;

1-[3-Aminobenzisoxazol-5'-yl)-3-trifluoromethyl-7-[2'-N-dimethylaminomethyl-3-fluoro-[1,1']-biphen-4-yl]-4,5,6,7-tetrahydropyrazolo-[3,4-c]-azepin-8-one;

1-[3-Aminobenzisoxazol-5'-yl]-3-trifluoromethyl-7-[2'-N-isopropylaminomethyl-3-fluoro-[1,1']-biphen-4-yl]-4,5,6,7-tetrahydropyrazolo-[3,4-c]-azepin-8-one;

1-[4-Methoxyphenyl]-3-trifluoromethyl-7-[4-(2-dimethylaminomethylimidazol-1'-yl)-3-fluorophenyl]-4,5,6,7-tetrahydropyrazolo-[3,4-c]-azepin-8-one;

1-[4-Methoxyphenyl]-3-trifluoromethyl-7-[4-(imidazol-1'-yl)-3-fluorophenyl]-4,5,6,7-tetrahydropyrazolo-[3,4-c]-azepin-8-one;

1-[2-Aminomethylphenyl]-3-trifluoromethyl-7-(2'-methylsulfonyl-[1,1']-biphen-4-yl]-4,5,6,7-tetrahydropyrazolo-[3,4-c]-azepin-8-one;

1-[3-Aminobenzisoxazol-5'-yl]-3-methyl-6-[2'-N-pyrrolidinylmethyl-[1,1']-biphen-4-yl]-1,4,5,6-tetrahydro-7H-pyrazolo-[3,4-c]-pyridin-7-one;

1-[3-Aminobenzisoxazol-5'-yl]-3-methyl-6-[2'-(3-(S)-hydroxy-N-pyrrolidinyl)methyl-[1,1']-biphen-4-yl]-1,4,5,6-tetrahydro-7H-pyrazolo-[3,4-c]-pyridin-7-one;

1-[3-Aminobenzisoxazol-5'-yl]-3-methyl-6-[2'-N-isopropylaminomethyl-[1,1']-biphen-4-yl]-1,4,5,6-tetrahydro-7H-pyrazolo-[3,4-c]-pyridin-7-one;

1-[3-Aminobenzisoxazol-5'-yl]-3-methyl-6-[2'-N,N-dimethylaminomethyl-[1,1']-biphen-4-yl]-1,4,5,6-tetrahydro-7H-pyrazolo-[3,4-c]-pyridin-7-one;

1-[3-Aminobenzisoxazol-5'-yl]-3-methyl-6-[2'-methylsulfonyl-[1,1']-biphen-4-yl]-1,4,5,6-tetrahydro-7H-pyrazolo-(3,4-c]-pyridin-7-one;

1-[3-Aminobenzisoxazol-5'-yl]-3-methyl-6-[2'-methylsulfonyl-3-fluoro-[1,1']-biphen-4-yl]-1,4,5,6-tetrahydro-7H-pyrazolo-[3,4-c]-pyridin-7-one;

1-[2-Aminomethylphenyl]-3-trifluoromethyl-6-[2'-methylsulfonyl-3-fluoro-[1,1']-biphen-4-yl]-1,4,5,6-tetrahydropyrazolo-[3,4-c]-pyridin-7-one;

1-[2-Aminomethylphenyl]-3-trifluoromethyl-6-[2'-aminosulfonyl-3-fluoro-[1,11]-biphen-4-yl]-1,4,5,6-tetrahydropyrazolo-[3,4-c]-pyridin-7-one;

1-[2-Aminomethylphenyl]-3-trifluoromethyl-6-[2'-methylsulfonyl-[1,1]-biphen-4-yl]-1,4,5,6-tetrahydropyrazolo-[3,4-c]-pyridin-7-one;

1-[2-Aminomethylphenyl]-3-trifluoromethyl-6-(2'-N,N-dimethylaminomethyl-3-fluoro-[1,1']-biphen-4-yl]-1,4,5,6-tetrahydropyrazolo-[3,4-c]-pyridin-7-one;

1-[2-Aminomethylphenyl]-3-trifluoromethyl-6-[2'-(3-(R)-hydroxy-N-pyrrolidinyl)methyl-3-fluoro-[1,1']-biphen-4-yl]1,4,5,6-tetrahydropyrazolo-[3,4-c]-pyridin-7-one;

1-[3-Aminobenzisoxazol-5'-yl]-3-trifluoromethyl-6-[2'-dimethylaminomethyl-3-fluoro-[1,1']-biphen-4-yl]-1,4,5,6-tetrahydropyrazolo-[3,4-c]-pyridin-7-one;

1-[3-Aminobenzisoxazol-5'-yl]-3-trifluoromethyl-6-[2'-(3-(R)-hydroxy-N-pyrrolidinyl)methyl-3-fluoro-[1,1']-biphen-4-yl]-1,4,5,6-tetrahydropyrazolo-[3,4-c]-pyridin-7-one;

1-[3-Aminobenzisoxazol-5'-yl]-3-trifluoromethyl-6-[2'-(3-(R)-hydroxy-N-pyrrolidinyl)methyl-[1,1']-biphen-4-yl]-1,4,5,6-tetrahydropyrazolo-[3,4-c]-pyridin-7-one;

1-[3-Aminobenzisoxazol-5'-yl]-3-trifluoromethyl-6-[2'-isopropylaminomethyl-3-fluoro-[1,1']-biphen-4-yl)-1,4,5,6-tetrahydropyrazolo-[3,4-c]-pyridin-7-one;

1-[3-Aminobenzisoxazol-5'-yl)-3-trifluoromethyl-6-[2'-N-(2-methylimidazol-1-yl)methyl-3-fluoro-[1,1')-biphen-4-yl]-1,4,5,6-tetrahydropyrazolo-[3,4-c]-pyridin-7-one;

1-[3-Aminobenzisoxazol-5'-yl]-3-trifluoromethyl-6-[2'-N-pyrrolidinomethyl-3-fluoro-[1,1']-biphen-4-yl)-1,4,5,6-tetrahydropyrazolo-[3,4-c]-pyridin-7-one;

1-[3-Aminobenzisoxazol-5l-yl]-3-trifluoromethyl-6-[2'-oximinomethyl-3-fluoro-[1,1']-biphen-4-yl]-1,4,5,6-tetrahydropyrazolo-[3,4-c]-pyridin-7-one;

1-[4-Methoxyphenyl]-3-trifluoromethyl-6-[2'-(3-(R)-hydroxy-N-pyrrolidinyl)methyl-3-fluoro-[1,1']-biphen-4-yl]-1,4,5,6-tetrahydropyrazolo-[3,4-c]-pyridin-7-one;

1-[3-Aminomethylphenyl]-3-trifluoromethyl-6-[2'-methylsulfonyl-3-fluoro-[1,1']-biphen-4-yl]-1,4,5,6-tetrahydropyrazolo-[3,4-c]-pyridin-7-one;

1-[4-Methoxyphenyl]-3-[(imidazol-1-yl)methyl]-5-methyl-6-[(2'-N-pyrrolidinylmethyl-[1,1']-biphen-4-yl)]-1,6-dihydropyrazolo-[4,3-d]-pyrimidin-7-one;

1-[4-Methoxyphenyl]-3-[(tetrazol-1-yl)methyl]-5-methyl-6-[(2'-N-pyrrolidinylmethyl-[1,1']-biphen-4-yl)]-1,6-dihydropyrazolo-[4,3-d]-pyrimidin-7-one;

1-[4-Methoxyphenyl]-3-[(tetrazol-2-yl)methyl]-5-methyl-6-[(21-N-pyrrolidinylmethyl-[1,1']-biphen-4-yl)]-1,6-dihydropyrazolo-[4,3-d]-pyrimidin-7-one;

1-[3-Aminobenzisoxazol-5'-yl]-3,5-dimethyl-6-[2'-N-dimethylaminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-N,N-dimethylaminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-N-isopropylaminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-(3-(R)-hydroxy-N-pyrrolidinyl)methyl-[1,1']-biphen-4-yl]-1,6-dihydropyrazolo-[4,3-d]-pyrimidin-7-one;

1-[3-Aminobenzisoxazol-5'-yl]-3-methyl-6-[4-(4,5-dihydroimidazol-1'-yl)phenyl]-1,6-dihydropyrazolo-[4,3-d]-pyrimidin-7-one;

1-[3-Aminobenzisoxazol-5'-yl]-3-methyl-6-[2'-N-(cyclopropylmethyl)aminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-N-pyrrolidinylmethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-(N-methyl-N-isopropyl)aminomethyl-[1,1']-biphen-4-yl]-1,6-dihydropyrazolo-[4,3-d]-pyrimidin-7-one;

1-[3-Aminobenzisoxazol-5'-yl]-3,5-dimethyl-6-[2'-(3-(R)-hydroxy-N-pyrrolidinyl)methyl-[1,1']-biphen-4-yl]-1,6-dihydropyrazolo-[4,3-d]-pyrimidin-7-one;

1-[3-Aminobenzisoxazol-5'-yl]-3-trifluoromethyl-6-[2'-N,N-dimethylaminomethyl-[1,1')-biphen-4-yl]-1,6-dihydropyrazolo-[4,3-d]-pyrimidin-7-one;

1-[3-Aminobenzisoxazol-5'-yl]-3-trifluoromethyl-6-[2'-N,N-dimethylaminomethyl-[1,1']-biphen-4-yl]-1,4,5,6-tetrahydropyrazolo-[4,3-d]-pyrimidin-7-one;

1-[3-Aminobenzisoxazol-5'-yl]-3-trifluoromethyl-6-[2'-(3-(R)-hydroxy-N-pyrrolidinyl)methyl-[1,1']-biphen-4-yl]-1,4,5,6-tetrahydropyrazolo-[4,3-d]-pyrimidin-7-one;

1-[3-Aminobenzisoxazol-5'-yl]-3-trifluoromethyl-6-[2'-(3-(S)-hydroxy-N-pyrrolidinyl)methyl-[1,1']-biphen-4-yl]-1, 4, 5, 6-tetrahydropyrazolo-[3,4-c]-pyridin-7-one;

1-[3-Aminobenzisoxazol-5'-yl]-3-trifluoromethyl-6-[2'-N-(pyrrolindinyl)methyl-[1,1']-biphen-4-yl]-1,4,5,6-tetrahydropyrazolo-[3,4-c]-pyridin-7-one;

1-[3-Aminobenzisoxazol-5'-yl]-3-trifluoromethyl-6-[2'-N-(morpholino)methyl-[1,1']-biphen-4-yl]-1,4,5,6-tetrahydropyrazolo-[3,4-c]-pyridin-7-one;

1-[3-Aminobenzisoxazol-5'-yl]-3-trifluoromethyl-6-[2'-N,N-dimethylaminomethyl-[1,1']-biphen-4-yl]-1,4,5,6-tetrahydropyrazolo-[3,4-c]-pyridin-7-one;

1-[3-Aminobenzisoxazol-5'-yl]-3-trifluoromethyl-7-[(3'-N-dimethylaminomethyl)-3-fluoro-[1,11]-biphen-4-yl]-4,5,6,7-tetrahydropyrazolo-[3,4-c]azepin-8-one;

1-[3-Aminobenzisoxazol-5'-yl]-3-trifluoromethyl-7-[(3'-N-pyrrolidinylmethyl)-3-fluoro-[1,1']-biphen-4-yl]-4,5,6,7-tetrahydropyrazolo-[3,4-c]azepin-8-one;

1-[4-Methoxyphenyl]-3-trifluoromethyl-7-[(3'-N-pyrrolidinylmethyl)-[1,1']-biphen-4-yl]-4,5,6,7-tetrahydropyrazolo-[3,4-c]azepin-8-one;

1-[4-Methoxyphenyl]-3-trifluoromethyl-7-[(3'-N-dimethylaminomethyl)-[1,1]-biphen-4-yl]-4,5,6,7-tetrahydropyrazolo-[3,4-c]azepin-8-one;

1-[4-Methoxyphenyl]-3-trifluoromethyl-7-[4-benzimidazol-1'-yl-3-fluorophenyl]-4,5,6,7-tetrahydropyrazolo-[3,4-c]azepin-8-one;

1-[3-Aminobenzisoxazo-5'-yl]-3-trifluoromethyl-7-[(2'-N-pyrrolidinylmethyl)-3-fluoro-[1,1']-biphen-4-yl]-6,7-dihydropyrazolo-[3,4-c]azepin-8-one;

1-[3-Aminobenzisoxazo-5'-yl]-3-trifluoromethyl-7-[(21'-N-dimethylaminomethyl)-3-fluoro-[1,1']-biphen-4-yl]-6,7-dihydropyrazolo-[3,4-c]azepin-8-one;

1-[3-Aminobenzisoxazo-5'-yl]-3-trifluoromethyl-7-[(2'-N-(R)-3-hydroxypyrrolidinylmethyl)-3-fluoro-[1,1')-biphen-4-yl]-6,7-dihydropyrazolo-[3,4-clazepin-8-one;

1-[3-Aminobenzisoxazo-5'-yl]-3-trifluoromethyl-7-[(2'-N—(R)-3-hydroxypyrrolidinylmethyl)-[1,1']-biphen-4-yl]-6,7-dihydropyrazolo-[3,4-c]azepin-8-one;

1-[3-Aminobenzisoxazo-5'-yl]-3-trifluoromethyl-7-[(2'-N-dimethylaminomethyl)-[1,1']-biphen-4-yl]-6,7-dihydropyrazolo-[3,4-c]azepin-8-one;

1-[4-Methoxyphenyl]-3-trifluoromethyl-7-[(2'-N-pyrrolidinylmethyl)-[1,1']-biphen-4-yl]-6,7-dihydropyrazolo-[3,4-c]azepin-8-one;

1-[4-Methoxyphenyl]-3-trifluoromethyl-7-[(2'-N,N-dimethylaminomethyl)-[1,1']-biphen-4-yl]-6,7-dihydropyrazolo-[3,4-c]azepin-8-one;

1[4-Methoxyphenyl]-3-trifluoromethyl-6-[(4-aminomethyl)phenyl]-1,4,5,6-tetrahydropyrazolo-[3,4-c]pyridin-7-one;

1-[3-Aminomethylphenyl]-3-methyl-6-[(2'-N-((3-(S)-hydroxy)pyrrolidinyl) methyl-[1,1']-biphen-4-yl)]-1,4,5,6-tetrahydro-7H-pyrazolo-[3,4-c]-pyridin-7-one;

1-[3-Aminomethylphenyl]-3-methyl-6-[(2'-methylsulfonyl-[1,1']-biphen-4-yl)]-1, 4, 5, 6-tetrahydro-7H-pyrazolo[3,4-c]pyridin-7-one;

1-[3-Aminobenzisoxazol-5'-yl]-3-methyl-6-[(3-fluoro-2'-N-(3 (S)-hydroxy)pyrrolidinylmethyl-[1,1']-biphen-4-yl)]-1,4,5,6-tetrahydro-7H-pyrazolo[3,4-c]pyridin-7-one;

1-[3-Aminobenzisoxazol-5'-yl]-3-methyl-6-[(3-fluoro-2'-N-pyrrolidinylmethyl-[1,1']-biphen-4-yl)]-1,4,5,6-tetrahydro-7H-pyrazolo[3,4-c]pyridin-7-one;

1-[1-Aminoisoquinolin-7'-yl]-3-trifluoromethyl-6-[4-(2-methylimidazol-1'-yl)phenyl]-1,4,5,6-tetrahydropyrazolo-[3,4-c]-pyridin-7-one;

1-[3-Aminobenzisoxazol-5'-yl]-3-methyl-6-[4-(2-methylimidazol-1'-yl)phenyl]-1,6-dihydropyrazolo-[4,3-d]-pyrimidin-7-one;

1-[3-Aminobenzisoxazol-5'-yl]-3-methyl-6-[4-(2-(dimethylaminomethyl)imidazol-1-yl)-2-fluorophenyl]-1,6-dihydropyrazolo-[4,3-d]-pyrimidin-7-one;

1-[3-Aminobenzisoxazol-5'-yl]-3-trifluoromethyl-6-[4-(2-(dimethylaminomethyl)imidazol-1'-yl)phenyl]-1,6-dihydropyrazolo-[4,3-d]-pyrimidin-7-one; and, 1-[3-Aminobenzisoxazol-5'-yl]-3-methyl-6-[4-(2-(dimethylaminomethyl)imidazol-1'-yl)-2-fluorophenyl]-1,4,5,6-tetrahydropyrazolo-[3,4-c]-pyridin-7-one; or a pharmaceutically acceptable salt form thereof.

In another embodiment, the present invention provides novel pharmaceutical compositions, comprising: a pharmaceutically acceptable carrier and a therapeutically effective amount of a compound of formula (I) or a pharmaceutically acceptable salt form thereof.

In another embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, C3, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example—$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, Cs, $C_6$, and $C_7$ cycloalkyl groups. Alkenyl" is intended to include hydrocarbon chains of either straight or branched configuration and one or more unsaturated carbon—carbon bonds that may occur in any stable point along the chain, such as ethenyl and propenyl. $C_{2-10}$ alkenyl is intended to include $C_2$, $C_3$, $C_4$, $C_5$, $C_6$, $C_7$, Cs, Cg, and $C_{10}$ alkenyl groups. "Alkynyl" is intended to include hydrocarbon chains of either straight or branched configuration and one or more triple carbon—carbon bonds that may occur in any stable point along the chain, such as ethynyl and propynyl. $C_{2-10}$ Alkynyl is intended to include $C_2$, C3, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue, is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Preferred prodrugs are amidine prodrugs wherein D is $C(=NR^7)NH_2$ or its tautomer $C(=NH)NHR^7$ and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amounts is intended to include an amount of a compound of the present invention or an amount of the combination of compounds claimed effective to inhibit factor Xa. The combination of compounds is preferably a synergistic combination. Synergy, as described, for example, by Chou and Talalay, Adv. Enzyme Regul. 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1991). All references cited herein are hereby incorporated in their entirety herein by reference.

The compounds of the present invention represented by Formula I consist of a group "D-E-G-$(CH_2)_s$-" and a group "-A-B" attached to a [5,6]- or [5,7]-heterobicyclic core structure of varying composition. The five-membered ring can be pyrazole, triazole, isoxazole or isothiazole and this ring can be fused to a variety of six- or seven membered rings including but not limited to piperidinone, pyridinone, pyrimidinone, pyrimidinedione, pyranone, diazepinone, diazepinedione. The following discussion and schemes will describe methods for the syntheses of the heterobicyclic cores and attachment to the groups "G-$(CH_2)_s$-" and "-A-B".

The 4-aminopyrazole-5-carboxylate V is a useful intermediate for the preparation of many of the pyrazole fused compounds of Formula I wherein the "G-$(CH_2)_s$-" residue is attached to a nitrogen atom of the pyrazole (Scheme I). This intermediate can be prepared in a variety of ways from hydrazines I. Hydrazines I are readily available starting materials. Aromatic hydrazines (G is aryl, s=0) are conveniently prepared from the corresponding aniline by diazotization with $NaNO_2$ in acidic media followed by reduction of the resulting diazonium ion with a suitable reducing agent, with $SnCl_2$ being a preferred reagent. Non-aromatic hydrazines represented by I are readily prepared by a variety of methods, such as by displacement of a suitable halogen compound with hydrazine or with a protected hydrazine followed by deprotection. Condensation of hydrazines I with a suitable hemiacetal or aldehyde followed by halogenation with NBS or NCS leads to hydrazidoyl halides II. Alternatively, the hydrazines I can be acylated with an acid chloride and converted to hydrazidoyl halides II by carbon tetrahalide/triphenylphosphine. The hydrazidoyl halides II are versatile intermediates for pyrazole synthesis (Shawali, A. S.; et. al. J. Het. Chem. 1980, 17, 833). The halide can be displaced with cyanide ion to afford cyanide III. Cyano compounds of this type (where G is aryl and s=0) can also be prepared more directly by diazotization of aniline IV followed by direct reaction with a cyano-containing active methylene compound, where $R^{1a}$ can include a variety of groups such as ester, ketone, cyano, trifluoromethyl, sulfone, aryl, etc. (Butler, R. N.; et. al. J. Chem. Soc. Chem. Commun. 1992, 20, 1481). Treatment of III with a bromoacetate in the presence of a suitable base such as carbonate or trialkylamine results in N-alkylation followed by ring closure to give the 4-aminopyrazole-5-carboxylate V. Alternatively, treatment of II with a nitropyruvate in the presence of a base such as alkoxide provides a 4-nitropyrazole by displacement of the halide followed by ring closure of the nitrogen onto the carbonyl group. Reduction of the nitro group can be accomplished by a variety of reducing agents, a preferred one of which is $SnCl_2$, to give the 4-aminopyrazole-5-carboxylate V. The hyrazidoyl halide II can also be reacted with a ketoester where R' represents a masked ester, preferably a 2-furyl residue, to give a pyrazole-4-carboxylate VI. Ester hydrolysis, conversion to an acyl azide, either via the acid chloride or anhydride, heating to generate an isocyanate via Curtius rearrangement, and finally treatment with water affords the 4-aminopyrazole VII. Alternatively, the amino can be masked as an appropriate carbamate by using an alcohol instead of water in the Curtius rearrangement. When R'=2-furyl, the furan can be oxidatively cleaved under a variety of conditions, such as sodium periodate with catalytic ruthenium trichloride, or $KMnO_4$, to afford a carboxylic acid which can be esterified to afford the 4-aminopyrazole-5-carboxylate V.

Another route to the 4-aminopyrazole V involves condensation of the hydrazine I with an appropriate diketone or monoprotected diketone to form a 3,5-disubstituted pyrazole in which the 5-substituent is a carboxylic ester. With proper choice of the G group, this pyrazole can be selectively nitrated at the 4-position with nitrating agents such as nitric acid or ammonium nitrate/trifluoroacetic anhydride. Reduction of the nitro group under a variety of conditions, such as with tin (II) chloride or catalytic hydrogenation, affords the 4-aminopyrazole V. This route can also be carried out using a diketone with a 2-furyl group as a latent carboxylate, giving initially a 3,5-disubstituted pyrazole in which the 5-substituent is the 2-furyl group. Oxidative cleavage of the furyl group to a carboxylate, nitration of the pyrazole 4-position, esterification and nitro reduction then affords 4-aminopyrazole V. It will be recognized by those skilled in the art that the synthetic route chosen to V will depend on additional functionality present in the molecule of interest and the route may require additional protection/deprotection sequences as well as modifications in the order of synthetic steps.

Scheme I

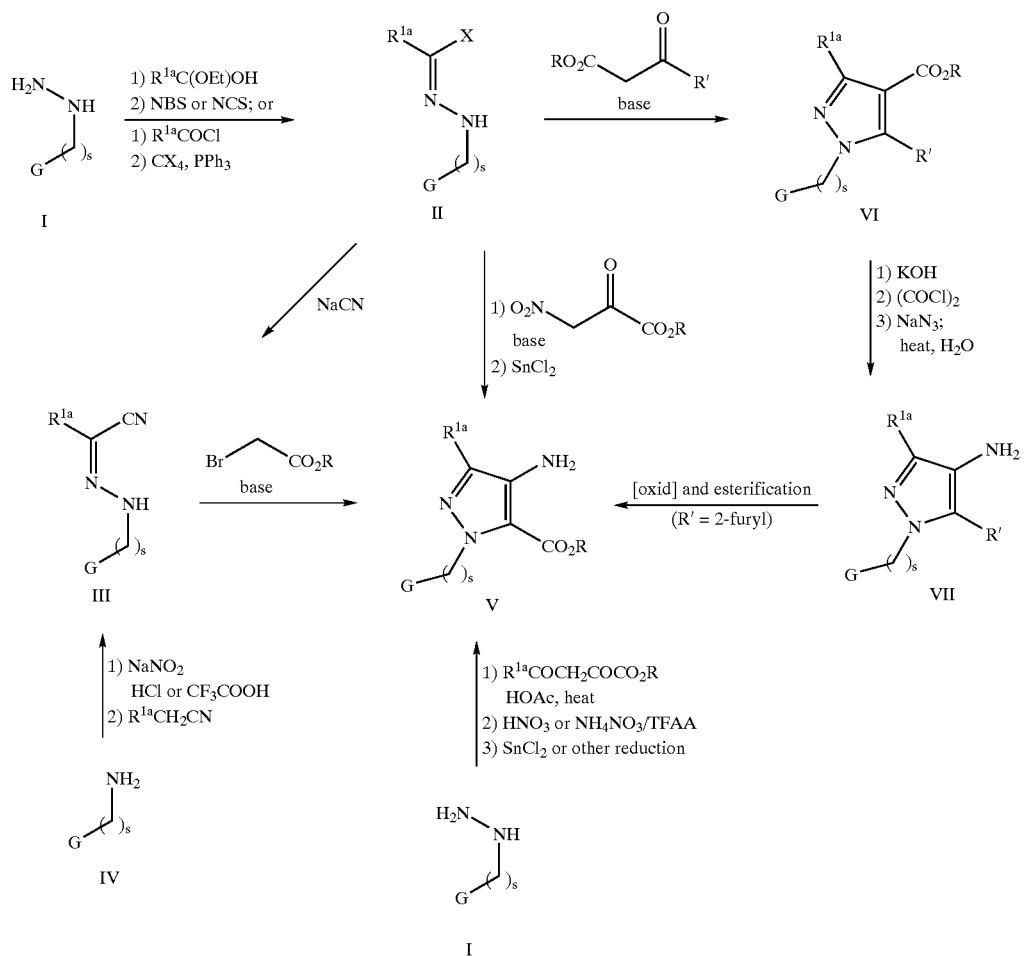

In Scheme II is shown how the 4-aminopyrazole-5-carboxylate V can be utilized to prepare a variety of structures described by Formula I where the A-B residue is connected to a nitrogen atom of the bicyclic core. The 4-amino group can be protected as a suitable carbamate (see Greene and Wuts, Protective Groups in Organic Synthesis, Wiley and Sons, 1991) or as an azide group (NaNO$_2$, acid, NaN$_3$). In some cases it may not be necessary to protect the amino functionality, as will be recognized by those skilled in the art. Unmasking of the ester residue involves either basic hydrolysis (R=Me, Et), hydrogenolysis (R=Bn) or trifluoroacetic acid (R=t-Bu). Coupling of the resulting acid with the appropriate amine H$_2$N-A-B can be accomplished by a wide variety of methods known to those skilled in the art, including dicyclohexylcarbodiimide and N,N-dimethylaminopyridine, the mixed anhydride method, the BOP reagent, and many others. Alternatively, the amide bond can be formed directly from the ester (R=Me, Et) by reacting the ester with an aluminum reagent prepared from the amine H$_2$N-A-B and trimethylaluminum. Deprotection of the amino group, if required, provides compounds VIII. Treating this amino amide with carbonyl diimidazole or other phosgene equivalent, such as triphosgene, provides pyrazolopyrimidinediones IX. Alternatively, aminocarboxylate V can be converted to pyrazolopyrimidinediones IX in a single step by heating with an appropriate isocyanate OCN-A-B in the presence of a base such as sodium hydride. Treating VIII with a substituted bromoacetyl chloride or bromide in the presence of a base such as triethylamine affords the pyrazolodiazepinediones X. Refluxing VIII in the presence of formic acid provides the pyrazolopyrimidinones XI (R$^3$=H). Substituted derivatives XI can be obtained by refluxing VIII in the presence of triethylorthoacetate (R$^3$= Me) or other orthoesters. Reduction of XI with catalytic hydrogenation, sodium borohydride in acidic medium or other reducing agent can provide compounds of type XII. Additionally, V can be treated with a bromoacetate in the presence of a base such as carbonate or sodium hydride to provide XIII. Selective hydrolysis of either ester of XIII followed by standard coupling with H$_2$N-A-B and subsequent heating affords compounds XIV, which are regioisomeric with X. Oxygen analogs of XIV are prepared by converting the amino group of V to a hydroxy group via a diazonium ion. Coupling with the amine H$_2$N-A-B by any of a wide variety of procedures yields XV. O-alkylation of XV with a bromoacetate in the presence of a base such as sodium hydride leads to XVI, the oxygen analogs of XIV. In the cases of compounds IX, X, XII and XIV the nitrogen atom can be further functionalized to provide additional analogs, such as by treating with methyl iodide in the presence of a base to afford the N-methyl derivatives.

Scheme II

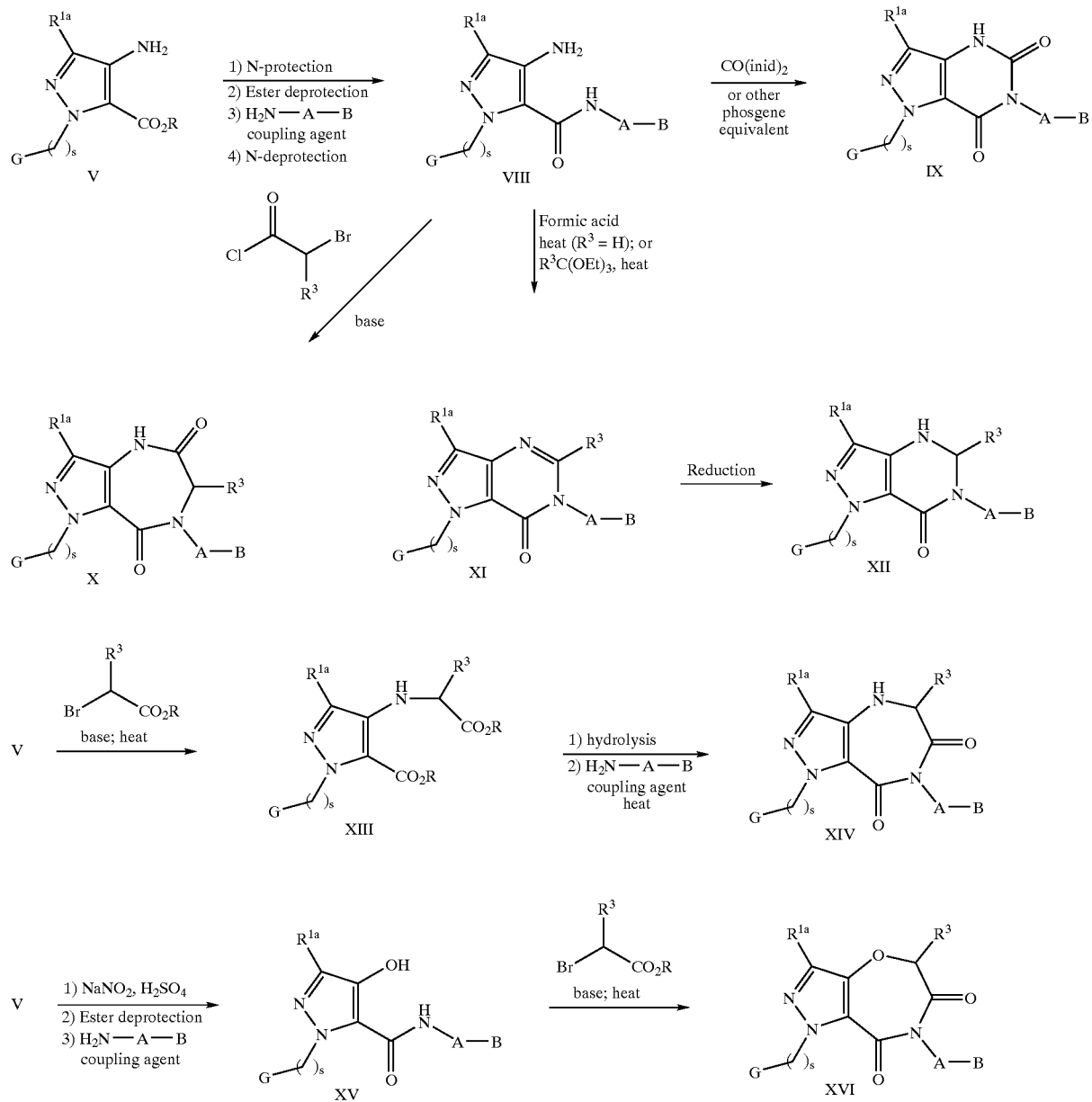

The 4-aminopyrazole-5-carboxylate can be used to prepare pyrazolopyranone and pyrazolopyridinone derivatives, in which the A-B residue is attached to a carbon atom of the bicyclic core, as shown in Scheme III. N-protection of V as described previously can be followed by straightforward conversion of the ester residue to an acid chloride. Treatment of this acid chloride with a zinc cuprate reagent derived from Br—$CH_2$-A-B (A=aryl) will afford the ketone XVII after N-deprotection. Heating XVII with dimethylformamide dimethylacetal or with an orthoester can provide the pyrazolopyridinone compounds XVIII. Conversion of the 4-amino residue of XVII to a hydroxyl group via the diazonium ion will lead to XIX, which will provide the pyrazolopyranone derivatives XX under similar cyclization conditions. Alternatively, treatment of the acid chloride XXI, obtained as described above where N-PG can represent a carbamate protected nitrogen or can represent conversion of the amino group to an azide group as described previously, with a suitable enamine in the presence of a base such as triethylamine can afford the ketone XXII. N-deprotection followed by heating will afford the pyrazolopyridinones XXIII (XVIII where R=H). Also, the ketone XVII can be prepared from the cyano compound III by treatment with a suitable bromoketone in the presence of a base such as carbonate or triethylamine. The required bromoketone is readily available by treating an appropriate acid chloride with diazomethane followed by HBr. It will be recognized by those skilled in the art that the syntheses of the compounds described in Scheme III may require additional protection/deprotection steps or modifications in the order of carrying out the steps, depending on additional functionality present in the compounds of interest.

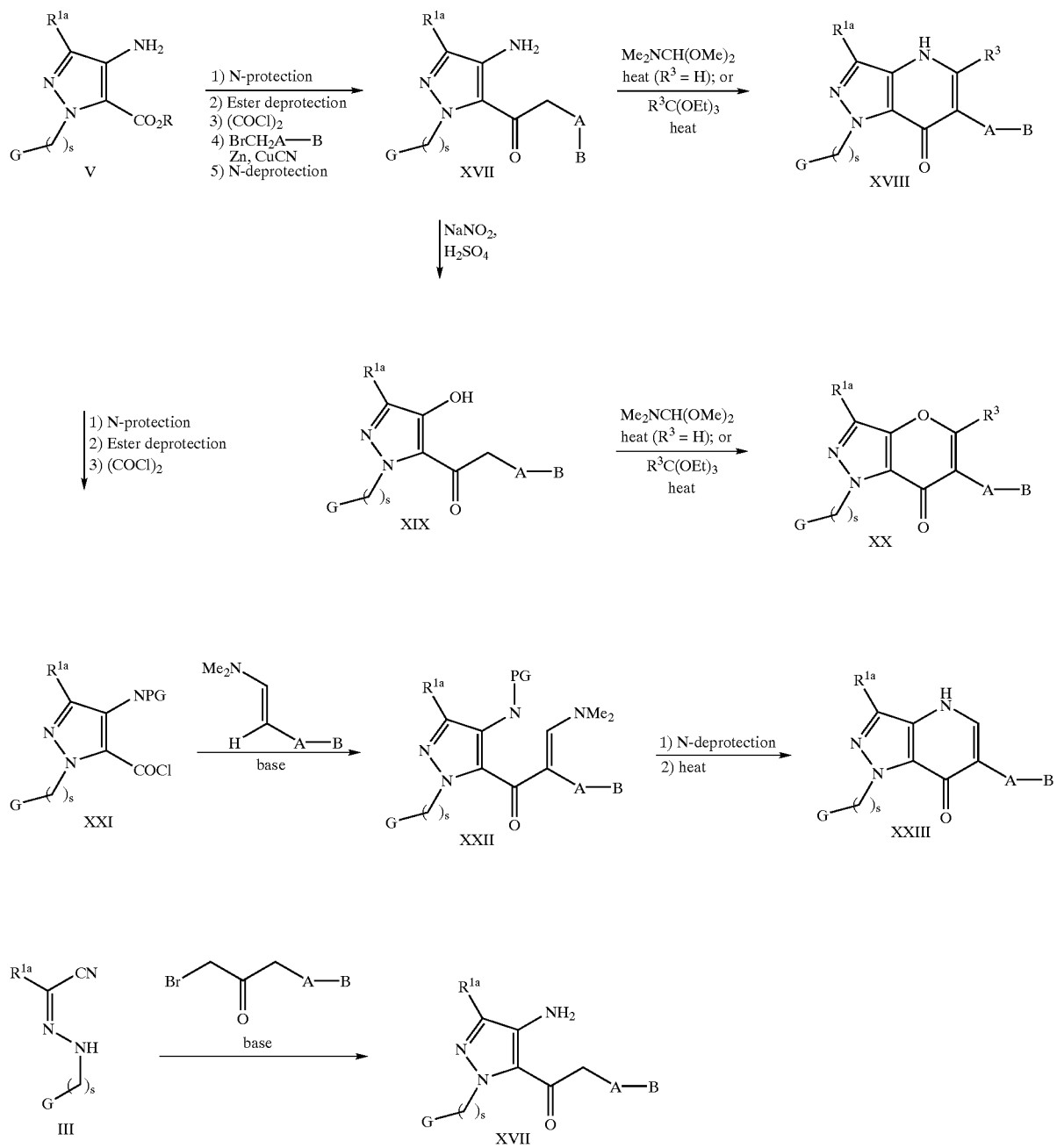

Scheme III

Additional oxygen-containing bicyclic systems can be prepared as shown in Scheme IV. The 4-amino-5-carboxylate V can be converted to its 4-hydroxy derivative via the diazonium ion to give XXIV. Ester deprotection and amide bond formation with an appropriate $H_2N$-A-B as described in Scheme II will afford the amide XXV. Alternatively, the amide bond can be formed directly from the ester by addition of the aluminum reagent derived from $H_2N$-A-B and trimethylaluminum. The 4-hydroxy substituent can be easily protected if required by any of a number of protecting groups, such as with t-butyldimethylsilyl ether (TBS), and then deprotected following amide bond formation. Treating the hydroxy amide XXV with carbonyl diimidazole or other phosgene equivalent, such as triphosgene, can provide the bicyclic core XXVI. Heating XXV in the presence of paraformaldehyde in the presence of a suitable acid such as p-toluenesulfonic acid will provide XXVII ($R^3$=H). Alternatively, XXV can be treated with dibromomethane in the presence of a suitable base such as carbonate to afford XXVII ($R^3$=H). Other aldehydes and substituted dibromomethanes can provide substituted derivatives of XXVII where $R^3$ is not hydrogen.

Scheme IV
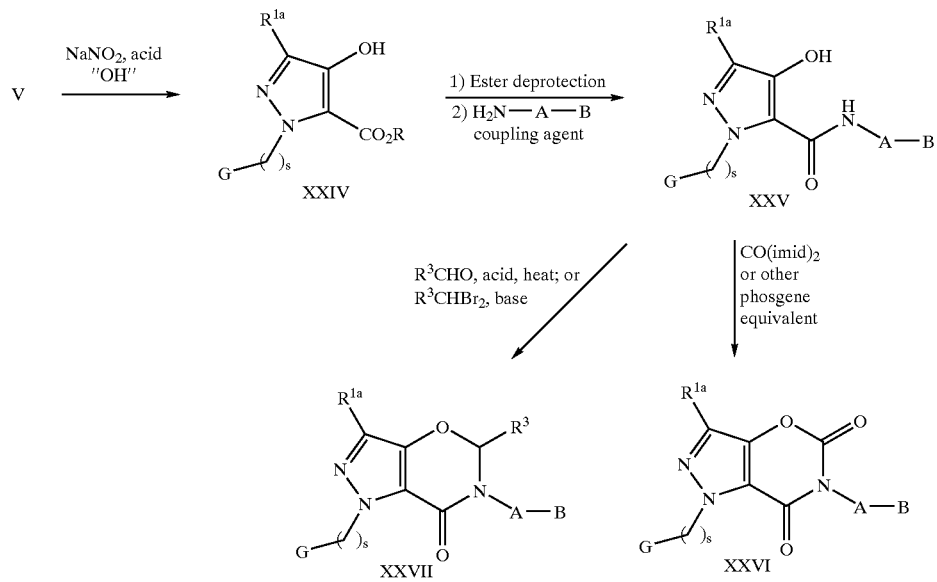
Scheme V
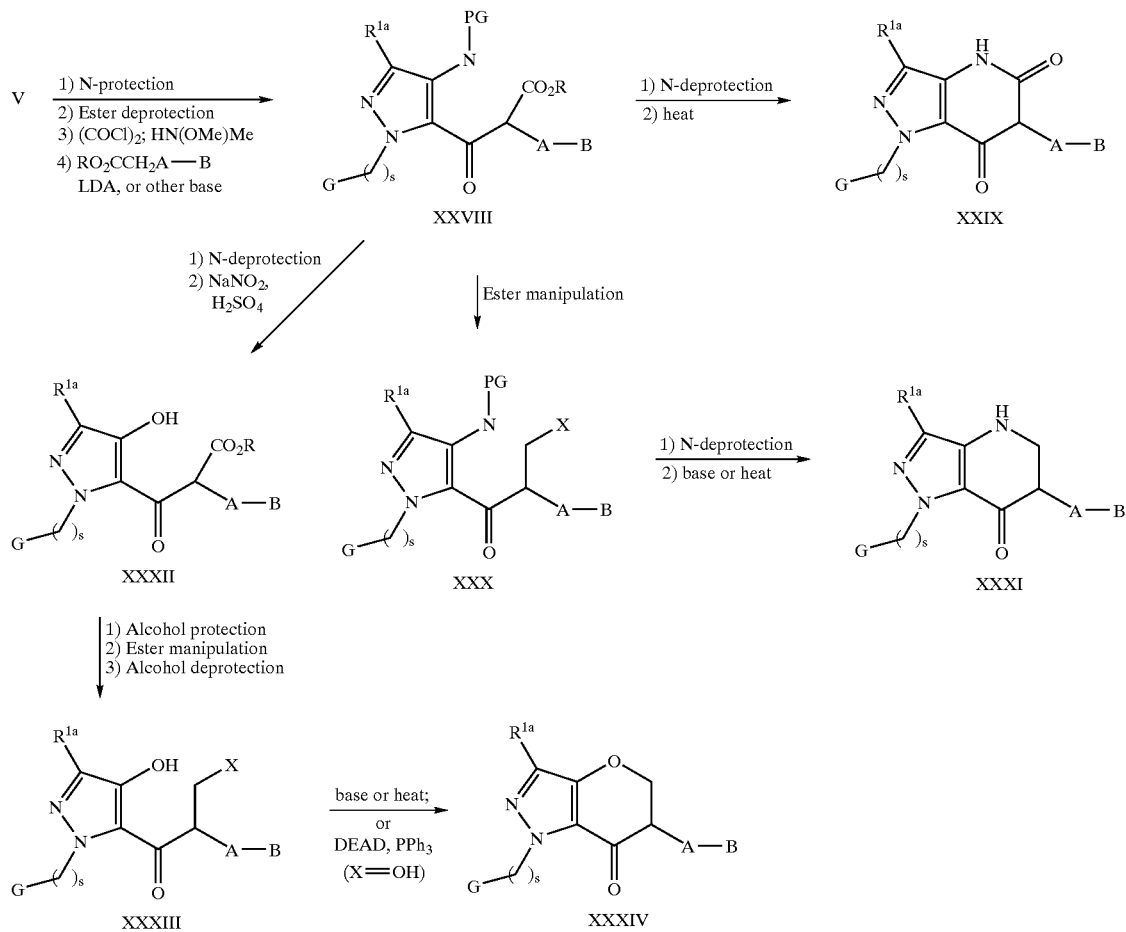

Additional bicyclic systems in which the A-B residue is substituted on a carbon atom can be prepared as shown in Scheme V. N-protection of 4-aminopyrazole-5-carboxylate V can be followed by manipulation of the ester to afford an acid chloride or an N-methoxy-N-methyl amide. Addition of an enolate derived from $RO_2CCH_2$-A-B and a base such as lithium diisopropylamide or lithium hexamnethyldisilazide provides XXVIII. The N-methoxy-N-methyl amide is the preferred reaction partner for this addition, as this functionality prevents the formation of overaddition products. Alternatively, the enolate addition reaction could be done on the ester as well. N-deprotection of the 4-amino substituent allows it to close onto the ester residue and provides the pyrazolopiperidinedione XXIX. Manipulation of the ester residue of XXVIII can lead to XXX where X represents a suitable leaving group such as a bromide or mesylate residue. A variety of methods can be utilized for the transformation of XXVIII to XXX, such as ketone protection, reduction of the ester to a primary alcohol, ketone deprotection and conversion of the primary alcohol to a bromide using $CBr_4/PPh_3$ or to a mesylate using methanesulfonyl chloride and a base such as triethylamine. Alternatively, the ester can be hydrolyzed to the acid that can be reduced to the primary alcohol with borane and converted to a leaving group as just described. N-deprotection liberates the 4-amino group, which provides compounds of structure XXXI upon heating or treatment with base. The corresponding oxygen derivative is also available from XXVIII. N-deprotection, diazotization with $NaNO_2$ in acidic medium and treatment with sulfuric acid produces the 4-hydroxy derivative XXXII. Protection of the alcohol functionality, for example as the TBS ether, followed by ester manipulation as described above and subsequent alcohol deprotection, produces XXXIII. Treatment of XXXIII with a suitable base such as carbonate leads to ring closure to afford compounds XXXIV. Alternatively, compounds XXXIII where X=OH can be closed to XXXIV via a Mitsunobu reaction by treatment with diethylazodicarboxylate and triphenylphosphine.

In scheme VI is shown how to make additional bicyclic systems in which the A-B residue is substituted on a carbon atom and the ring is substituted with an $R^3$ group. Ester XXVIII can be converted under standard conditions to the N-methoxy-N-methyl amide XXXV. Addition of an appropriate Grignard reagent $R^3MgBr$ produces a ketone, which upon N-deprotection and heating in acidic conditions leads to the substituted pyridones XXXVI. Hydride reduction, with REDAL for example, will produce the piperidone XXXVII. Alternatively, diisobutylaluminum hydride reduction of the N-methoxy-N-methyl amide gives an aldehyde which will add a suitable Grignard reagent $R^3MgBr$ to afford XXXVIII. Conversion of the alcohol to a leaving group, for example by making the mesylate with methanesulfonyl chloride and a trialkylamine base, followed by N-deprotection leads to ring closure to piperidones XXXVII. The alcohol XXXVIII can also be prepared from enamine XXII from Scheme III by hydrolysis to the corresponding aldehyde followed by addition of the appropriate Grignard reagent R MgBr.

Scheme VI

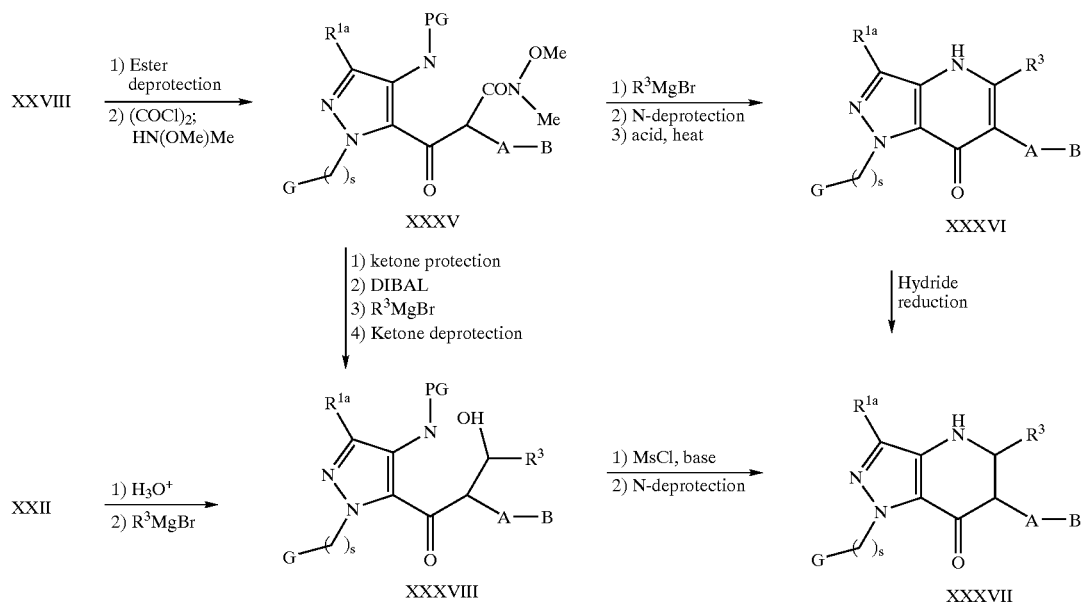

Preparation of a bicyclic system containing a seven-membered ring in which the A-B residue is attached to a carbon atom is described in Scheme VII. N-protection of aminoketone XVII, where N-PG represents preferably an N-protected nitrogen wherein both N—H groups are masked, such as by conversion to an azide group, is followed by formation of a ketone enolate, with a base such as lithium diisopropylamide, and reaction with a bromoacetate to afford XXXIX. N-deprotection followed by heating of the resulting amino ester affords XL. Alternatively, the ester can be converted by straightforward means to a more reactive species prior to ring closure, such as a mixed anhydride or acid chloride. Treatment of XVII with bromoacetyl bromide and a base such as triethylamine gives the acylamine XLI that can be cyclized by formation of the ketone enolate with a base such as lithium diisopropylamide.

Scheme VII

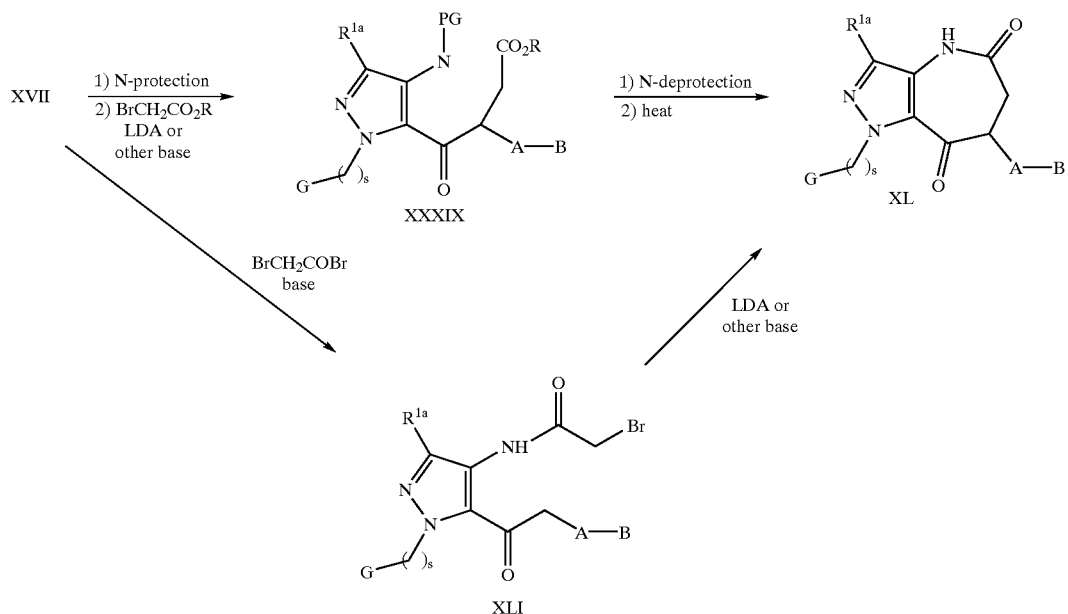

Additional seven-membered ring-containing bicyclic systems can be prepared as shown in Scheme VIII. The hydrazidoyl halide II, prepared as shown in Scheme I, can be cyclized with a cyanopyruvate in the presence of a base such as alkoxide to afford 4-cyanopyrazole XLII. Ester deprotection and coupling with $H_2N$-A-B as described in previous schemes yields cyanoamide XLIII. Reduction of the nitrile can be accomplished by various methods, such as by catalytic hydrogenation or by reduction with sodium borohydride in the presence of cobalt chloride. Cyclization of the resulting aminoamide using carbonyl diimidazole or other phosgene equivalent as described previously affords compounds XLIV. For the corresponding compound wherein the A-B residue is attached to carbon, the ester XLII can be converted to the N-methoxy-N-methyl amide as described previously. Treatment of this amide with the enolate derived from $RO_2CCH_2$A-B yields the ketone XLV. Catalytic hydrogenation of the nitrile affords an amine that upon heating undergoes cyclization to afford XLVI. The oxygen containing analog corresponding to XLIV is obtained from ester VI, prepared as described in Scheme I. The group R' represents preferably a 2-furyl residue as a masked carboxylic acid. Reduction of the ester group of VI with a hydride reducing agent such as diisobutylaluminum hydride is followed by protection of the resulting primary alcohol, such as by a TBS ether. When R' is 2-furyl, the carboxylic acid can be unmasked by oxidation by a variety of reagents, including ozone, potassium permanganate, and sodium periodate in the presence of ruthenium trichloride. Coupling with a suitable with $H_2N$-A-B as described in previous schemes yields the amide XLVII. Deprotection of the alcohol affords a hydroxy amide, which can be cyclized using carbonyl diimidazole as described previously to afford compounds XLVIII.

Scheme VIII

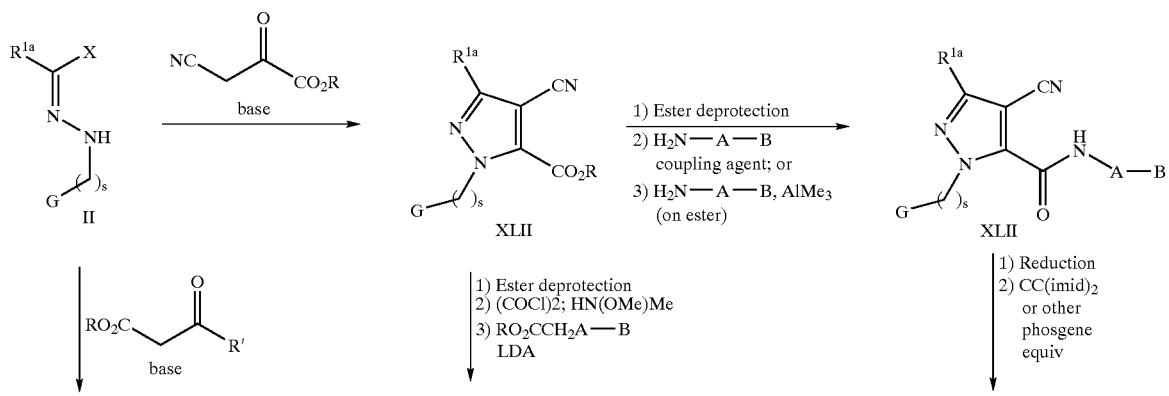

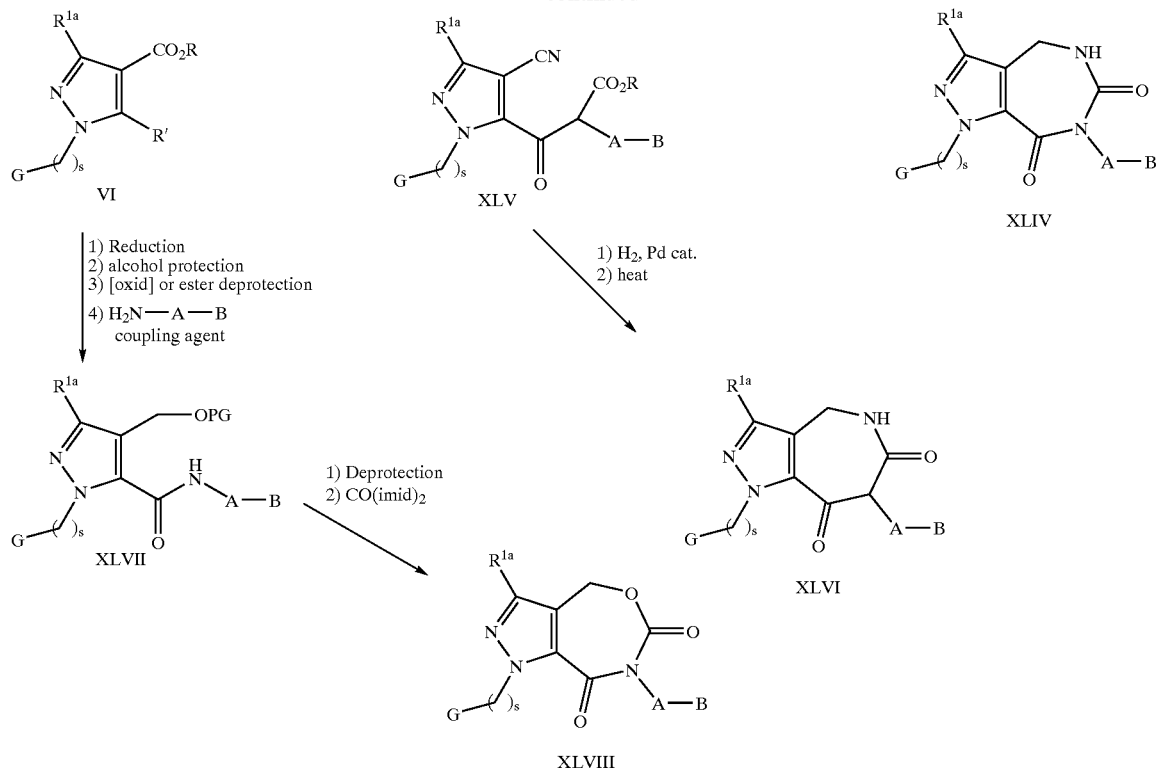
Bicyclic compounds of Formula I containing a carbon atom at the pyrazole 4-position are prepared by a [3+2] cycloaddition strategy as shown in Scheme IX (for a review of [3+2] cycloadditions, see 1,3-Dipolar Cycloaddition Chemistry (Padwa, ed.), Wiley, New York, 1984).
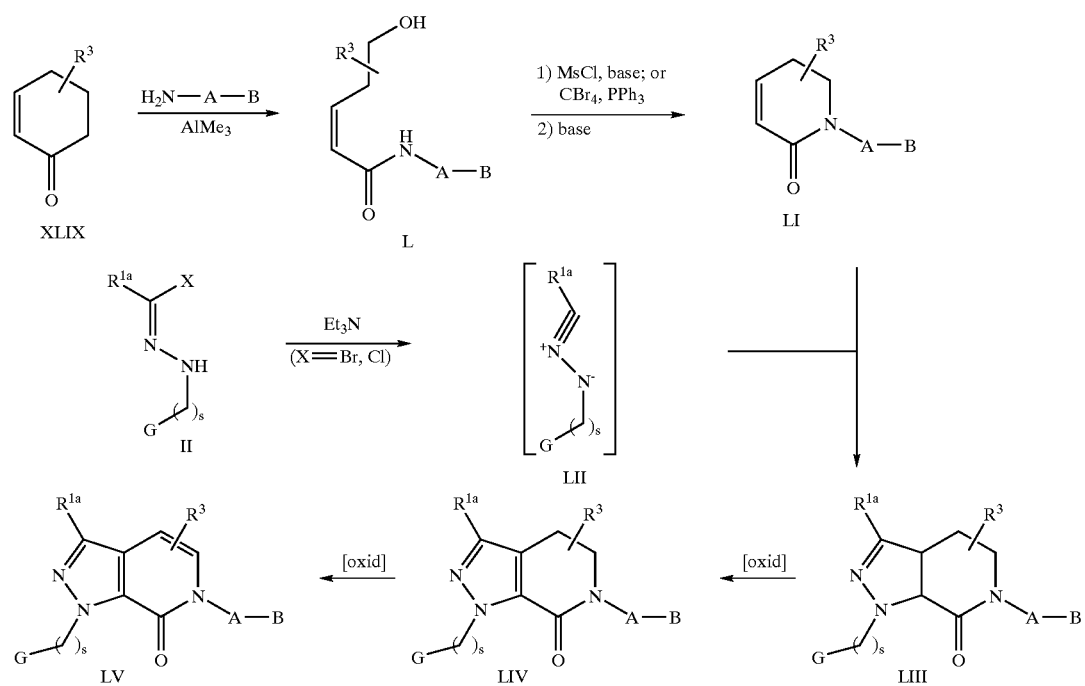

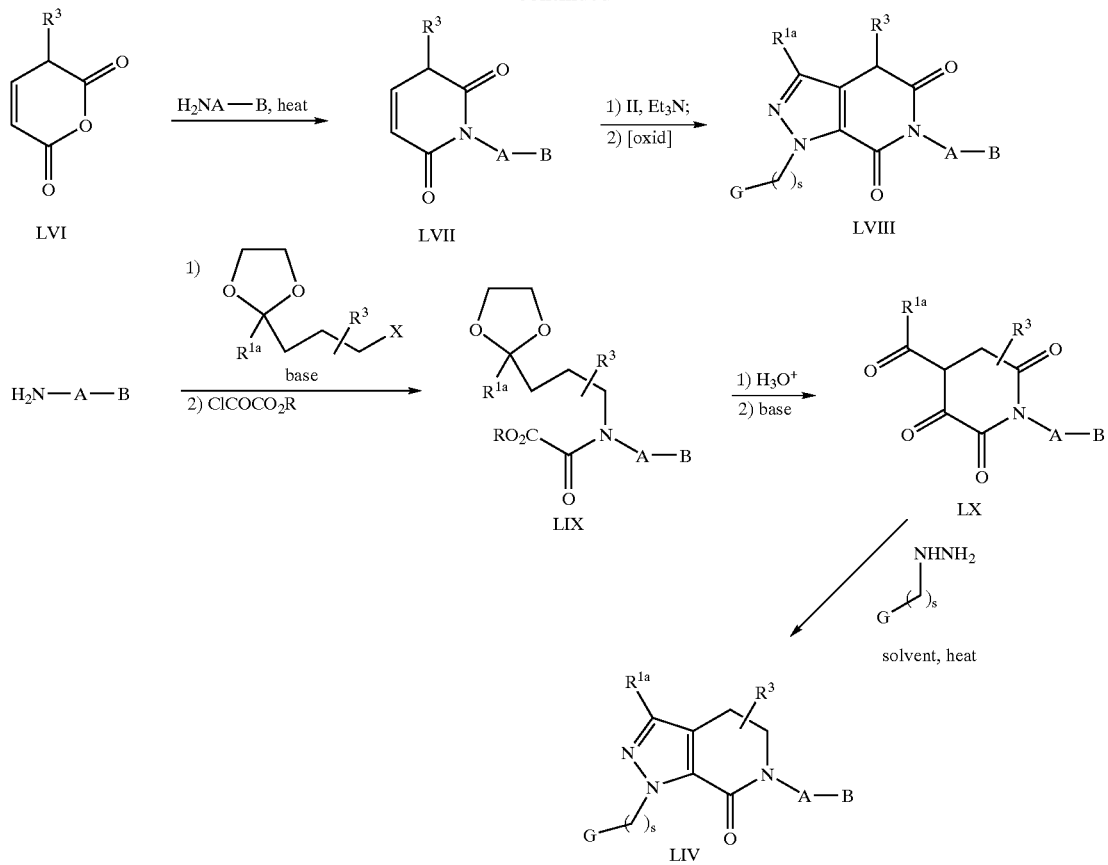

Treatment of unsaturated lactone XLIX, which is readily available by standard procedures known to those skilled in the art, with an aluminum reagent prepared from an appropriate amine $H_2N$-A-B and trimethylaluminum affords the ring-opened amide L. Conversion of the primary alcohol under standard conditions to a suitable leaving group, such as a bromide or mesylate, and subjection to basic conditions affords the required unsaturated lactam LI. Treatment of hydrazidoyl halide II, prepared as shown in Scheme I where X=Cl or Br, with triethylamine generates a 1,3-dipolar intermediate LII, which can undergo a [3+2] cycloaddition with the olefin LI to produce the bicyclic pyrazolidine LIII as the predominant regioisomer. Mild oxidation with reagents such as chloranil or nickel peroxide will produce the pyrazolopiperidones LIV. Further oxidation, such as with DDQ, can produce the unsaturated derivatives LV. These steps can be reversed such that initial complete oxidation to LV can be followed by reduction, such as by catalytic hydrogenation, to produce LIV. The ketone derivatives can be prepared by condensation of an appropriate amine $H_2N$-A-B with the cyclic anhydride LVI to give LVII. Alternatively, a saturated derivative of LVI can be condensed with an appropriate amine $H_2N$-A-B followed by oxidation to the unsaturated derivative LVII, such as by treatment with LDA/PhSeSePh and subsequent oxidative selenoxide elimination. The olefin LVII undergoes similar [3+2] cycloaddition to give a pyrazolidine intermediate that is readily oxidized to the pyrazolopiperidinedione derivatives LVIII by a variety of oxidizing agents.

An alternative preparation of compound LIV is also described. A standard alkylation/acylation sequence on the amine $H_2N$-A-B affords amide ester LIX, which contains a protected ketone functionality. A variety of reaction conditions can be employed for these transformations, which are known to those skilled in the art. Deprotection of the ketone followed by Dieckmann condensation under basic conditions affords the cyclic diketoamides LX. Condensation of LX with an appropriate hydrazine is readily accomplished by heating in a solvent such as acetic acid or ethanol to afford the previously described LIV.

Pyrazolopiperidone compounds LXVI (where n=1) wherein the pyrazole 4-substituent $R^{1a}$ is a trifluoromethyl group can be prepared via the method outlined in Scheme X. Coupling of the acid LXI with amines $H_2N$-A-B can be accomplished under a variety of conditions, such as via the acid chloride, giving amide LXII. A straightforward sequence involving cleavage of the tetrahydrofuran ring and intramolecular cyclization on the amide nitrogen affords the ketolactam LXIII. This compound can also be prepared from the lactam LXIV by introduction of sulfur substituents and subsequent oxidation to the ketolactam LXIII. Formation of the morpholine or related enamine followed by reaction with trifluoroacetic anhydride leads to the trifluoroacetylated intermediate LXV. Alternatively, dichlorination of lactam LXIV with $PCl_5$ or analogous reagents, heating with excess morpholine or related amine, and reacting the enamine derived in this way with trifluoroacetic anhydride also yields the trifluoroacetylated intermediate LXV. This compound can be readily condensed with an appropriate hydrazine to afford the pyrazolopiperidone compounds LXVI. Analogous chemistry can be utilized to afford [5,7]-fused ring systems (where n=2).

Unsaturated analogs of the above compounds can be prepared as shown in the bottom of Scheme X. Bromination of LXVII, prepared as described in Scheme IX and the top of Scheme X, affords bromo analog LXVIII. Elimination of HBr by treatment with any of a variety of bases, such as DBU, will afford the unsaturated bicylic analogs LXIX. Additional analogs can be prepared by displacement of the bromide LXVIII by any of a wide variety of nitrogen-, oxygen- and sulfur-based nucleophiles.

tetrahydro-1,4-oxazepin-5(2H)-one and tetrahydro-1,4-thiazepin-5(2H)-one. Compounds LXXI where X is NH or NR can be prepared by Schmidt rearrangement of 4-piperidone monohydrate hydrochloride or protected 4-piperidone (Groves, J. T. and Chambers, R. R. Jr. J. Am. Chem. Soc. 1984, 106, 630–638). Ullmann coupling of the lactam with I(Br)-A-B provides the lactam LXXII with an

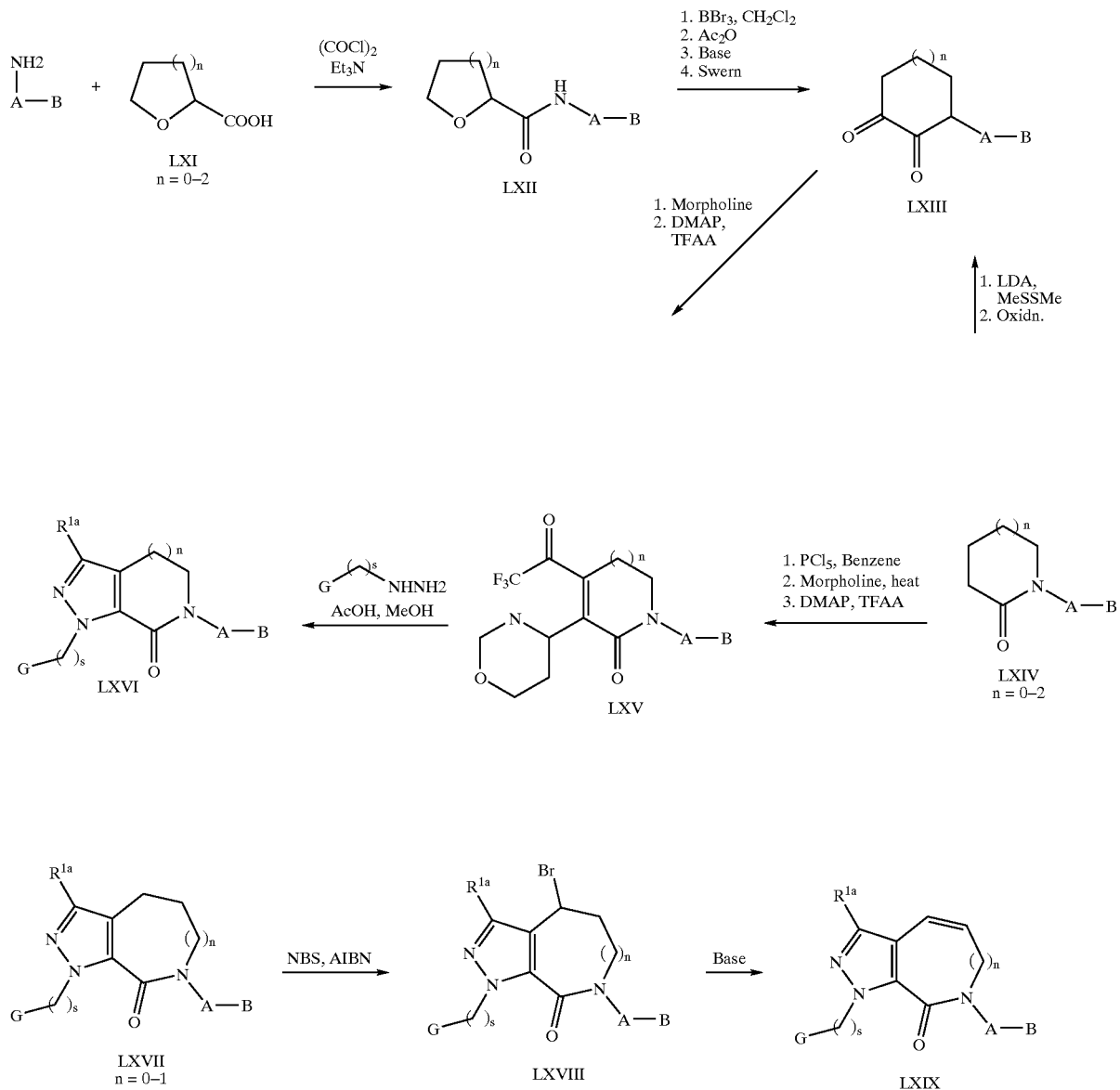

Additional [5,7]-fused bicyclic systems which contain an additional heteroatom in the seven-membered ring can be prepared as shown in Scheme XI. Compounds LXXI where X is O or S can be prepared from commercially available tetrahydro-4H-pyran-4-one and tetrahydrothiopyran-4-one. Photoinduced Schmidt rearrangement of (triisopropylsilyl) azidohydrin (Evans, P. A. and Modi, D. P. J. Org. Chem. 1995, 60, 6662–6663), which is formed from tetrahydro-4H-pyran-4-one and tetrahydrothiopyran-4-one, provides A-B residue. Dichloronation with phosphorus pentachloride or related reagent affords a dichlorinated intermediate which can react with morpholine to give the enamine LXXIII. Reaction of LXXIII with DMAP and an appropriate acid chloride or acid anhydride provides the acylenamine intermediate LXXIV which can be condensed with an appropriate hydrazine in acetic acid to afford the [5,7]-fused bicyclic compounds LXXV.

Scheme XI

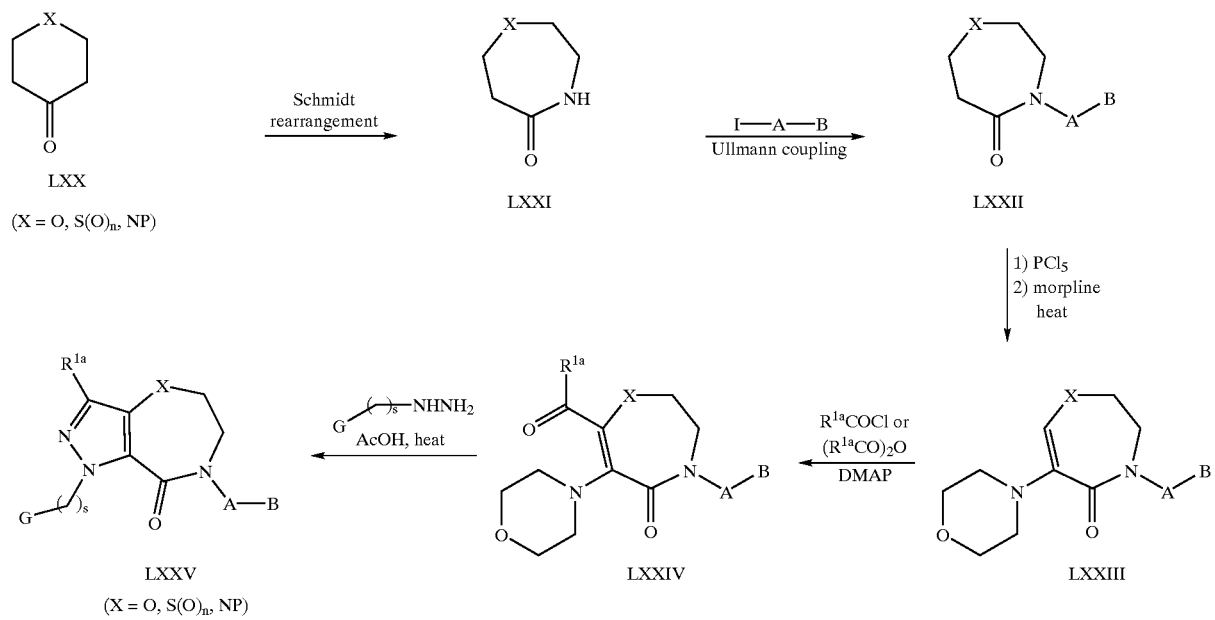

Bicyclic compounds of Formula I which contain a carbon atom at the pyrazole 4-position and wherein the A-B residue is attached to a carbon atom are also prepared by a [3+2] cycloaddition strategy as shown in Scheme XII. Unsaturated cyclic ketones LXXVI are readily available by standard synthetic methods known to those skilled in the art. The [3+2] cycloaddition with the 1,3-dipole generated from II as described previously gives a pyrazolidine intermediate that can be readily oxidized to the pyrazolocyclohexanone LXX- VII. Introduction of a double bond, such as by treating with LDA and PhSeSePh followed by oxidative selenoxide elimination, gives the unsaturated derivative LXXVIII. Incorporation of a residue such as a protected alcohol into the unsaturated ketone, represented by LXXIX, leads to pyrazolocyclohexanone LXXX following [3+2] cycloaddition and subsequent oxidation. Deprotection of the alcohol and oxidation by a variety of reagents affords the pyrazolo-cyclohexanedione LXXXI.

Scheme XII

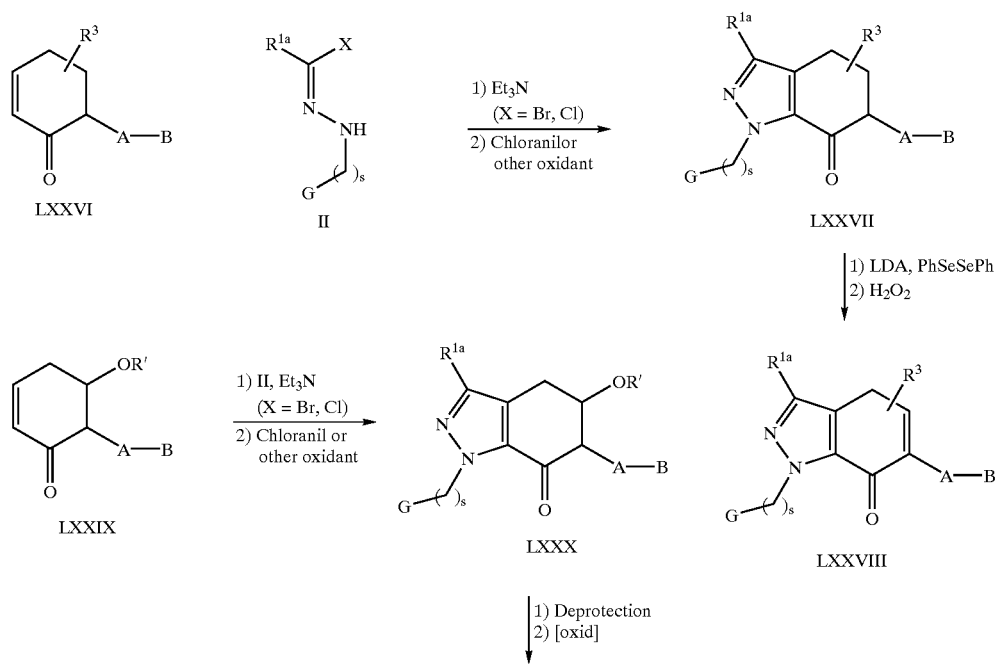

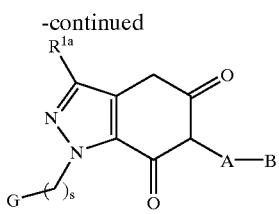

LXXXI

Additional bicyclic compounds of Formula I containing a carbon atom at the pyrazole 4-position are described in Scheme XIII. Condensation of hydrazidoyl halide II with a diketoester in the presence of a base such as alkoxide affords pyrazoles LXXXII. Heating this ketoester in the presence of readily available hydrazines A-B-NHNH$_2$ affords the pyrazolopyridazinones LXXXIII. For preparation of pyrazolopyridazinones where R$^3$ is hydrogen, the hydrazidoyl halide II can be cyclized with a furyl ketoester in the presence of alkoxide base to afford LXXXIV. Standard functional group manipulations, involving ester reduction and protection, furyl oxidation and esterification leads to LXXXV, although not necessarily in that order. Those skilled in the art will be able to determine a proper order and appropriate reagents for achieving these transformations. Alcohol deprotection and oxidation, such as by manganese dioxide, affords an aldehyde ester which readily produces LXXXVI upon heating in the presence of a hydrazine A-B-NHNH$_2$. Appropriate functional group manipulation of LXXXIV, of which many methods are available, can also afford ester acids LXXXVII. Activation of the carboxylic acid, such as by formation of the acid chloride with oxalyl chloride, followed by heating in the presence of a hydrazine A-B-NHNH$_2$ affords the pyrazolopyridazinedione LXXXVIII.

Scheme XIII

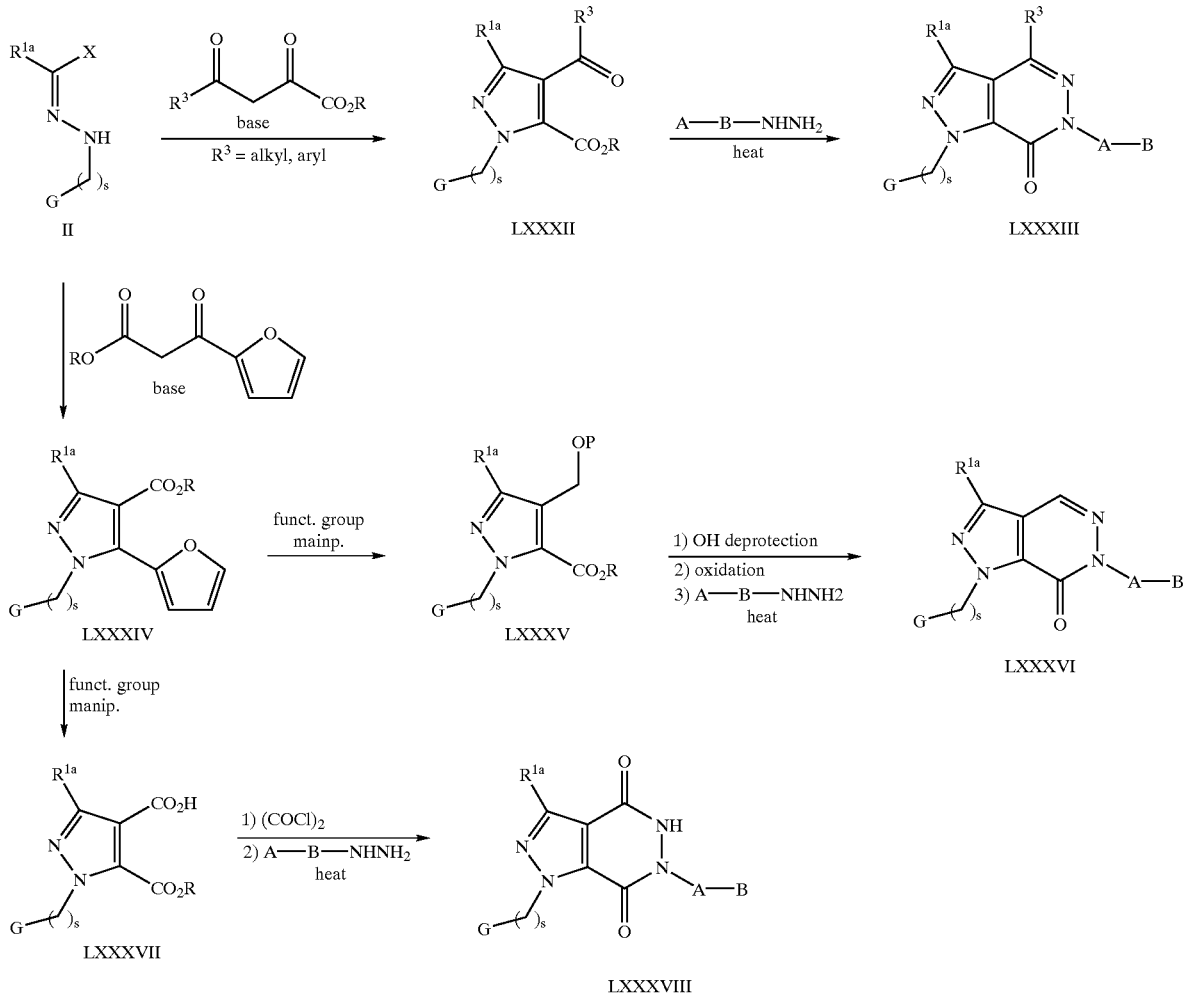

The preparation of the compounds of Formula I where the five-membered ring is triazole is accomplished using azide intermediates. Azides readily undergo [3+2] cycloaddition reactions with a variety of olefins and alkynes, and the application of this reaction to the synthesis of the triazole-fused bicyclic compounds of Formula I is shown in Scheme XIV. As described for the pyrazole-fused compounds previously, the 4-amino-1,2,3-triazole-5-carboxylate XCII is a particularly useful intermediate for the preparation of many of the triazole-fused bicyclic systems. The required azides LXXXIX are readily available. Aliphatic azides are easily prepared from the corresponding bromide by displacement with sodium azide in solvents such as dimethylformamide and dimethyl sulfoxide. Where "G-(CH$_2$)$_s$-" represents an aryl azide (G is aryl, s=0), the azides are readily available from the corresponding aniline by diazotization with NaNO$_2$ in acidic medium followed by displacement of the diazonium ion with sodium azide. The [3+2] cycloaddition of azides LXXXIX with nitroolefins XC (R'=Me, 2-furyl) affords the triazoles XCI as the major product, in which initial cyclization to a triazoline intermediate is followed by autooxidation to the triazole products (Cailleux, P.; et. al. Bull. Soc. Chim. Belg. 1996, 105, 45). These reactions can be performed in refluxing benzene or similar solvents at similar temperatures. Conversion of XCI to the 4-amino-1,2,3-triazole-5-carboxylate XCII is straightforward. When R' is methyl, oxidation of the methyl group with an oxidant such as KMnO$_4$ gives the carboxylic acid which can be esterified to an appropriate ester. Reduction of the nitro group by any of a variety of reducing agents, preferably SnCl$_2$ or catalytic hydrogenation, gives XCII. When R' is 2-furyl, the carboxylic acid can be unmasked by a variety of oxidizing agents, including ozone, KMnO$_4$ and sodium periodate/ruthenium trichloride, to give the carboxylic acid which can be esterified and reduced as described above to afford XCII. The 4-hydroxy-1,2,3-triazole-5-carboxylates can be obtained via the diazonium ion of XCII as described for the pyrazole series to afford XCIV.

The reaction of azides LXXXIX with active methylene compounds is also illustrated in Scheme XIV. Treating LXXIX with cyano- or nitropyruvates in the presence of a base such as alkoxide affords triazoles XCIII. The triazole-4-carboxylate derivatives can be prepared by treating LXXXIX with a furyl ketoester in the presence of alkoxide base to afford XCV. These reactions are analogous to those described in Scheme I for the pyrazole derivatives. The triazole-containing bicyclic systems having a carbon atom at the 4-position of the triazole can be prepared by [3+2] cycloaddition of an appropriate azide LXXXIX with an unsaturated lactam LI or an unsaturated cyclic ketone LXXVI. These cycloadditions are performed by heating in an appropriate solvent, such as benzene or toluene. The resulting triazoline intermediates are readily oxidized to the fused triazoles using chloroanil, nickel peroxide or other mild oxidant to give XCVI and XCVII, respectively. The triazole intermediates XCI, XCII, XCIII, XCIV, XCV, XCVI and XCVII can be transformed into the final triazole-containing bicyclic compounds described by Formula I following the procedures described for the corresponding pyrazole derivatives in Schemes II–XI. The nitro group present in XCI and XCIII can correspond to the "N-PG" residue described in Schemes II–VIII, or alternatively, the nitro group can be reduced at an appropriate time and further protected as a suitable carbamate derivative or as an azido group.

Scheme XIV

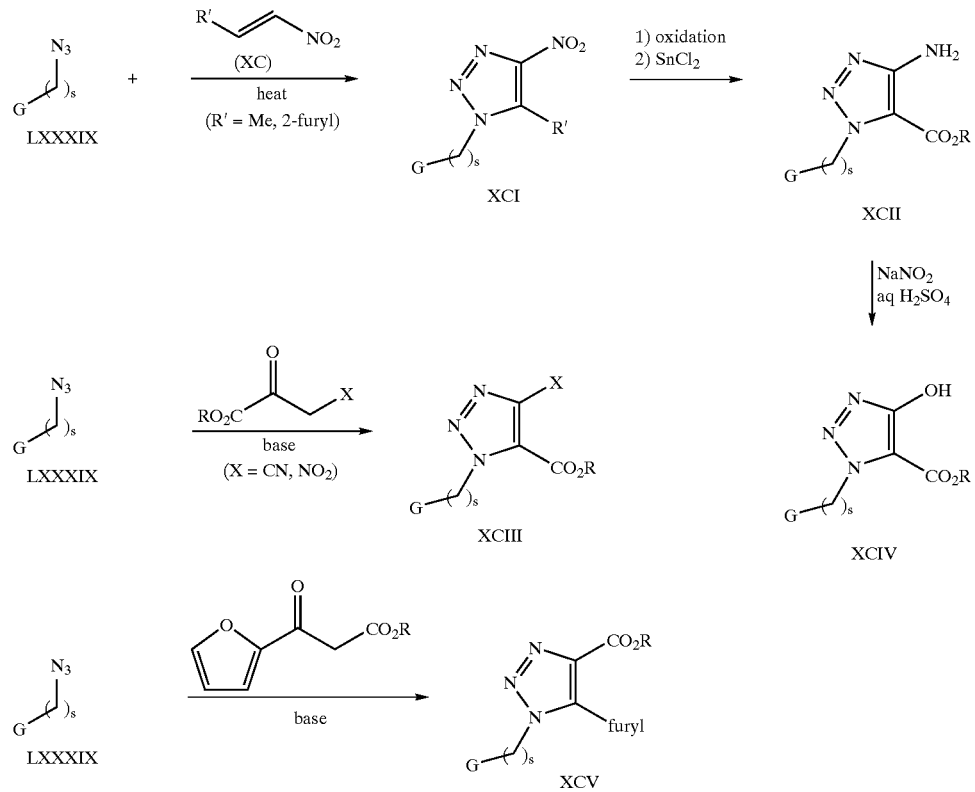

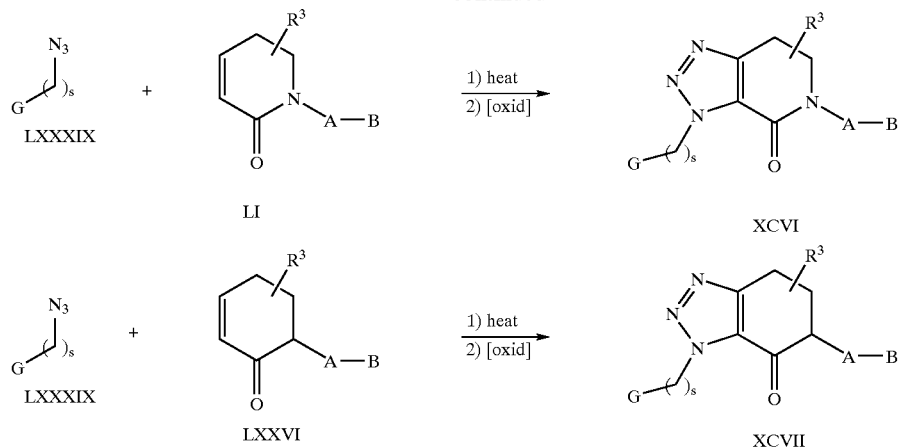

The preparation of the compounds of Formula I where the five-membered ring is isoxazole is accomplished as shown in Scheme XV. The hydroximinoyl chloride XCIX is a useful intermediate for the preparation of isoxazole-fused compounds. This intermediate is readily available from appropriate aldehydes XCVIII by oxime formation with hydroxylamine followed by chlorination with N-chlorosuccinimide. Treatment of XCIX with a cyanoacetate in the presence of a base such as carbonate results in cyclization to give a 5-aminoisoxazole-4-carboxylate C. The amino residue of C can be readily converted into the corresponding hydroxy or cyano derivatives CI and CII, respectively, via the diazonium ion, as described earlier for the pyrazole and triazole compounds.

The isoxazole-5-carboxylates are available from cyclization of XCIX with a furan ketoester to give CIII. Oxidation of the furan to a carboxylic acid residue is accomplished by a variety of oxidizing agents as described earlier.

The hydroxyiminoyl chloride XCIX can also be treated with a base such as triethylamine to generate a nitrile oxide intermediate, which can undergo [3+2] cycloaddition reactions with appropriate olefins or alkynes. This is a convenient method by which to prepare bicyclic compounds containing a carbon atom at the 5-position of the isoxazole ring. For example, cycloaddition with the unsaturated lactam LI leads to formation of a fused isoxazoline intermediate which is readily oxidized with reagents such as nickel peroxide, chloranil or DDQ to afford CIV. Cycloaddition with unsaturated cyclic ketone and oxidation under the same conditions affords the ketone analog Cv. The isoxazole-fused intermediates C, CI, CII, CIII, CIV and CV can be transformed into the final isoxazole-containing bicyclic compounds described by Formula I following the procedures described for the corresponding pyrazole derivatives in Schemes II–XI.

Scheme XV

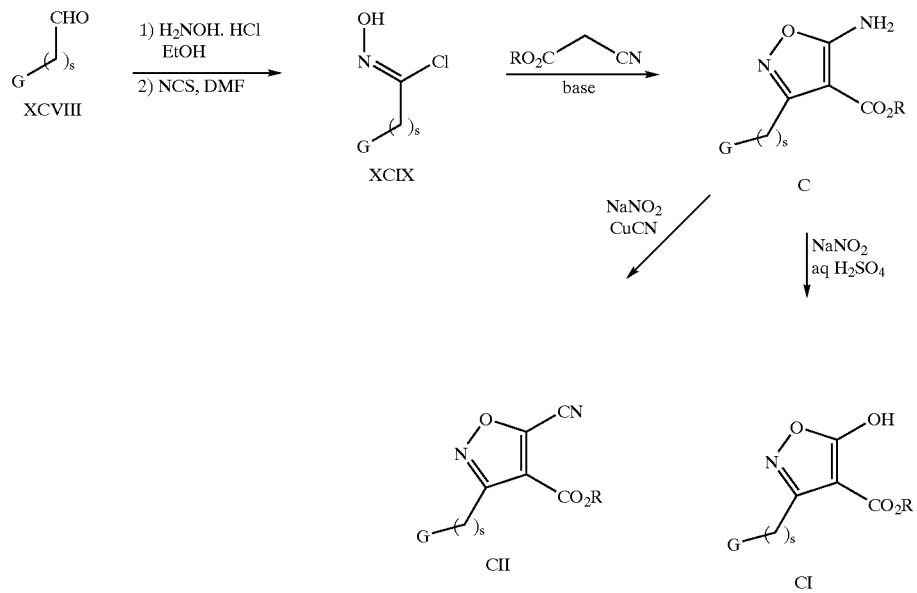

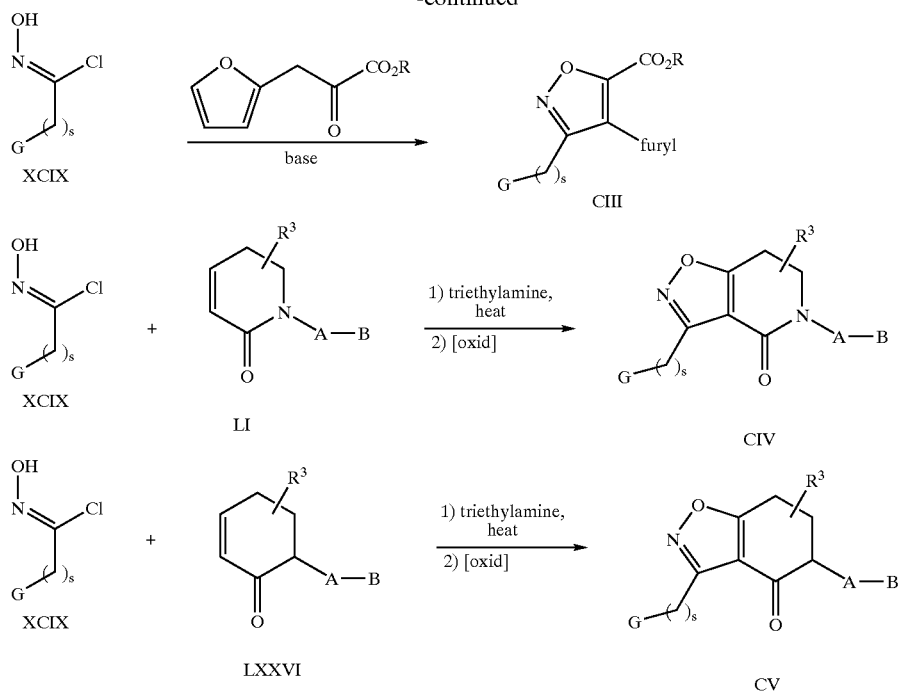

The preparation of the compounds of Formula I where the five-membered ring is isothiazole is accomplished as shown in Scheme XVI. One method for preparing the 5-aminoisothiazole-4-carboxylate intermediate CVIII proceeds from readily available acid chloride CVI. Condensation of CVI with a cyanoacetate in the presence of a base such as a magnesium alkoxide followed by treatment with ammonia in an alcoholic solvent gives an aminonitrile CVII. Treatment with hydrogen sulfide in the presence of a base such as triethylamine affords a thioamide that can undergo an oxidative cyclization to CVIII upon treatment with hydrogen peroxide or bromine. As described in previous schemes, the amino residue can easily be converted into the corresponding hydroxyl or cyano derivatives CIX or CX, respectively.

Another useful intermediate for the preparation of isothiazole compounds of the present invention is the nitrile sulfide CXIII. This intermediate can be generated conveniently from heterocycle CXII, which itself can be prepared from amides CXI either by treating with chlorocarbonylsulfenyl chloride or by treating with trichlorbmethanesulfenyl chloride followed by aqueous sodium hydroxide. Thermolysis of heterocycle CXII affords the nitrile sulfide CXIII, which can undergo many of the same reactions as the corresponding nitrile oxide intermediates. For example, [3+2] cycloaddition of CXIII with olefins LI and LXXVI can afford, after subsequent mild oxidation as described previously, the isothiazole-fused compounds CXIV and CXV, respectively. Isothiazole intermediates CVIII, CIX, CX, CXIV and CXV can be transformed into the final isothiazole-containing bicyclic compounds described by Formula I following the procedures described for the corresponding pyrazole derivatives in Schemes II–XI.

Scheme XVI

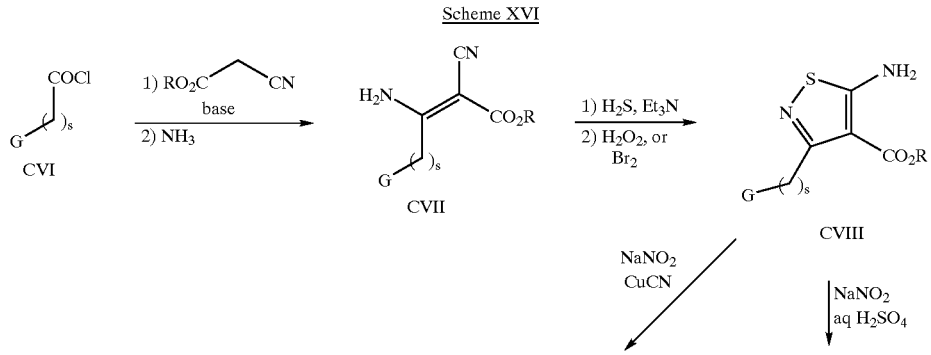

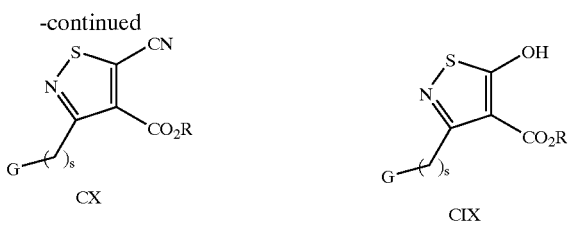

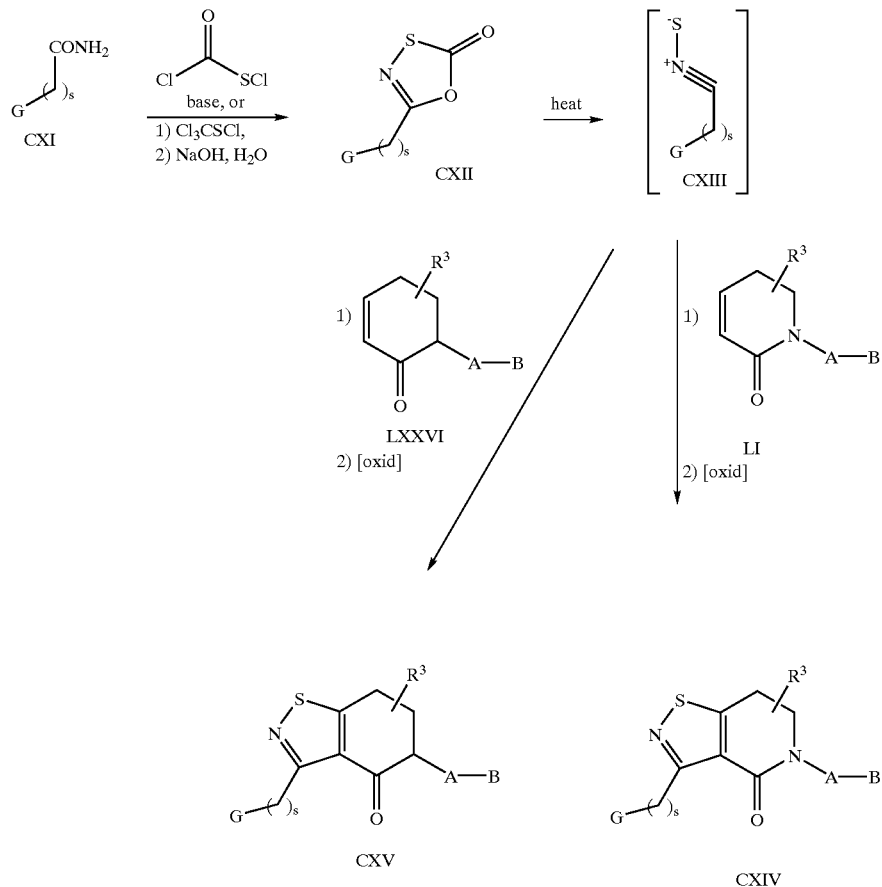

Formula I also describes pyrazole-fused bicyclic compounds in which the "G-(CH$_2$)$_s$-" group resides on a carbon atom of the pyrazole ring. These compounds can be prepared as shown in Scheme XVII. Condensation of acid chlorides CVI with cyanoacetates in the presence of a base such as magnesium methoxide affords an enol derivative that is converted to the enol ether CXVI (X=OMe) with diazomethane or to the chloro derivative CXVI (X=Cl) with POCl$_3$. Heating with hydrazine (R'=H) or a substituted hydrazine affords 5-amino-4-carboxylate CXVII. The amino residue of CXVII can be converted to the hydroxyl or cyano derivative CXVIII or CXIX, respectively via the diazonium ion as described previously.

The 5-carboxylate derivatives can be prepared by condensing a substituted hydrazine with a hemiacetal or related derivative represented by CXX. Chlorination or bromination with NCS or NBS, respectively, affords the hydrazidoyl halides CXXI. Reaction of CXXI with the anion of a furyl ketoester affords the 5-carboxylate CXXII, the furan residue of which can be oxidized to a carboxylic acid residue by methods described previously.

The hydrazidoyl halides CXXI can also participate in [3+2] cycloadditions as described previously to afford, after oxidation of the intermediate pyrazolines, the pyrazole-fused compounds CXXIII and CXXIV. The intermediates CXVII, CXVIII, CXIX, CXXII, CXXIII and CXXIV can be transformed into the final C-linked pyrazole-containing bicyclic compounds described by Formula I following the procedures described for the corresponding N-linked pyrazole derivatives in Schemes II–XI.

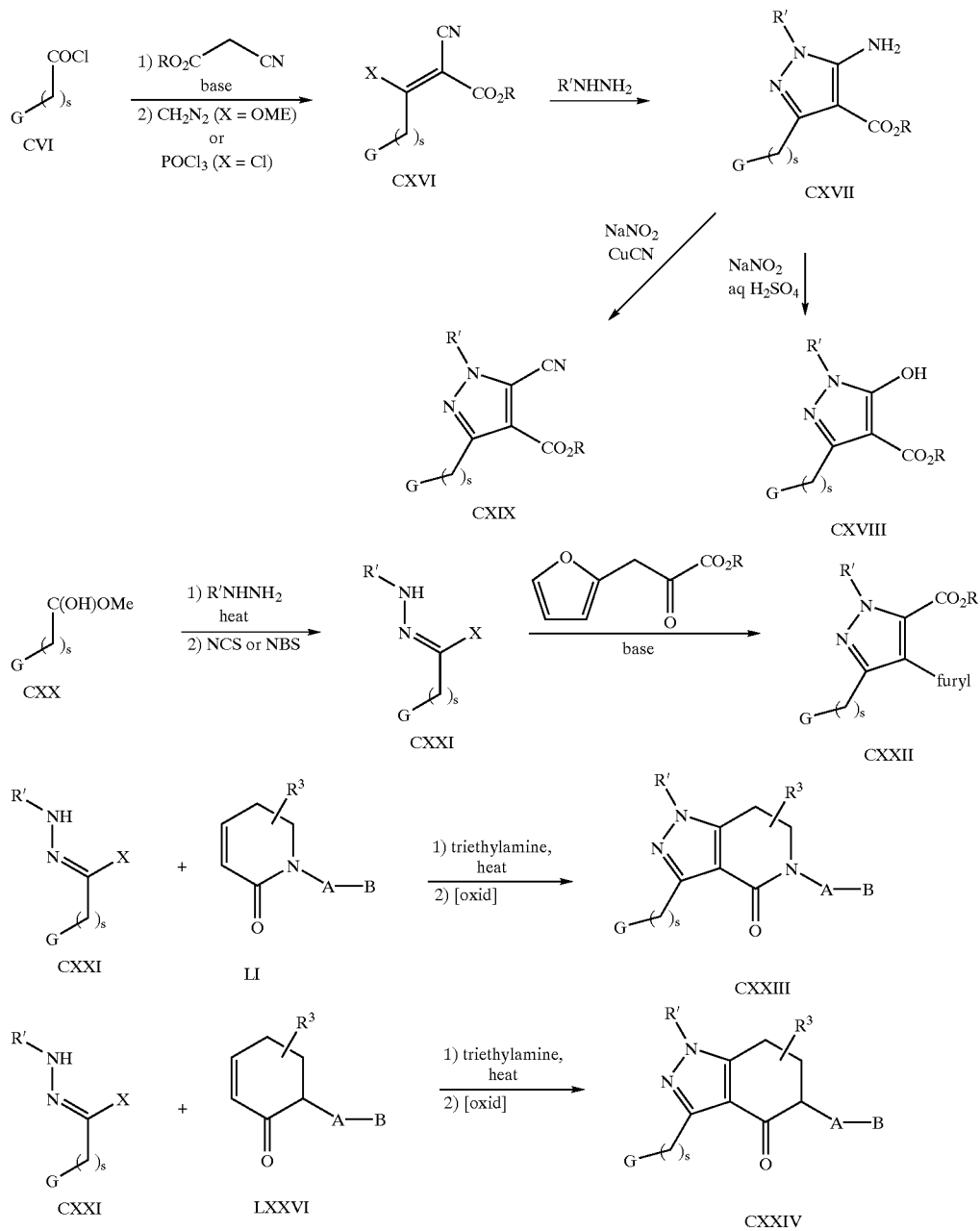

Scheme XVII

Bicyclic compounds of the present invention in which the five membered ring is pyrrole and the G-containing group is attached to a carbon atom can be prepared as shown in Scheme XVIII. For compounds of this type wherein a nitrogen atom is required at the pyrrolo 2-position, the 2-aminopyrrole CXXVI is a useful intermediate. This compound can be prepared by condensation of readily obtained aminocarbonyl compounds CXXV with an appropriate cyanoacetate. This condensation can be carried out under basic conditions or by heating with azeotropic removal of water. The 2-aminopyrroles CXXVI can be diazotized and subsequently converted into the 2-cyano- and 2-hydroxypyrroles CXXVII, which are suitable intermediates for a variety of the bicyclic compounds of this invention. Pyrrole 2,3-dicarboxylates can also be prepared from aminocarbonyl compounds CXXV. Michael addition under basic conditions with acetylenedicarboxylate esters is followed by in situ ring closure to afford the pyrrole 2,3-dicarboxylate diester. Selective hydrolysis of one of the esters, typically the 2-ester, affords the pyrrole 2-carboxylic acid CXXVIII. Curtius rearrangement of CXXVIII affords another route to the 2-aminopyrrole CXXVI. Also, the carboxylic acid can be reduced to the alcohol CXXIX using borane or by sodium borohydride reduction of the derived mixed anhydride. Following procedures described in Schemes II–VIII and Scheme XIII, the intermediates CXXVI, CXXVII, CXXVIII and CXXIX can be converted to the final pyrrolo-fused bicyclic compounds of Formula I. Other procedures not described here are also known to those skilled in the art and can be used to prepare the pyrrolo-fused bicyclic compounds of Formula I.

Scheme XVIII

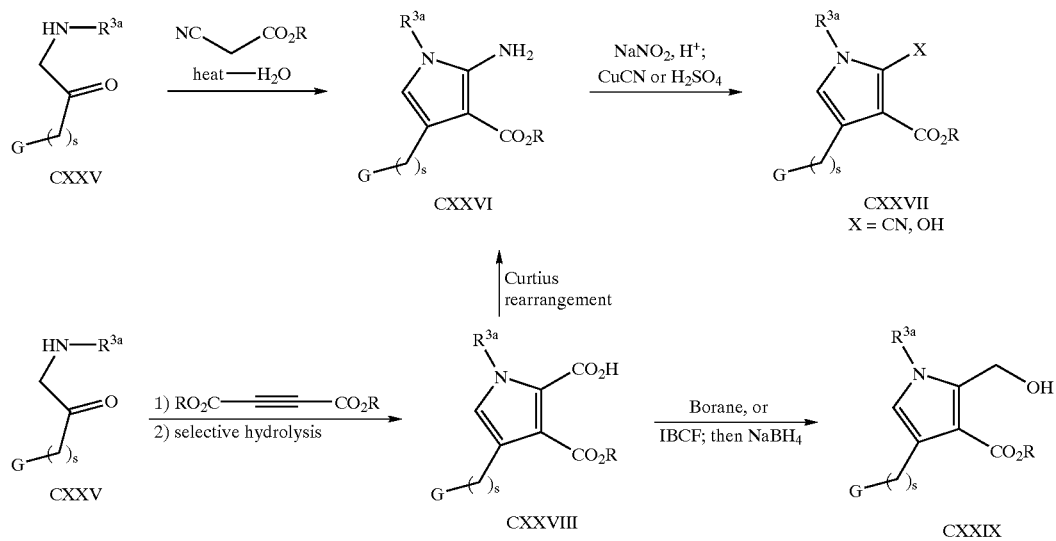

Bicyclic compounds of the present invention in which the five membered ring is furan and the G-containing group is attached to a carbon atom can be prepared as shown in Scheme XIX. For compounds of this type wherein a nitrogen atom is required at the furyl 2-position, the 2-aminofuran CXXXI is a useful intermediate. These compounds can be prepared analogously to the pyrrole analogs described in Scheme XVIII. Thus, condensation of readily obtained hydroxycarbonyl compounds CXXX with an appropriate cyanoacetate affords the 2-aminofurans CXXXI. This condensation can be carried out under basic conditions or by heating with azeotropic removal of water. The 2-aminofurans CXXXI can be diazotized and subsequently converted into the 2-cyano- and 2-hydroxyfurans CXXXII, which are suitable intermediates for a variety of the bicyclic compounds of this invention. Furan 2,3-dicarboxylates can also be prepared from hydroxycarbonyl compounds CXXX, analogously to the pyrrole analogs described in Scheme XVIII. Michael addition of CXXX under basic conditions with acetylenedicarboxylate esters is followed by in situ ring closure to afford the furan 2,3-dicarboxylate diester. Selective hydrolysis of one of the esters, typically the 2-ester, affords the furan 2-carboxylic acid CXXXIII. Curtius rearrangement of CXXXIII affords another route to the 2-aminofurans CXXXI. Also, the carboxylic acid can be reduced to the alcohol CXXXIV using borane or by sodium borohydride reduction of the derived mixed anhydride. Following procedures described in Schemes II–VIII and Scheme XIII, the intermediates CXXXI, CXXXII, CXXIII and CXXXIV can be converted to the final furan-fused bicyclic compounds of Formula I. Other procedures not described here are also known to those skilled in the art and can be used to prepare the furan-fused bicyclic compounds of Formula I.

Scheme XIX

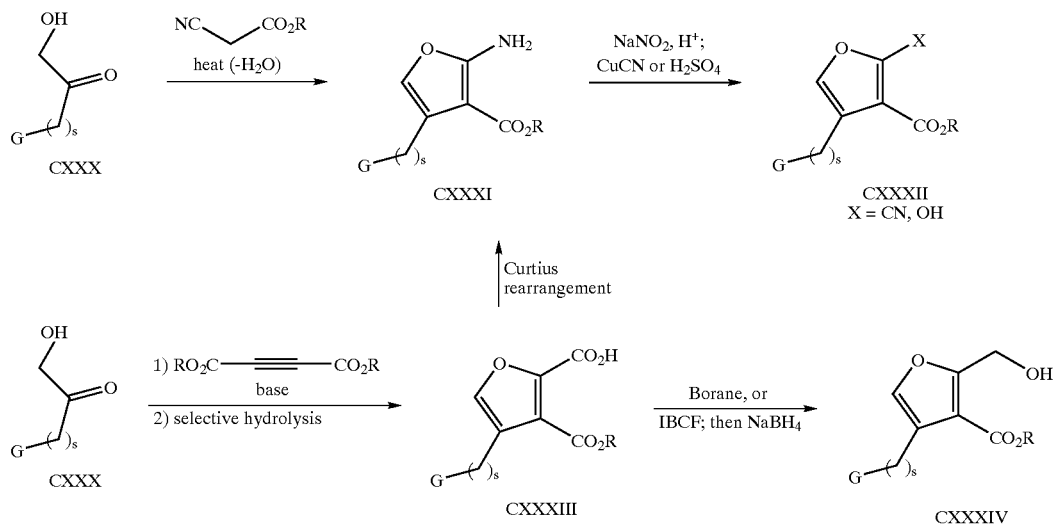

Bicyclic compounds of the present invention in which the five membered ring is thiophene and the G-containing group is attached to a carbon atom can be prepared as shown in Scheme XX. For compounds of this type wherein a nitrogen atom is required at the thiophene 2-position, the 2-aminothiophene CXXXVI is a useful intermediate. These compounds can be prepared analogously to the pyrrole analogs described in Scheme XVIII. Thus, condensation of readily obtained mercaptocarbonyl compounds CXXXV with an appropriate cyanoacetate affords the 2-aminothiophenes CXXXVI. This condensation can be carried out under basic conditions or by heating with azeotropic removal of water. Alternatively, condensation of the cyanoacetate with ketone CXXXVIII affords olefin CXXXIX. In a subsequent step, CXXXIX can be converted into 2-aminothiophenes CXXXVI by treatment with $S_8$ and a base such as triethylamine. The 2-aminothiophenes CXXXVI can be diazotized and subsequently converted into the 2-cyano- and 2-hydroxythiophenes CXXXVII, which are suitable intermediates for a variety of the bicyclic compounds of this invention. Thiophene 2,3-dicarboxylates can be prepared from alkali-metal acetylenethiolates CXL. These compounds react with acetylenedicarboxylate esters in a [3+2] cycloaddition to afford thiophene 2,3-dicarboxylate diesters. Selective hydrolysis of one of the esters, typically the 2-ester, affords the thiophene 2-carboxylic acid CXLI. Curtius rearrangement of CXLI affords another route to the 2-aminothiophenes CXXXVI. Also, the carboxylic acid can be reduced to the alcohols CXLII using borane or by sodium borohydride reduction of the derived mixed anhydride. Following procedures described in Schemes II–VIII and Scheme XIII, the intermediates CXXXVI, CXXXVII, CXLI and CXLII can be converted to the final thiophene-fused bicyclic compounds of Formula I. Other procedures not described here are also known to those skilled in the art and can be used to prepare the thiophene-fused bicyclic compounds of Formula I.

Bicyclic compounds of the present invention in which the five membered ring is imidazole and the G-containing group is attached to a nitrogen atom can be prepared as shown in Scheme XXI. These compounds CXLIII through CLXIV, where the R group may be alkyl, aryl or a protecting group PG, are available either from commercial sources or through known prior art and can be represented generically by CLXV. Suitable protection of the imidazole nitrogen affords compounds of the type CLXVI, which are further elaborated via a cupric mediated coupling of appropriate A-B containing boronic acid to yield CLXVII. Subsequent removal of the imidazole-protecting group PG affords compounds such as CLXVIII. The introduction of a substituent G is accomplished as before by the coupling of a G-containing boronic acid in a manner such that the G-group is transferred to the imidazole nitrogen as depicted by CLVIX.

Scheme XXI

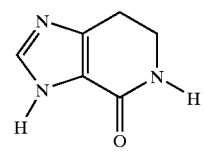

CXLIII

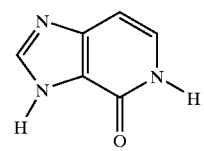

CXLIV

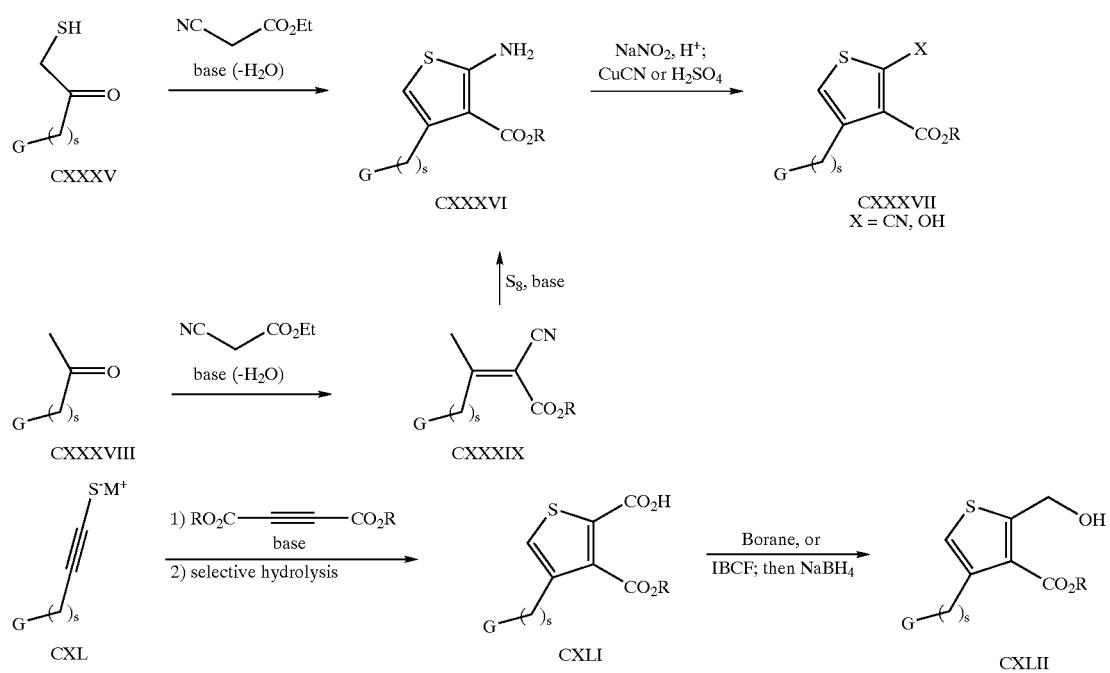

Scheme XX

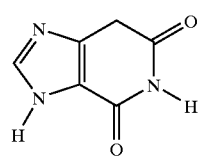
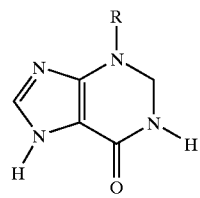
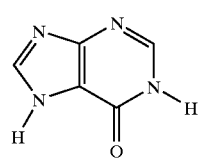
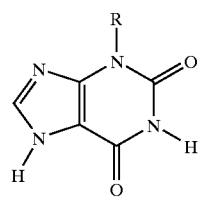
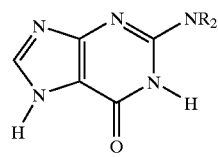
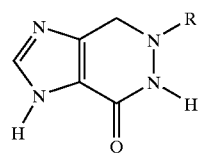
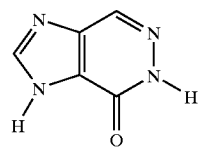
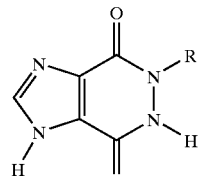
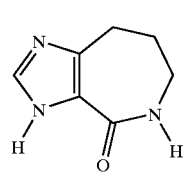
CXLV 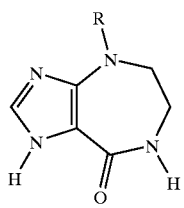
CXLVI
CXLVII 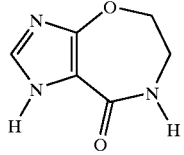
CXLVIII
CXLIX 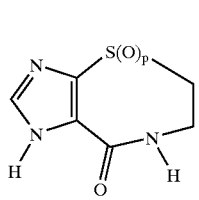
CL
CLI 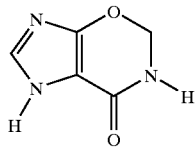
CLII
CLIII
CLIV
CLV 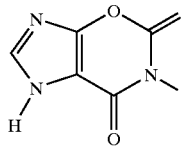
CLVI
CLVII 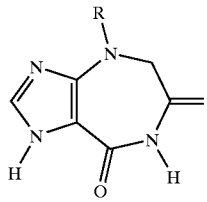
CLVIII
CLIX 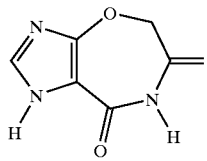
CLX 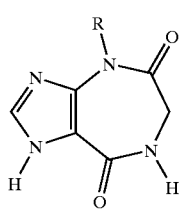
CLXI 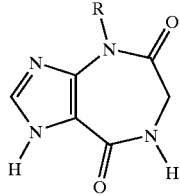

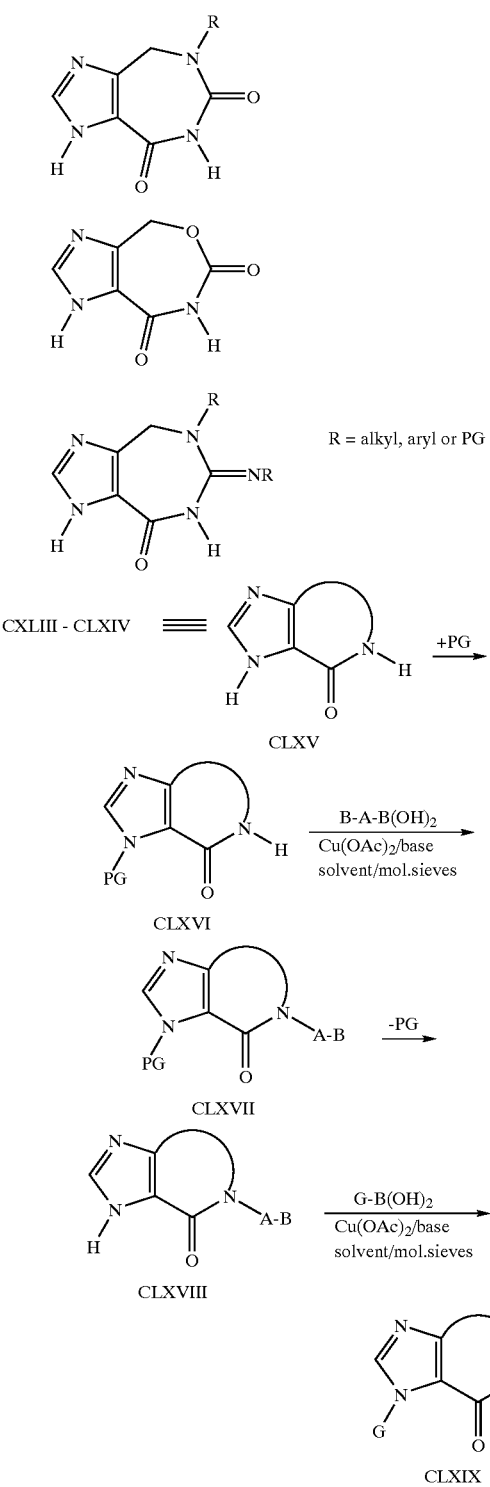

CXLIII - CLXIV ≡

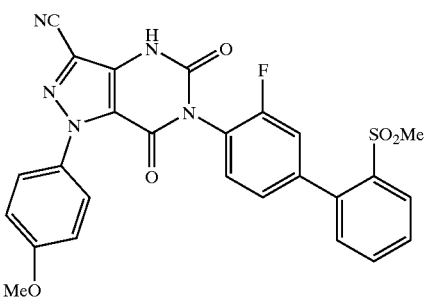

The A-B moieties can be prepared by methods known to those of skill in the art. The following publications, the contents of which are incorporated herein by reference, describe and exemplify means of preparing A-B moieties: WO97/23212, WO97/30971, WO97/38984, WO98/06694, WO98/01428, WO98/28269, and WO98/28282.

Other features of the invention will become apparent in the course of the following descriptions of exemplary embodiments that are given for illustration of the invention and are not intended to be limiting thereof.

EXAMPLES

Example 1

1-[4-methoxyphenyl]-3-cyano-6-[2'-methylsulfonyl-3-fluoro-[1,1']-biphen-4-yl]-1,4-dihydropyrazolo-[4,3-d]-pyrimidine-5,7-dione.

Part A. □, □-Dicyano-4-methoxyphenyl hydrazine imine

Anisidine (18.84 g, 152.99 mmol) was dissolved in 225 mL of water followed by the addition of 32.7 mL (392.4 mmol) of concentrated HCl and then the mixture was cooled in an ice bath. $NaNO_2$ (13.72 g, 198.89 mmol) was dissolved in 45 mL of water and added in several portions. The solution was stirred for 10 minutes and poured into a flask containing a solution of 10.10 g (152.99 mmol) of malononitrile and sodium acetate (27.61 g, 336.59 mmol) in 36 mL of methanol and 75 mL of water. A heavy yellow precipitate immediately formed (29.9 g, 97%) and was isolated as the title compound by suction filtration. LRMS ($NH_3$—Cl): 218.2 $(M+NH_4)^+$.

Part B. Methyl(1-[4-Methoxyphenyl]-3-cyano-4-amino) pyrazole-5-carboxylate.

□, □-Dicyano-4-methoxyphenyl hydrazine imine (20.00 g, 99.92 mmol), methyl bromoacetate (16.81 g, 109.90 mmol), 4-N,N-dimethyl pyridine (1.22 g, 9.99 mmol) and potassium carbonate (34.52 g, 249.79 mmol) were dissolved in N,N-dimethyl formamide and heated to 100° C. for several hours. The solution was diluted with ethyl acetate and washed 4 times with brine. The organics were dried over $MgSO_4$, filtered through a pad of silica gel and the volatiles were removed. The title compound was purified by dissolving in hot diethyl ether and collecting the solids (9.18 g, 34%) that formed upon cooling by filtration. LRMS ($ES^+$): 273.2 $(M+H)^+$.

Part C. Methyl(1-[4-Methoxyphenyl]-3-cyano-4-azido) pyrazole-5-carboxylate.

Methyl(1-[4-Methoxyphenyl]-3-cyano-4-amino) pyrazole-5-carboxylate (3.36 g, 12.34 mmol) was dissolved in TFA and cooled to 0° C. followed by the addition of $NaNO_2$ (0.94 g, 13.57 mmol) and then the reaction was stirred at that temperature for 45 min. $NaN_3$ (0.80 g, 12.34 mmol) was dissolved in a minimal amount of water and added in portions to the TFA solution. The solution was allowed to stir at 0° C. for 45 min and added slowly to a saturated water solution of $NaHCO_3$. The solution was diluted with ethyl acetate and washed twice with brine. The organics were dried over $MgSO_4$, filtered through a plug of silica gel and the volatiles were removed to give the title compound as a tan solid (1.0 g, 57%). LRMS ($NH_3$—Cl): 316.3 $(M+NH_4)^+$.

Part D. 1-[4-methoxyphenyl]-3-cyano-4-azido-5-[2'-methylsulfonyl-3-fluoro-[1,1']-biphen-4-yl[aminocarbonyl]pyrazole.

[2'-methylsulfonyl-3-fluoro-[1,1']-biphen-4-yl]amine hydrochloride (1.00 g, 3.31 mmol) was dissolved in anhydrous methylene chloride followed by the addition of trimethylaluminum (9.94 mL. 19.88 mmol) as 2.0 M solution in toluene. The solution was stirred at ambient temperature until gas evolution ceased. Methyl(1-[4-Methoxyphenyl]-3-cyano-4-azido)pyrazole-5-carboxylate (0.988 g, 3.31 mmol) was added and the solution stirred overnight at room temperature and refluxed for an additional 2 hrs. The solution was allowed to cool to room temperature and the solution slowly quenched with a saturated solution of ammonium chloride. The reaction was diluted with ethyl acetate and washed twice with a 5% solution of citric acid. The organics were dried over $MgSO_4$ and filtered through a plug of silica gel. The title compound was purified by column chromatography eluting with 1:1 hexane/ethyl acetate (0.09 g, 5%). LRMS (ES-): 530.1 (M-H)-.

Part E. 1-[4-methoxyphenyl]-3-cyano-4-amino-5-[2'-methylsulfonyl-3-fluoro-[1,1']-biphen-4-yl]aminocarbonyl]pyrazole.

1-[4-methoxyphenyl]-3-cyano-4-azido-5-[2'-methylsulfonyl-3-fluoro-[1,1']-biphen-4-yl]aminocarbonyl]pyrazole (0.09 g, 0.169 mmol) was dissolved in methanol followed by the addition of $SnCl_2 2 H_2O$ (0.321 g, 1.69 mmol) and the solution refluxed for 1 hr. The volatile were removed under reduced pressure and the residue stirred in TFA, filtered through a pad of Celite® and the residue purified by preparative HPLC chromatography to yield the title compound as a white solid (30 mg 19%). LRMS (ES+): 506.3 (M+H)[31].

Part F. 1-[4-methoxyphenyl]-3-3-cyano-6-[2'-methylsulfonyl-3-fluoro-[1,1']-biphen-4-yl]-1,4-dihydropyrazolo-[4,3-d]-pyrimidine-5,7-dione.

1-[4-methoxyphenyl]-3-cyano-4-amino-5-[2'-methylsulfonyl-3-fluoro-[1,1']-biphen-4-yl]aminocarbonyl]pyrazole (0.02 g, 0.032 mmol) was dissolved in THF followed by the addition of carbonyl diimidazole (0.010 g, 0.064 mmol) and the solution was stirred at room temperature for 48 hrs. and then at reflux for 0.5 hrs. The volatiles were removed under reduced pressure and the product purified by preparative HPLC (C18 reverse phase column, elution with a $H_2O/CH_3CN$ gradient with 0.5% TFA) and lyophilized to afford the title compound of Example 1 as a white powder (1.9 mg, 11%). LRMS (ES-): 530.2 (M-H)-

Example 2

1-[4-methoxyphenyl]-3-(methoxycarbonyl)-6-[2'-aminosulfonyl-3-fluoro-[1,1']-biphen-4-yl]-1,6-dihydropyrazolo-[4,3-d]-pyrimidin-7-one.

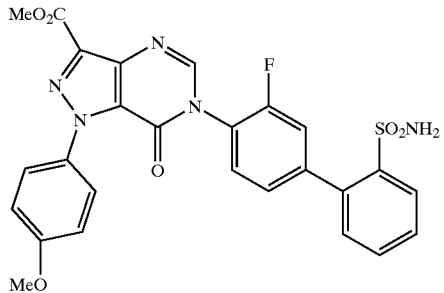

Part A. (1-[4-Methoxyphenyl]-3-cyano-4-azido)pyrazole-5-carboxylic acid.

Methyl(1-[4-Methoxyphenyl]-3-cyano-4-azido)pyrazole-5-carboxylate (5.9 g, 19.78 mmol) was dissolved in a 1:1:1 mixture of $MeOH/H_2O/THF$ followed by the addition of NaOH (1.58 g, 39.56 mmol) and the reaction was allowed to stir at room temperature until all of the starting material was consumed by TLC. The solution was acidified with 10% HCl and the product was extracted with ethyl acetate. The organic layer was washed twice with brine and the solvent was dried over $MgSO_4$, filtered and the volatiles were removed under reduced pressure to yield the title compound as a tan solid (4.00, 71%). LRMS (ES-): 539.0 (M-H—$CO_2$)[31].

Part B. 1-[4-methoxyphenyl]-3-cyano-4-azido-5-[2-fluoro-4-bromophenyl) aminocarbonyl]pyrazole.

1-[4-methoxyphenyl]-3-cyano-4-azidopyrazole-5-carboxylic acid (4.00 g, 14.07 mmol) was dissolved in $CH_2Cl_2$ followed by the addition of oxalyl chloride (1.84 mL, 21.11 mmol) and 1 drop of DMF. The mixture was allowed to stir at room temperature for 2 hrs. The volatiles were removed under reduced pressure and the residue dried under high vacuum for 1 hr. The residue was dissolved in $CH_2Cl_2$ followed by the addition of DMAP (3.44 g, 28.15 mmol) and 2-fluoro-4-bromo-aniline (2.67 g, 14.07 mmol) and the solution stirred overnight at room temperature. The volatiles were removed under vacuum and the product purified by trituration of the residue with ether/hexanes to afford the title compound (1.50 g, 23%). LRMS (ES-): 454.0 (M-H)-.

Part C. 1-[4-methoxyphenyl]-3-(methoxycarbonyl)-4-amino-5-[2-fluoro-4-bromophenyl) aminocarbonyl]pyrazole.

1-[4-methoxyphenyl]-3-cyano-4-azido-5-[2-fluoro-4-bromophenyl)aminocarbonyl]pyrazole (1.50 g, 3.28 mmol) was dissolved in MeOH followed by the addition of tin (II) chloride dihydrate (6.23, 32.88 mmol) and the solution refluxed for 2 hrs. The solution was dissolved in EtOAc and basified by the addition of 10% NaOH solution. The organics were washed twice with brine and dried over $MgSO_4$ filtered through a pad of silica gel and dried under vacuum to give the title compound (0.55 g, 39%). LRMS (ES+): 463.1 (M+H)+.

Part D. 1-[4-methoxyphenyl]-3-(methoxycarbonyl)-6-[2-fluoro-4-bromophenyl]-1,6-dihydropyrazolo-[4,3-d]-pyrimidin-7-one.

1-[4-methoxyphenyl]-3-methoxycarbonyl-4-amino-5-[2-fluoro-4-bromophenyl)aminocarbonyl]pyrazole (0.55 g, 1.27 mmol) was dissolved in 25 mL of 96% formic acid and refluxed for 3 hrs. The volatile were removed and the residue dissolved in EtOAc and washed with a saturated solution of $NaHCO_3$. The organics were dried over a solution of $MgSO_4$, filtered through a plug of silica gel and the volatiles were removed to yield the title compound as a white solid (0.30 g, 50%). LRMS (ES+): 473.1 (M+H)+.

Part E. 1-[4-methoxyphenyl]-3-(methoxycarbonyl)-6-[2'-aminosulfonyl-3-fluoro-[1,1']-biphen-4-yl]-1,6-dihydropyrazolo-[4,3-d]-pyrimidin-7-one.

1-[4-methoxyphenyl]-3-(methoxycarbonyl)-6-[2-fluoro-4-bromophenyl]-1,6-dihydropyrazolo-[4,3-d]-pyrimidin-7-one (0.30 g, 0.633 mmol), TBAB (0.02 g, 0.06 mmol), aqueous $Na_2CO_3$ (2M, 0.7 mL, 0.88 mmol), and 2-(N-tert-butyl)phenylsulfonamide boronic acid (0.22 g, 0.88 mmol) were dissolved in 100 mL of benzene and degassed with nitrogen for 30 minutes. Following the purge, tetrakis(triphenylphosphine)palladium(0) (0.036 g, 0.03 mol) was added and the solution stirred overnight at reflux. The solution was diluted with EtOAc and washed twice with brine and the organics dried over $MgSO_4$, filtered and the volatiles were removed under reduced pressure. Purification by column chromatography, eluting with 1:1 hexane/EtOAc, afforded 0.20 g (52%) of a tert-butyl sulfonamide. This compound (0.20 g, 0.33 mmol) was dissolved in 25 mL of TFA and refluxed for 1 hour. The volatiles were removed under reduced pressure and the product was purified by reverse phase HPLC (C18 reverse phase column, elution with a $H_2O/CH_3CN$ gradient with 0.5% TFA) and lyophilized to afford the title compound of Example 2 as a white solid. LRMS (ES$^+$): 550.2 (M+H)$^+$.

Example 3

1-[4-methoxyphenyl]-3-(aminocarbonyl)-6-[2'-aminosulfonyl-3-fluoro-[1,1']-biphen-4-yl]-1,6-dihydropyrazolo-[4,3-d]-pyrimidin-7-one.

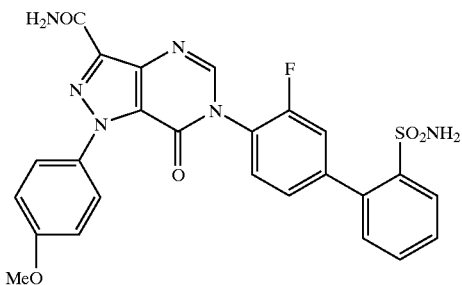

Part A. (1-[4-Methoxyphenyl]-3-cyano-4-azido)pyrazole-5-carboxylic acid.

Methyl(1-[4-Methoxyphenyl]-3-cyano-4-azido)pyrazole-5-carboxylate from Example 1, Part C (14.0 gr, 46.94 mmol) was dissolved in a 1:1 solution of THF/H$_2$O followed by the addition of lithium hydroxide monohydrate (5.90 g, 140.84 mmol) and the solution stirred at room temperature for 4 hours. The solution was acidified with HCl, the organics were extracted with EtOAc and washed with brine. The organic layer was dried over MgSO$_4$, filtered through a plug of silica gel and the volatiles removed under reduced pressure to yield 8.72 g (65%) of the title compound as a tan solid. LRMS (ES–): 283.1 (M–H)$^–$.

Part B. 1-[4-methoxyphenyl]-3-cyano-4-azido-5-[(2-fluoro-4-bromophenyl) aminocarbonyl pyrazole.

To a solution of (1-[4-Methoxyphenyl]-3-cyano-4-azido) pyrazole-5-carboxylic acid (8.22 g, 28.92 mmol) in CH$_2$Cl$_2$ was added oxallyl chloride (3.78 mL, 43.38 mmol) and 1 drop of DMF. The mixture was allowed to stir at room temperature for 2 hours. The volatiles were removed under reduced pressure and the residue dried under high vacuum for 1 hour. The residue was dissolved in CH$_2$Cl$_2$ followed by the addition of DMAP (7.06 g, 57.84 mmol) and 2-fluoro-4-bromoaniline (5.49 g, 28.92 mmol) and the solution stirred overnight at room temperature. The volatiles were removed under vacuum and the product was purified by trituration of the residue with hexane/ether to give 7.9 g (60%) of the title compound as a solid. LRMS (ES–): 454.0/456.0 (M–H)$^–$.

Part C. 1-[4-methoxyphenyl]-3-(aminocarbonyl)-4-azido-5-[(2-fluoro-4-bromophenyl) aminocarbonyl]pyrazole.

A solution of 1-[4-methoxyphenyl]-3-cyano-4-azido-5-[(2-fluoro-4-bromophenyl)aminocarbonyl]pyrazole (1.00 g, 2.32 mmol) in a 1:1 mixture of MeOH:MeOAc was cooled in an ice/water bath. Gaseous HCl was bubbled through the cooled solution for 15 minutes and the solution was stirred, with warming to room temperature, overnight. The volatiles were removed under reduced pressure followed by the addition of 25 mL of MeOH and 20 mL of 1 M HCl and the resulting solution was stirred at room temperature for 2 hours. The solution was diluted with EtOAc, washed with brine, the organics were dried over MgSO$_4$, filtered through a pad of silica gel and the volatiles were removed under reduced pressure to give 0.99 g (95%) of the title compound as a tan solid. LRMS (ES+): 458.1/460.1 (M+H)$^+$.

Part D. 1-[4-methoxyphenyl]-3-(aminocarbonyl)-6-[2-fluoro-4-bromophenyl]-1,6-dihyropyrazolo-[4,3-d]-pyrimidin-7-one.

To a solution of 1-[4-methoxyphenyl]-3-(aminocarbonyl)-4-azido-5-[(2-fluoro-4-bromophenyl) aminocarbonyl]pyrazole (0.99 g, 2.20 mmol) in methanol was added tin (II) chloride dihydrate (6.23, 32.88 mmol) and the solution refluxed for 2 hrs. The solution was dissolved in EtOAc and basified by the addition of 10% NaOH solution. The organics were washed twice with brine and dried over MgSO$_4$ filtered through a pad of silica gel and dried under vacuum. The residue was dissolved in 50 mL of 95% formic acid was stirred at reflux for 2 hours. The volatiles were removed under reduced pressure and the residue was heated in methanol and filtered to afford 0.69 g (68%) of the title compound as a solid. LRMS (ES$^+$): 458.1/460.1 (M+H)$^+$.

Part E. 1-[4-methoxyphenyl]-3-(aminocarbonyl)-6-[2'-N-tert-butylaminosulfonyl-3-fluoro-[1,1']-biphen-4-yl]-1,6-dihydropyrazolo-[4,3-d]-pyrimidin-7-one.

1-[4-Methoxyphenyl]-3-(aminocarbonyl)-6-[2-fluoro-4-bromophenyl]-1,6-dihydropyrazolo-[4,3-d]-pyrimidin-7-one (0.69 g, 1.50 mmol), TBAB (0.048 g, 0.15 mmol), aqueous Na$_2$CO$_3$ (2M, 3.0 mL, 6.0 mmol) and 2-(tert-butylaminosulfonyl)phenylboronic acid (0.54 g, 2.1 mmol) were dissolved in 100 mL of benzene and degassed with nitrogen for 30 minutes. Following the purge, tetrakis (triphenylphosphine)palladium(0) (0.087 g, 0.075 mmol) was added and the solution stirred overnight at reflux. The solution was diluted with EtOAc and washed twice with brine and the organics dried over MgSO$_4$, filtered and the volatiles removed under reduced pressure. The title compound was purified by column chromatography eluting with 1:1 hexane/EtOAc to afford 0.26 g (29%) of the title compound. LRMS (ES$^+$): 573.3 (M+H)$^+$.

Part F. 1-[4-methoxyphenyl]-3-(aminocarbonyl)-6-[2'-aminosulfonyl-3-fluoro-[1,1']-biphen-4-yl]-1,6-dihydropyrazolo-[4,3-d]-pyrimidin-7-one.

A solution of 1-(4-methoxyphenyl)-3-(aminocarbonyl)-6-[2'-N-tert-butylaminosulfonyl-3-fluoro-[1,1']-biphen-4-yl]-1,6-dihydropyrazolo-[4,3-d]-pyrimidin-7-one (0.26 g, 0.44 mmol) in 25 mL of TFA was refluxed for 1 hour. The volatiles were removed under reduced pressure and the product purified by reverse phase HPLC (C18 reverse phase column, elution with a H$_2$O/CH$_3$CN gradient with 0.5% TFA) and lyophilized to afford the title compound of Example 3 as a white solid. LRMS (ES$^+$): 535.2 (M+H)$^+$.

Example 4

1-[4-methoxyphenyl]-3-(methoxycarbonyl)-6-[2'-aminosulfonyl-[1,1']-biphen-4-yl]-1,6-dihydropyrazolo-[4,3-d]-pyrimidin-7-one.

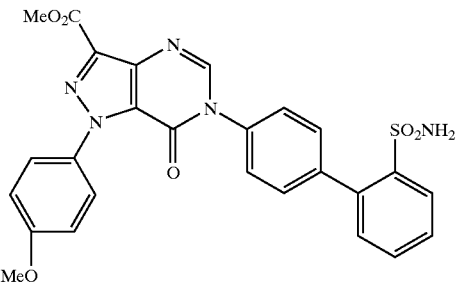

Part A. □-Cyano-.□-(methoxycarbonyl)-4-methoxyphenyl hydrazine imine

Anisidine (55.0 g, 446.57 mmol) was dissolved in 675 mL of water followed by the addition of 98.1 mL (1.1 mol) of concentrated HCl and the mixture cooled in an ice bath. $NaNO_2$ (40.05 g, 580.54 mmol) was dissolved in 100 mL of water and added in several portions. The solution was stirred for 10 minutes and poured into a flask containing a solution of 44.25 g (446.57 mmol) of methyl cyanoacetate and sodium acetate trihydrate (133.69 g, 446.57 mmol) in a solution of methanol and water (108:225 mL). A heavy yellow precipitate immediately formed and was isolated by suction filtration and dried on a lyophilizer to give 82.0 g (79%) of the title compound as a yellow solid. LRMS (ES$^+$): 232.1 (M–H)$^-$.

Part B. tert-Butyl(1-[4-Methoxyphenyl]-3-(methoxycarbonyl)-4-amino)pyrazole-5-carboxylate.

□-Cyano-□-(methoxycarbonyl)-4-methoxyphenyl hydrazine imine (105.7 g, 455.2 mmol), tert-butyl bromoacetate (106.5 g, 546.2 mmol), and potassium carbonate (157.3 g, 1.13 mol) were dissolved in N,N-dimethylformamide and heated to 100° C. for several hours. The solution was diluted with ethyl acetate and washed 4 times with brine. The organics were dried over $MgSO_4$, filtered through a pad of silica gel and the volatiles removed. The title compound was obtained as a dark viscous liquid and used without any further purification (136.7 g, 86%). LRMS ($NH_3$—Cl): 348.3 (M+H)$^+$.

Part C. (1-[4-Methoxyphenyl]-3-(methoxycarbonyl)-4-azido)pyrazole-5-carboxylic acid.

To a solution of tert-butyl (1-[4-Methoxyphenyl]-3-(methoxycarbonyl)-4-amino)pyrazole-5-carboxylate (16.89 g, 48.62 mmol) in 100 mL of TFA at 0° C. was added $NaNO_2$ (4.02 g, 58.34 mmol) and the mixture was stirred for 45 min. $NaN_3$ (3.79 g, 58.34 mmol) was dissolved in a minimal amount of water and added in portions to the TFA solution. The solution was allowed to sir at 0° C. for 45 min. and added slowly to a saturated aqueous solution of $NaHCO_3$. The solution was diluted with ethyl acetate and washed three times with water. The aqueous layer was acidified with 10% aqueous HCl and extracted with EtOAc. The organics were dried over $MgSO_4$, filtered through a plug of silica gel. The product was obtained by flushing the silica gel with 1:1 EtOAc:MeOH. The volatiles were removed under reduced pressure to give 3.0 g (32%) of the title compound as a tan solid. LRMS (ES–): 316.1 (M–H)$^{31}$ Part D. 1-[4-methoxyphenyl]-3-(methoxycarbonyl)-4-azido-5-[4-bromophenylaminocarbonyl]pyrazole.

To a solution of (1-[4-Methoxyphenyl]-3-(methoxycarbonyl)-4-azido)pyrazole-5-carboxylic acid (3.00 g, 9.45 mmol) in 20 mL of $CH_2Cl_2$ was added oxallyl chloride (1.24 mL, 14.18 mmol) and 1 drop of DMF. The mixture was allowed to stir at room temperature for 2 hours. The volatiles were removed under reduced pressure and the residue dried under high vacuum for 1 hour. The residue was dissolved in $CH_2Cl_2$ followed by the addition of DMAP (4.0 g, 33.1 mmol) and 4-bromoaniline (1.62 g, 9.45 mmol) and the solution stirred overnight at room temperature. The volatiles were removed under vacuum and the product purified by trituration of the residue with ether/hexanes to afford the title compound (1.5 g, 33%). LRMS (ES–): 454.0 (M–H)$^-$ Part E. 1-[4-methoxyphenyl]-3-(methoxycarbonyl)-6-[4-bromophenyl]-1,6-dihydropyrazolo-[4,3-d]-pyrimidin-7-one.

To a solution of 1-[4-methoxyphenyl]-3-(methoxycarbonyl)-4-azido-5-[4-bromophenylaminocarbonyl]pyrazole (1.5 g, 3.18 mmol) in isopropanol was added tin (II) chloride dihydrate (0.43 g, 2.28 mmol) and the solution was warmed for 5 minutes. The solution was filtered through a pad of silica gel and the silica rinsed with EtOAc. The volatiles were removed under reduced pressure and the residue was refluxed for 2 hours in 95% formic acid. The volatiles were removed under reduced pressure and the solid residue was washed with cold EtOAc and collected by suction filtration to afford 1.44 g (93%) of the title compound as a solid. LRMS (ES$^+$): 455.1/457.1 (M+H)$^+$ Part F. 1-[4-methoxyphenyl]-3-(methoxycarbonyl)-6-[2'-aminosulfonyl-[1,1']-biphen-4-yl]-1,6-dihydropyrazolo-14,3-d]-pyrimidin-7-one.

A solution of 1-[4-methoxyphenyl]-3-(methoxycarbonyl)-6-[4-bromophenyl]-1,6-dihydropyrazolo-[4,3-d]-pyrimidin-7-one (0.60 g, 1.32 mmol), TBAB (0.04 g, 0.13 mmol), aqueous $Na_2CO_3$ (2M, 2.6 mL, 5.28 mmol), and 2-(tert-butylaminosulfonyl) phenylboronic acid (0.47 g, 1.84 mmol) in 100 mL of benzene was degassed with a stream of nitrogen for 30 minutes. Following the purge, tetrakis(triphenylphosphine)palladium(0) (0.076 g, 0.066 mmol) was added and the solution was stirred overnight at reflux. The solution was diluted with EtOAc and washed twice with brine and the organics dried over $MgSO_4$, filtered and the volatiles removed under reduced pressure. The residue was purified by column chromatography (elution with 1:1 hexane/EtOAc) to afford 0.2 g (52%) of a t-butylsulfonamide. A portion of this compound (0.08 g, 0.136 mmol) was dissolved in 30 mL of TFA and refluxed for 1 hour. The volatiles were removed under reduced pressure and the product was purified by reverse phase HPLC (C18 reverse phase column, elution with a $H_2O/CH_3CN$ gradient with 0.5% TFA) and lyophilized to afford the title compound of Example 4 as a white solid. LRMS (ES$^+$): 532.2 (M+H)$^+$.

Example 5

1-[4-methoxyphenyl]-6-[2'-aminosulfonyl-[1,1']-biphen-4-yl]-1,6-dihydropyrazolo-[4,3-d]-pyrimidin-7-one-3-carboxylic acid.

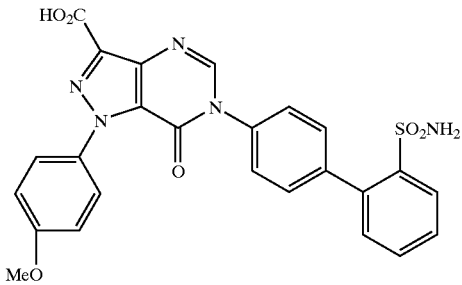

To a solution of 1-[4-methoxyphenyl]-3-(methoxycarbonyl)-6-[2'-aminosulfonyl-[1,1']-biphen-4-yl]-1,6-dihydropyrazolo-[4,3-d]-pyrimidin-7-one from Example 4, Part F (150 mg, 0.28 mmol) in a 1:1 mixture of MeOH:H$_2$O was added LiOH (120 mg, 2.82 mmol) and the reaction was followed by TLC. The solution was quenched by the addition of 10% HCl until acidic to litmus and the product purified by reverse phase HPLC (C18 reverse phase column, elution with a H$_2$O/CH$_3$CN gradient with 0.5% TFA) and lyophilized to afford the title compound of Example 5 as a white solid. LRMS (ES): 516.1 (M–H)$^-$

Example 6

1-[4-methoxyphenyl]-3-(aminocarbonyl)-6-[2'-aminosulfonyl-[1,1']-biphen-4-yl]-1,6-dihydropyrazolo-[4,3-d]-pyrimidin-7-one.

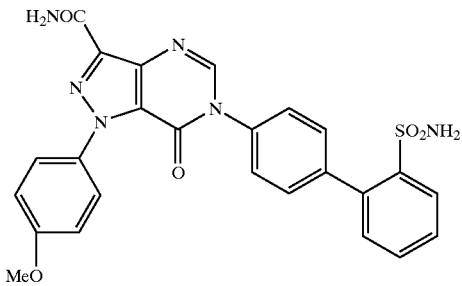

To a solution of 1-[4-methoxyphenyl]-3-(methoxycarbonyl)-6-[2'-aminosulfonyl-[1,1']-biphen-4-yl]-1,6-dihydropyrazolo-[4,3-d]-pyrimidin-7-one from Example 4, Part F (1.00 gr, 1.70 mmol) in 20 mL of 1,4-dioxane was added 25 mL of aqueous (28%) ammonia and the reaction was stirred at room temperature overnight. The solution was diluted with EtOAc and washed with 100 mL of brine. The organics were dried over MgSO$_4$, filtered through a plug of silica gel and the volatiles removed under reduced pressure. The residue (0.08 g, 0.139 mmol) was dissolved in 30 mL of TFA and refluxed for 1 hour. The volatiles were removed under reduced pressure and the product purified by reverse phase HPLC (C18 reverse phase column, elution with a H$_2$O/CH$_3$CN gradient with 0.5% TFA) and lyophilized to afford the title compound of Example 6 as a white solid. LRMS (ES$^+$): 535.1 (M+H)$^+$.

Example 7

1-[4-methoxyphenyl]-3-cyano-6-[2'-aminosulfonyl-[1,1']-biphen-4-yl]-1,6-dihydropyrazolo-[4,3-d]-pyrimidin-7-one.

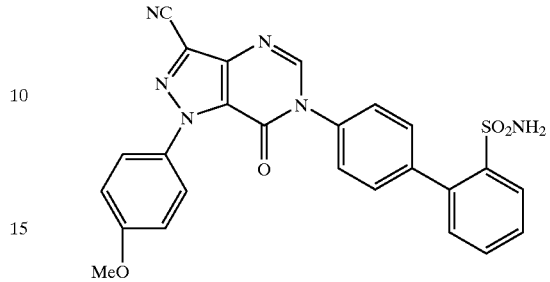

To a solution of 1-[4-methoxyphenyl]-3-(aminocarbonyl)-6-[2'-aminosulfonyl-[1,1']-biphen-4-yl]-1,6-dihydropyrazolo-[4,3-d]-pyrimidin-7-one from Example 6, Part A (0.25 g, 0.436 mmol) in 50 mL of anhydrous benzene was added phosphorous oxychloride (0.33 g, 2.18 mmol) and the reaction was allowed to reflux for 3 hours. The solution was quenched with H$_2$O and the product extracted with EtOAc, dried over MgSO$_4$, filtered through a plug of silica gel and the volatiles removed under reduced pressure. The residue was dissolved in 30 mL of TFA and refluxed for 1 hour. The volatiles were removed under reduced pressure and the product purified by reverse phase HPLC (C18 reverse phase column, elution with a H$_2$O/CH$_3$CN gradient with 0.5% TFA) and lyophilized to afford the title compound of Example 7 as a white solid. LRMS (ES$^+$): 499.2 (M+H)$^+$.

Example 8

1-[4-methoxyphenyl]-3-(aminomethyl)-6-[2'-aminosulfonyl-[1,1']-biphen-4-yl]-1,6-dihydropyrazolo-[4,3-d]-pyrimidin-7-one trifluoroacetic acid salt.

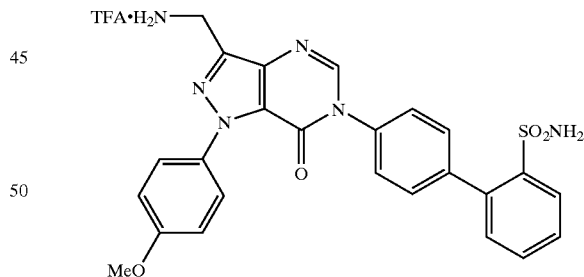

To a solution of 1-[4-methoxyphenyl]-3-cyano-6-[2'-aminosulfonyl-[1,1']-biphen-4-yl]-1,6-dihydropyrazolo-[4,3-d]-pyrimidin-7-one from Example 7, Part A (0.50 g, 1.00 mmol) in 75 mL of absolute EtOH containing 1 mL of TFA was added 10% Pd/C (50 mg) and the reaction was stirred overnight under a balloon of H$_2$ gas. The solution was filtered through a pad of Celite® and the volatiles were removed under reduced pressure and the product purified by reverse phase HPLC (C18 reverse phase column, elution with a H$_2$O/CH$_3$CN gradient with 0.5% TFA) and lyophilized to afford the title compound of Example 8 as a white solid. LRMS (ES$^+$): 503.3 (M+H)$^+$.

Example 9

1-[4-methoxyphenyl]-3-(ethoxycarbonyl)-6-[4-(2-methylimidazol-1'-yl)phenyl]-1,6-dihydropyrazolo-[4,3-d]-pyrimidin-7-one.

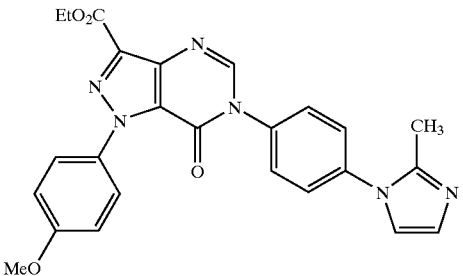

Part A. □-Cyano-.□-(ethoxycarbonyl)-4-methoxyphenyl hydrazine imine.

Anisidine (110 g, 0.89 mol) was dissolved in 1 L of water followed by the addition of 196 mL (2.35 mol) of concentrated HCl and then the mixture was cooled in an ice bath. NaNO₂ (67.8 g, 0.98 mol) was dissolved in 250 mL of water and added in several portions. The solution was stirred for 15 minutes and then poured into a flask containing a solution of ethyl cyanoacetate (111 g, 0.98 mol) and sodium acetate trihydrate (267 g, 1.96 mol) in 215 mL of methanol and 450 mL of water at 0° C. A heavy yellow precipitate immediately formed. After 30 minutes 187 g (84%) of the title compound was isolated by suction filtration and was used without further purification.

Part B. 3-Ethyl-5-methyl (1-[4-Methoxyphenyl]-4-amino) pyrazole-3,5-dicarboxylate.

□-Cyano-.□-(ethoxycarbonyl)-4-methoxyphenyl hydrazine imine (81.8 g, 331 mmol), methyl bromoacetate (55.7 g, 364 mmol) and potassium carbonate (114 g, 0.827 mmol) were dissolved in N,N-dimethyl formamide and heated to 100° C. for several hours. The solution was diluted with ethyl acetate and washed 4 times with brine. The organics were dried over MgSO₄, filtered through a pad of silica gel and the volatiles were removed. The title compound was purified by dissolving in hot diethyl ether and collecting the solids (24.3 g, 23%) that formed upon cooling by filtration. This material was used without further purification.

Part C. 3-Ethyl-5-methyl (1-[4-Methoxyphenyl]-4-azido) pyrazole-3,5-dicarboxylate.

3-Ethyl-5-methyl (1-[4-Methoxyphenyl]-4-amino) pyrazole-3,5-dicarboxylate (41.0 g, 128.4 mmol) was dissolved in TFA and cooled to 0° C. followed by the portionwise addition of NaNO₂ (10.6 g, 154.1 mmol) and then the reaction was stirred at that temperature for 45 min. NaN₃ (10.0 g, 154.1 mmol) was dissolved in a minimal amount of water and added in portions to the TFA solution. The solution was allowed to stir at 0° C. for 45 min and added slowly to a saturated aqueous solution of NaHCO₃. The solution was diluted with ethyl acetate and washed twice with brine. The organics were dried over MgSO₄1 filtered through a plug of silica gel and the volatiles were removed. The residue was recrystallized from ether/hexanes to give the title compound as a tan solid (39.9 g, 90%). LRMS (ES⁺): 346.1 (M+H)⁺.

Part D. (1-[4-Methoxyphenyl]-3-(ethoxycarbonyl)-47 azido)pyrazole-5-carboxylic acid.

To a solution of 3-ethyl-5-methyl (1-[4-Methoxyphenyl]-4-azido)pyrazole-3,5-dicarboxylate (14.0 g, 40.5 mmol) in 50 mL of tetrahydrofuran and 50 mL of water was added lithium hydroxide (0.97 g, 40.5 mmol) and the reaction was stirred at ambient temperature for several hours. The reaction was diluted with water and hexanes and made basic with saturated aqueous sodium bicarbonate. The organic layer was separated. The aqueous layer was acidified with aqueous HCl and then was extracted with ethyl acetate. The organics were washed with brine, dried over MgSO₄, and concentrated to afford 10.1 g (75%) of the title compound that was used without purification. LRMS (ES⁺): 332.1 (M+H)⁺.

Part E. 1-[4-methoxyphenyl]-3-(ethoxycarbonyl)-6-[4-(2-methylimidazol-1'-yl)phenyl]-1,6-dihydropyrazolo-[4,3-d]-pyrimidin-7-one.

To a solution of (1-[4-Methoxyphenyl]-3-(ethoxycarbonyl)-4-azido)pyrazole-5-carboxylic acid (1.50 g, 4.52 mmol) in 20 mL of CH₂Cl₂ was added oxallyl chloride (0.60 mL, 6.80 mmol) and 1 drop of DMF. The mixture was allowed to stir at room temperature for 2 hours. The volatiles were removed under reduced pressure and the residue dried under high vacuum for 1 hour. The residue was dissolved in CH₂Cl₂ followed by the addition of DMAP (1.38 g, 11.3 mmol) and 4-(2-methylimidazol-1'-yl) aniline (0.78 g, 4.52 mmol) and the solution stirred overnight at room temperature. The volatiles were removed under vacuum and the residue was taken up in ethyl acetate and filtered through a plug of silica gel. The product was obtained by flushing the silica gel with methanol. The volatiles were removed under vacuum and the residue was used without further purification. The crude product was dissolved in ethanol and then there was added tin (II) chloride dihydrate (2.57 g, 13.6 mmol) and the solution was warmed for 15 minutes. The solution was diluted with ethyl acetate, washed with 10% aqueous sodium hydroxide and brine, dried MgSO₄) and the volatiles were removed under reduced pressure. The residue was refluxed for 2 hours in 95% formic acid. The volatiles were removed under reduced pressure and the residue was purified by reverse phase HPLC (C18 reverse phase column, elution with a H₂O/CH₃CN gradient with 0.5% TFA) and lyophilized to afford 0.16 g of the title compound of Example 9 as a white solid. LRMS (ES⁺): 471.2 (M+H)⁺.

Example 10

1-[4-methoxyphenyl]-3-(aminocarbonyl)-6-[4-(2-methylimidazol-1'-yl)phenyl]-1,6-dihydropyrazolo-[4,3-d]-pyrimidin-7-one.

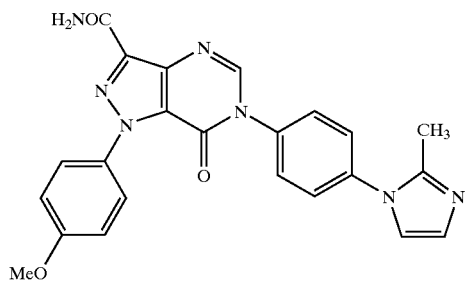

To a solution of 1-[4-methoxyphenyl]-3-(ethoxycarbonyl)-6-[4-(2-methylimidazol-1'-yl)phenyl]-1,6-dihydropyrazolo-[4,3-d]-pyrimidin-7-one from Example 9, Part E (0.50 g, 0.85 mmol) in 20 mL of 1,4-dioxane was added 20 mL of aqueous (28%) ammonia and the reaction was stirred at room temperature overnight. The solution was diluted with EtOAc and washed with 100 mL of brine. The organics were dried over MgSO₄ and the volatiles removed under reduced pressure. The residue was purified by reverse phase HPLC (C18 reverse phase column, elution with a H₂O/CH₃CN gradient with 0.5% TFA) and lyophilized to afford the title compound of Example 10 as a white solid. LRMS (ES⁺): 442.1 (M+H)⁺.

Examples 11 and 12

1-[4-methoxyphenyl]-3-(ethoxycarbonyl)-6-[2'-N-pyrrolidinylmethyl-[1,1']-biphen-4-yl]-1,6-dihydropyrazolo-[4,3-d]-pyrimidin-7-one trifluoroacetic acid salt (Example 11) and 1-[4-methoxyphenyl]-3-(ethoxycarbonyl)-6-[2'-N-pyrrolidinylmethyl-[1,1']-biphen-4-yl]-1,4,5,6-tetrahydropyrazolo-[4,3-d]-pyrimidin-7-one trifluoroacetic acid salt (Example 12).

Example 11

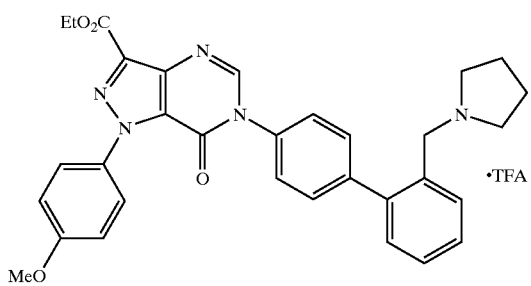

Example 12

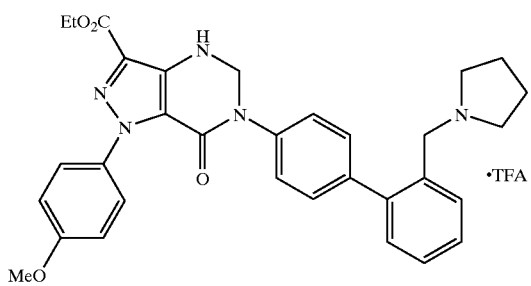

Part A. 1-[4-methoxyphenyl]-3-(ethoxycarbonyl)-4-azido-5-[4-bromophenylaminocarbonyl]pyrazole.

To a solution of (1-[4-Methoxyphenyl]-3-(ethoxycarbonyl)-4-azido)pyrazole-5-carboxylic acid from Example 9, Part D (3.6 g, 10.9 mmol) in 40 mL of CH₂Cl₂ was added oxallyl chloride (1.42 mL, 16.3 mmol) and 1 drop of DMF. The mixture was allowed to stir at room temperature for 2 hours. The volatiles were removed under reduced pressure and the residue dried under high vacuum for 1 hour. The residue was dissolved in CH₂Cl₂ followed by the addition of DMAP (3.32 g, 27.2 mmol) and 4-bromoaniline (1.86 g, 10.9 mmol) and the solution stirred overnight at room temperature. The volatiles were removed under vacuum and the product purified by trituration of the residue with ether/hexanes to afford the title compound (2.6 g, 49%). LRMS (ES⁺): 485.0/487.0 (M+H)⁺.

Part B. 1-[4-methoxyphenyl]-3-(ethoxycarbonyl)-6-[4-bromophenyl]-1,6-dihydropyrazolo-[4,3-d]-pyrimidin-7-one.

To a solution of 1-[4-methoxyphenyl]-3-(ethoxycarbonyl)-4-azido-5-[4-bromophenylaminocarbonyl]pyrazole (2.62 g, 5.40 mmol) in ethanol was added tin (II) chloride dihydrate (3.07 g, 16.2 mmol) and the solution was warmed for 15 minutes. The solution was filtered through a pad of silica gel and the silica rinsed with EtOAc. The volatiles were removed under reduced pressure and the residue was refluxed for 2 hours in 95% formic acid. The volatiles were removed under reduced pressure and the solid residue was washed with cold EtOAc and collected by suction filtration to afford 1.1 g (44%) of the title compound as a solid. LRMS (ES⁺): 469.0/471.0 (M+H)⁺.

Part C. 1-[4-methoxyphenyl]-3-(ethoxycarbonyl)-6-[2'-formyl-[1,1'-biphen-4-yl]-1,6-dihydropyrazolo-[4,3-d]-pyrimidin-7-one.

A solution of 1-[4-methoxyphenyl)-3-(ethoxycarbonyl)-6-[4-bromophenyl]-1,6-dihydropyrazolo-(4,3-d]-pyrimidin-7-one (1.1 g, 2.34 mmol), TBAB (0.07 g, 0.23 mmol), aqueous Na₂CO₃ (2M, 5.0 mL, 9.3 mmol), and 2-formylphenylboronic acid (0.49 g, 3.28 mmol) in 30 mL of benzene was degassed with a stream of nitrogen for 15 minutes. Following the purge, tetrakis(triphenylphosphine)palladium(0) (0.14 g, 0.12 mmol) was added and the solution was stirred overnight at reflux. The solution was diluted with EtOAc, washed twice with brine and dried over MgSO₄, filtered through a pad of silica gel and the volatiles were removed under reduced pressure to afford the title compound that was used without further purification. LRMS (ES⁺): 495.1 (M+H)⁺.

Part D. 1-[4-methoxyphenyl]-3-(ethoxycarbonyl)-6-[2'-N-pyrrolidinylmethyl-[1,1']-biphen-4-yl]-1,6-dihydropyrazolo-[4,3-d]-pyrimidin-7-one trifluoroacetic acid salt (Example 11) and 1-[4-methoxyphenyl]-3-(ethoxycarbonyl)-6-[2'-N-pyrrolidinylmethyl-[1,1']-biphen-4-yl]-1,4,5,6-tetrahydropyrazolo-[4,3-d]-pyrimidin-7-one trifluoroacetic acid salt (Example 12).

To a solution of 1-[4-methoxyphenyl]-3-(ethoxycarbonyl)-6-[2'-formyl-[1,1']-biphen-4-yl]-1,6-dihydropyrazolo-[4,3-d]-pyrimidin-7-one (2.68 g, 5.42 mmol) in 20 mL of dimethyl formamide was added pyrrolidine (0.77 g, 10.8 mmol) and acetic acid dropwise until pH was about 5–6. Then there was added sodium cyanoborohydride (0.68 g, 10.8 mmol) and the resulting solution was allowed to sir for 18 h. The reaction mixture was quenched with water and was partitioned between saturated aqueous sodium bicarbonate and ethyl acetate. The organics were washed with water and brine, dried (MgSO₄) and the volatiles were removed under vacuum. The residue was purified by prep HPLC (C18 reverse phase column, elution with a H₂O/CH₃CN gradient with 0.5% TFA) to afford 0.3 g (10%) of the title compound of Example 11 and 0.5 g (17%) of the title compound of Example 12. Example 11 LRMS (ES⁺): 550.2 (M+H)⁺. Example 12 LRMS (ES⁺): 552.2 (M+H)⁺.

Example 13

1-[4-methoxyphenyl]-3-(aminocarbonyl)-6-[2'-N-pyrrolidinylmethyl-1,1']-biphen-4-yl]-1,6-dihydropyrazolo-[4,3-d]-pyrimidin-7-one trifluoroacetic acid salt

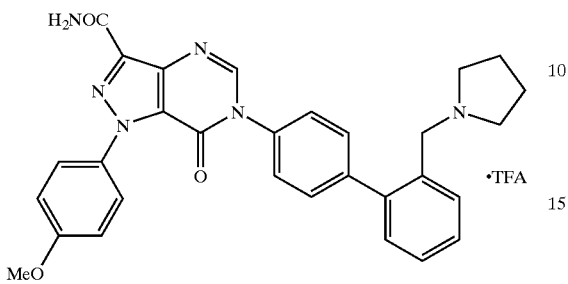

To a solution of 1-[4-methoxyphenyl]-3-(ethoxycarbonyl)-6-[2'-N-pyrrolidinylmethyl-[1,1']-biphen-4-yl]-1,6-dihydropyrazolo-[4,3-d]-pyrimidin-7-one trifluoroacetic acid salt from Example 11, Part D (0.32 g, 0.48 mmol) in 20 mL of 1,4-dioxane was added 20 mL of aqueous (28%) ammonia and the reaction was stirred at room temperature overnight. The solution was diluted with EtOAc and washed with 100 mL of brine. The organics were dried over MgSO$_4$ and the volatiles removed under reduced pressure. The residue was purified by reverse phase HPLC (C18 reverse phase column, elution with a H$_2$O/CH$_3$CN gradient with 0.5% TFA) and lyophilized to afford the title compound of Example 13 as a white solid. LRMS (ES$^+$): 521.1 (M+H)$^+$.

Example 14

1-[4-methoxyphenyl]-3-cyano-6-[2'-N-pyrrolidinylmethyl-[1,1']-biphen-4-yl]-1,6-dihydropyrazolo-[4,3-d]-pyrimidin-7-one trifluoroacetic acid salt

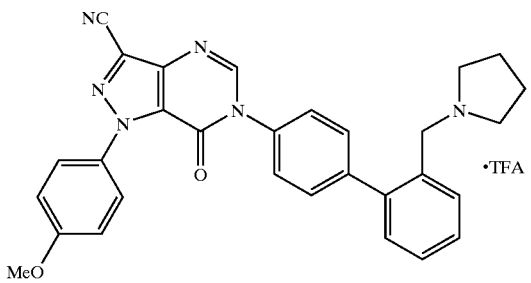

To a solution of 1-[4-methoxyphenyl]-3-(aminocarbonyl)-6-[2'-N-pyrrolidinylmethyl-[1,1']-biphen-4-yl]-1,6-dihydropyrazolo-[4,3-d]-pyrimidin-7-one from Example 13 (0.20 g, 32 mmol) in 10 mL of anhydrous benzene was added phosphorous oxychloride (0.24 g, 1.57 mmol) and the reaction was allowed to reflux for 4 hours. The solution was quenched with H$_2$O and the volatiles were removed under reduced pressure. The residue was purified by reverse phase HPLC (C18 reverse phase column, elution with a H$_2$O/CH$_3$CN gradient with 0.5% TFA) and lyophilized to afford the title compound of Example 14 as a white solid. LRMS (ES$^+$): 503.1 (M+H)$^+$.

Example 15

1-[4-methoxyphenyl]-3-(ethoxycarbonyl)-6-(2-fluoro-4-(2-dimethylaminomethylimidazol-1'-yl)phenyl]-1,6-dihydropyrazolo-[4,3-d]-pyrimidin-7-one trifluoroacetic acid salt

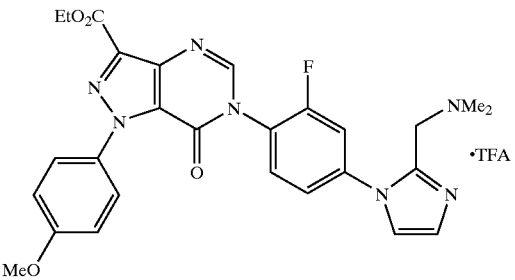

Following the procedures described in Example 9, Part E, the title compound of Example 15 was prepared. LRMS (ES$^+$): 532.1 (M+H)$^+$.

Example 16

1-[2-aminomethylphenyl]-3-(ethoxycarbonyl)-6-[2'-methylsulfonyl-[1,1']-biphen-4-yl]-1,6-dihydropyrazolo-[4,3-d]-pyrimidin-7-one trifluoroacetic acid salt

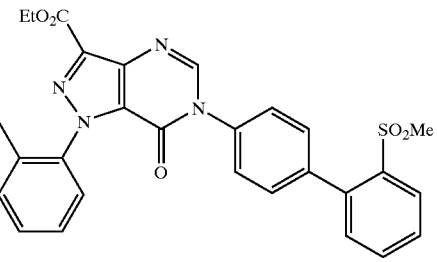

Part A. □-Cyano-.□-(ethoxycarbonyl)-2-methylphenyl hydrazine imine.

To a solution of o-toluidine (20.0 g, 187 mmol) in 320 mL of water at 0° C. was added of 44 mL of concentrated HCl followed by sodium nitrite (16.7 g, 243 mmol) portionwise. The solution was stirred for 15 minutes and then poured into a flask containing a solution of ethyl cyanoacetate (21.1 g, 187 mmol) and sodium acetate trihydrate (55.9 g, 410 mmol) in 100 mL of methanol and 200 mL of water at 0° C. A heavy yellow precipitate immediately formed. After 30 minutes the solid was filtered, washed with water and dried under vacuum to afford 32.4 g (75%) of the title compound, that was used without further purification. $^1$H NMR (CDCl$_3$): □ 9.29 (broad S, 1H), 7.63 (d, 1H), 7.28 (t, 1H), 7.20 (d, 1H), 7.11 (t, 1H), 4.40 (q, 2H), 2.40 (s, 3H), 1.40 (t, 3H)

Part B. 3-Ethyl-5-methyl1-(2-methylphenyl)-4-aminopyrazole-3,5-dicarboxylate.

□-Cyano-.□(ethoxycarbonyl)-2-methylphenyl hydrazine imine (14.0 g, 60 mmol), methyl bromoacetate (8.6 mL, 91 mmol) and potassium carbonate (31.3 g, 226 mmol) were dissolved in 150 mL of N,N-dimethyl formamide and heated to 100° C. for several hours. The solution was diluted with ethyl acetate and washed 4 times with brine. The organics were dried over MgSO$_4$, filtered through a pad of silica gel and the volatiles were removed. The residue was purified by flash chromatography (elution with 3:1 hexanes/ethyl acetate) to afford 5.15 g (28%) of the title compound. $^1$H NMR (CDCl$_3$): □ 7.30–7.15 (m, 4H), 5.25 (broad s, 2H), 4.40 (q, 2H), 3.67 (s, 3H), 2.01 (s, 3H), 1.38 (t, 3H).

Part C. 1-(2-methylphenyl)-3-(ethoxycarbonyl)-4-azidopyrazole-5-carboxylic acid.

3-Ethyl-5-methyl 1-(2-methylphenyl)-4-aminopyrazole-3,5-dicarboxylate (5.2 g, 17.0 mmol) was dissolved in 100 mL of TFA and cooled to 0° C. followed by the addition of NaNO$_2$ (1.4 g, 20.4 mmol) and then the reaction was stirred at that temperature for 45 min. Sodium azide (1.3 g, 20.4 mmol) was dissolved in a minimal amount of water and added in portions to the TFA solution. The solution was allowed to stir at 0° C. for 45 min and added slowly to a saturated aqueous solution of NaHCO$_3$. The solution was diluted with ethyl acetate and washed twice with brine. The organics were dried over MgSO$_4$, filtered through a plug of silica gel and the volatiles were removed. The residue was triturated with ether to afford a crude azide that was used without purification.

To a solution of 1.0 g (3.0 mmol) of the residue in 20 mL of tetrahydrofuran and 20 mL of water was added lithium hydroxide (60 mg, 2.7 mmol) and the reaction was stirred at ambient temperature for several hours. The reaction was diluted with water and hexanes and made basic with saturated aqueous sodium bicarbonate. The organic layer was separated. The aqueous layer was acidified with aqueous HCl and then was extracted with ethyl acetate. The organics were washed with brine, dried over MgSO$_4$, and concentrated to afford 0.65 g (69%) of the title compound that was used without purification. LRMS (ES−): 314.2 (M−H)$^+$.

Part D. 1-(2-methylphenyl)-3-(ethoxycarbonyl)-4-azido-5-[2'-methylsulfonyl-[1,1']-biphen-4-yl]aminocarbonyl]pyrazole.

To a solution of 1-(2-methylphenyl)-3-(ethoxycarbonyl)-4-azidopyrazole-5-carboxylic acid (0.69 g, 2.2 mmol) in 50 mL of CH$_2$Cl$_2$ was added oxallyl chloride (0.29 mL, 3.3 mmol) and 1 drop of DMF. The mixture was allowed to stir at room temperature for 2 hours. The volatiles were removed under reduced pressure and the residue dried under high vacuum for 1 hour. The residue was dissolved in CH$_2$Cl$_2$ followed by the addition of DMAP (0.81 g, 6.6 mmol) and [2'-methylsulfonyl-[1,1']-biphen-4-yl]amine hydrochloride (0.62 g, 2.2 mmol) and the solution was stirred overnight at room temperature. The volatiles were removed under vacuum and the residue was taken up in ethyl acetate, washed with saturated aqueous sodium bicarbonate and brine, dried (MgSO$_4$) and filtered through a plug of silica gel. The volatiles were removed under vacuum to afford 1.0 g (83%) of the title compound that was used without further purification. LRMS (ES−): 543.1 (M−H)$^-$.

Part E. 1-(2-methylphenyl)-3-(ethoxycarbonyl)-6-[2'-methylsulfonyl-[1,1']-biphen-4-yl]-1,6-dihydropyrazolo-[4,3-d]-pyrimidin-7-one.

To a solution of 1-(2-methylphenyl)-3-(ethoxycarbonyl)-4-azido-5-[2'-methylsulfonyl-[1,1']-biphen-4-yl]aminocarbonyl]pyrazole (0.98 g, 1.8 mmol) in absolute ethanol was added tin (II) chloride dihydrate (1.22 g, 5.4 mmol) and the solution was warmed for 15 minutes. The solution was filtered through a pad of silica gel and the silica rinsed with EtOAc. The volatiles were removed under reduced pressure and the residue was refluxed for 2 hours in 95% formic acid. The volatiles were removed under reduced pressure and the solid residue was purified by flash chromatography (elution with 1:1 hexanes/ethyl acetate) to afford 0.21 g (22%) of the title compound as a solid. LRMS (ES$^+$): 529.2 (M+H)$^+$.

Part F. 1-[2-bromomethylphenyl]-3-(ethoxycarbonyl)-6-[2'-methylsulfonyl-[1,1']-biphen-4-yl]-1,6-dihydropyrazolo-[4,3-d]-pyrimidin-7-one.

To a solution of 1-(2-methylphenyl)-3-(ethoxycarbonyl)-6-[2'-methylsulfonyl-[1,1']-biphen-4-yl]-1,6-dihydropyrazolo-[4,3-d]-pyrimidin-7-one (0.21 g, 0.4 mmol) in 50 mL of carbon tetrachloride was added N-bromosuccinimide (0.08 g, 0.44 mmol) and a small amount of AIBN. The reaction was stirred at reflux for 5 h and then was cooled and diluted with ethyl acetate. The organics were washed with brine, dried (MgSO$_4$) and concentrated in vacuo to afford 0.24 g (99%) of the title compound that was used without purification. LRMS (ES$^+$): 607.0/609.0 (M+H)$^+$.

Part G. 1-[2-aminomethylphenyl]-3-(ethoxycarbonyl)-6-[2'-methylsulfonyl-[1,1']-biphen-4-yl]-1,6-dihydropyrazolo-[4,3-d]-pyrimidin-7-one trifluoroacetic acid salt To a solution of 1-[2-bromomethylphenyl]-3-(ethoxycarbonyl)-6-[2'-methylsulfonyl-[1,1']-biphen-4-yl]-1,6-dihydropyrazolo-[4,3-d]-pyrimidin-7-one (0.24 g, 0.4 mmol) in 20 mL of dimethyl formamide was added sodium azide (0.04 g, 0.6=mol) and the reaction was stirred at ambient temperature for 3 h. The reaction was poured into water and extracted with ethyl acetate. The organics were washed with brine, dried (MgSO$_4$) and concentrated in vacuo to afford 0.21 g (91%) of an azide that was used without further purification. This azide was taken up in 20 mL of absolute ethanol and 10 mL of tetrahydrofuran and then there was added tin (II) chloride dihydrate (0.061 g, 0.27 mmol). The reaction was allowed to stir at reflux for 18 h. The voltiles were removed in vacuo and the residue was purified by prep HPLC (C18 reverse phase column, elution with a H$_2$O/CH$_3$CN gradient with 0.5% TFA) and lyophilized to afford the title compound of Example 16 as a white solid. LRMS (ES$^+$): 544.2 (M+H)$^+$.

Example 17

1-[3-aminoiminomethylphenyl]-3-methyl-6-[2'-aminosulfonyl-[1,1']-biphen-4-yl]-1,4,5,6-tetrahydropyrazolo-[3,4-c]-pyridin-7-one trifluoroacetic acid salt

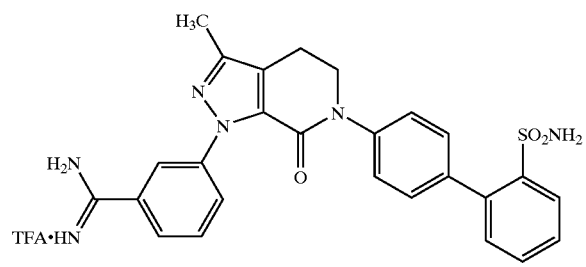

Part A. 1-[4-bromophenyl]-4-acetyl-2,3-dioxopiperidine.

This intermediate was prepared in four steps in 10% overall yield by the following sequence of reactions. Commercially available 4-bromoaniline was treated with commercially available 5-chloro-2-pentanone ethylene ketal in dimethylformamide in the presence of potassium carbonate for three days. The crude alkylated aniline was treated with ethyloxalyl chloride in THF the presence of triethylamine. Hydrolysis of the ketal was accomplished by treating with aqueous HCl and the resulting material was subjected to Dieckmann cyclization conditions (NaOMe, methanol). The crude dioxopiperidine was purified by flash chromatography (elution with 4:1 hexanes/ethylacetate) to afford the title compound. $^1$H NMR (dmso d6): □ 7.56 (d, 2H, J=8 Hz), 7.26 (d, 2H, J=8 Hz), 3.60 (t, 2H), 3.28 (t, 2H), 2.30 (s, 3H). LRMS (ES$^+$): 281.0 (M+H)$^+$.

Part B. 1-[3-aminoiminomethylphenyl]-3-methyl-6-[2'-aminosulfonyl-[1,1']-biphen-4-yl]-1,4,5,6-tetrahydropyrazolo-[3,4-c]-pyridin-7-one trifluoroacetic acid salt.

To a solution of 1-[4-bromophenyl]-4-acetyl-2,3-dioxopiperidine in glacial acetic acid was added 3-cyanophenyl hydrazine. The reaction mixture was stirred at reflux for 3 h and then was cooled to ambient temperature. The volatiles were removed and the residue was taken up in ethyl acetate. The organics were washed with saturated aq sodium bicarbonate and brine, dried (MgSO$_4$) and concentrated.

The residue was dissolved in benzene and then there was added tetrabutylammonium bromide, aqueous Na$_2$CO$_3$ and 2-(tert-butylaminosulfonyl)phenylboronic. This solution was degassed with a stream of nitrogen for 30 minutes. Following the purge, tetrakis(triphenylphosphine)palladium (0) was added and the solution was stirred overnight at reflux. The solution was diluted with EtOAc and washed twice with brine and the organics dried over MgSO$_4$, filtered and the volatiles removed under reduced pressure. The residue was purified by column chromatography (elution with 1:1 hexane/EtOAc) to afford an intermediate biphenyl compound.

This material was dissolved in 50 mL of anhydrous methanol and was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in anhydrous methanol and ammonium carbonate was added and the mixture was allowed to stir at room temperature for 24 h. The reaction mixture was concentrated in vacuo. The residue was dissolved in trifluoroacetic acid and stirred at reflux for 20 minutes. The volatiles were removed in vacuo and the residue was purified by prep HPLC (C18 reverse phase column, elution with a H$_2$O/CH$_3$CN gradient with 0.5% TFA) and lyophilized to afford the title compound of Example 17 as a white powder. $^1$H NMR (dmso d6): □ 9.40 (broad s, 1.5H), 9.28 (broad s, 1.5H), 8.04 (ds, 2H), 7.94 (d, 1H), 7.81 (d, 1H), 7.78–7.48 (m, 4H), 7.40–7.30 (m, 4H), 4.18 (t, 2H), 2.95 (t, 2H), 2.30 (s, 3H). LRMS (ES$^+$): 501.0 (M+H)$^+$.

Example 18

1-[2-aminomethylphenyl]-3-methyl-6-[2'-aminosulfonyl-[1,1']-biphen-4-yl]-1,4,5,6-tetrahydropyrazolo-[3,4-c]-pyridin-7-one trifluoroacetic acid salt

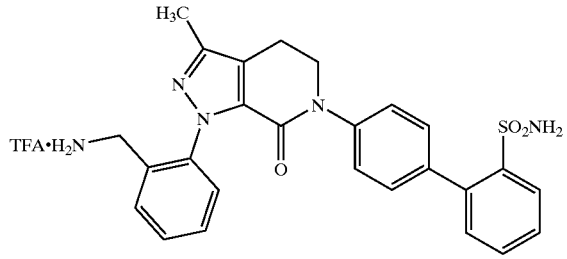

Part A. 1-[2-trifluoroacetamidomethylphenyl]-3-methyl-6-[4-bromophenyl]-1,4,5,6-tetrahydropyrazolo-[3,4-c]-pyridin-7-one.

To solution of 2-(trifluoroacetamidomethyl) aniline (6.5 g, 0.029 mol), prepared from 2-(aminomethyl) aniline and ethyl trifluoroacetate, was added conc. HCl (50 mL) with cooling in an ice bath. The temperature was maintained between 0° C. and 100° C. and sodium nitrite (2 g, 0.029 mol) in water (40 mL) was added. The diazonium was stirred cold for 2 h, then stannous chloride dihydrate (15.4 g, 0.069 mol) in conc. HCl (5 mL) and water (50 mL) was added slowly. The reaction was stirred 0.5 h, saturated with NaCl, extracted with ether, dried (Na$_2$SO$_4$) and concentrated. A portion of the crude hydrazine tin salt (2 g) was combined with 1-[4-bromophenyl]-4-acetyl-2,3-dioxopiperidine from Example 17, Part A (0.46 g, 1.5 mmol) and acetic acid (20 mL) and heated to reflux for 8 h. The reaction was concentrated, taken up in ethyl acetate, washed successively with sat'd NaHCO$_3$ and sat'd NaCl, dried (Na$_2$SO$_4$) and concentrated. The residue was purified by flash chromatography (elution with 1:1 hexanes/ethyl acetate) to afford 0.24 g (32%) of the title compound as a yellow oil. LRMS (ES+): 507/509 (M+H)$^+$.

Part B. 1-[2-aminomethylphenyl]-3-methyl-6-[2'-aminosulfonyl-[1,1']-biphen-4-yl]-1,4,5,6-tetrahydropyrazolo-[3,4-c]-pyridin-7-one trifluoroacetic acid salt.

To a solution of 1-[2-trifluoroacetamidomethylphenyl]-3-methyl-6-[4-bromophenyl]-1,4,5,6-tetrahydropyrazolo-[3,4-c]-pyridin-7-one (0.24 g, 0.47 mmol) in dioxane (15 mL) was added 2-tert-butylsulfonamide benzeneboronic acid (0.16 g, 0.62 mmol), potassium phosphate tribasic (0.3 g, 1.4 mmol), and the mixture was degassed with N$_2$ for 0.5 h. Tetrakis(triphenylphosphine)palladium(0) (50 mg) was added and the reaction was heated to reflux for 4 h. The reaction was filtered through Celite® and the filtrate concentrated. Trifluoroacetic acid (10 mL) was added to the crude residue and the mixture was heated to reflux for 0.25 h. The reaction was concentrated and the residue was purified by flash chromatography (elution with 2:1 hexanes/ethyl acetate) to afford 0.13 g (49%) of the trifluoroacetamide as a tan foam. The trifluoroacetamide was placed in MeOH (10 mL), water (2 mL) and K$_2$CO$_3$ (0.15 g) and heated to reflux for 4 h. The reaction was concentrated, acidified with TFA, purified by prep HPLC (C18 reverse phase column, elution with a H$_2$O/CH$_3$CN gradient with 0.5% TFA) and lyophilized to afford the title compound of Example 18 as a white powder. $^1$H NMR (DMSO-d6) □ 8.19 (broad s, 2H), 8.05 (dd, J=1.1, 7.4 Hz, 1H), 7.65–7.28 (m, 13H), 4.17 (t, J=6.6 Hz, 2H), 3.88 (m, 2H), 3.01 (t, J=6.2, 2H), 2.31 (s, 3H). LRMS (ES$^+$): 488.3 (M+H)$'$.

Example 19

1-[3-Aminobenzisoxazol-5'-yl]-3-methyl-6-[2'-aminosulfonyl-[1,1']-biphen-4-yl]-1,4,5,6-tetrahydropyrazolo-[3,4-c]-pyridin-7-one.

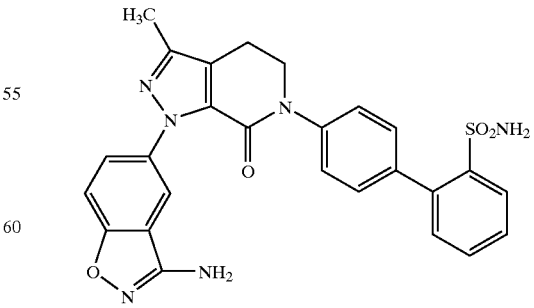

Part A. 1-[3-cyano-4-fluorophenyl]-3-methyl-6-[4-bromophenyl]-1,4,5,6-tetrahydropyrazolo-[3,4-c]-pyridin-7-one.

To 1-[4-bromophenyl]-4-acetyl-2,3-dioxopiperidine from Example 17, Part A (0.3 g, 0.97 mmol) in acetic acid (20 mL) was added 3-cyano-4-fluorophenylhydrazine stannyl chloride hydrochloride (0.39 g, 1.16 mmol) and the mixture was heated to reflux for 8 h. The reaction was concentrated, taken up in ethyl acetate, washed successively with sat'd NaHCO$_3$ and sat'd NaCl, dried (Na$_2$SO$_4$) and concentrated. Purification by silica gel chromatography using 1:1 hexanes/ethyl acetate as eluent afforded 0.31 g (76%) of the title compound as a white solid. $^1$H NMR (CDCl$_3$) □ 7.88 (m, 2H), 7.53 (d, J=8.4 Hz, 2H), 7.25 (m, 1H), 7.21 (d, J=8.4 Hz, 2H), 4.13 (t, J=7.0 Hz, 2H), 2.98 (t, J=6.6 Hz, 2H), 2.35 (s, 3H). LRM (ES$^+$): 425.1/427.1 (M+H)$^+$.

Part B. 1-[3-cyano-4-fluorophenyl]-3-methyl-6-[2-tert-butylaminosulfonyl-[1,1']-biphen-4-yl]-1,4,5,6-tetrahydropyrazolo-[3,4-c]-pyridin-7-one.

To a solution of 1-[3-cyano-4-fluorophenyl]-3-methyl-6-[4-bromophenyl]-1,4,5,6-tetrahydropyrazolo-[3,4-c]-pyridin-7-one (0.31 g, 0.73 mmol) in 15 mL of dioxane was added 2-tert-butylsulfonamide benzeneboronic acid (0.24 g, 0.95 mmol), potassium phosphate tribasic (0.47 g, 2.2 mmol), and the mixture was degassed with N$_2$ for 0.5 h. Tetrakis(triphenylphosphine)palladium(0) (60 mg) was added and the reaction was heated in a 70–80° C. bath for 18 h. The reaction was filtered through Celite® and the filtrate concentrated. Purification by silica gel chromatography using 1:1 hexanes/ethyl acetate as eluent afforded 0.24 g (59%) of a yellow solid. $^1$H NMR (CDCl$_3$): □ 8.18 (dd, J=1.4, 7.7 Hz, 1H), 7.91 (m, 2H), 7.59 (m, 4H), 7.42 (d, J=8.4 Hz, 2H), 7.32 (dd, J=1.5, 7.5 Hz, 1H), 7.24 (d, J=8.8 Hz, 1H), 4.19 (t, J=6.5 Hz, 2H), 3.68 (s, 1H), 3.68 (t, J=6.9 Hz, 2H), 2.36 (3H, s), 1.04 (s, 9H). LRMS (ES$^+$): 580.3 (M+Na)$^+$.

Part C. 1-[3-Aminobenzisoxazol-5'-yl]-3-methyl-6-[2'-aminosulfonyl-[1,1']-biphen-4-yl]-1,4,5,6-tetrahydropyrazolo-[3,4-c]-pyridin-7-one.

Trifluoroacetic acid (10 mL) was added to 1-[3-cyano-4-fluorophenyl]-3-methyl-6-[2'-tert-butylaminosulfonyl-[1,1']-biphen-4-yl]-1,4,5,6-tetrahydropyrazolo-[3,4-c]-pyridin-7-one and the mixture was heated to reflux for 0.25 h. The reaction was concentrated and the residue dried in vacuo for 2 h. To the crude residue was added DMF (5 mL), K$_2$CO$_3$ (0.18 g, 1.3 mmol), and acetohydroxamic acid (97 mg, 1.3 mmol) and the reaction was stirred at ambient temperature. After 0.25 h excess K$_2$CO$_3$ and acetohydroxamic acid were added to counter residual TFA and the rection was stirred 18 h. Water (10 mL) was added and the precipitate filtered off. The solid was acidifed in TFA/CH$_3$CN, concentrated and purified by prep HPLC (C18 reverse phase column, elution with a H$_2$O/CH$_3$CN gradient with 0.5% TFA) and lyophilized to afford the title compound of Example 19 as a white powder. LRMS (ES$^+$): 515.2 (M+H)$^+$, 537 (M+Na)$^+$.

Example 20

1-[4-methoxyphenyl]-3-cyano-6-[2'-N,N-dimethylaminomethyl-[1,1']-biphen-4-yl]-1,6-dihydropyrazolo-[4,3-d]-pyrimidin-7-one trifluoroacetic acid salt.

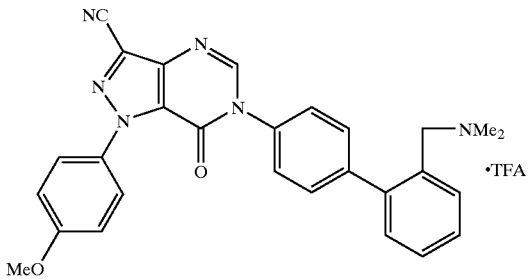

Part A. 1-[4-methoxyphenyl]-3-cyano-4-azido-5-[4-bromophenylaminocarbonyl]pyrazole.

1-[4-Methoxyphenyl]-3-cyano-4-azidopyrazole-5-carboxylic acid from Example 2, Part A (2.92 g, 10.3 mmol) was dissolved in CH$_2$Cl$_2$ followed by the addition of oxalyl chloride (1.34 mL, 15.4 mmol) and 2 drops of DMF. The mixture was allowed to stir at room temperature for 2 hrs. The volatiles were removed under reduced pressure and the residue dried under high vacuum for 1 hr. The residue was dissolved in CH$_2$Cl$_2$ followed by the addition of DMAP (3.78 g, 30.9 mmol) and 4-bromo-aniline (1.77 g, 10.3 mmol) and the solution stirred overnight at room temperature. The reaction mixture was diluted with ethyl acetate, washed sequentially with 10% aqueous HCl, saturated aqueous sodium bicarbonate and brine, dried (MgSO$_4$) and filtered through a plug of silica gel. The volatiles were removed under vacuum to afford 3.9 g (87%) of the title compound that was used without further purification. $^1$H NMR (CDCl$_3$)-8.41 (broad s, 1H), 7.43 (app s, 4H), 7.31 (d, 2H), 6.98 (d, 2H), 3.86 (s, 3H).

Part B. 1-[4-methoxyphenyl]-3-cyano-4-amino-5-[4-bromophenyl)aminocarbonyl]pyrazole.

To a solution of 1-[4-methoxyphenyl]-3-cyano-4-azido-5-[4-bromophenylaminocarbonyl]pyrazole (3.9 g, 8.9 mmol) in 30 mL of isopropanol was added tin (II) chloride dihydrate (8.0 g, 35.6 mmol) and the solution was stirred at 80° C. for 2 hrs. The solution was cooled, dissolved in EtOAc, washed with 10% aqueous NaOH solution and brine, dried over MgSO$_4$, filtered through a pad of silica gel and dried under vacuum to give the title compound (3.0 g, 82%). $^1$H NMR (dmso-D6) n 10.26 (s, 1H), 7.46 (app s, 4H), 7.35(d, 2H), 6.98 (d, 2H), 5.46 (broad s, 2H), 3.74 (s, 3H).

Part C. 1-[4-methoxyphenyl]-3-cyano-6-[4-bromophenyl]-1,6-dihydropyrazolo-[4,3-d]-pyrimidin-7-one.

1[4-methoxyphenyl]-3-cyano-4-amino-5-[4-bromophenylaminocarbonyl]pyrazole (0.60 g, 1.45 mmol) was dissolved in 5 mL of N,N-dimethylformamide dimethyl acetal and stirred at 100° C. for 1 h. The volatiles were removed and the residue was dissolved in 95% formic acid and stirred at 100° C. for 1 h. The volatiles were removed in vacuo and the residue was dissolved in EtOAc and washed with saturated NaHCO$_3$ and brine. The organics were dried over MgSO$_4$, filtered through a plug of silica gel and the volatiles were removed to yield the title compound as an off-white solid (0.56 g, 91%). $^1$H NMR (dmso-D6) □ 8.45 (s, 1H), 7.75 (app d, 2H), 7.62(app d, 2H), 7.45 (app d, 2H), 7.05 (app d, 2H), 3.79 (s, 3H).

Part D. 1-[4-methoxyphenyl]-3-cyano-6-[2'-formyl-[1,1']-biphen-4-yl]-1,6-dihydropyrazolo-[4,3-d]-pyrimidin-7-one.

To a solution of 1-[4-methoxyphenyl]-3-cyano-6-[4-bromophenyl]-1,6-dihydropyrazolo-[4,3-d]-pyrimidin-7-one (0.40 g, 0.95 mmol) in 10 mL of 1,4-dioxane was added 2-formylphenylboronic acid (0.22 g, 1.43 mmol) and potassium phosphate tribasic (0.71 g, 3.33 mmol). This mixture was degassed with a stream of nitrogen for 15 minutes. Following the purge, tetrakis(triphenylphosphine)palladium (0) (0.04 g, 0.035 mmol) was added and the solution was stirred overnight at 100° C. The solution was cooled, diluted with EtOAc, washed twice with brine and the organics were dried over MgSO₄, filtered through a pad of silica gel and concentrated to afford 0.30 g (71%) of the title compound that was sufficiently pure to be used without purification. ¹H NMR (CDCl₃) □ 10.02 (s, 1H), 8.21 (s, 1H), 8.06 (dd, 1H), 7.70–7.40 (m, 9H), 7.00 (app d, 2H), 3.86 (s, 3H).

Part E. 1-[4-methoxyphenyl]-3-cyano-6-[2'-hydroxymethyl-[1,1']-biphen-4-yl]-1,6-dihydropyrazolo-[4,3-d]-pyrimidin-7-one.

To a solution of 1-[4-methoxyphenyl]-3-cyano-6-[2'-formyl-[1,1']-biphen-4-yl]-1,6-dihydropyrazolo-[4,3-d]-pyrimidin-7-one (0.30 g, 0.67 mmol) in 10 mL of 1:1 DMF/THF was added sodium borohydride (38 mg, 1.0 mmol) and the reaction was stirred at ambient temperature for 1 h. The reaction was quenched with 10% aqueous HCl and then diluted with ethyl acetate. The organics were washed with water and brine, dried (MgSO₄) and concentrated. The residue was purified by flash chromatography (elution with 2:1 hexanes/ethyl acetate) to afford 150 mg (50%) of the title compound. ¹H NMR (dmso-D6)□ 8.53 (s, 1H), 7.65 (app d, 2H), 7.62–7.54 (m, 5H), 7.42–7.30 (m, 2H), 7.23 (dd, 1H), 7.07 (app d, 2H), 5.19 (t, 1 h), 4.39 (s, 2H), 3.80 (s, 3H).

Part F. 1-[4-methoxyphenyl]-3-cyano-6-[2'-N,N-dimethyaminomethyl-[1,1'-biphen-4-yl]-1,6-dihydropyrazolo-[4,3-d]-pyrimidin-7-one trifluoroacetic acid salt.

To a solution of 1-(4-methoxyphenyl]-3-cyano-6-[2'-hydroxymethyl-[1,1']-biphen-4-yl]-1,6-dihydropyrazolo-[4,3-d]-pyrimidin-7-one (120 mg, 0.27 mmol) in 5 mL of CH₂Cl₂ was added phosphorous tribromide (144 mg, 0.53 mmol) and the reaction mixture was allowed to stir at ambient temperature for 1 h. The reaction was diluted with ethyl acetate, washed with brine, dried (MgSO₄), filtered through a pad of silica gel and concentrated to afford 115 mg of a crude bromide. To a portion of this residue (65 mg, 0.13 mmol) in 2 mL of acetonitrile was added dimethylamine (0.13 mL of a 2M solution in methanol, 0.26 mmol). The reaction was allowed to stir at ambient temperature for 2 h. The reaction was concentrated and the residue was purified by prep HPLC (C18 reverse phase column, elution with a H₂O/CH₃CN gradient with 0.5% TFA) and lyophilized to afford 38 mg (50%) of the title compound of Example 20 as a white powder. ¹H NMR (dmso-D6)□ 9.68 (broad s, 1H), 8.48 (s, 1H), 7.72–7.50 (m, 9H), 7.36 (dd, 1H), 7.07 (app d, 2H), 4.30 (broad s, 2H), 3.80 (s, 3H), 2.55 (s, 6H). LRMS (ES⁺): 477.3 (M+H)⁺.

Example 21
1-[4-methoxyphenyl]-3-cyano-5-methyl-6-[2'-N,N-dimethylaminomethyl-[1,1']-biphen-4-yl]-1,6-dihydropyrazolo-[4,3-d]-pyrimidin-7-one trifluoroacetic acid salt

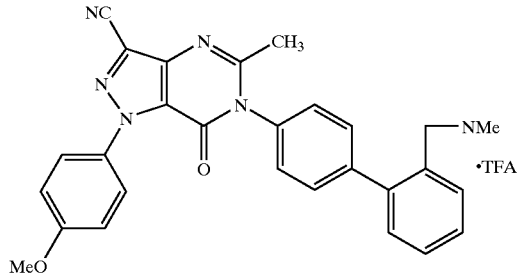

Part A. 1-[4-methoxyphenyl]-3-cyano-5-methyl-6-[4-bromophenyl]-1,6-dihydropyrazolo-[4,3-d]-pyrimidin-7-one.

1-[4-methoxyphenyl]-3-cyano-4-amino-5-[4-bromophenyl)aminocarbonyl]pyrazole from Example 20, Part B (1.0 g, 2.4 mmol) was dissolved in 5 mL of N,N-dimethylacetamide dimethyl acetal and stirred at 100° C. for 1 h. The volatiles were removed and the residue was dissolved in glacial acetic acid and stirred at 100° C. for 1 h. The volatiles were removed in vacuo and the residue was dissolved in EtOAc and washed with saturated NaHCO₃ and brine. The organics were dried over MgSO₄, filtered through a plug of silica gel and the volatiles were removed to yield the title compound as an off-white solid (0.95 g, 90%). ¹H NMR (dmso-D6) □ 7.75 (app d, 2H), 7.58 (app d, 2H), 7.37 (app d, 2H), 7.04 (app d, 2H), 3.78 (s, 3H), 2.15 (s, 3H).

Part B. 1-[4-methoxyphenyl]-3-cyano-5-methyl-6-[2'-formyl-[1,1'-biphen-4-yl]-1,6-dihydropyrazolo-[4,3-d3-pyrimidin-7-one.

To a solution of 1-[4-methoxyphenyl]-3-cyano-6-[4-bromophenyl]-1,6-dihydropyrazolo-[4,3-d]-5-methyl-pyrimidin-7-one (0.24 g, 0.55 mmol) in 10 mL of 1,4-dioxane was added 2-formylphenylboronic acid (0.12 g, 0.83 mmol) and potassium phosphate tribasic (0.41 g, 1.93 mmol). This mixture was degassed with a stream of nitrogen for 15 minutes. Following the purge, tetrakis (triphenylphosphine)palladium(0) (0.025 g) was added and the solution was stirred at 100° C. for 4 h. The solution was cooled, diluted with EtOAc, washed twice with brine and the organics were dried over MgSO₄, filtered through a pad of silica gel and concentrated. The residue was purified by flash chromatography (elution with 2:1 hexanes/ethyl acetate) to afford 0.10 g (40%) of the title compound. ¹H NMR (CDCl₃) □ 10.02 (s, 1H), 8.05 (dd, 1H), 7.69 (td, 1H), 7.65–7.55 (m, 5H), 7.46 (dd, 1H), 7.36 (app d, 2H), 6.98(app d, 2H), 3.83 (s, 3H), 2.38 (s, 3H).

Part C. 1-[4-methoxyphenyl]-3-cyano-5-methyl-6-[2'-N,N-dimethylaminomethyl-[1,1']-biphen-4-yl]-1,6-dihydropyrazolo-[4,3-d3-pyrimidin-7-one trifluoroacetic acid salt.

To a solution of 1-[4-methoxyphenyl]-3-cyano-6-[2'-formyl-[1,1']-biphen-4-yl]-1,6-dihydropyrazolo-[4,3-d]-5-methyl-pyrimidin-7-one (80 mg, 0.17 mmol) in 5 mL of THF was added dimethylamine (0.34 mL of a 2M solution in methanol, 0.68 mmol) and then sodium triacetoxyborohydride (73 mg, 0.35 mmol) and 2 drops of glacial acetic acid. The reaction was allowed to stir at ambient temperature for 3 h. The reaction was quenched with water and diluted with ethyl acetate and saturated aqueous NaHCO₃. The organics were washed with brine, dried (MgSO₄) and concentrated. The residue was purified by prep HPLC (C18 reverse phase column, elution with a H₂O/CH₃CN gradient with 0.5% TFA) and lyophilized to afford 45 mg (44%) of the title compound of Example 21 as a white powder. ¹H NMR (dmso-D6) □ 9.60 (broad s, 1H), 7.70 (m, 1H), 7.60 (app d, 2H), 7.65–7.48 (m, 6H), 7.39 (m, 1H), 7.05 (app d, 2H), 4.31 (broad s, 2H), 3.79 (s, 3H), 2.53 (s, 6H), 2.24 (s, 3H). LRMS (ES⁺): 491.3 (M+H)⁺.

Example 22

1-[2-aminomethylphenyl]-3-cyano-6-[2-methylsulfonyl-3-fluoro-[1,1']-biphen-4-yl]-1,6-dihydropyrazolo-[4,3-d]-pyrimidin-7-one trifluoroacetic acid salt

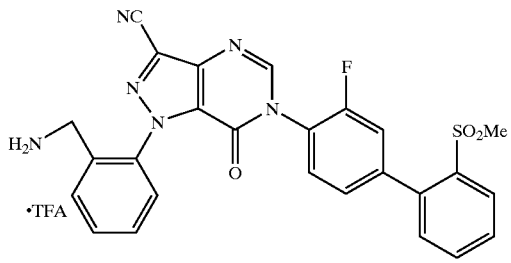

Part A. □,□-Dicyano-2-methylphenyl hydrazine imine.

To a solution of o-toluidine (10.0 g, 93.3 mmol) in 160 mL of water at 0° C. was added of 22 mL of concentrated HCl followed by sodium nitrite (8.4 g, 121 mmol) portionwise. The solution was stirred for 15 minutes and then poured into a flask containing a solution of malononitrile (6.2 g, 93.3 mmol) and sodium acetate trihydrate (28 g, 205 mmol) in 50 mL of methanol and 100 mL of water at 0° C. A heavy yellow precipitate immediately formed. After 30 minutes the solid was filtered, washed with water and dried under vacuum to afford 16 g (93%) of the title compound, that was used without further purification. $^1$H NMR (CDCl$_3$):⁻ 9.60 (broad s, 1H), 7.53 (d, 1H), 7.31 (t, 1H), 7.22 (m, 2H), 2.40 (s, 3H).

Part B. Methyl1-(2-methylphenyl)-3-cyano-4-aminopyrazole-5-carboxylate.

□,□-Dicyano-2-methylphenyl hydrazine imine (12.0 g, 65.1 mmol), methyl bromoacetate (9.3 mL, 97.7 mmol) and potassium carbonate (22.5 g, 163 mmol) were dissolved in 100 mL of N,N-dimethyl formamide and heated to 100° C. for 3 h. The solution was cooled, diluted with ethyl acetate and washed 2 times with brine. The organics were dried over MgSO$_4$, filtered through a pad of silica gel and the volatiles were removed. The residue was purified by flash chromatography (elution with 3:1 hexanes/ethyl acetate) to afford 5.1 g (31%) of the title compound. $^1$H NMR (CDCl$_3$): □ 7.39 (t, 1H), 7.28 (m, 2H), 7.17 (d, 1H), 3.71 (s, 3H), 2.04 (s, 3H). LRMS (ESI): 255.1 (M−H)—.

Part C. 1-(2-methylphenyl)-3-cyano-4-azidopyrazole-5-carboxylic acid.

To a solution of methyl 1-(2-methylphenyl)-3-cyano-4-aminopyrazole-5-carboxylate (5.1 g, 19.9 mmol) in 100 mL of TFA at 0° C. was added NaNO$_2$ (1.65 g, 23.9 mmol) and then the reaction was stirred at that temperature for 45 min. Sodium azide (1.55 g, 23.9 mmol) was dissolved in a minimal amount of water and added in portions to the TFA solution. The solution was allowed to stir at 0° C. for 45 min and added slowly to a saturated aqueous solution of NaHCO$_3$. The solution was diluted with ethyl acetate and washed twice with brine. The organics were dried over MgSO$_4$, filtered through a plug of silica gel and the volatiles were removed to afford 5.26 g of crude azide that was used without purification. To a solution of crude azide (5.26 g, 18.6 mmol) in 100 mL of tetrahydrofuran and 50 mL of water at 0° C. was added lithium hydroxide (0.53 g, 22.3 mmol) and the reaction was stirred at ambient temperature for 3 h. The reaction was diluted with water and ethyl acetate and made basic with saturated aqueous sodium bicarbonate. The organic layer was separated. The aqueous layer was acidified with aqueous HCl and then was extracted with ethyl acetate. The organics were washed with brine, dried over MgSO$_4$, and concentrated to afford 5.18 g of the title compound that was used without purification. $^1$H NMR (CDCl$_3$): _9.56 (broad s, 1H), 7.42 (t, 1H), 7.30 (m, 2H), 7.15(d, 1H), 2.03 (s, 3H).

Part D. 1-(2-methylphenyl)-3-cyano-4-azido-5-[2'-methylsulfonyl-3-fluoro-[1,1']-biphen-4-yl]aminocarbonyl]pyrazole.

To a solution of 1-(2-methylphenyl)-3-cyano-4-azidopyrazole-5-carboxylic acid (2.25 g, 8.37 mmol) in 50 mL of CH$_2$Cl$_2$ was added oxalyl chloride (1.1 mL, 12.6 mmol) and 2 drops of DMF. The mixture was allowed to stir at room temperature for 2 hours. The volatiles were removed under reduced pressure and the residue dried under high vacuum for 1 hour. The residue was dissolved in CH$_2$Cl$_2$ followed by the addition of DMAP (3.07 g, 25.1 mmol) and [2'-methylsulfonyl-3-fluoro-[1,1']-biphen-4-yl]amine hydrochloride (2.53 g, 8.37 mmol) and the solution was stirred overnight at room temperature. The volatiles were removed under vacuum and the residue was taken up in ethyl acetate, washed with 10% aqueous HCl, saturated aqueous sodium bicarbonate and brine, dried (MgSO$_4$) and filtered through a plug of silica gel. The volatiles were removed under vacuum to afford 4.1 g (95%) of the title compound that was used without further purification. $^1$H NMR (CDCl$_3$): □ 8.94 (d, 1H), 8.30 (t, 1H), 8.20 (dd, 1H), 7.64 (td, 1H), 7.57 (td, 1H), 7.46 (t, 1H), 7.37–7.30 (m, 4H), 7.23 (m, 1H), 7.13 (d, 1H), 2.68 (s, 3H), 2.08 (s, 3H).

Part E. 1-(2-methylphenyl)-3-cyano-6-[2'-methylsulfonyl-3-fluoro-[1,1']-biphen-4-yl]-1,6-dihydropyrazolo-[4,3-d]-pyrimidin-7-one.

To a solution of 1-(2-methylphenyl)-3-cyano-4-azido-5-[2'-methylsulfonyl-3-fluoro-[1,1']-biphen-4-yl]aminocarbonyl]pyrazole (2.06 g, 4.0 mmol) in absolute ethanol was added tin (II) chloride dihydrate (2.71 g, 12.0 mmol) and the solution was stirred at reflux for 2 h. The reaction was cooled and concentrated. The residue was taken up in ethyl acetate, washed with dilute aqueous sodium hydroxide and brine, dried (MgSO$_4$) and concentrated. The residue was dissolved in 25 mL of N,N-dimethylformamide dimethyl acetal and stirred at 100° C. for 2 h. The reaction was cooled and concentrated in vacuo. The residue was taken up in 95% formic acid and stirred at 100° C. for 2 h. The reaction was cooled and concentrated. The residue was diluted with ethyl acetate and washed with saturated NaHCO$_3$ and brine, dried (MgSO$_4$) and concentrated to afford 0.60 g (30%) of the title compound that was used without purification. $^1$H NMR (CDCl$_3$): □ 8.23 (dd, 1H), 8.13 (s, 1H), 7.67 (symm m, 2H), 7.50–7.30 (m, 8H), 2.76 (s, 3H), 2.17 (s, 3H).

Part F. 1-[2-aminomethylphenyl]-3-cyano-6-[2'-methylsulfonyl-3-fluoro-[1,1']-biphen-4-yl]-1,6-dihydropyrazolo-[4,3-d]-pyrimidin-7-one trifluoroacetic acid salt.

To a solution of 1-(2-methylphenyl)-3-cyano-6-[2'-methylsulfonyl-3-fluoro-[1,1']-biphen-4-yl]-1,6-dihydropyrazolo-[4,3-d]-pyrimidin-7-one (0.30 g, 0.60 mmol) in 50 mL of 1,2-dichloroethane was added N-bromosuccinimide (0.13 g, 0.72 mmol) and a small amount of AIBN. The reaction was stirred at reflux for 16 h and then was cooled and diluted with ethyl acetate. The organics were washed with brine, dried (MgSO$_4$) and concentrated in vacuo to afford 0.35 g of a 4:1 mixture of desired bromide/starting material that was used without purification.

To this residue in 20 mL of dimethyl formamide was added sodium azide (0.06 g, 0.9 mmol) and the reaction was stirred at ambient temperature for 16 h. The reaction was poured into water and extracted with ethyl acetate. The organics were washed with brine, dried (MgSO$_4$) and concentrated in vacuo to afford 0.21 g (91%) of an azide that was used without further purification. This azide was taken up in 20 mL of isopropanol and 10 mL of tetrahydrofuran and then there was added tin (II) chloride dihydrate (0.41 g, 1.8 mmol). The reaction was allowed to stir at reflux for 18 h. The volatiles were removed in vacuo and the residue was purified by prep HPLC (C18 reverse phase column, elution with a $H_2O/CH_3CN$ gradient with 0.5% TFA) and lyophilized to afford the title compound of Example 22 as a white solid. $^1$H NMR (dmso-D6) □ 8.66 (s, 1H), 8.21 (broad s, 3H), 8.09 (dd, 1H), 7.80–7.50 (m, 8H), 7.42 (m, 2H), 3.99 (broad s, 2H), 2.94 (s, 3H). LRMS (ES$^+$): 515.1 (M+H)$^+$.

Example 23

1-[4-methoxyphenyl]-3-trifluoromethyl-4-methyl-6-[2'-aminosulfonyl-[1,1']-biphen-4-yl]-1,6-dihydropyrazolo-[3,4-d]-pyridazin-7-one.

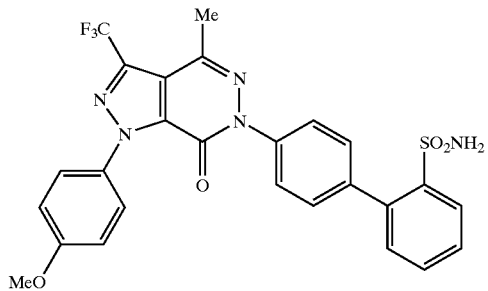

Part A. Ethyl 1-[4-methoxyphenyl]-3-trifluoromethyl-4-acetylpyrazole-5-carboxylate.

To a solution of □bromo-□-.□-trifluoromethyl-4-methoxyphenyl hydrazine imine (2.0 g, 6.7 mmol) in 200 mL of absolute ethanol was added ethyl 2,4-dioxovalerate (2.33 g, 14.7 mmol) and sodium ethoxide (5.0 mL of a 21% wt solution in ethanol, 13.4 mmol). The reaction mixture was stirred at ambient temperature overnight. The ethanol was removed and the residue was diluted with ethyl acetate, washed sequentially with 10% aq HCl, sat'd aq NaHCO$_3$ and brine, dried (MgSO$_4$) and concentrated. The residue was purified by flash chromatography (elution with 4:1 hexanes/ethyl acetate) to afford 0.48 g (20%) of the title compound. $^1$H NMR (CDCl$_3$): □ 7.37 (d, 2H), 6.97 (d, 2H), 4.27 (q, 2H), 3.85 (s, 3H), 2.57 (s, 3H), 1.22 (t, 3H).

Part B. 1-[4-methoxyphenyl]-3-trifluoromethyl-4-methyl-6-[4-bromophenyl]-1,6-dihydropyrazolo-[3,4-d]-pyridazin-7-one.

To a solution of ethyl 1-[4-methoxyphenyl]-3-trifluoromethyl-4-acetylpyrazole-5-carboxylate (1.5 g, 4.2 mmol) in 100 mL of absolute ethanol was added 4-bromophenyl hydrazine hydrochloride (0.94 g, 4.2 mmol) and the resulting mixture was stirred at reflux overnight. Upon cooling a solid fell out of solution. The mixture was filtered and the solid was dried in vacuo to afford 0.77 g (38%) of the title compound. $^1$H NMR (CDCl$_3$): □ 7.60-7.45 (m, 6H), 7.00 (d, 2H), 3.85 (s, 3H), 2.69 (s, 3H).

Part C. 1-[4-methoxyphenyl]-3-trifluoromethyl-4-methyl-6-[2'-aminosulfonyl-[1,1']-biphen-4-yl]-1,6-dihydropyrazolo-[3,4-d]-pyridazin-7-one.

To a solution of 1-[4-methoxyphenyl]-3-trifluoromethyl-4-methyl-6-[4-bromophenyl]-1,6-dihydropyrazolo-[3,4-d]-pyridazin-7-one (0.10 g, 0.21 mmol) in 20 mL of benzene was added 2-(tert-butylaminosulfonyl)phenyl boronic acid (0.08 g, 0.29 mmol), tetrabutylammonium bromide (7 mg, 0.02 mmol), sodium carbonate (0.07 g, 0.63 mmol) and 1 mL of water. This mixture was degassed with a stream of nitrogen for 15 minutes and then there was added tetrakis (triphenylphosphine) palladium (0.02 g, 0.02 mmol). The reaction mixture was stirred at reflux for 16 h. The mixture was cooled, diluted with ethyl acetate and washed with sat'd aq NaHCO$_3$ and brine, dried (MgSO$_4$) and concentrated. The residue was taken up in 10 mL of trifluoroacetic acid and stirred at reflux for 30 min and concentrated in vacuo. The residue was purified by prep HPLC (C18 reverse phase column, elution with a $H_2O/CH_3CN$ gradient with 0.5% TFA) and lyophilized to afford the title compound of Example 23 as a white solid. $^1$H NMR (dmso-D6) □ 8.01 (dd, 1H), 7.64–7.56 (m, 3H), 7.49 (m, 4H), 7.34 (m, 2H), 7.05 (d, 2H), 3.80 (s, 3H), 2.58 (s, 3H). LRMS (ES$^+$): 556.0 (M+H).

Example 24

1-[4-methoxyphenyl]-3-trifluoromethyl-4-methyl-6-[2'-N-pyrrolidinylmethyl-[1,1']-biphen-4-yl-1,6-dihydropyrazolo-[3,4-d]-pyridazin-7-one, trifluoroacetic acid salt.

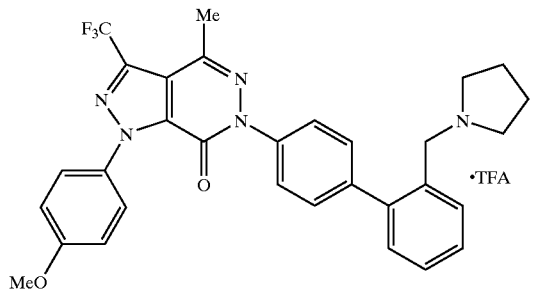

To a solution of 1-[4-methoxyphenyl]-3-trifluoromethyl-4-methyl-6-[4-bromophenyl]-1,6-dihydropyrazolo-[3,4-d]-pyridazin-7-one from Example 23, Part B (0.10 g, 0.21 mmol) in 10 mL of toluene and 10 mL of water was added 2-formylphenylboronic acid (0.04 g, 0.29 mmol) and potassium fluoride (0.02 g, 0.42 mmol). This mixture was degassed with a stream of nitrogen for 15 minutes and then there was added tetrakis (triphenylphosphine) palladium (0.02 g, 0.02 mmol). The reaction mixture was stirred at reflux for 16 h. The mixture was cooled, diluted with ethyl acetate and washed with sat'd aq NaHCO$_3$ and brine, dried (MgSO$_4$) and concentrated to give 0.11 g of an aldehyde. This aldehyde was dissolved in 10 mL of DMF and then there was added pyrrolidine (0.02 mL, 0.26 mmol). This mixture was allowed to stir at ambient temperature for 1 h. The pH was adjusted to 6 by addition of acetic acid and then there was added sodium cyanoborohydride (0.03 g, 0.42 mmol). The reaction was allowed to stir at ambient temperature overnight. The reaction was quenched with dilute aq HCl, diluted with ethyl acetate, washed with brine, dried (MgSO$_4$) and concentrated. The residue was purified by prep HPLC (C18 reverse phase column, elution with a $H_2O/CH_3CN$ gradient with 0.5% TFA) and lyophilized to afford the title compound of Example 24 as a white solid. $^1$H NMR (dmso-D6) □ 7.72 (m, 1H), 7.70–7.60 (m, 4H), 7.51 (m, 2H), 7.46 (d, 2H), 7.35 (m, 1H), 7.06 (d, 2H), 4.39 (broad s, 2H), 3.81 (s, 3H), 3.35 (m, 2H), 2.80 (m, 2H), 2.58 (s, 3H), 1.77 (m, 4H). LRMS (ES$^+$): 560.2 (M+H)$^+$.

Example 25

1-[3-Aminobenzisoxazol-5'-yl]-3-trifluoromethyl-6-[4-(1-methylimidazol-2'-yl)phenyl]-1,6-dihydropyrazolo-14,3-d]-pyrimidin-7-one trifluoroacetic acid salt

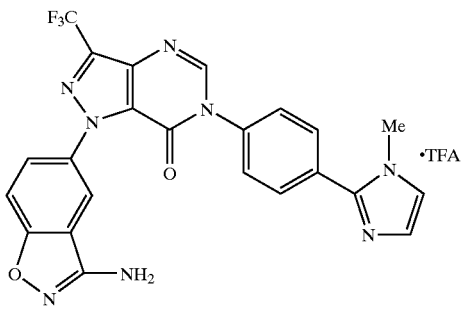

Part A. 1-[3-cyano-4-fluorophenyl]-3-trifluoromethyl-4-nitropyrazole-5-carboxylate.

To a solution of 1-[3-cyano-4-fluorophenyl]-3-trifluoromethylpyrazole-5-carboxylate (2.30 g, 7.7 mmol) in 70 mL of trifluoroacetic acid was added ammonium nitrate (0.92 g, 11.6 mmol). Stirred for 15 minutes and then cooled to 0° C. and added trifluoroacetic anhydride (5.4 mL, 38.5 mmol). The reaction was allowed to stir overnight with warming to room temperature. The reaction was concentrated, poured into water, diluted with ethyl acetate, washed with saturated NaHCO$_3$ and brine, dried (MgSO$_4$) and concentrated. The residue was a mixture of nitrated compound and starting material. It was dissolved in warm water and remaining solid was filtered (starting material). Pure title compound (0.65 g, 25%) was obtained by extracting the water with ethyl acetate, drying (MgSO$_4$) and concentrating. $^1$H NMR (CD$_3$OD):□ 8.12 (dd, 1H), 8.00 (m, 1H), 7.58 (t, 1H).

Part B. 1-[3-cyano-4-fluorophenyl]-3-trifluoromethyl-4-nitro-5-[4-(1-methylimidazol-2'-yl)aminocarbonyl]pyrazole.

To a solution of 1-[3-cyano-4-fluorophenyl]-3-trifluoromethyl-4-nitropyrazole-5-carboxylate (0.76 g, 2.2 mmol) in 100 mL of methylene chloride was added oxalyl chloride (0.29 mL, 3.3 mmol) and 2 drops of DMF. The reaction was allowed to stir at ambient temperature for 3 h, at which time gas evolution had ceased. The reaction was concentrated in vacuo. The residue was taken up in 100 mL of methylene chloride and then there was added 4-dimethylaminopyridine (0.81 g, 6.6 mmol) and 4-(1-methylimidazol-2'-yl) aniline (0.38 g, 2.2 mmol). The reaction was allowed to stir at ambient temparature overnight. The reaction was diluted with ethyl acetate, washed with 10% aq HCl, sat'd aq NaHCO$_3$ and brine, dried (MgSO$_4$) and concentrated. The residue was purified by flash chromatography to afford 0.45 g (41%) of the title compound. $^1$H NMR (CD$_3$OD):□ 8.12 (dd, 1H), 8.03 (m, 1H), 7.70–7.50 (m, 5H), 7.13 (d, 1H), 6.98 (d, 1H), 3.72 (s, 3H). LRMS (ES$^+$): 500.1 (M+H)$^+$.

Part C. 1-[3-cyano-4-fluorophenyl]-3-trifluoromethyl-6-[4-(1-methylimidazol-2'-yl)phenyl]-1,6-dihydropyrazolo-[4,3-d]-pyrimidin-7-one.

To a solution of 1-[3-cyano-4-fluorophenyl]-3-trifluoromethyl-4-nitro-5-[4-(1-methylimidazol-2'-yl) aminocarbonyl]pyrazole (113 mg, 0.23 mmol) in 20 mL of methanol was added copper (I) chloride (0.27 g, 2.7 mmol) and potassium borohydride (0.17 g, 3.2 mmol). The reaction was allowed to stir at ambient temperature for 2 h. The reaction was diluted with ethyl acetate, washed with sat'd ammonium chloride and brine, dried (MgSO$_4$) and concentrated. The residue was taken up in 10 mL of 95% formic acid and stirred at 100° C. for 2 h. The reaction was cooled and concentrated, diluted with ethyl acetate, washed with saturated NaHCO$_3$ and brine, dried (MgSO$_4$) and concentrated to afford the title compound that was used without purification. LRMS (ES$^+$): 480.2 (M+H)$^+$.

Part D. 1-[3-Aminobenzisoxazol-5'-yl]-3-trifluoromethyl-6-[4-(1-methylimidazol-2'-yl)phenyl]-1,6-dihydropyrazolo-[4,3-d]-pyrimidin-7-one trifluoroacetic acid salt.

To a solution of 1-[3-cyano-4-fluorophenyl]-3-trifluoromethyl-6-[4-(1-methylimidazol-2'-yl)phenyl]-1,6-dihydropyrazolo-[4,3-d]-pyrimidin-7-one (53 mg, 0.11 mmol) in 5 mL of DMF and 1 mL of water was added N-acetylhydroxylamine (0.02 g, 0.33 mmol) and potassium carbonate (0.06 g, 0.44 mmol). The reaction was allowed to stir at ambient temperature overnight. The reaction was diluted with ethyl acetate, washed with brine, dried (MgSO$_4$) and concentrated. The residue was purified by prep HPLC (C18 reverse phase column, elution with a H$_2$O/CH$_3$CN gradient with 0.5% TFA) and lyophilized to afford the title compound of Example 25 as a white solid. LRMS (ES$^+$): 493.3 (M+H)$^+$.

Example 26

1-[4-methoxyphenyl]-3-(ethoxycarbonyl)-6-[2'-hydroxymethyl-3-fluoro-[1,1']-biphen-4-yl]-1,6-dihydropyrazolo-[4,3-d]-pyrimidin-7-one

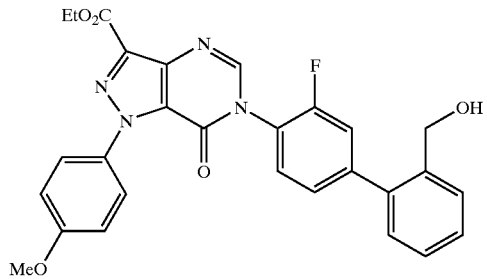

To a solution of 1-[4-Methoxyphenyl]-3-(ethoxycarbonyl)-4-azidopyrazole-5-carboxylic acid (5.77 g, 17.44) in a 1:1 mixture of tetrahydrofuran and methylene chloride (200 mL) was added oxalyl chloride (1.90 mL, 21.81 mmol) and 1 drop of N,N-dimethylformamide. The solution was allowed to stir at ambient temperature for several hours. The volatiles were removed under reduced pressure and the residue dried under high vacuum for several hours. The residue was then dissolved in 200 mL of methylene chloride followed by the addition of 4-dimethylamino pyridine (4.44 g, 36.35 mmol) and [2'-tert-butyldimethylsiloxymethyl-3-fluoro-[1,1']-biphen-4-yl]amine (4.82 g, 14.54 mmol) and the solution allowed to stir at ambient temperature overnight. The solution was filtered though a pad of silica gel and the volatiles were removed in vacuum. The residue was purified by column chromatography using 1:1 hexane/ethyl acetate to give the title compound as a white solid (7.51 g, 67%). LRMS (ESI): 643.2 (M–H)$^-$.

Part B. 1-[4-methoxyphenyl]-3-(ethoxycarbonyl)-6-[2'-hydroxymethyl-3-fluoro-[1,1]-biphen-4-yl]-1,6-dihydropyrazolo-[4,3-d]-pyrimidin-7-one.

(1-[4-Methoxyphenyl]-3-(ethoxycarbonyl)-4-azido)-5-[(2'-tert-butyldimethylsiloxymethyl-3-fluoro-[1,1']-biphen-4-yl)aminocarbonyl]pyrazole (7.51 g, 11.64 mmol) was dissolved in 300 mL of ethanol followed by the addition of stannous chloride dihydrate (5.52 g, 29.12 mmol) and the solution was warmed gently for 2 minutes. The solution was poured through a plug of silica gel and the volatiles removed. The crude product was dissolved in 100 mL of 95% formic acid and refluxed for 1 hr. The volatiles were removed under vacuum and the residue dried overnight. The product was then dissolved in 200 mL of ethanol and cooled in an ice/water bath followed by the addition of lithium hydroxide (1.26 g, 3.3 mmol) in 30 mL of water and the reaction stirred at ambient temperature for 2 hours. The solution was diluted with ethyl acetate and washed with brine. The organics were dried over magnesium sulfate and the residue was purified by prep HPLC (C18 reverse phase column, elution with a H$_2$O/CH$_3$CN gradient with 0.5% TFA) and lyophilized to afford the title compound of Example 26 as a white solid. LRMS (ESI): 515.1 (M+H)$^+$.

Example 27

1-[4-methoxyphenyl]-3-(ethoxycarbonyl)-6-[2'-N-pyrrolidinylmethyl-3-fluoro-[1,1']1-biphen-4-yl]-1,6-dihydropyrazolo-[4,3-d]-pyrimidin-7-one, trifluoroacetic acid salt

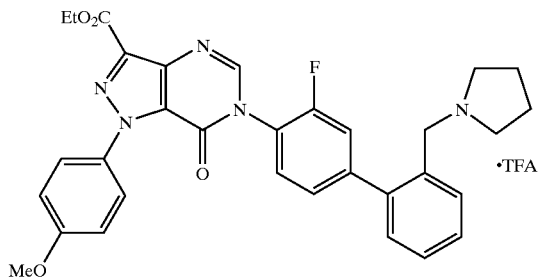

To a solution of 1-[4-methoxyphenyl]-3-(ethoxycarbonyl)-6-[2'-hydroxymethyl-3-fluoro-[1,1']-biphen-4-yl]-1,6-dihydropyrazolo-[4,3-d]-pyrimidin-7-one from Example 26, Part B (0.20 g, 0.39 mmol) in 150 mL of methylene chloride was added phosphorous tribromide (0.074 mL, 0.77 mmol) and the reaction was stirred at ambient temperature overnight. The solution was slowly quenched with water and the organics extracted with ethyl acetate. The organics were dried over magnesium sulfate, filtered and the volatiles were removed under reduced pressure. The crude benzyl bromide (0.22 g, 0.39 mmol) was dissolved in 50 mL of acetonitrile followed by the addition of pyrrolidine (0.11 mL, 1.34 mmol) and stirred at ambient temperature overnight. The volatiles were removed under reduced pressure and the residue was purified by prep HPLC (C18 reverse phase column, elution with a H$_2$O/CH$_3$CN gradient with 0.5% TFA) and lyophilized to afford the title compound of Example 27 as a white solid. LRMS (ESI): 568.2 (M+H)$^+$.

Example 28
1-[4-methoxyphenyl]-3-[2'-N-pyrrolidinylmethyl-3-fluoro-[1,1']-biphen-4-yl]-1,6-dihydropyrazolo-[4,3-d]-pyrimidin-7-one, trifluoroacetic acid salt

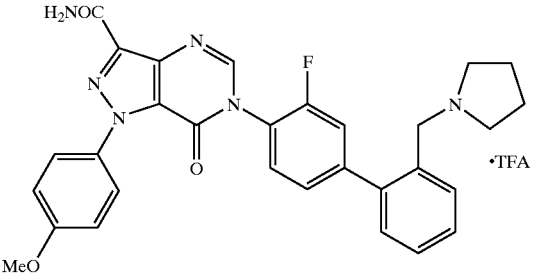

1-[4-methoxyphenyl]-3-(ethoxycarbonyl)-6-[(2'-N-pyrrolidinylmethyl-3-fluoro-[1,1']-biphen-4-yl) aminocarbonyl]pyrazole (0.60 g, 0.92 mmol) was dissolved in 200 mL of methanol followed by the addition of 50 mL of a 28% ammonium hydroxide solution and allowed the reaction to stir overnight at ambient temperature. The reaction was concentrated and the residue was purified by prep HPLC (C18 reverse phase column, elution with a H$_2$O/CH$_3$CN gradient with 0.5% TFA) and lyophilized to afford the title compound of Example 28 as a white solid. LRMS (ESI): 539.1 (M+H)$^+$.

Example 29
1-[4-methoxyphenyl]-3-(aminocarbonyl)-6-[2-(3-(R)-hydroxy-N-pyrrolidinylmethyl)-3-fluoro-[1,1']-biphen-4-yl]-1,6-dihydropyrazolo-[4,3-d]-pyrimidin-7-one, trifluoroacetic acid salt

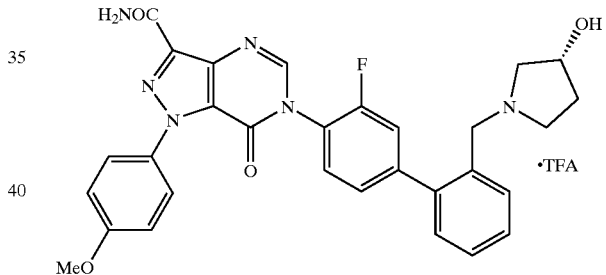

1-[4-methoxyphenyl]-3-(ethoxycarbonyl)-6-[2'-hydroxymethyl-3-fluoro-[1,1']-biphen-4-yl]-1,6-dihydropyrazolo-[4,3-d]-pyrimidin-7-one (0.85 g, 1.71 mmol) was dissolved in 150 mL of methylene chloride followed by the addition of phosphorous tribromide (0.32 mL, 3.42 mmol) and stirred at ambient temperature overnight. The solution was slowly quenched with water and the organics extracted with ethyl acetate. The organics were dried over magnesium sulfate, filtered and the volatiles removed under reduced pressure. The crude benzyl bromide (0.42 g, 0.75 mmol) was dissolved in 50 mL of acetonitrile followed by the addition of 3-(R)-pyrrolidinol hydrochloride (0.55 mL, 4.50 mmol) and stirred at ambient temperature overnight. The volatiles were removed under reduced pressure and the residue was purified by prep HPLC (C18 reverse phase column, elution with a H$_2$O/CH$_3$CN gradient with 0.5% TFA) and lyophilized to afford 0.2 g (17%) of the title compound as a white solid. LRMS (ESI): 566.3 (M+H)$^+$.
Part B. 1-[4-methoxyphenyl]-3-(aminocarbonyl)-6-[2'-(3-(R)-hydroxy-N-pyrrolidinylmethyl)-3-fluoro-[1,1']-biphen-4-yl]-1,6-dihydropyrazolo-[4,3-d]-pyrimidin-7-one, trifluoroacetic acid salt.
1-[4-methoxyphenyl]-3-(ethoxycarbonyl)-6-[2'-(3-(R)-hydroxy-N-pyrrolidinylmethyl)-3-fluoro-[1,1']-biphen-4- yl]-1,6-dihydropyrazolo-[4,3-d]-pyrimidin-7-one (0.120 g, 0.20 mmol) was dissolved in 200 mL of methanol followed by the addition of 50 mL of a 28% ammonium hydroxide solution and allowed the reaction to stir overnight at ambient temperature. The reaction was concentrated and the residue was purified by prep HPLC (C18 reverse phase column, elution with a H₂O/CH₃CN gradient with 0.5% TFA) and lyophilized to afford the title compound of Example 29 as a white solid.

LRMS (ESI): 537.2 (M+H)+

Example 30

1-[4-methoxyphenyl]-3-(N-formylaminomethyl)-6-[2'-methylsulfonyl-3-fluoro-[1,1']-biphen-4-yl]-1,6-dihydropyrazolo-[4,3-d]-pyrimidin-7-one

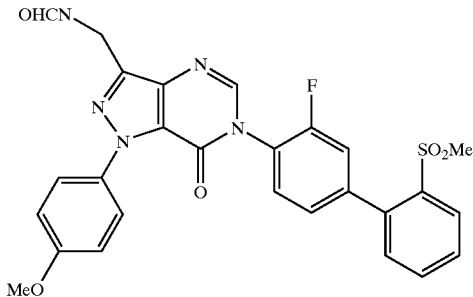

1-(4-methoxyphenyl)-3-cyano-4-amino-5-[2'-methylsulfonyl-3-fluoro-[1,1']-biphen-4-yl]aminocarbonyl] pyrazole (0.30 g, 0.59 mmol) was dissolved in 100 mL of ethanol followed by the addition of 5 mL of trifluoroacetic acid and a catalytic amount of 10% palladium on carbon (0.03 g) and the reaction was stirred overnight at ambient temperature under a balloon of hydrogen gas. The solution was filtered through a plug of Celite® and the volatiles were removed to give the title product as a grey/white solid (0.30 g, 99%). LRMS (ESI); 510.1 (M+H)⁺.

Part B. 1-[4-methoxyphenyl]-3-(N-formylaminomethyl)-6-[2'-methylsulfonyl-3-fluoro-[1,1']-biphen-4-yl]-1,6-dihydropyrazolo-[4,3-d]-pyrimidin-7-one.

1-[4-Methoxyphenyl]-3-aminomethyl-4-amino-5-[2'-methylsulfonyl-3-fluoro-[1, 1']-biphen-4-yl]aminocarbonyl) pyrazole (0.30 g, 0.59 mmol) was refluxed for 3 hours in 75 mL of 95% formic acid. The volatiles were removed under vacuum and the residue was purified by prep HPLC (C18 reverse phase column, elution with a H₂O/CH₃CN gradient with 0.5% TFA) and lyophilized to afford the title compound of Example 30 as a white solid. LRMS (ESI): 548.1 (M+H)⁺.

Example 31

1-[3-Aminobenzisoxazol-5'-yl]-3-(ethoxycarbonyl)-6-[2'-hydroxymethyl-[1,1'-biphen-4-yl]-1,6-dihydropyrazolo-[4,3-d]-pyrimidin-7-one

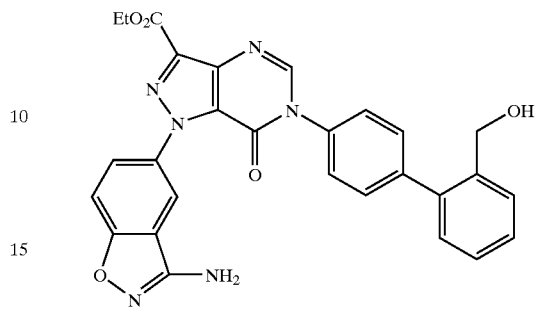

Part A. ☐-Cyano-.☐-ethoxycarbonyl-[4-fluoro-3-cyano) phenyl hydrazine imine.

To a solution of 4-fluoro-3-cyanoaniline (11.78 g, 86.5 mmol) in concentrated HCl (20.2 mL, 173.0 mmol) was added 131 mL of water and the entire reaction was cooled in an ice/water bath. Sodium nitrite (6.5 g, 95.20 mmol) was dissolved in 20 mL of water and slowly added to the reaction mixture. After stirring for 30 minutes, the diazonium solution was poured into a solution of ethyl cyanoacetate (7.60 mL, 95.20 mmol) and sodium acetate trihydrate (25.91 g, 190.40 mmol) in a mixture of 21 mL of methanol and 44 mL of water at 0° C. The reaction was stirred at 0° C. for 20 minutes during which time a heavy yellow precipitate of the title compound formed. The product was isolated and dried by suction filtration to afford 8.9 g (39%) of bright yellow product.

Part B. 3-Ethyl-5-methyl1-(4-fluoro-3-cyano)phenyl-4-aminopyrazole-3,5-dicarboxylate.

☐-Cyano-.☐-ethoxycarbonyl-[4-fluoro-3-cyano)phenyl] hydrazine imine (4.00 g, 15.37 mmol), methyl bromoacetate, (1.85 mL, 19.98 mmol) and potassium carbonate (5.31 g, 38.43 mmol) were dissolved in N,N-dimethyl formamide and heated to 100° C. for several hours. The solution was diluted with ethyl acetate and washed 2 times with brine. The organics were dried over MgSO₄, filtered through a pad of silica gel and the volatiles were removed. The title compound was purified by dissolving in hot diethyl ether and collecting the solids (2.82 g, 55%).

Part C. 3-Ethyl-5-methyl1-(4-fluoro-3-cyano)phenyl-4-azidopyrazole-3,5-dicarboxylate.

3-Ethyl-5-methyl 1-(4-fluoro-3-cyano)phenyl-4-aminopyrazole-3,5-dicarboxylate (2.82 g, 8.48 mmol) was dissolved in TFA and cooled to 0° C. followed by the addition of NaNO₂ (0.70 g, 10.18 mmol) and then the reaction was stirred at that temperature for 45 min. NaN₃ was dissolved in a minimal amount of water and added in portions to the TFA solution. The solution was allowed to stir at 00 C for 45 min and added slowly to a saturated solution of NaHCO₃. The organics were dried over MgSO₄, filtered through a plug of silica gel and the volatiles were removed to give the title compound as a tan solid (0.13 g, 4.2%).

Part D. 1-(4-fluoro-3-cyano)phenyl-3-(ethoxycarbonyl)-4-azidopyrazole-5-carboxylic acid.

3-Ethyl-5-methyl 1-(4-fluoro-3-cyano)phenyl-4-azidopyrazole-3,5-dicarboxylate (0.40 g, 1.11 mmol) was dissolved in a 1:1 mixture of 1,4-dioxane/water and cooled in an ice water bath. Lithium hydroxide (0.04 g, 1.67 mmol) was predissolved in a minimal amount of water and added to the stirring solution in one portion. The reaction was allowed to warm to ambient temperature and the reaction was followed by thin layer chromatography. The solution was extracted with water, the aqueous layer acidified with 10% hydrochloric acid and the product extracted with ethyl acetate to yield the title compound as a white solid (0.35 g, 92%) LRMS (ESI): 687.2 (2M-H)⁻. 1-(4-fluoro-3-cyano) phenyl-3-(ethoxycarbonyl)-4-azidopyrazole-5-carboxylic acid (0.35 g, 1.0 mmol) was dissolved in a 1:1 mixture of tetrahydrofuran and methylene chloride (200 mL) followed by the addition of oxalyl chloride (0.130 mL, 17.58 mmol) and 1 drop of N,N-dimethylformamide. The solution was allowed to stir at ambient temperature for several hours. The volatiles were removed under reduced pressure and the residue dried under high vacuum for several hours. The residue was then dissolved in 200 mL of methylene chloride followed by the addition of N,N-dimethylaminopyridine (3.58 g, 29.31 mmol) and [2'-tert-butyldimethylsiloxymethyl-3-fluoro-[1,1']-biphen-4-yl] amine (3.88 g, 11.72 mmol) and the solution allowed to stir at ambient temperature overnight. The solution was filtered though a pad of silica gel and the volatiles were removed in vacuum. The residue was used without further purification (0.55 g, 86%). LRMS (ESI): 508.1(M-OSi(t-Bu)Me₂+H)⁺.

Part F. 1-(4-fluoro-3-cyano)phenyl-3-(ethoxycarbonyl)-6-[2'-formylhydroxymethyl-[1,1'-biphen-4-yl]-1,6-dihydropyrazolo-[4,3-d]-pyrimidin-7-one.

(1-(4-fluoro-3-cyano)phenyl-3-(ethoxycarbonyl)-4-azido-5-[2'-tert-butyldimethylsiloxy)methyl-[1,1']-biphen-4-yl]aminocarbonyl]pyrazole (0.55 g, 0.86 mmol) was dissolved in 100 mL of ethanol followed by the addition of stannous chloride dihydrate (0.49 g, 2.57 mmol) and the solution warmed gently for several minutes. The solution was then filtered through a pad of silica gel and the volatiles removed under reduced pressure. The residue was dissolved in 100 mL of 96% formic acid and refluxed for 2 hours. The volatiles were removed under reduced pressure and the residue dissolved in ethylacetate and the solution filtered through a pad of silica gel and the volatiles removed under reduced pressure. The title product was purified by column chromatography using 1:1 hexane:ethylacetate and isolated as a white solid (0.40 g, 86%), LRMS (ESI): 560.1 (M+Na)⁺.

Part G. 1-[3-Aminobenzisoxazol-5'-yl]-3-(ethoxycarbonyl)-6-[2'-hydroxymethyl-1,1']-biphen-4-yl]-1,6-dihydropyrazolo-[4,3-d]-pyrimidin-7-one.

1-(4-fluoro-3-cyano)phenyl-3-(ethoxycarbonyl)-6-[2'-formylhydroxymethyl-[1,1']-biphen-4-yl]-1,6-dihydropyrazolo-(4,3-d]-pyrimidin-7-one (0.40 g, 0.74 mmol) was dissolved in N,N-dimethylformamide followed by the addition of acetohydroxamic acid (0.22 g, 2.97 mmol) and potassium carbonate (0.41 g, 2.97 mmol) and stirred overnight at ambient temperature. Potassium carbonate in 10 mL of ethanol was added to the solution and heated to 80° C. for 1 hour. The solution was diluted with water and the product immediately precipitated out and was isolated by filtration. The residue was purified by prep HPLC (C18 reverse phase column, elution with a H₂O/CH₃CN gradient with 0.5% TFA) and lyophilized to afford the title compound of Example 31 as a white solid. LRMS (ESI): 523.1 (M+H)⁺.

Example 32

1-[3-Aminobenzisoxazol-5'-yl]-3-(ethoxycarbonyl)-6-[2'-N-pyrrolidinylmethyl-[1,1']-biphen-4-yl]-1,6-dihydropyrazolo-[4,3-d]-pyrimidin-7-one, trifluoroacetic acid salt

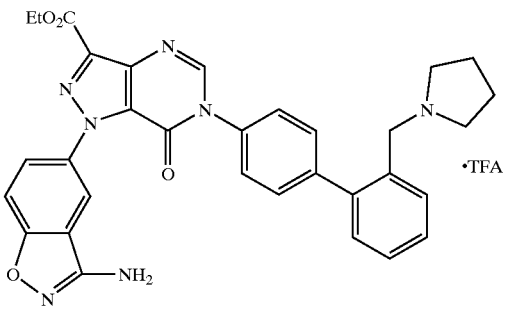

1-[3-Aminobenzisoxazol-5'-yl]-3-(ethoxycarbonyl)-6-[2'-N-hydroxymethyl-[1,1']-biphen-4-yl]-1,6-dihydropyrazolo-[4,3-d]-pyrimidin-7-one (0.05 g, 0.08 mmol) was dissolved in 10 mL of methylene chloride followed by the addition of phosphorous tribromide (0.022 mL, 0.23 mmol) and stirred at ambient temperature overnight. The solution was slowly quenched with water and the organics extracted with ethyl acetate. The organics were dried over magnesium sulfate, filtered and the volatiles removed under reduced pressure. The crude benzyl bromide was dissolved in 10 mL of acetonitrile followed by the addition of pyrrolidine (0.04 mL, 0.47 mmol) and stirred at ambient temperature overnight. The volatiles were removed under reduced pressure and the residue was purified by prep HPLC (C18 reverse phase column, elution with a H₂O/CH₃CN gradient with 0.5% TFA) and lyophilized to afford the title compound of Example 32 as a white solid. LRMS (ESI): 576.3 (M+H)⁺.

Example 33

1-[4-Methoxyphenyl]-3-trifluoromethyl-7-[2'-methylsulfonyl-[1,1']-biphen-4-yl]-4,5,6,7-tetrahydropyrazolo-[3,4-c]-azepin-8-one

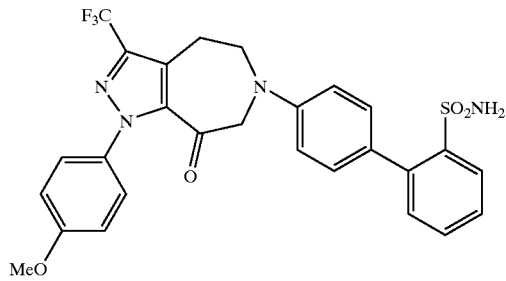

Part A. N-[4-bromophenyl]caprolactam

4-Bromoaniline (20.0 g, 11.62 mmol) and triethylamine (17.8 mL, 12.78 mmol) were dissolved in 250 mL of methylene chloride. 6-Bromohexanoyl chloride (19.6 mL, 12.78 mmol) was added dropwise via an addition funnel. The reaction mixture was stirred under N₂ for ½ h after the addition was completed. It was diluted with methylene chloride and washed with water, 1N aqueous HCl, 1N aqueous NaOH, and brine. It was then dried over MgSO₄ and concentrated to a white solid (37.20 g).

A solution of the above solid in 100 mL of DMF was added dropwise at room temperature to a mixture of NaH (5.00 g of 60% dispersion, 12.47 mmol) in 150 mL of DMF. The reaction mixture was stirred at room temperature for 2 h under $N_2$. It was then poured into 500 mL of water and extracted with EtOAc. The combined organic mixture was washed with brine, dried over $MgSO_4$, and concentrated to colorless oil. The title compound was then purified by chromatography on silica gel eluted with methylene chloride to give 24.5 g of white solid (78%). LRXS (ES+): 268.0, 270.0 (M+H)+. $^1$H NMR (CDCl$_3$): δ 7.49 (d, 2H), 7.12 (d, 2H), 3.73 (m,2H), 2.69 (m, 2H), 1.82 (m, 6H).

Part B. N-[4-bromophenyl]-3-oxocaprolactam

N,N-Diisopropylamine (11.0 mL, 78.4 mmol) was dissolved in 20 mL of dry THF and cooled at 0° C. n-BuLi (29.4 mL of 2.5 M solution in hexane) was added. The mixture was stirred at 0 CC under $N_2$ for 30 minutes and then cooled to −78° C. It was then cannulated to a solution of N-[4-bromophenyl]caprolactam (6.57 g, 24.5 mmol) in 100 mL of THF at −78° C. The mixture was stirred at −78° C. under $N_2$ for 1 h, and methyl methanethiosulfonate (8.1 mL, 78.4 mmol) was added. The cooling bath was removed, the mixture was allowed to warm up to room temperature and stirred for 12 h. It was quenched with $H_2O$ and the THF was removed in vacuo. The residue was dissolved in EtOAc and washed with water and brine. It was then dried over $MgSO_4$ and concentrated. Chromatography on silica gel with 20% EtOAc in hexane gave 1.40 g of N-[4-bromophenyl]-3-bis (thiomethoxy) caprolactam and 4.42 g of N-[4-bromophenyl]-3-mono(thiomethoxy) caprolactam. The N-[4-bromophenyl]-3-mono(thiomethoxy) caprolactam isolated was resubjected to the above conditions, and a total of 6.38 g of N-[4-bromophenyl]-3-bis(thiomethoxy) caprolactam was isolated. LRMS (AP+): 361.9, (M+H)+.

N-[4-bromophenyl]-3-bis(thiomethoxy) caprolactam from above was dissolved in 100 mL of $CH_3CN$ and 25 mL of $H_2O$ was added. Ceric ammonium nitrate (38.86 g, 70.89 mmol) was then added. After stirring for five minutes, water (300 mL) was added and the mixture was extracted with EtOAc. The combined organic mixture was washed with water and brine. It was dried over $MgSO_4$ and concentrated. The desired product was purified by chromatography on silica gel eluted with 30% EtOAc in hexane to give 1.25 g of light yellow oil (18%). LRMS (AP+): 283.9, (M+H)+. $^1$H NMR (CDCl$_3$): δ 7.56 (d, 2H), 7.22 (d, 2H), 3.77 (t, 2H), 2.67 (t, 2H), 2.09 (m, 2H), 1.98 (m, 2H).

Part C. 1-[4-methoxyphenyl]-3-trifluoromethyl-7-[4-bromophenyl]-4,5,6,7-tetrahydropyrazolo-13,4-c]-azepin-8-one N-[4-bromophenyl]-3-oxocaprolactam (0.37 g, 1.13 mmol), morpholine (0.25 mL, 2.81 mmol), and p-toluenesulfonic acid (catalytic amount) were refluxed with 30 mL benzene using a Dean Stark apparatus under $N_2$ for 12 h. The solvent was removed in vacuo and the residue was dried under vacuum to give 1,5,6,7-tetrahydro-1-(4-bromophenyl]-3-(morpholin-4-yl)-2H-azepin-2-one. LRMS (AP+): 351.0, 353.0, (M+H)+.

4-Dimethylaminopyridine (0.13 g, 1.13 mmol) was dissolved in 5 mL of methylene chloride and cooled in an ice-bath. Trifluoroacetic anhydride (0.16 mL, 1.13 mmol) was added. The mixture was stirred at 0° C. for ½ h, and a solution of 1,5,6,7-tetrahydro-1-[4-bromophenyl]-3-(morpholin-4-yl)-2H-azepin-2-one in 5 mL of methylene chloride was added. The ice-bath was removed, and the reaction mixture was stirred at room temperature under $N_2$ for 12 h. The reaction mixture was diluted with methylene chloride and washed with water and brine. After drying over $MgSO_4$, it was concentrated to give 1,5,6,7-tetrahydro-1-[4-bromophenyl]-3-(morpholin-4-yl)-4-trifluoroacetyl-2H-azepin-2-one as brown oil. LRMS (AP+): 446.0, 448.0, (M+H)+.

The brown oil above and p-methoxyphenylhydrazine hydrochloride (0.20 g, 1.13 mmol) were refluxed with 50 mL of acetic acid under $N_2$ for 20 h. The solvent was removed, the residue was dissolved in EtOAc and washed with water, Saturated $NaHCO_3$, and brine. It was dried over $MgSO_4$, concentrated, and chromatographed on silica gel with 15–20% EtOAc in hexane to give 0.24 g of the desired product (40%) and 0.17 g of the regioisomer (28%). LRMS (ES+): 528.0, (M+H)+. $^1$H NMR (CDCl$_3$): δ 7.71 (d, 2H), 7.39 (d, 2H), 7.06 (d, 2H), 6.92 (d, 2H), 3.89 (t, 2H), 3.82 (s, 3H), 3.04 (t, 2H), 2.22 (m, 2H).

Part D. 1-[4-methoxyphenyl]-3-trifluoromethyl-7-[2'-aminosulfonyl-[1,1']-biphen-4-yl]-4,5,6,7-tetrahydropyrazolo-[3,4-c]-azepin-S-one.

1-[4-Methoxyphenyl]-3-trifluoromethyl-7-[4-bromophenyl]-4,5,6,7-tetrahydropyrazolo-[3,4-c]-azepin-8-one (0.12 g, 0.23 mmol), 2-(tert-butylaminosulfonyl) phenylboronic acid (63.0 mg, 0.25 mmol), tetrabutylammonium bromide (4 mg, 5 mol %), tetrakis (triphenylphosphine)palladium(0) (13 mg, 5 mol %) were refluxed with 20 mL of benzene under $N_2$ for 12 h. The reaction was cooled. It was filtered through Celite® and washed with EtOAc. The mixture was washed with water and brine, dried over $MgSO_4$, concentrated, and chromatographed on silica gel with 15–30% EtOAc in hexane to give 26 mg of the desired product (18%) and 96 mg of the starting material. LRMS (ES+): 613.4, (M+H)+.

The product above was refluxed with 10 mL of trifluoroacetic acid for ½ h. The solvent was removed. It was purified by prep HPLC (C18 reverse phase column, eluted with a $H_2O/CH_3CN$ gradient with 0.05% TFA) and lyophilized to afford 5.7 mg of the title compound of Example 33 as a white powder (24%). LRMS (ES+): 557.3, (M+H)+. $^1$H NMR (CDCl$_3$): δ 8.12 (d, 1H), 7.59 (t, 1H), 7.51 (m, 3H), 7.38 (m, 4H), 7.29 (d, 1H), 6.82 (d, 2H), 4.51 (s, 2H), 4.00 (t, 2H), 3.82 (s, 3H), 3.10 (t, 2H), 2.31 (m, 2H).

Example 34

1-[4-Methoxyphenyl]-3-trifluoromethyl-7-[2'-aminosulfonyl-3-fluoro-[1,1's-biphen-4-yl]-4,5,6,7-tetrahydropyrazolo-[3,4-c]-azepin-8-one

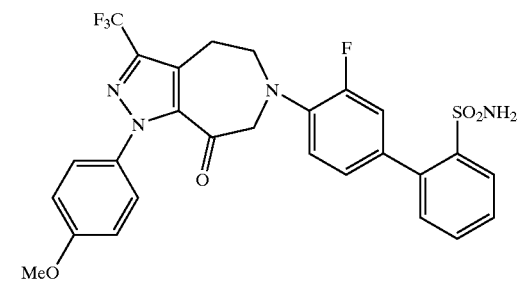

The title compound was prepared by the same procedures as shown for Example 1 using 4-bromo-2-fluoroaniline as starting material. LRMS (ES+): 575.2, (M+H)+. $^1$HNMR (CDCl$_3$) δ 8.15(d, 1H), 7.57 (m, 2H), 7.39 (t, 2H), 7.32 (d, 2H), 7.27 (d, 2H), 6.93 (d, 2H), 4.51 (s, 2H), 3.93(t, 2H), 3.82 (s, 3H), 3.11 (t, 2H), 2.27 (m, 2H).

Example 35

1-[4-Methoxyphenyl]-3-trifluoromethyl-7-[2'-N-pyrrolidinylmethyl-[1,1']-biphen-4-yl]-4,5,6,7-tetrahydropyrazolo-[3,4-c]-azepin-8-one, trifluoroacetic acid salt

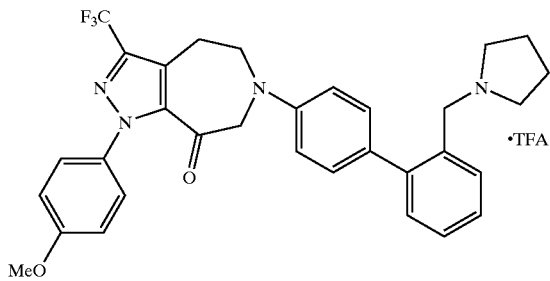

Part A. 1-[4-methoxyphenyl]-3-trifluoromethyl-7-[2'-formyl-[1,1']-biphen-4-yl]-4,5,6,7-tetrahydropyrazolo-[3,4-c]-azepin-8-one 1-[4-Methoxyphenyl]-3-trifluoromethyl-7-[4-bromophenyl]-4,5,6,7-tetrahydropyrazolo-[3,4-c]-azepin-8-one from Part C of Example 33 (0.17 g, 0.32 mmol), 2-formylphenylboronic acid (97.0 mg, 0.64 mmol), potassium phosphate (273.0 mg, 1.28 mmol) and tetrakis(triphenylphosphine)palladium (0) (19 mg) were refluxed with 20 mL of dioxane under N$_2$ for 12 h. It was filtered through Celite® and washed with EtOAc. The mixture was washed with water and brine, dried over MgSO$_4$, concentrated, and chromatographed on silica gel with 10–15% EtOAc in hexane to give 0.10 g of the desired product (62%). LRMS (ES$^+$): 506.4, (M+H)$^+$. $^1$H NMR (CDCl$_3$): δ 10.02 (s, 1H), 8.02 (d, 1H), 7.64 (t, 1H), 7.52 (t, 1H), 7.42 (m, 6H), 6.83 (d, 2H), 3.99(t, 2H), 3.82 (s, 3H), 3.10 (t, 2H), 2.29 (m, 2H).

Part B. 1-[4-methoxyphenyl]-3-trifluoromethyl-7-[2'-N-pyrrolidinylmethyl-[1,1']-biphen-4-yl]-4,5,6,7-tetrahydropyrazolo-[3,4-c]-azepin-8-one, trifluoroacetic acid salt.

The product from Part A was dissolved in 15 mL of MeOH. Pyrrolidine (0.049 mL, 0.59 mmol) and NaBH$_4$ (13 mg, 0.40 mmol) were added. The mixture was stirred at room temperature under N$_2$ for 12 h. It was quenched with water, extracted with methylene chloride, dried over MgSO$_{41}$ concentrated, and purified by prep HPLC (C18 reverse phase column, eluted with a H$_2$O/CH$_3$CN gradient with 0.05% TFA) and lyophilized to afford 24 mg of the title compound of Example 35 as a TFA salt (18%). LRMS (ES$^+$): 557.3, (M+H)$^+$. $^1$H NMR (CD$_3$OD): δ 7.66 (m, 1H), 7.35–7.56 (m, 9H), 6.98 (d, 2H), 4.40 (s, 2H), 4.01 (t, 2H), 3.81 (s, 3H), 3.32 (m, 2H), 3.08 (t, 2H), 2.80 (m, 2H), 2.29 (m, 2H), 1.88 (m, 4H).

Example 36

1-[3-Aminobenzisoxazol-5'-yl]-3-trifluoromethyl-7-[2'-N-pyrrolidinylmethyl-[1,1']-biphen-4-yl]-4,5,6,7-tetrahydropyrazolo-[3,4-c]-azepin-8-one, trifluoroacetic acid salt

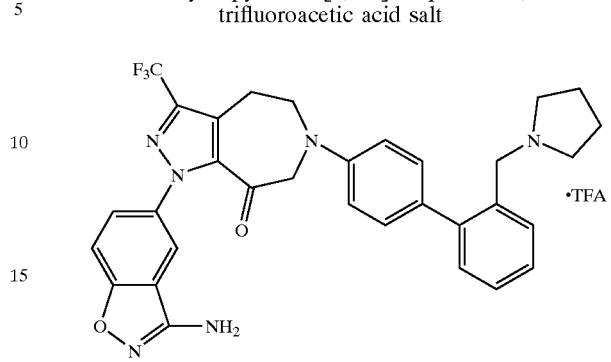

Part A. 1-[3-Cyano-4-fluorophenyl]-3-trifluoromethyl-7-[4-bromophenyl]-4,5,6,7-tetrahydropyrazolo-[3,4-c]-azepin-8-one N-[4-bromophenyl]-3-oxocaprolactam (1.31 g, 4.63 mmol), morpholine (1.60 mL, 18.52 mmol), and p-toluenesulfonic acid (catalytic amount) were refluxed with 50 mL benzene using a Dean Stark apparatus under N$_2$ for 12 h. The solvent was then removed in vacuo and the residue was dried under vacuum to give 1,5,6,7-tetrahydro-1-[4-bromophenyl]-3-(morpholin-4-yl)-2H-azepin-2-one as a yellow solid. LRMS (AP$^+$): 351.0, 353.0, (M+H)$^+$.

4-Dimethylaminopyridine (0.68 g, 5.56 mmol) was dissolved in 20 mL of methylene chloride and cooled in an ice-bath. Trifluoroacetic anhydride (0.79 mL, 5.56 mmol) was added. The mixture was stirred at 0° C. for ½ h, and a solution of the solid formed above in 20 mL of methylene chloride was added. The ice-bath was removed, and the reaction mixture was stirred at room temperature under N$_2$ for 12 h. It was diluted with methylene chloride and washed with water and brine. After dried over MgSO$_4$, it was concentrated to give 1,5,6,7-tetrahydro-1-[4-bromophenyl]-3-(morpholin-4-yl)-4-trifluoroacetyl-2H-azepin-2-one as brown oil. LRMS (AP$^{31}$): 446.0, 448.0, (M+H)$^+$.

The brown oil above and 3-cyano-4-fluorophenylhydrazine hydrochloride (1.31 g, 6.95 mmol) were refluxed with 100 mL of acetic acid under N$_2$ for 20 h. The solvent was removed, the residue was dissolved in EtOAc and washed with water, saturated NaHCO$_3$, and brine. It was dried over MgSO$_4$, concentrated, and chromatographed on silica gel with 15–20% EtOAc in hexane to give 1.06 g of the desired product (46%). LRMS (ES$^+$): 493.1, (M+H)$^+$. $^1$H NMR (CDCl$_3$): 37.77 (m, 2H), 7.54 (d, 2H), 7.28 (m, 3H), 7.15 (d, 2H), 3.91 (t, 2H), 3.10 (t, 2H), 2.28 (m, 2H).

Part B. 1-[3-Cyano-4-fluorophenyl]-3-trifluoromethyl-7-[2'-formyl-[1,1']-biphen-4-yl]-4,5,6,7-tetrahydropyrazolo-[3,4-c]-azepin-8-one.

1-[3-Cyano-4-fluorophenyl)-3-trifluoromethyl-7-[4-bromophenyl]-4,5,6,7-tetrahydropyrazolo-[3,4-c]-azepin-8-one (1.06 g, 2.15 mmol), 2-formylphenylboronic acid (0.65 g, 4.30 mmol), potassium phosphate (1.83 g, 8.60 mmol), tetrakis(triphenylphosphine)palladium (0) (124 mg) were refluxed with 80 mL of dioxane under N$_2$ for 12 h. It was filtered through Celite® and washed with EtOAc. The mixture was washed with water and brine, dried over MgSO$_4$, concentrated, and chromatographed on silica gel with 15–25% EtOAc in hexane to give 0.90 g of the desired product (81%). LRMS (ES$^+$): 519.3, (M+H)$^+$. $^1$H NMR (CDCl$_3$): δ 10.02 (s, 1H), 8.04 (d, 1H), 7.80 (m, 2H), 7.68 (t, 1H), 7.54 (t, 1H), 7.43 (m, 4H), 7.30 (m, 1H), 4.02 (m, 2H), 3.12 (t, 2H), 2.32 (m, 2H).

Part C. 1-[3-Aminobenzisoxazol-5'-yl]-3-trifluoromethyl-7-[2'-hydroxymethyl-[1,1']-biphen-4-yl]-4,5,6,7-tetrahydropyrazolo-[3,4-c]-azepin-8-one.

1-[3-Cyano-4-fluorophenyl]-3-trifluoromethyl-7-[2'-formyl-[1,1']-biphen-4-yl]-4,5,6,7-tetrahydropyrazolo-[3,4-c]-azepin-8-one (0.90 g, 1.74 mmol) was dissolved in 20 mL of methanol and cooled at 0° C. NaBH$_4$ (76.0 mg, 2.00 mmol) was added. After stirring for ½ h at 0° C., it was quenched with water. The solvent was removed. The residue was partitioned between methylene chloride and water. The aqueous layer was extracted with methylene chloride. The combined organic solution was washed with brine, dried over MgSO$_4$, concentrated to yellow foam. The alcohol formed such was used in the next step without further purification.

N-Acetylhydroxylamine (0.39 g, 5.22 mmol) was dissolved in 10 mL of DMF. Potassium carbonate (0.96 g, 6.96 mmol) was added, followed by 2 mL of water. After stirring for ½ h, a solution of the alcohol from above in 5 mL of DMF was added. The reaction mixture was stirred at room temperature under N$_2$ for 12 h. Water was added, the precipitate was filtered and dried to give 0.90 g of the desired product (97%). LRMS (AP$^+$): 534.2, (M+H)$^+$. $^1$H NMR (CDCl$_3$): δ 7.67 (m, 2H), 7.50 (m, 1H), 7.42–7.20 (m, 8H), 4.52 (s, 2H), 3.97 (m, 2H), 3.10 (t, 2H), 2.30 (m, 2H), 2.06 (bs, 1H).

Part D. 1-[3-Aminobenzisoxazol-5'-yl]-3-trifluoromethyl-7-[2'-N-pyrrolidinylmethyl-[1,1']-biphen-4-yl]-4,5,6,7-tetrahydropyrazolo-[3,4-c]-azepin-8-one, trifluoroacetic acid salt.

1-[3-Aminobenzisoxazol-5'-yl]-3-trifluoromethyl-7-[2'-hydroxymethyl-[1,1']-biphen-4-yl]-4,5,6,7-tetrahydropyrazolo-[3,4-c]-azepin-8-one (0.15 g, 0.28 mmol) was dissolved in 6 mL of dry methylene chloride. PBr$_3$ (0.037 mL, 0.39 mmol) was added and the mixture was stirred at room temperature under N$_2$ for 30 minute. The reaction mixture was quenched with water and extracted with methylene chloride. The methylene chloride extract was washed with brine, dried over MgSO$_4$, and concentrated to yellow foam.

The foam was then dissolved in 10 mL of CH$_3$CN, and pyrrolidine (0.070 mL, 0.84 mmol) was added. The mixture was stirred at room temperature for 12 h. It was concentrated, and purified by prep HPLC (C18 reverse phase column, eluted with a H$_2$O/CH$_3$CN gradient with 0.05% TFA) and lyophilized to afford 0.11 of the title compound of Example 36 as a TFA salt (56%). LRMS (ES$^+$): 587.3, (M+H)$^+$. $^1$H NMR (CD$_3$OD): δ 7.96 (m, 1H), 7.73–7.60 (m, 3H), 7.58–7.34 (m, 7H), 4.38 (s, 2H), 4.04 (t, 2H), 3.33 (m, 2H), 3.14 (t, 2H), 2.78 (m, 2H), 2.32 (m, 2H), 1.86 (m, 4H).

Example 37

1-[3-Aminobenzisoxazol-51-yl]-3-trifluoromethyl-7-[2'-N-dimethylaminomethyl-[1,1']-biphen-4-yl]-4,5,6,7-tetrahydropyrazolo-[3,4-c3-azepin-8-one, trifluoroacetic acid salt

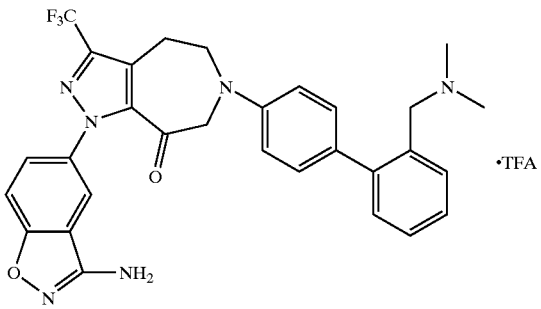

The title compound of Example 37 was prepared by the same methods described in Example 36. LRMS (ES$^+$): 561.4, (M+H)$^+$. $^1$H NMR (CD$_3$OD): δ 7.96 (d, 1H), 7.71 (dd, 1H), 7.63 (m, 1H), 7.55 (m, 2H), 7.50 (m, 2H), 7.40 (m, 4H), 4.34 (s, 2H), 4.07 (t, 2H), 3.15 (t, 2H), 2.60 (s, 6H), 2.34 (m, 2H).

Example 38

1-[3-Aminobenzisoxazol-51-yl]-3-trifluoromethyl-7-[2'-N-isopropylaminomethyl-1,1']-biphen-4-yl]-4,5,6,7-tetrahydropyrazolo-[3,4-c]-azepin-8-one, trifluoroacetic acid salt

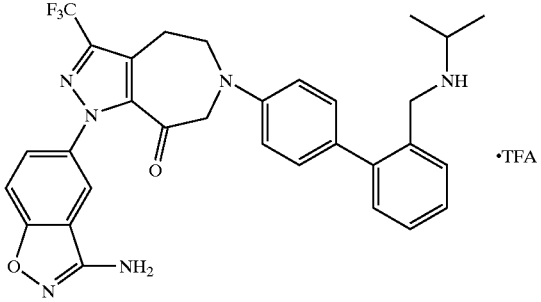

The title compound of Example 38 was prepared by the same methods described in Example 36. LRMS (ES$^+$): 575.4, (M+H)$^+$. $^1$H NMR (CD$_3$OD): δ 7.97 (s, 1H), 7.71 (m, 1H), 7.62 (m, 1H), 7.53–7.36 (m, 8H), 4.18 (s, 2H), 4.07 (t, 2H), 3.20 (m,1H), 3.15 (t, 2H), 2.33 (t, 2H), 1.14 (d, 6H).

Example 39

1-[3-Aminobenzisoxazol-5I-yl]-3-trifluoromethyl-7-[2'-(3-(R)-hydroxy-N-pyrrolidinyl)methyl-[1,1']-biphen-4-yl]-4,5,6,7-tetrahydropyrazolo-[3,4-c3-azepin-8-one, trifluoroacetic acid salt

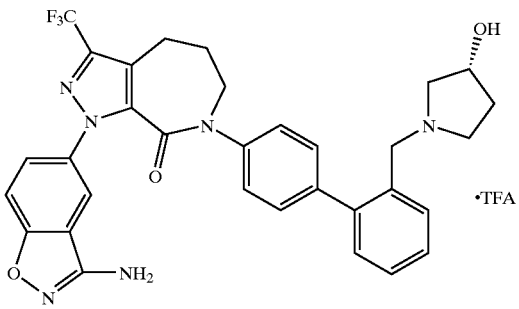

The title compound of Example 39 was prepared by the same methods described in Example 36. LRMS (ES$^+$): 603.4, (M+H)$^+$. $^1$H NMR (CD$_3$OD): δ 7.98 (d, 1H), 7.70 (m, 2H), 7.58–7.37 (m, 8H), 4.58–4.30 (m, 3H), 4.08 (t, 2H), 3.60–3.35 (m, 1H), 3.15 (t, 2H), 3.00–2.78 (m, 2H), 2.34 (m, 2H), 2.20–1.79 (m, 2H).

Example 40

1-[3-Aminobenzisoxazol-5'-yl]-3-trifluoromethyl-7-[2'-(3-(R)-hydroxy-N-pyrrolidinyl)methyl-3-fluoro-[1,1']-biphen-4-yl]-4,5,6,7-tetrahydropyrazolo-[3,4-c]-azepin-8-one, trifluoroacetic acid salt

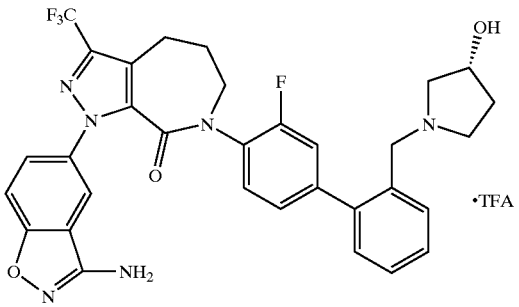

Part A. N-(4-Bromo-2-fluorophenyl)caprolactam

4-Bromo-2-fluoroaniline (11.80 g, 62.1 mmol) and triethylamine (9.00 mL, 64.6 mmol) were dissolved in 200 mL of methylene chloride. 6-Bromohexanoyl chloride (13.26 g, 62.1 mmol) was added dropwise via an addition funnel. The reaction mixture was stirred under N$_2$ for M h after the addition was completed. It was diluted with methylene chloride and washed with water, 1N aqueous HCl, 1N aqueous NaOH, and brine. It was the dried over MgSO$_4$ and concentrated to a white solid (21.75 g).

A solution of the above solid in 200 mL of DMF was added dropwise at room temperature to a mixture of NaH (2.85 g of 60% dispersion, 71.3 mmol) in 100 mL of DMF. The reaction mixture was stirred at room temperature for 2 h under N$_2$. It was then poured into 500 mL of water and extracted with EtOAc. The combined organic mixture was washed with brine, dried over MgSO$_4$, and concentrated to orange oil. The title compound was then purified by chromatography on silica gel eluted with 10–50% EtOAc in hexane to give 16.27 g of orange oil (92%). LRMS (ES$^+$): 286.1, 288.1 (M+H)$^+$. $^1$H NMR (CDCl$_3$): δ 7.29 (m, 2H), 7.09 (t, 1H), 3.65 (t, 2H), 2.71 (t, 2H), 1.82 (m, 6H).

Part B. N-(4-Bromo-2-fluorophenyl)-3,3-dichlorocaprolactam

N-[4-bromo-2-fluorophenyl]caprolactam (6.96 g, 24.33 mmol) and phosphorus pentachloride (15.20 g, 72.99 mmol) were added together with 200 mL of benzene and refluxed under N$_2$ for 2 h. The reaction mixture was cooled and quenched with water and saturated aqueous NaHCO$_3$. It was diluted with EtOAc and washed with water and brine. The organic mixture was then dried over MgSO$_4$, concentrated, and chromatographed on silica gel eluted with 10% EtOAc in hexane to give 4.97 g of the desired product (58%). LRMS (ES$^+$): 355.9 (M+H)$^+$, $^1$H NMR (CDCl$_3$): δ 7.32 (m, 2H), 7.10 (t, 1H), 3.84 (m, 2H), 2.75 (t, 2H), 2.10 (m, 2H), 1.82 (m, 2H).

Part C. 1-[3-Cyano-4-fluorophenyl]-3-trifluoromethyl-7-[4-bromo-2-fluorophenyl]-4,5,6,7-tetrahydropyrazolo-13,4-c]-azepin-8-one N-[4-bromo-2-fluorophenyl]-3,3-dichlorocaprolactam (0.49 g, 1.38 mmol) was refluxed with 10 mL of morpholine under N$_2$ for 1 h. The solvent was then removed in vacuo. Toluene was added and the solid was filtered off. The filtrate was concentrated and dried under vacuum to give 1,5,6,7-tetrahydro-1-[4-bromo-2-fluorophenyl]-3-(morpholin-4-yl)-2H-azepin-2-one as brown oil (0.55 g). LRMS (AP$^+$): 369.0, 371.0, (M+H)$^+$.

4-Dimethylaminopyridine (0.22 g, 1.79 mmol) was dissolved in 5 mL of methylene chloride and cooled in an ice-bath. Trifluoroacetic anhydride (0.0.42 mL, 2.98 mmol) was added. The mixture was stirred at 0° C. for % h, and a solution of 1,5,6,7-tetrahydro-1-[4-bromo-2-fluorophenyl]-3-(morpholin-4-yl)-2H-azepin-2-one in 15 mL of methylene chloride was added. The ice-bath was removed, and the reaction mixture was stirred at room temperature under N$_2$ for 12 h. It was diluted with methylene chloride and washed with water and brine. After drying over MgSO$_4$, it was concentrated to give 1,5,6,7-tetrahydro-1-[4-bromo-2-fluorophenyl]-3-(morpholin-4-yl)-4-trifluoroacetyl-2H-azepin-2-one as brown oil. LRMS (AP$^+$): 465.0.0, 467.0, (M+H)$^+$.

1,5,6,7-Tetrahydro-1-[4-bromo-2-fluorophenyl]-3-(morpholin-4-yl)-4-trifluoroacetyl-2H-azepin-2-one formed above and 3-cyano-4-fluorophenylhydrazine hydrochloride (0.42 g, 2.24 mmol) were refluxed with 25 mL of acetic acid under N$_2$ for 20 h. The solvent was removed, the residue was dissolved in EtOAc and washed with water, saturated NaHCO$_3$, and brine. It was dried over MgSO$_4$, concentrated, and chromatographed on silica gel with 25% EtOAc in hexane to give 0.15 g of the desired product (19%). LRMS (AP$^+$): 511.0, 513.0, (M+H)$^+$. $^1$H NMR (CDCl$_3$): δ 7.76 (m, 2H), 7.36 (m, 2H), 7.28 (m,1H), 7.17 (m, 1H), 3.85 (t, 2H), 3.12 (t, 2H), 2.26 (m, 2H).

Part D. 1-[3-Cyano-4-fluorophenyl]-3-trifluoromethyl-7-[2'-formyl-3-fluoro-[1,1']-biphen-4-yl]-4,5,6,7-tetrahydropyrazolo-[3,4-c]-azepin-8-one 1-(3-Cyano-4-fluoro)phenyl-3-trifluoromethyl-7-[4-bromo-2-fluorophenyl]-4,5,6,7-tetrahydropyrazolo-[3,4-c]-azepin-8-one (0.15 g, 0.29 mmol), 2-formylphenylboronic acid (88.0 mg, 0.58 mmol), potassium phosphate (0.25 g, 1.16 mmol), tetrakis(triphenylphosphine)palladium (0) (34 mg) were refluxed with 20 mL of dioxane under N$_2$ for 12 h. It was filtered through Celite® and washed with EtOAc. The mixture was washed with water and brine, dried over MgSO$_4$, concentrated, and chromatographed on silica gel with 25% EtOAc in hexane to give 93.0 mg of the desired product (60%). LRMS (AP$^+$): 537.1, (M+H)$^+$. $^1$H NMR (CDCl$_3$): δ 10.02 (s, 1H), 8.04 (d, 1H), 7.80 (m, 2H), 7.68 (t, 1H), 7.54 (t, 1H), 7.40–7.20 (m, 6H), 3.97 (m, 2H), 3.15 (t, 2H), 2.33 (m, 2H).

Part B. 1-[3-Aminobenzisoxazol-5'-yl]-3-trifluoromethyl-7-[2'-hydroxymethyl-3-fluoro-1,1']-biphen-4-yl]-4,5,6,7-tetrahydropyrazolo-[3,4-c]-azepin-8-one 1-(3-Cyano-4-fluoro)phenyl-3-trifluoromethyl-7-[2'-formyl-3-fluoro-[1,1']-biphen-4-yl]-4,5,6,7-tetrahydropyrazolo-[3,4-c]-azepin-8-one (93.0 mg, 0.17 mmol) was dissolved in 10 mL of THF and cooled at 0° C. NaBH$_4$ (17 mg, 0.45 mmol) was added. After stirred for ½ h at 0° C., it was quenched with water and extracted with EtOAc. The combined organic solution was washed with brine, dried over MgSO$_4$, concentrated. The alcohol formed such was used in the next step without further purification.

N-Acetylhydroxylamine (38 mg, 0.51 mmol) was dissolved in 2 mL of DMF. Potassium carbonate (94 mg, 0.68 mmol) was added, followed by 2 drops of water. After stirred for ½ h, a solution of the alcohol from above in 3 mL of DMF was added. The reaction mixture was stirred at room temperature under N$_2$ for 12 h. Water was added, the milky mixture was extracted with EtOAc. The combined organic solution was washed with brine, dried over MgSO$_4$, concentrated and dried to give 89 mg of the desired product (95%). LRMS (AP$^+$): 552.2, (M+H)$^+$. $^1$H NMR (CDCl$_3$): δ 8.01 (s, 1H), 7.76 (d, 1H), 7.63 (dd, 1H), 7.54 (dd, 1H), 7.47–7.20 (m, 6H), 4.55 (s, 2H), 4.47 (s, 2H), 3.83 (t, 2H), 3.13 (t, 2H), 2.30 (m, 2H), 1.68 (bs, 1H).

Part F. 1-[3-Aminobenzisoxazol-5'-yl]-3-trifluoromethyl-7-[2'-N-pyrrolidinylmethyl-3-fluoro-[1,1']-biphen-4-yl-4,5,6,7-tetrahydropyrazolo-[3,4-c]-azepin-8-one, trifluoroacetic acid salt.

1-[3-Aminobenzisoxazol-5'-yl]-3-trifluoromethyl-7-[2'-hydroxymethyl-3-fluoro-[1,1']-biphen-4-yl]-4,5,6,7-tetrahydropyrazolo-[3,4-c]-azepin-8-one (89 mg, 0.16 mmol) was dissolved in 10 mL of dry methylene chloride. PBr$_3$ (0.021 mL, 0.22 mmol) was added and the mixture was stirred at room temperature under N$_2$ for 30 minute. The reaction mixture was quenched with water and extracted with methylene chloride. The methylene chloride extract was washed with brine, dried over MgSO$_4$, and concentrated to yellow foam.

The foam was then dissolved in 10 mL of CH$_3$CN, and (R)-3-pyrrolidinol (0.050 mL, 0.60 mmol) was added. The mixture was stirred at room temperature for 12 h. It was concentrated, and purified by prep HPLC (C18 reverse phase column, eluted with a H$_2$O/CH$_3$CN gradient with 0.05% TFA) and lyophilized to afford 49 mg of the title compound of Example 40 as a TFA salt (42%). LRMS (ES$^+$): 621.3, (M+H)$^+$. $^1$H NMR (CD$_3$OD): δ 7.96 (d, 1H), 7.64 (m, 2H), 7.58–7.36 (m, 5H), 7.25 (m, 2H), 4.58–4.30 (m, 3H), 4.02 (t, 2H), 3.60–3.35 (m, 2H), 3.15 (t, 2H), 3.00–2.78 (m, 2H), 2.34 (m, 2H), 2.20–1.79 (m, 2H).

Example 41

1-[3-Aminobenzisoxazol-5'-yl]-3-trifluoromethyl-7-[2'-N-pyrrolidinylmethyl-3-fluoro-[1,1']-biphen-4-yl]-4,5,6,7-tetrahydropyrazolo-[3,4-c]-azepin-8-one, trifluoroacetic acid salt

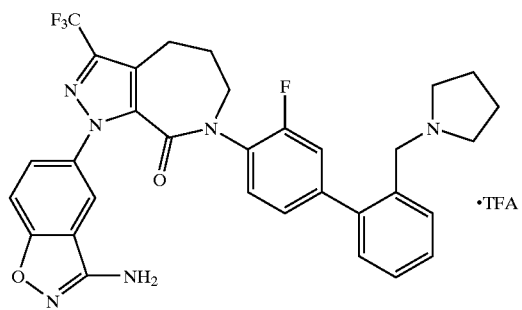

The title compound of Example 41 was prepared by the same methods described in Example 40. LRMS (ES$^+$): 605.3, (M+H)$^+$. $^1$H NMR (CD$_3$OD): δ 7.97 (d, 1H), 7.67 (m, 2H), 7.57 (m, 3H), 7.50 (d, 1H), 7.42 (m, 1H), 7.27 (dd, 2H), 4.41 (s, 2H), 4.03 (t, 2H), 3.36 (m,1H), 3.15 (t, 2H), 2.82 (m, 2H), 2.33 (m, 2H), 1.90 (m, 4H).

Example 42

1-[3-Aminobenzisoxazol-5'-yl]-3-trifluoromethyl-7-[2'-N-dimethylaminomethyl-3-fluoro-[1,1']-biphen-4-yl]-4,5,6,7-tetrahydropyrazolo-[3,4-c]-azepin-8-one, trifluoroacetic acid salt

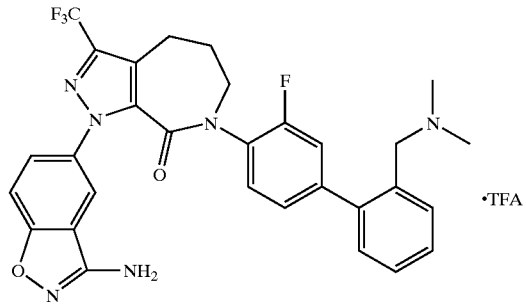

The title compound of Example 42 was prepared by the same methods described in Example 40. LRMS (ES$^+$): 579.3, (M+H)$^+$. $^1$H NMR (CD$_3$OD): δ 7.97 (d, 1H), 7.68 (dd, 1H), 7.62 (m, 1H), 7.57 (m, 3H), 7.47 (t, 1H), 7.42 (m, 1H), 7.25 (dd, 2H), 4.34 (s, 2H), 4.04 (t, 2H), 3.15 (t, 2H), 2.62 (6, 6H), 2.32 (m, 2H).

Example 43

1-[3-Aminobenzisoxazol-5l-yl]-3-trifluoromethyl-7-[2'-N-isopropylaminomethyl-3-fluoro-[1,1']-biphen-4-yl]-4,5,6,7-tetrahydropyrazolo-[3,4-c]-azepin-8-one, trifluoroacetic acid salt

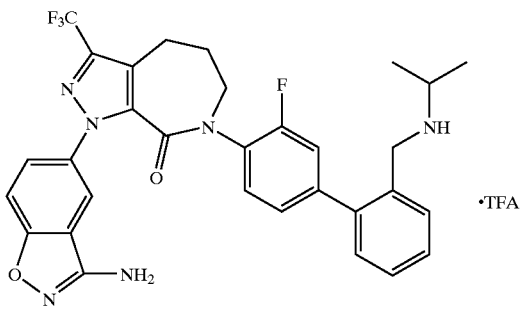

The title compound of Example 43 was prepared by the same methods described in Example 40. LRMS (ES+): 593.3, (M+H)+. 1H NMR (CD3OD): δ 7.97 (d, 1H), 7.66 (dd, 1H), 7.59 (m, 1H), 7.53 (m, 3H), 7.47 (d, 1H), 7.40 (m, 1H), 7.28 (m, 2H), 4.18 (s, 2H), 4.02 (t, 2H), 3.24 (m,1H), 3.15 (t, 2H), 2.32 (m, 2H), 1.16 (d, 6H).

Example 44

1-[4-Methoxyphenyl]-3-trifluoromethyl-7-[4-(2-dimethylaminomethylimidazol-1'-yl)-3-fluorophenyl]-4,5,6,7-tetrahydropyrazolo-[3,4-c]-azepin-8-one, trifluoroacetic acid salt

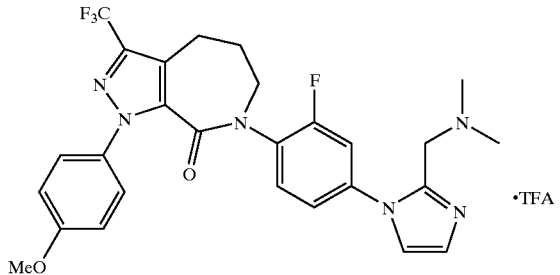

1-[4-Methoxyphenyl]-3-trifluoromethyl-7-[2-fluoro-4-iodophenyl]-4,5,6,7-tetrahydropyrazolo-[3,4-c]-azepin-8-one (prepared by the procedures described in Example 40) (0.22 g, 0.40 mmol), 2-(N,N-dimethylaminomethyl) imidazole (61 mg, 0.48 mmol), potassium carbonate (61 mg, 0,44 mmol), CuI (12 mg), and 1,10-phenanthroline (11 mg) were heated with 8 mL of DMSO at 130° C. under N2 for 12 h. The reaction mixture was cooled and 14% aqueous NH4OH was added. It was extracted with EtOAc, washed with brine, dried over MgSO4, concentrated, and chromatographed on silica gel eluted with 5% MeOH in CH2Cl2. Final purification by prep HPLC (C18 reverse phase column, eluted with a H2O/CH3CN gradient with 0.05% TFA) afforded 53.2 mg of the title compound of Example 44 as a TFA salt (20%). LRMS (ES+): 543.3, (M+H)+. 1H NMR (CD3OD): δ 7.68 (t, 1H), 7.54–7.36 (m, 5H), 7.27 (d, 1H), 6.98 (d, 2H), 4.42 (s, 2H), 3.87 (t, 2H), 3.80 (s, 3H), 3.08 (t, 2H), 2.83 (s, 6H), 2.25 (m, 2H).

Example 45

1-[4-Methoxyphenyl]-3-trifluoromethyl-7-[4-(imidazol-1'-yl)-3-fluorophenyl]-4,5,6,7-tetrahydropyrazolo-[3,4-c3-azepin-8-one, trifluoroacetic acid salt

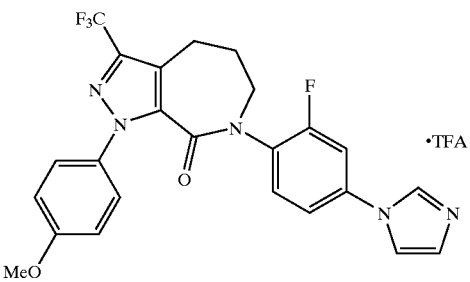

The title compound of Example 45 was prepared by the same methods described in Example 44. LRMS (ES+): 485.4, (M+H)+. 1H NMR (CD3OD): δ 9.50(s, 1H), 8.12 (s, 1H), 7.82–7.66 (m, 4H), 7.43 (d, 2H), 7.00 (d, 2H), 3.97 (t, 2H), 3.82 (s, 3H), 3.10 (t, 2H), 2.28 (m, 2H).

Example 46

1-[2-Aminomethylphenyl]-3-trifluoromethyl-7-[2'-methylsulfonyl-[1,1']-biphen-4-yl]-4,5,6,7-tetrahydropyrazolo-[3,4-c]-azepin-8-one, trifluoroacetic acid salt

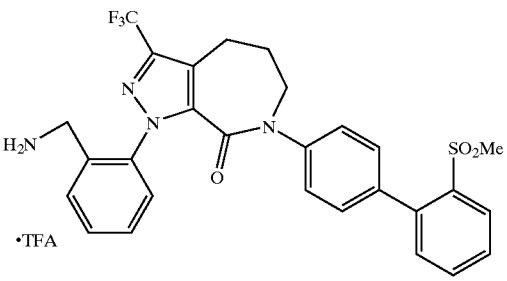

Part A. 1-[2-Trifluoroacetamidomethylphenyl]-3-trifluoromethyl-7-[4-bromophenyl]-4,5,6,7-tetrahydropyrazolo-[3,4-c]-azepin-8-one To a solution of 2-(trifluoroacetamidomethyl) aniline (0.64 g, 2.94 mmol) in 5 mL of acetic acid at 0° C. was added 5 mL concentrated HCl, followed by sodium nitrite (220 mg, 3.19 mmol) in 5 mL of H2O. After stirred at 0° C. for 2 h, stannous chloride dihydrate (1.53 g, 6.73 mmol) in 3 mL of concentrated HCl and 3 mL of H2O was slowly added. After stirring at 0° C. for 1 h, a solution of 1,5,6,7-tetrahydro-1-[4-bromophenyl]-3-(morpholin-4-yl)-4-trifluoroacetyl-2H-azepin-2-one (prepared in Part C of Example 33) (0.57 g, 1.18 mmol) in 20 mL of MeOH was added. The mixture was heated at 70° C. for 3 h. The solvent was removed. The residue was dissolved in EtOAc and washed with water, saturated NaHCO3, and brine. It was dried over MgSO4, concentrated, and chromatographed on silica gel with 10–30% EtOAc in hexane to give 0.13 g of the desired product (19%). LRMS (AP+): 575.1, (M+H)+.

Part B. 1-[2-Trifluoroacetamidomethylphenyl]-3-trifluoromethyl-7-[2'-thiomethyl-1,1']-biphen-4-yl]-4,5,6,7-tetrahydropyrazolo-[3,4-c]-azepin-8-one 1-[2-Trifluoroacetamidomethylphenyl])-3-trifluoromethyl-7-[4-bromophenyl]-4,5,6,7- tetrahydropyrazolo-[3,4-c]-azepin-8-one (0.132 g, 0.23 mmol), 2-thiomethylphenylboronic acid (79 mg, 0.46 mmol), potassium phosphate (0.19 g, 0.92 mmol), tetrakis (triphenylphosphine)palladium (0) (13 mg) were refluxed with 20 mL of dioxane under $N_2$ for 12 h. It was filtered through Celite® and washed with EtOAc. The mixture was washed with water and brine, dried over $MgSO_4$, concentrated, and chromatographed on silica gel with 25% EtOAc in hexane to give 80.0 mg of the desired product (56%). LRMS (AP+): 619.1, (M+H)+.

Part C. 1-[2-Trifluoroacetamidomethylphenyl]-3-trifluoromethyl-7-[2'-methylsulfonyl-[1,1']-biphen-4-yl]-4,5,6,7-tetrahydropyrazolo-[3,4-c]-azepin-8-one To a solution of 1-[2-trifluoroacetamidomethylphenyl]-3-trifluoromethyl-7-[2'-thiomethyl-[1,1']-biphen-4-yl]-4,5,6,7-tetrahydropyrazolo-[3,4-c]-azepin-8-one (80 mg, 0.13 mmol) in 10 mL of $CH_2Cl_2$ was added MCPBA (111 mg, 0.33 mmol) at 0° C. The mixture was allowed to warm up to room temperature and stirred for 12 h. It was diluted with $CH_2Cl_2$ and washed with saturated aqueous $NaHCO_3$ and brine. It was dried over $MgSO_4$, concentrated, chromatographed on silica gel eluted with 50% EtOAc in hexane to give 25 mg of white solid. LRMS (AP−): 649.1, (M−H)−.

Part D. 1-[2-Aminomethylphenyl]-3-trifluoromethyl-7-[2'-methylsulfonyl-[1,1']-biphen-4-yl]-4,5,6,7-tetrahydropyrazolo-[3,4-c]-azepin-8-one, trifluoroacetic acid salt.

1-(2-Trifluoroacetamidomethylphenyl]-3-trifluoromethyl-7-[2'-methylsulfonyl-[1,1']-biphen-4-yl]-4,5,6,7-tetrahydropyrazolo-[3,4-c]-azepin-8-one (25 mg, 0.039 mmol) and potassium carbonate (11 mg) were stirred with 6 mL of MeOH and a few drops of $H_2O$ under $N_2$ for 12 h. It was concentrated and purified by prep HPLC (C18 reverse phase column, eluted with a $H_2O/CH_3CN$ gradient with 0.05% TFA) afforded 5 mg of the title compound of Example 46 as a TFA salt. LRMS (ES+): 555.3, (M+H)+.

Example 47

1-[3-Aminobenzisoxazol-5'-yl]-3-methyl-6-[2'-N-pyrrolidinyl methyl-[1,1']-biphen-4-yl]-1,4,5,6-tetrahydro-79-pyrazolo-[3,4-c]-pyridin-7-one trifluoroacetic acid salt

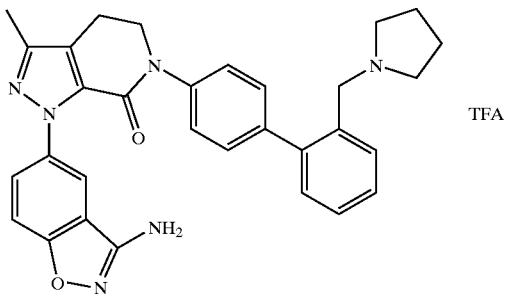

Part A. 1-[4-bromophenyl]-3-hydroxy-4-acetyl-5,6-dihydropyridin-2-one.

Levulinic acid (10 g, 86.1 mmol) in $CH_2Cl_2$ (100 mL) was cooled to 0° C. and oxalyl chloride (90.4 mmol, 11.48 g) and a few drops of DMF were added. The reaction was allowed to warm to ambient temperature and stirred 18 h. The reaction was evaporated and the residue dissolved in $CH_2Cl_2$ (50 mL) and added dropwise to a solution of 4-bromoaniline (81.1 mmol, 13.95 g), $Et_3N$ (100 mmol, 10.12 g) and DMAP (81.1 mmol, 9.9 g) in $CH_2Cl_2$ (100 mL) at 0° C. The reaction was allowed to warm to ambient temperature and stirred 18 h. The reaction was filtered, washed with 1N HCl (3×) and 1N NaOH (3×), dried ($MgSO_4$) and evaporated. There was obtained 9.4 g of N-[4-bromophenyl]-4-oxopentamide. Crystallization from EtOAc gave material with mp 156.2° C.

N-[4-bromophenyl]-4-oxopentamide (18.5 mmol, 5 g) was added dropwise to a suspension of $LiAlH_4$ (74 mmol, 2.8 g) in THF (50 mL). When the addition was completed, the reaction mixture was heated at reflux for 1 h. The reaction was cooled to ambient temperature and water (2.8 mL), 1N NaOH (2.8 mL) and water (8.4 mL) were carefully added sequentially to the reaction mixture. Low resolution mass spectroscopy (LRMS), showed only product, N-[4-bromophenyl]-4-hydroxypentylamine, (M+H)+: 258.0/260.0 m/z.

This solution was cooled to 0° C., then 4-methylmorpholine (37 mmol, 3.75 g) and ethyl oxalyl chloride (37 mmol, 5.1 g) were added. The reaction was allowed to warm to ambient temperature and stirred 3 h. LRMS showed the major portion of the product mixture to be the mono-acylation product [M+H)+358.0/360.0 m/z] and a small amount of the di-acylation product [M+H)+: 458.0/460.0 m/z]. The reaction mixture was evaporated, dissolved in EtOAc, and washed with 1N HCl (3×), 1N NaOH (2×), dried ($MgSO_4$) and evaporated. There was obtained 4.34 g of material.

The product mixture from above was dissolved in MeOH (100 mL), cooled to 0° C. and a freshly prepared solution of NaOMe in MeOH (ca. 0.2 g of Na metal in 10 mL of MeOH) added. The reaction was stirred at 0° C. for 2 h whereupon all of the diacylation product was consumed and the ethyl ester in the monoacylation product was transesterified to the methyl ester. The reaction was evaporated, dissolved in $CHCl_3$ and washed with 1N HCl, dried ($MgSO_4$) and evaporated to give 3.9 g of methyl N-[4-bromophenyl]-N-(4-hydroxypentyl)oxalyl amide; LRMS (M+H)+: 344.0/346.0 m/z.

DMSO (74 mmol, 5.8 g) was added dropwise to a solution of oxalyl chloride (34 mmol, 17 mL of a 2M solution in $CH_2Cl_2$) in $CH_2Cl_2$ (50 mL) at −63° C. (dry ice/AcCN bath). The reaction was maintained at −63° C. for 15 min then methyl N-[4-bromophenyl]-N-(4-hydroxypentyl)oxalyl amide (3.9 g, 11.3 mmol) in $CH_2Cl_2$ (50 mL) was added dropwise. After 3 h at −63° C., $Et_3N$ (96.4 mmol, 9.75 g) was added and the cooling bath removed. After the reaction warmed to ambient temperature and stirred for 1 h, water was added (150 mL), the layers were separated, washed with 1N HCl (2×) and brine, dried ($MgSO_4$) and evaporated. There was obtained 3.4 g (9.8 mmol) of methyl N-[4-bromophenyl]-N-(4-oxopentyl)oxalyl amide; LRMS (M+H)+342.0/344.0 m/z.

Methyl N-[4-bromophenyl]-N-(4-oxopentyl)oxalyl amide (9.8 mmol, 3.4 g) was added to a solution of NaOMe in MeOH (from 0.53 g of Na metal (23 mg atom) in 20 mL of MeOH). This mixture was stirred at ambient temperature for 1 h, then 10 mL of 3N HCl was added. This suspension was diluted further by the addition of more water (100 mL) and the product collected by filtration and air-dried. There was obtained 1.72 g (5.6 mmol) of 1-[4-bromophenyl]-3-hydroxy-4-acetyl-5,6-dihydropyridin-2-one; LRMS (M+H)−310.2/312.2 m/z.

Part B. 1-[3-Cyano-4-fluorophenyl]-3-methyl-6-[4-bromophenyl]-1,4,5,6-tetrahydro-7H-pyrazolo-[3,4-c]-pyridin-7-one.

3-Cyano-4-fluoroaniline (3.7 mmol, 0.5 g) in conc. HCl (4 mL) was cooled to 0° C. and $NaNO_2$ (4.4 mmol, 0.3 g) in water (3 mL). This was stirred at 0° C. for 30 min, then acetic acid (1.3 mL) was added. $SnCl_2·(H_2O)_2$ (8.5 mmol, 1.9 g) in 1:1 water:conc. HCl (3 mL) was added dropwise to the cold solution and stirred for an additional 30 min. To this mixture 1-[4-bromophenyl]-3-hydroxy-4-acetyl-5,6-dihydropyridin-2-one (3.9 mmol, 1.2 g) was slurried in MeOH (20 mL) and added with the aid of additional MeOH (6 mL). The suspension was heated at 50° C. for 3 h, then cooled at 10° C. for 18 h. The product, 1-[3-cyano-4-fluorophenyl]-3-methyl-6-[4-bromophenyl]-1,4,5,6-tetrahydro-7H-pyrazolo[3,4-c]pyridin-7-one, was isolated by filtration. There was obtained 1.34 g (3.2 mmol) of product; mp 237.6° C., LRMS (M+H)$^+$: 425.2/427.1 m/z.

Part C. 1-[3-Aminobenzisoxazol-5'-yl]-3-methyl-6-[2-formyl-[1,1']-biphen-4-yl]-1,4,5,6-tetrahydro-7H-pyrazolo-[3,4-c]-pyridin-7-one.

1-[3-Cyano-4-fluorophenyl]-3-methyl-6-[4-bromophenyl]-1,4,5,6-tetrahydro-7H-pyrazolo-[3,4-c]-pyridin-7-one (1.34 g, 3.2 mmol), 2-formylphenylboronic acid (0.68 g, 4.5 mmol) and Bu$_4$NBr (0.06 g) in C$_6$H$_6$ (50 mL) and 2N Na$_2$CO$_3$ (10 mL) was purged with a stream of N$_2$ gas. Palladium tetrakis (triphenyl) phosphine (0.19 g, 5 mol %) was added and the mixture heated at reflux for 18 h. To the cooled reaction mixture, brine and EtOAc was added and the layers separated. The organic layer was dried (MgSO$_4$) and evaporated to give 1.58 g (3.2 mmol) of 1-[3-cyano-4-fluorophenyl]-3-methyl-6-[2'-formyl-[1,1']-biphen-4-yl]-1,4,5,6-tetrahydro-7H-pyrazolo[3,4-c]pyridin-7-one; LRMS (M+Na)$^+$: 473.3 m/z.

1-[3-Cyano-4-fluorophenyl]-3-methyl-6-[2'-formyl-[1,1']-biphen-4-yl]-1,4,5,6-tetrahydro-7H-pyrazolo-[3,4-c]-pyridin-7-one (3.4 g, 7.5 mmol) was cooled to 0° C. in MeOH (75 mL) and NaBH$_4$ (0.43 g, 11.3 mmol) added. After 3 h, 1N HCl (50 mL) was added, the reaction was evaporated and EtOAc added. The organic layer was washed with 1N HCl, dried (MgSO$_4$) and evaporated to give 2.48 g (5.5 mmol) of 1-[3-cyano-4-fluorophenyl]-3-methyl-6-[2'-hydroxymethyl-[1,1']-biphen-4-yl]-1,4,5,6-tetrahydro-7H-pyrazolo-[3,4-c]-pyridin-7-one.

The product from above (2.48 g, 5.5 mmol), N-acetylhydroxylamine (1.24 g, 16.4 mmol) and K$_2$CO$_3$ (4.54 g, 33 mmol) in DMF (75 mL) and water (7.5 mL) were stirred at ambient temperature for 18 h. The solvent was removed by distillation and the residue applied to a flash silica gel column (200 g) and eluted with a gradient of 2:1 to 1:1 hexane:EtOAc. There was obtained 1.65 g of 1-[3-Aminobenzisoxazol-5-yl]-3-methyl-6-[2'-hydroxymethyl-[1,1']-biphenyl-4-yl)-1,4,5,6-tetrahydro-7H-pyrazolo-[3,4-c]-pyridin-7-one; LRMS (M$^-$) 464.0 m/z.

1-[3-Aminobenzisoxazol-5'-yl]-3-methyl-6-[2'-hydroxymethyl-[1,1']-biphenyl-4-yl)-1,4,5,6-tetrahydro-7H-pyrazolo-[3,4-c]-pyridin-7-one (0.1 g, 0.22 mmol) in acetone (5 mL) and CH$_2$Cl$_2$ (20 mL) was stirred with activated MnO$_2$ (0.3 g, 3.3 mmol). After 3 h the suspension was filtered through a pad of Celite® and evaporated to give 0.09 g of 1-[3-Aminobenzisoxazol-5'-yl]-3-methyl-6-[2'-formyl-[1,1']-biphen-4-yl]-1,4, 5,6-tetrahydro-7H-pyrazolo-[3,4-c]-pyridin-7-one; LRMS (M+H)$^-$: 464.2 m/z.

Part D. 1-(3-Aminobenzisoxazol-5'-yl]-3-methyl-6-[2'-N-pyrrolidinylmethyl-[1,1']-biphen-4-yl]-1,4,5,6-tetrahydro-7H-pyrazolo-[3,4-c]-pyridin-7-one trifluoroacetic acid salt.

To 0.09 g of 1-[3-Aminobenzisoxazol-5'-yl]-3-methyl-6-[2'-formyl-[1,1']-biphen-4-yl]-1,4,5,6-tetrahydro-7H-pyrazolo-[3,4-c]-pyridin-7-one (0.22 mmol) in 1:1 CHCl$_3$ THF (40 mL) was added pyrrolidine (0.064 g, 0.88 mmol), acetic acid (0.44 mmol) and sodium triacetoxyborohydride (0.094 g, 0.44 mmol). After 18 h at ambient temperature more CHCl$_3$ was added (100 mL) and the organics washed with water, dried (MgSO$_4$) and evaporated. The residue (0.11 g) was purified by HPLC on a C$_{18}$ column by elution with a gradient of water (0.05% TFA, solvent A) and acetonitrile (0.05% TFA, solvent B). There was obtained 0.066 g of 1-(3-Aminobenzisoxazol-5'-yl]-3-methyl-6-[2'-N-pyrrolidinyl methyl)-[1,1']-biphen-4-yl]-1,4,5,6-tetrahydro-7H-pyrazolo-[3,4-c]-pyridin-7-one trifluoroacetic acid salt with a purity of >99%; mp 108.9° C., HRMS (C$_{31}$H$_{31}$O$_2$N$_6$)$^+$: 519.2517 m/z.

Example 48

1-[3-Aminobenzisoxazol-5'-yl]-3-methyl-6-[2'-(3-(S)-hydroxy-N-pyrrolidinyl)methyl-[1,1']-biphen-4-yl]-1,4,5,6-tetrahydro-7H-pyrazolo-[3,4-c]-pyridin-7-one trifluoroacetic acid salt

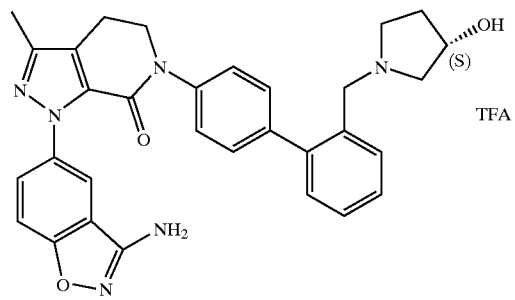

This compound was prepared and purified by the same procedure outlined in Example 47, Part D from a mixture of 1-(3-Aminobenzisoxazol-5'-yl]-3-methyl-6-[2'-formyl-[1,1']-biphen-4-yl]-1,4,5,6-tetrahydro-7H-pyrazolo-[(3,4-c]-pyridin-7-one and 3-(S)-hydroxypyrrolidine. There was obtained 0.047 g of the title compound of Example 48 with a purity >98%; mp 137.7° C.; HRMS (C$_{31}$H$_{31}$N$_6$O$_3$)$^+$: 535.2452.

Example 49

1-[3-Aminobenzisoxazol-51-yl]-3-methyl-6-[2'-N-isopropylaminomethyl-[1,1']-biphen-4-yl]-1,4,5,6-tetrahydro-7H-pyrazolo-[3, 4-c]-pyridin-7-one trifluoroacetic acid salt

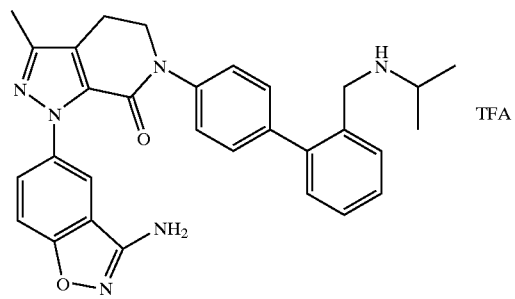

This compound was prepared and purified by the same procedure outlined in Example 47, Part D from a mixture of 1-[3-Aminobenzisoxazol-5'-yl]-3-methyl-6-[2'-formyl-[1,1']-biphen-4-yl]-1,4,5,6-tetrahydro-7H-pyrazolo-[3,4-c]-pyridin-7-one and isopropylamine. There was obtained 0.065 g of the title compound of Example 49 with a purity >95%; mp 71.5° C.; HRMS (C$_3$H$_{31}$N$_6$O$_2$)$^+$: 507.2501.

Example 50

1-[3-Aminobenzisoxazol-5'-yl]-3-methyl-6-[2'-N,N-dimethylaminomethyl-[1,1']-biphen-4-yl]-1,4,5,6-tetrahydro-7H-pyrazolo-[3,4-c]-pyridin-7-one trifluoroacetic acid salt

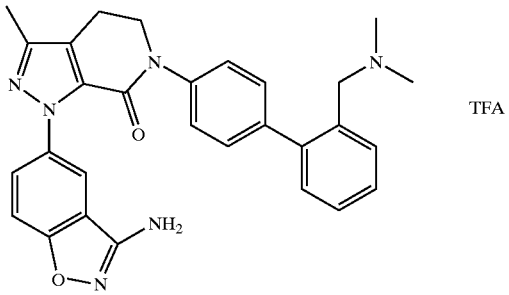

This compound was prepared and purified by the same procedure outlined in Example 47, Part D from a mixture of 1-[3-Aminobenzisoxazol-5'-yl]-3-methyl-6-[2'-formyl-[1,1']-biphen-4-yl]-1,4,5,6-tetrahydro-7H-pyrazolo-[3,4-c]-pyridin-7-one and a 2M THF solution of dimethylamine. There was obtained 0.040 g of the title compound of Example 50 with a purity >95%; mp 51.6° C.; HRMS ($C_{29}H_{29}N_6O_2$): 493.2355.

Example 51

1-[3-Aminobenzisoxazol-5'-yl]-3-methyl-6-[2'-methylsulfonyl-[1,1']-biphen-4-yl]-1,4,5,6-tetrahydro-7H-pyrazolo-[3,4-c]-pyridin-7-one trifluoroacetic acid salt

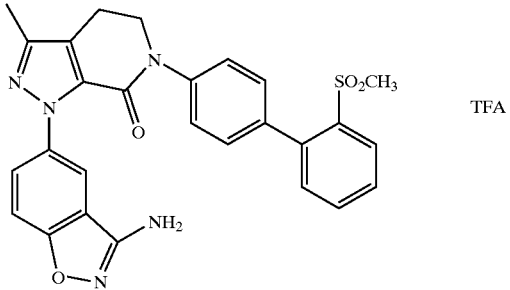

Part A. 1-[3-Aminobenzisoxazol-5'-yl]-3-methyl-6-[2'-thiomethyl-[1,1']-biphen-4-yl]-1,4,5,6-tetrahydro-7H-pyrazolo-[3,4-c]-pyridin-7-one.

1-[3-Cyano-4-fluorophenyl)-3-methyl-6-[4-bromophenyl]-1,4,5,6-tetrahydro-7H-pyrazolo-[3,4-c]-pyridin-7-one (Example 47, Part B; 0.23 g, 0.54 mmol), 2-thiomethylphenylboronic acid (0.13 g, 0.76 mmol) and Bu$_4$NBr (0.011 g) in C$_6$H$_6$ (20 mL) and 2N Na$_2$CO$_3$ (4 mL) was purged with a stream of N$_2$ gas. Palladium tetrakis (triphenyl) phosphine (0.032 g, 0.028 mmol) was added and the mixture heated at reflux for 18 h. To the cooled reaction mixture, brine and EtOAc was added and the layers sepa rated. The organic layer was dried (MgSO$_4$) and evaporated then the residue was purified by silica gel chromatography (100 g of SiO$_2$, eluted with 1:1 hexane:EtOAc) to give 0.17 g (3.2 mmol) of 1-[3-cyano-4-fluorophenyl]-3-methyl-6-[2'-thiomethyl)-[1,1']-biphen-4-yl]-1,4,5,6-tetrahydro-7H-pyrazolo-[3,4-c]-pyridin-7-one; LRMS (M+H)$^+$: 469.0 m/z.

The product from above (0.17 g, 0.36 mmol), N-acetylhydroxylamine (0.08 g, 1.09 mmol) and K$_2$CO$_3$ (0.30 g, 2.2 mmol) in DMF (5 mL) and water (0.5 mL) were stirred at ambient temperature for 18 h. The reaction was diluted with EtOAc and washed with water (5×), dried (MgSO$_4$) and evaporated. The residue was applied to a flash silica gel column (50 g) and eluted with 1:1 hexane:EtOAc. There was obtained 0.09 g of 1-[3-Aminobenzisoxazol-5'-yl]-3-methyl-6-[2'-thiomethyl)-[1,1']-biphen-4-yl]-1,4,5,6-tetrahydro-7H-pyrazolo-[3,4-c]-pyridin-7-one.

A mixture of 1-[3-Aminobenzisoxazol-5'-yl]-3-methyl-6-[2'-thiomethyl-[1,1']-biphen-4-yl]-1,4,5,6-tetrahydro-7H-pyrazolo-[3,4-c]-pyridin-7-one (0.09 g, 0.19 mmol) and m-chloroperbenzoic acid (0.10 g, 0.56 mmol) in CH$_2$Cl$_2$ were stirred for 18 h. Saturated NaHCO3 was added and the layers separated. The basic layer was extracted into CH$_2$Cl$_2$, then the organic layers were combined, dried (MgSO$_4$) and evaporated. The residue was purified by HPLC on a C$_{18}$ column by elution with a gradient of water (0.05% TFA, solvent A) and acetonitrile (0.05% TFA, solvent B). There was obtained 0.036 g of 1-[3-Aminobenzisoxazol-5'-yl]-3-methyl-6-[2'-methylsulfonyl)-[1,1']-biphen-4-yl]-1,4,5,6-tetrahydro-7H-pyrazolo-[3,4-c]-pyridin-7-one trifluoroacetic acid salt with a purity of >96%; mp 274.5° C., HRMS ($C_{27}H_{24}O_4N_5S)^+$: 514.1527 m/z.

Example 52

1-[3-Aminobenzisoxazol-5'-yl]-3-methyl-6-[2'-methylsulfonyl-3-fluoro-[1,1']-biphen-4-yl]-1,4,5,6-tetrahydro-7H-pyrazolo-[3,4-c]-pyridin-7-one trifluoroacetic acid salt

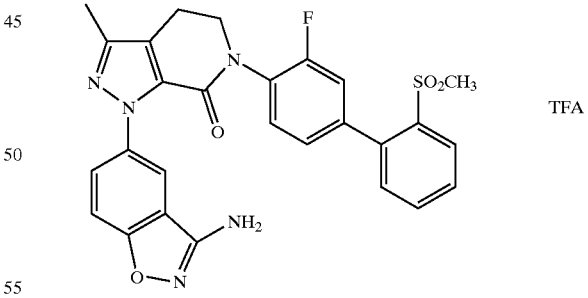

The title compound was prepared by the same methods disclosed for Example 51. After HPLC purification there was obtained 0.24 g of 1-[3-Aminobenzisoxazol-5'-yl]-3-methyl-6-[2'-methylsulfonyl-3-fluoro-[1,1']-biphen-4-yl]-1,4,5,6-tetrahydro-7H-pyrazolo-[3,4-c]-pyridin-7-one trifluoroacetic acid salt with a purity of >96%; mp 250.3° C., CHN for $C_{27}H_{22}N_5O_4FS$ ·½ $C_2F_3O_2H$: Calcd. %C: 58.98, %H: 4.00, %N: 12.50, Found. %C: 59.02, %H: 4.17, %N: 12.56; HRMS ($C_{27}H_{23}O_4N_5SF)^-$: 532.1471 m/z.

Examples 53 and 54

1-[2-Aminomethylphenyl]-3-trifluoromethyl-6-[2'-methylsulfonyl-3-fluoro-[1,1']-biphen-4-yl]-1,4,5,6-tetrahydropyrazolo-[3,4-c]-pyridin-7-one trifluoroacetic acid salt (Example 53) and cyclized byproduct (Example 54).

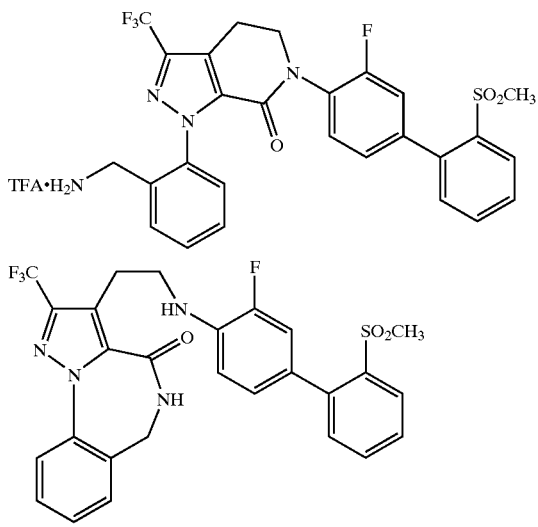

Part A. 1,5,6-Trihydro-1-[4-bromo-2-fluorophenyl]-3-(morpholin-4-yl)-pyridin-2-one.

To DMSO (16.6 mL) in CH$_2$Cl$_2$' (200 mL) at −60° C. was added dropwise trifluoroacetic anhydride (29.9 mL, 0.21 mol). This mixture was stirred 15 min then 1-[4-bromo-2-fluorophenyl]-3-hydroxypiperidin-2-one (21 g, 0.073 mol, prepared following the procedures in Marinelli et. al. Tetrahedron 1996, 11176) in CH$_2$Cl$_2$ (100 mL) was added dropwise. After 2 h triethylamine (61.2 mL, 0.44 mol) was slowly added. The reaction was stirred 1.5 h then poured into 1N HCl and the CH$_2$Cl$_2$ layer was separated and concentrated. The residue was taken up in EtOAc and washed with water, saturated aq NaHCO$_3$ and brine, dried (Na$_2$SO$_4$) and concentrated. The dione was placed in a Dean-Stark apparatus in benzene (200 mL) with morpholine (13 mL) and p-toluenesulfonic acid (50 mg) and heated to reflux 18 h. The reaction was concentrated and purification by chromatography on silica with (2:1) hexanes/EtOAc as eluent afforded 17.2 g (66%) of a pale yellow foam. $^1$H NMR (CDCl$_3$): □ 7.41–7.12 (m, 3H), 5.68 (t, j=4.7, 1H), 3.83 (4H, j=4.4 Hz, 4H), 3.71 (t, j=6.6 Hz, 2H), 2.93 (t,j=4.8 Hz, 4H), 2.55 (dd, j=4.8, 6.6 Hz, 2H).

Part B. 1-[2-Trifluoroacetamidomethylphenyl]-3-trifluoromethyl-6-[4-bromo-2-fluorophenyl]-1,4,5,6-tetrahydropyrazolo-[3,4-c]-pyridin-7-one.

To DMAP (0.5 g, 4.1 mmol) in CH$_2$Cl$_2$ (25 mL) at 0° C. was added TFAA (0.58 mL, 4.1 mmol). After 30 minutes 1,5,6-trihydro-1-[4-bromophenyl]-3-[morpholin-4-yl]-pyridin-2-one (1.2 g, 3.3 mmol) in CH$_2$Cl$_2$ (30 mL) was added. The reaction was stirred 24 h at rt. The solvent was removed and purification by chromatography on silica with (2:1) hexanes/EtOAc as eluent afforded 0.79 g (52%) of a yellow solid. LRMS (ES−): 449–450.9 (M−H)$^-$. The compound was heated to reflux for 3 h in THF (45 mL) containing 20% HCl (15 mL). The reaction was cooled and extracted with diethyl ether, washed successively with NaHCO$_3$, brine and dried (Na$_2$SO$_4$). The trione intermediate was obtained as a green-yellow foam (0.64 g, 90%). LRMS (ES$^+$): 783–785 (2M+Na). To this product (0.62 g, 1.6 mmol) was added 2-hydrazino benzyltrifluoroacetamide hydrochloride (1.0 g, 3.7 mmol) and acetic acid (20 mL) and the mixture was heated to reflux 24 h. The acetic acid was removed and the residue dissolved in EtOAc, washed successively with NaHCO$_3$, brine and dried (Na$_2$SO$_4$). Purification by chromatography on silica with (4:1) hexanes/EtOAc as eluent afforded 0.3 g (32%) of the title compound. LRMS (ES−): 577–579.1 (M−H)$^-$.

Part C. 1-[2-Aminomethylphenyl]-3-trifluoromethyl-6-[2'-methylsulfonyl-3-fluoro-[1,1']-biphen-4-yl]-1,4,5,6-tetrahydropyrazolo-[3,4-c]-pyridin-7-one trifluoroacetic acid salt 1-[2-Trifluoroacetamidomethylphenyl]-3-trifluoromethyl-7-[4-bromophenyl]-1,4,5,6-tetrahydropyrazolo-[3,4-c]-pyridin-7-one (0.3 g, 0.052 mmol) was coupled with 2-thiomethylphenyl boronic acid (0.113 g, 0.06 mmol) via standard Suzuki coupling procedures with Pd°. Purification by chromatography on silica with (2:1) hexanes/EtOAc as eluent afforded 0.35 g of the desired thiomethyl intermediate. The thiomethyl intermediate was dissolved in CH$_2$Cl$_2$, cooled to 0° C. and oxidized with m-chloroperbenzoic acid (0.39 g, 1.3 mmol). After stirring for 2.5 h the reaction mixture was washed successively with sat'd sodium bisulfate, brine and dried (MgSO$_4$). Purification by chromatography on silica with (1:1) hexanes/EtOAc as eluent afforded 0.2 g of a foam. LRMS (ES−): 653.1 (M−H)$^-$. The trifluoroacetamide group was removed by heating to reflux the previous compound in a mixture of MeOH (10 mL), water (3 mL), and K$_2$CO$_3$ (0.17 g, 1.2 mmol) for 3 h. The reaction was cooled, acidified with TFA, concentrated and purified via HPLC (C18 reverse phase column, elution with a H$_2$O/CH$_3$CN gradient with 0.5% TFA) to afford two products. First the desired ortho-benzyl amine (Example 53), 0.064 mg (32% from sulfone) was recovered: Mass Spec m/z (ESI) (M+H)+559.1; HRMS (M+H)$^+$ for C$_{27}$H$_{23}$F$_4$N$_4$O$_3$S$_1$: 599.1427; $^1$H NMR (DMSO) □ 8.23 (s, 2H), 8.12 (dd, j=1.1, 7.7 Hz, 1H) 7.82 (dt, j=1.5, 7.3 Hz, 1H), 7.74 (dt, j=1.5, 7.7 Hz, 1H), 7.67 (m, 2H), 7.55 (m, 2H), 7.53 (d, 1j=8 Hz, 1H), 7.42 (m, 2H), 7.32 dd, j=1.8, 8 Hz, 1H), 4.18 (t, j=6.6 Hz, 2H), 3.88 (q, j=5.8 Hz, 2H), 3.23 (t, j=6.2 Hz, 2H), 2.91 (s, 3H). A second byproduct the cyclic lactam (Example 54), 25 mg (12% from sulfone), was recovered: HRMS (M+H)$^+$ for C$_{27}$H$_{23}$F$_4$N$_4$O$_3$S$_1$: 599.1429; $^1$H NMR (DMSO) □ 8.21 (dd, j=1.1, 7.7 Hz, 1H), 7.86 (d, j=8 Hz, 1H), 7.65 (m, 2H), 7.56 (m, 2H), 7.45 (dt, j=1.1, 7.3 Hz, 1H), 7.36 (m, 2H), 7.16 (dd, j=2.2, 12.5 Hz, 1H), 7.06 (dd, j=1.5, 8.4 Hz, 1H), 6.81 (t, j=8.7 Hz, 1H), 4.25 (d, j=5.9 Hz, 2H), 3.59 (t, j=6.2 Hz, 2H), 3.30 (m, 2H), 2.74 (s+m, 4H).

Example 55

1-[2-Aminomethylphenyl]-3-trifluoromethyl-6-[2'-aminosulfonyl-3-fluoro-[1,1']-biphen-4-yl]-1,4,5,6-tetrahydropyrazolo-[3,4-c]-pyridin-7-one trifluoroacetic acid salt

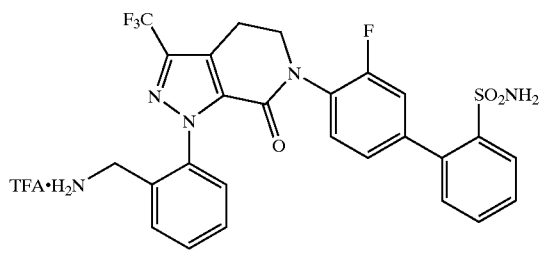

The product from Example 53, Part B (0.33 g, 0.057 mmol) was coupled with 2-(tert-butylaminosulfonyl)phenyl boronic acid (0.22 g, 0.08 mmol) via the Suzuki procedure.

Purification by chromatography on silica with (2:1) hexanes/EtOAc as eluent afforded 0.23 g (56%) of a pale yellow solid. LRMS (ES−): 710.2 (M−H)⁻. The protecting groups were removed sequentially by, first, stirring the previous compound in a mixture of MeOH (30 mL), water (10 mL), and $K_2CO_3$ (0.086 g, 0.6 mmol) for 18 h. The reaction was acidified with TFA and heated to reflux for 10 min. The reaction was concentrated and purified by HPLC (C18 reverse phase column, elution with a $H_2O/CH_3CN$ gradient with 0.5% TFA) and freeze-dried to afford 92 mg (44%) of the title compound of Example 55. HRMS (M+H)⁺ for $C_{26}H_{22}F_4N_5O_3S_1$: 560.1377. ¹H NMR (DMSO-d6) ☐ 8.21 (2H, s), 8.04 (dd, j=2.2, 5.1 Hz, 1H), 7.67 (m, 4H), 7.55 (m, 2H), 7.49 (t, j=8.1 Hz, 1H), 7.39 (s, 2H), 7.35 (m, 2H), 7.28 (dd, j=1.8, 8 Hz, 1H), 4.16 (t, j=6.3 Hz, 2H), 3.89 (q, j=5.9 Hz, 2H), 3.23 (t, j=6.2 Hz, 2H). Analysis calc'd for $C_{26}H_{22}F_4N_5O_3S_1$ (TFA) $(H_2O)_2$: C: 47.39; H:3.69; N:9.87; found C:47.35; H:3.22; N:9.55.

Example 56

1-[2-Aminomethylphenyl]-3-trifluoromethyl-6-[2'-methylsulfonyl-[1,1']-biphen-4-yl]-1,4,5,6-tetrahydropyrazolo-[3,4-c]-pyridin-7-one trifluoroacetic acid salt

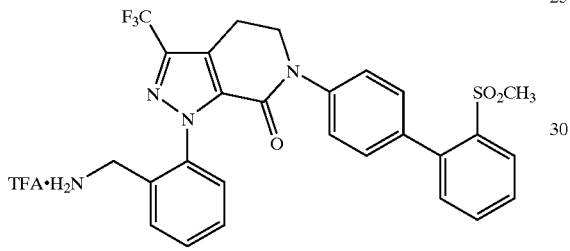

The title compound of Example 56 was prepared in a similar fashion to that described for example 53. LRMS (ES⁺): 541.3 (M+H)⁺. ¹H NMR (DMSO-d6): 8.18 (bm, 2H), 8.09 (dd, 2H), 7.78–7.64 (cp, 6H), 7.54 (m, 2H), 7.38 (m, 2H), 4.22 (t, 2H), 3.86 (m, 2H), 3.35 (bm, 1H), 3.20 (t, 2H), 2.83 (s, 3H).

Example 57

1-[2-Aminomethylphenyl]-3-trifluoromethyl-6-[2'-N,N-dimethylaminomethyl-3-fluoro-[1,1']-biphen-4-yl]-1,4,5,6-tetrahydropyrazolo-[3,4-c]-pyridin-7-one trifluoroacetic acid salt

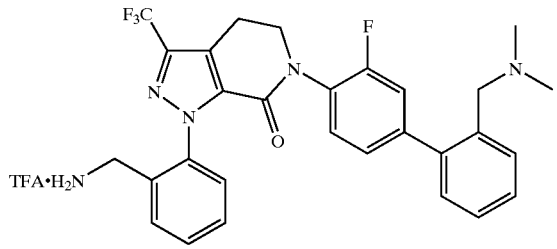

Part A. 1-[2-Trifluoroacetamidomethylphenyl]-3-trifluoromethyl-6-[2'-formyl-3-fluoro-[1,1']-biphen-4-yl]-1,4,5,6-tetrahydropyrazolo-[3,4-c]-pyridin-7-one The product from Example 53, Part B above (0.8 g, 1.4 mmol) was coupled with 2-formylphenylboronic acid (0.311 g, 2.1 mmol) via standard Suzuki methodology. Purification by chromatography on silica with (2:1) hexanes/EtOAc as eluent afforded 0.5 g (59%) of the aldehyde intermediate. LRMS (ES−): 603.2 (M−H)⁻.

Part B. 1-[2-Aminomethylphenyl]-3-trifluoromethyl-6-[2'-N,N-dimethylaminomethyl-3-fluoro-[1,1']-biphen-4-yl]-1,4,5,6-tetrahydropyrazolo-13,4-c]-pyridin-7-one trifluoroacetic acid salt.

The aldehyde from part A (0.16 g, 0.26 mmol) was hydrogenated at 40 psi in EtOH with 5% Pd/C (35 mg) and excess dimethylamine hydrochloride (50 mg) for 6 h. The incomplete reaction was filtered through Celite®, concentrated and purification by chromatography on silica with 10% $MeOH/CH_2Cl_2$ as eluent afforded 77 mg (32%) of the trifluoroacetamide. The protecting group was removed in a mixture of MeOH (15 mL), water (8 mL), and $K_2CO_3$ (34 mg, 0.2 mmol) for 18 h. The reaction was acidified with TFA, concentrated, combined with another 60 mg of additional crude product and purified via HPLC (C18 reverse phase column, elution with a $H_2O/CH_3CN$ gradient with 0.5% TFA) to afford 94 mg (67%) of the title compound of Example 57. HRMS (M+H)⁺ for $C_{34}H_{29}F_3N_2O$ 538.2234; ¹H NMR (DMSO-d6) .☐ 8.26 (s, 2H), 7.73 (m, 1H), 7.67 (m, 2H), 7.58 (m, 5H), 7.41 (dd, j=1.9, 11.4 Hz, 1H), 7.36 (m, 1H), 7.26 (dd, j=1.4, 8 Hz, 1H), 4.31 (d, j=4.4 Hz, 2H), 4.17 (t, j=6.2 Hz, 2H), 3.88 (q, j=5.5 Hz, 2H), 3.24 (t, j=6.6 Hz, 2H), 2.58 (s, 3H), 2.56 (s, 3H).

Example 58

1-[2-Aminomethylphenyl]-3-trifluoromethyl-6-[2-(3-(R)-hydroxy-N-pyrrolidinyl)methyl-3-fluoro-[1,1']-biphen-4-yl]-1,4,5,6-tetrahydropyrazolo-[3,4-c]-pyridin-7-one trifluoroacetic acid salt

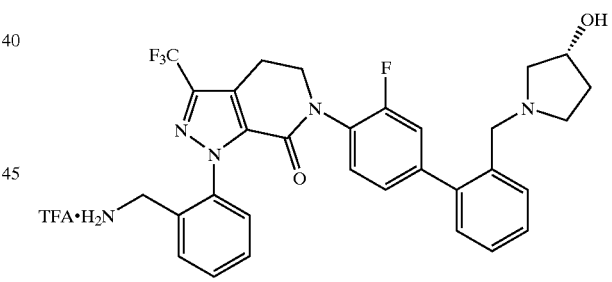

The aldehyde from Example 57, Part A (0.225 g, 0.37 mmol) was reductively aminated, with (S)-3-pyrrolidinol (100 mg, 1.1 mmol) and then deprotected with $K_2CO_3$/MeOH/water, as in Example 57. Purification by HPLC (C18 reverse phase column, elution with a $H_2O/CH_3CN$ gradient with 0.5% TFA) and freeze-drying afforded 80 mg (27%) of the title compound of Example 58 as a white solid: HRMS (M+H)⁻ for $C_{31}H_{30}F_4N_5O_2$: 580.2313; ¹H NMR (DMSO-d6) ☐ 8.27 (m, 2H), 7.78 (m, 1H), 7.67 (m, 2H), 7.55 (m, 5H), 7.40 (dd, j=1.8, 11.4 Hz, 1H), 7.33 (m, 1H), 7.27 (dd, j=1.4, 8 Hz, 1H), 4.46 (m, 3H), 4.16 w; (t, j=5.5 Hz, 2H), 3.87 (g, j=5.5 Hz, 2H), 3.50 m, 1H), 3.24 (t, j=6.6 Hz, 2H), 3.10–2.51 (m, 3H), 2.10–1.60 (m, 3H). Analysis calc'd for $C_{31}H_{30}F_4N_5O_2$ $(TFA)_2(H_2O)_{1.5}$: C: 50.37; H: 4.11; N: 8.39; found C: 50.05; H: 3.78; N:8.01.

Example 59

1-[3-Aminobenzisoxazol-5'-yl]-3-trifluoromethyl-6-[2'-dimethylaminomethyl-3-fluoro-[1,1']-biphen-4-yl]-1,4,5,6-tetrahydropyrazolo-[3,4-c]-pyridin-7-one trifluoroacetic acid salt

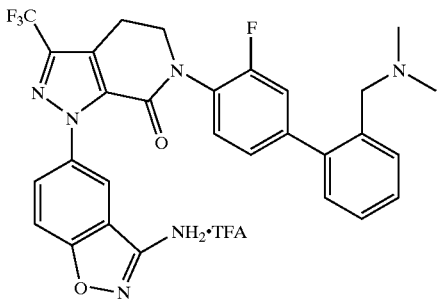

Part A. 1-[3-Cyano-4-fluorophenyl]-3-trifluoromethyl-6-[4-bromo-2-fluorophenyl]-1,4,5,6-tetrahydropyrazolo-[3,4-c]-pyridin-7-one.

The trione intermediate from Example 53, Part B (4.1 g, 11 mmol) was condensed with 3-cyano-4-fluorophenyl hydrazine (4.5 g, 13 mmol) in refluxing AcOH (60 mL) for 18 h. The reaction was cooled, concentrated and the residue taken up in EtOAc. The organic layer was washed successively with NaHCO$_3$, brine and dried (Na$_2$SO$_4$). Purification by chromatography on silica with (4:1) hexanes/EtOAc as eluent afforded 3.68 g (67%) of the title compound as a foam. LRMS (ES−): 497–499 (M−H)$^-$.

Part B. 1-[3-Cyano-4-fluorophenyl]-3-trifluoromethyl-6-[2'-formyl-3-fluoro-[1,1']-biphen-4-yl]-1,4,5,6-tetrahydropyrazolo-[3,4-c]-pyridin-7-one 1-[3-Cyano-4-fluorophenyl]-3-trifluoromethyl-6-[4-bromo-2-fluorophenyl]-1,4,5,6-tetrahydropyrazolo-[3,4-c]-pyridin-7-one (3.6 g, 7 mmol) was coupled with 2-formyl phenyl boronic acid (1.6 g, 10.9 mmol) via Suzuki methodology. Purification by chromatography on silica with (2:1) hexanes/EtOAc as eluent afforded 2.7 g (71.4%) of the title compound as a yellow foam. LRMS (ES−): 520.9 (M−H)$^-$; 635 (M−H+TFA).

Part C. 1-[3-Aminobenzisoxazol-5'-yl]-3-trifluoromethyl-6-[2'-hydroxymethyl-3-fluoro-[1,1']-biphen-4-yl]-1,4,5,6-tetrahydropyrazolo-[3,4-c]-pyridin-7-one.

To the aldehyde from Part B (3.68 g, 7.1 mmol) in MeOH (25 mL) at 0° C. was added NaBH$_4$ (0.31 g, 8 mmol) and the reaction was stirred 20 min. The MeOH was removed and the crude alcohol dissolved in CH$_2$Cl$_2$, washed with water, brine and dried (MgSO$_4$). To N-acetylhydroxylamine (1.6 g, 21 mmol) in DMF (15 mL) and water (1 mL) was added K$_2$CO$_3$ (3.9 g, 28 mmol). After 30 min. the above alcohol in DMF (15 mL) was added and the reaction was stirred 6 h. Water (75 mL) was added and the precipitated product filtered off, dried in vacuo and used in the next step. LRMS (ES−): 536.1 (M−H)$^-$.

Part D. 1-[3-Aminobenzisoxazol-5'-yl]-3-trifluoromethyl-6-[2'-dimethylaminomethyl-3-fluoro-[1,1']-biphen-4-yl]-1,4,5,6-tetrahydropyrazolo-[3,4-c]-pyridin-7-one trifluoroacetic acid salt.

To a suspension of the alcohol from Part C (2.99 g, 5.6 mmol) in CH$_2$Cl$_2$ (100 mL) was added PBr$_3$ (0.74 mL, 7.8 mmol). After 30 min. the reaction was quenched with ice water. The aqueous layer was extracted with CH$_2$Cl$_2$, washed with brine and dried (Na$_2$SO$_4$) to afford 3.6 g. The crude bromide was used in the next step. To a portion of this intermediate bromide (0.5 g, 0.8 mmol) in CH$_3$CN (15 mL) was added excess 40% aqueous dimethylamine (1 mL, 9 mmol). After 24 h the reaction was concentrated and purification by HPLC (C18 reverse phase column, elution with a H$_2$O/CH$_3$CN gradient with 0.5% TFA) and freeze-drying afforded 257 mg (45%) of the title compound of Example 59 as a white solid: HRMS (M+H)+ for C$_{29}$H$_{25}$F$_4$N$_6$O$_2$: 565.1967; $^1$H NMR (DMSO-d6) 9.50 (m, 2H), 8.11 (d, j=2.2 Hz, 1H), 7.79 (dd, j=2.2, 8.8 Hz, 1H), 7.72 (m, 1H), 7.59 (m, 4H), 7.41 (m, 2H), 7.26 (dd, j=1.4, 8 Hz, 1H), 4.32 (d, j=5.1 Hz, 2H), 4.17 (t, j=6.2 Hz, 2H), 3.23 (t, j=6.6 Hz, 2H), 2.58 (s, 0.3H), 2.57 (s, 3H).

Example 60

1-[3-Aminobenzisoxazol-51-yl]-3-trifluoromethyl-6-[2'-(3-(R)-hydroxy-N-pyrrolidinyl)methyl-3-fluoro-[1,1']-biphen-4-yl]-1,4,5,6-tetrahydropyrazolo-[3,4-c]-pyridin-7-one trifluoroacetic acid salt

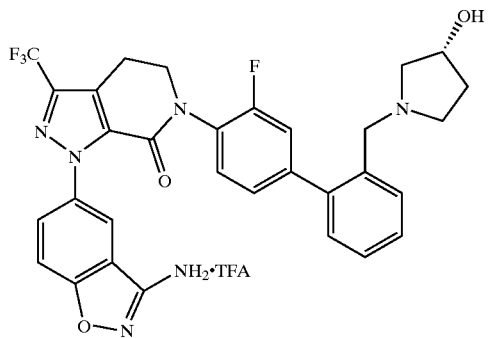

To the intermediate bromide from Example 59, Part D (0.5 g, 0.8 mmol) in CH$_3$CN (15 mL) was added (R)-3-pyrrolidinol (0.22 g, 2.5 mmol). After 24 h the reaction was concentrated and purification by HPLC (C18 reverse phase column, elution with a H$_2$O/CH$_3$CN gradient with 0.5% TFA) and freeze-drying afforded 283 mg (47%) of the title compound of Example 60 as a white solid: HRMS (M+H)+ for C$_{31}$H$_{27}$F$_4$N$_6$O$_3$: 607.2075; $^1$H NMR (DMSO-d6) 8.11 (d, j=1.8 Hz, 1H), 7.79 (dd, j=2.2, 8.8 Hz, 2H), 7.60 (m, 4H), 7.40 (m, 2H), 7.27 (dd, j=1.4, 8 Hz, 1H), 4.48 (d, j=5.5 Hz, 1H), 4.38 (m, 1H), 4.31 (m, 1H), 4.15 (t, j=6.2 Hz, 2H), 3.40 (m, 2H), 3.22 (t, j=6.3 Hz, 2H), 3.15–2.70 (m, 4H), 2.20–1.70 (m, 3H).

Example 61

1-[3-Aminobenzisoxazol-5'-yl]-3-trifluoromethyl-6-[2'-(3-(R)-hydroxy-N-pyrrolidinyl)methyl-[1,1']-biphen-4-yl]-1,4,5,6-tetrahydropyrazolo-[3,4-c]-pyridin-7-one trifluoroacetic acid salt

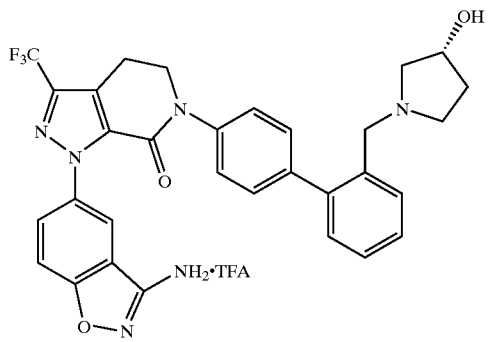

The title compound of Example 61 was prepared in a similar fashion to that described above. HRMS (M+H)+ for $C_{31}H_{28}F_3O_3N_6$ 589.216 $^1$H NMR (DMSO-d6): 8.11 (d, j=1.8 Hz, 1H), 8.81–7.65 (m, 2H), 7.58–7.45 (m, 5H), 7.40–7.31 (m, 3H), 6.60 (b, 1H), 4.48 (d, j=5.5 Hz, 1H), 4.38 (m, 1H), 4.31 (m, 1H), 4.15 (t, j=6.2 Hz, 2H), 3.40 (m, 2H), 3.22 (t, j=6.3 Hz, 2H), 3.15–2.70 (m, 4H), 2.20–1.70 (m, 3H).

Example 62

1-[3-Aminobenzisoxazol-5'-yl]-3-trifluoromethyl-6-[2'-isopropylaminomethyl-3-fluoro-[1,1'-biphen-4-yl]-1,4,5,6-tetrahydropyrazolo-[3,4-c]-pyridin-7-one trifluoroacetic acid salt

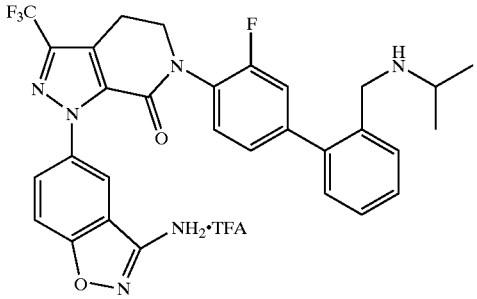

To the intermediate bromide from Example 59, Part D (0.62 g, 1.3 mmol) in CH$_3$CN (25 mL) was added isopropylamine (0.52 mL, 6.2 mmol). After 24 h the reaction was concentrated and purification by HPLC (C18 reverse phase column, elution with a H$_2$O/CH$_3$CN gradient with 0.5% TFA) and freeze-drying afforded 308 mg (43%) of the title compound of Example 62 as a white solid: HRMS (M+H)$^+$ for $C_{30}H_{27}F_4N_6O_2$: 579.2158; $^1$H NMR (DMSO-d6) □ 8.73 (m, 2H), 8.12 (d, j=1.8 Hz, 1H), 7.79 (dd, j=2.2, 8.8 Hz, 1H), 7.72 (dd, j=1.8, 7.3 Hz, 1H), 7.63–7.49 (m, 4H), 7.43 (m+s, 2H), 7.31 (dd, j=1.4, 8 Hz, 1H), 6.60 (m, 1H), 4.16 (t, j=6.2 Hz, 2H), 4.11 (m, 2H), 3.26 (m, 1H), 3.20 (t, j=6.2 Hz, 2H), 1.14 (d, j=6.6 Hz, 6H).

Example 63

1-[3-Aminobenzisoxazol-5'-yl]-3-trifluoromethyl-6-[2'-N-(2-methylimidazol-1-yl)methyl-3-fluoro-[1,1']-biphen-4-yl]-1,4,5,6-tetrahydropyrazolo-[3,4-c]-pyridin-7-one trifluoroacetic acid salt

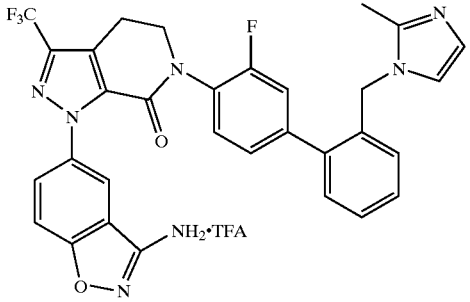

To the intermediate bromide from Example 59, Part D (0.2 g, 0.3 mmol) in CH$_3$CN (15 mL) was added 2-methylimidazole (0.11 mL, 1.3 mmol). After 24 h the reaction was concentrated and purification by HPLC (C18 reverse phase column, elution with a H$_2$O/CH$_3$CN gradient with 0.5% TFA) and freeze-drying afforded 80 mg (34%) of the title compound of Example 63 as a white solid: HRMS (M+H)$^+$ for $C_{31}H_{24}F_4N_7O_2$: 602.1908; $^1$H NMR (DMSO-d6) □ 8.12 d, j=1.8 Hz, 1H), 7.79 dd, j=2.1, 9.1 Hz, 1H), 7.60 (m, 2H), 7.48 (dt, j=2.2, 4.7 Hz, 1H), 7.43–7.33 (m, 4H), 7.31 (d, j=1.8 Hz, 1H), 7.28 (dd, j=1.8, 8.1 Hz, 1H), 7.12 (dd, j=8.2 Hz, 1H), 6.58 (m, 2H), 5.35 (s, 2H), 4.15 (t, j=6.6 Hz, 2H), 3.22 (t, j=6.3 Hz, 2H), 2.31 (s, 3H). HRMS (M+H)$^-$ for $C_{31}H_{24}F_4N_7O_2$: 602.1908.

Example 64

1-[3-Aminobenzisoxazol-5'-yl]-3-trifluoromethyl-6-[2'-N-pyrrolidinomethyl-3-fluoro-[1,1']-biphen-4-yl]-1,4,5,6-tetrahydropyrazolo-[3,4-c]-pyridin-7-one trifluoroacetic acid salt

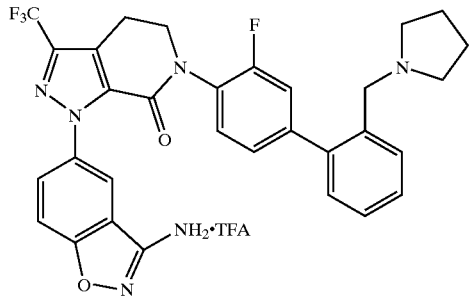

To the intermediate bromide from Example 59, Part D (0.27 g, 0.45 mmol) in CH$_3$CN (20 mL) was added pyrrolidine (0.17 g, 2.7 mmol). After 18 h the reaction was concentrated and purification by HPLC (C18 reverse phase column, elution with a H$_2$O/CH$_3$CN gradient with 0.5% TFA) and freeze-drying afforded 113 mg (36%) of the title compound of Example 64 as a white solid. HRMS (M+H)$^+$ for $C_{31}H_{27}F_4N_6O_2$: 591.2141; $^1$H NMR (DMSO-d6) □ 8.11 (d, j=2.2 Hz, 1H), 7.79 (dd, j=2.1, 9.1 Hz, 1H), 7.74 m, 1H), 7.58 (m, 4H), 7.42 (m, 2H), 7.28 (dd, j=1.5, 8.1 Hz, 1H), 6.58 (m, 2H), 4.39 (d, j=5.5 Hz, 2H), 4.16 (t, j=6.6 Hz, 2H), 3.35 m, 2H), 3.22 (t, j=6.2 Hz, 2H), 2.82 (m, 2H), 1.81 (m, 4H).

Example 65

1-[3-Aminobenzisoxazol-5'-yl]-3-trifluoromethyl-6-[2'-oximinomethyl-3-fluoro-[1,1']-biphen-4-yl]-1,4,5,6-tetrahydropyrazolo-[3,4-c]-pyridin-7-one trifluoroacetic acid salt

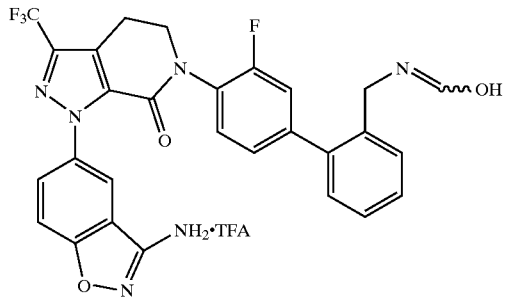

1-[3-Cyano-4-fluorophenyl]-3-trifluoromethyl-6-[2'-4' formyl-3-fluoro-[1,1']-biphen-4-yl]-1,4,5,6-tetrahydropyrazolo-[3,4-c]-pyridin-7-one from Example 59, Part B (2 g, 3.8 mmol) was reacted with N-acetylhydroxylamine (0.57 g, 7.6 mmol) and K$_2$CO$_3$ (1.6 g, 11.5 mmol) in DMF (15 mL). The reaction was stirred 18 h, then extracted with EtOAc, washed with water, brine and dried (MgSO$_4$). Purification through silica using (2:1) hexanes/EtOAc as eluent afforded 1.6 g of a white solid. A portion (100 mgs) of this solid was further purified by HPLC (C18 reverse phase column, elution with a H$_2$O/CH$_3$CN gradient with 0.5% TFA) and freeze-dried to afford 48 mg of the title compound of Example 65. HRMS (M+H)$^+$ for C$_{27}$H$_{19}$F$_4$N$_6$O$_3$: 551.1436; Analysis calc'd for C$_{27}$H$_{18}$F$_4$N$_6$O$_3$ (TFA)0.6: C:54.73; H:3.03; N:13.58; found C:54.71; H:3.10; N:13.55

Example 66

1-[4-Methoxyphenyl]-3-trifluoromethyl-6-[2'-(3-(R)-hydroxy-N-pyrrolidinyl)methyl-3-fluoro-[1,1']-biphen-4-yl]-1,4,5,6-tetrahydropyrazolo-[3,4-c]-pyridin-7-one trifluoroacetic acid salt

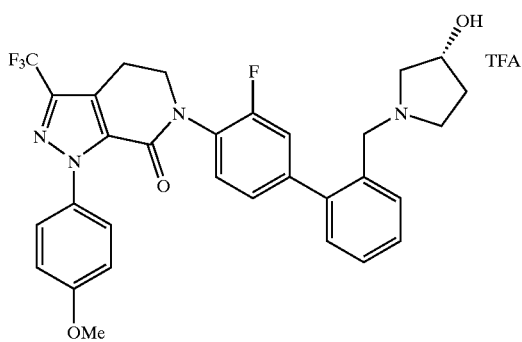

Part A. 1-[4-Methoxyphenyl]-3-trifluoromethyl-6-[4-bromo-2-fluorophenyl]-1,4,5,6-tetrahydropyrazolo-[3,4-c]-pyridin-7-one.

The trione intermediate from Example 53, Part B (0.49 g, 1.3 mmol) and 4-methoxyphenylhydrazine hydrochloride (0.29 g, 1.7 mmol) were heated to reflux in a mixture of MeOH (30 mL) and AcOH (10 mL) for 18 h. The reaction was cooled, concentrated and dissolved in EtOAc. The EtOAc layer was washed with NaHCO$_3$, brine, and dried (Na$_2$SO$_4$). Purification through silica using (4:1) hexanes/EtOAc as eluent afforded 0.22 g (35%) of the title compound as a yellow oil. LRMS (ES+): 484–486 (M+H)$^+$.

Part B. 1-[4-Methoxyphenyl]-3-trifluoromethyl-6-[2'-hydroxymethyl-3-fluoro-[1,1']-biphen-4-yl]-1,4,5,6-tetrahydropyrazolo-[3,4-c]-pyridin-7-one.

1-[4-Methoxyphenyl]-3-trifluoromethyl-6-[4-bromo-2-fluorophenyl]-1,4,5,6-tetrahydropyrazolo-[3,4-c]-pyridin-7-one (0.22 g, 0.45 mmol) was coupled with 2-formylphenyl boronic acid (0.102 g, 0.6 mmol) via Suzuki procedure. After 18 h the reaction was filtered, concentrated, and the crude aldehyde used in next step. LRMS (ES–): 508 (M–H)$^-$. To the aldehyde in MeOH (10 mL) at 0° C. was added NaBH$_4$ (21 mg, 0.5 mmol). After 2 h the reaction was quenched with water, extracted with EtOAc and dried (MgSO$_4$). Purification by chromatography on silica with (2:1) hexanes/EtOAc as eluent afforded 0.1 g (43%) of the title compound as a clear oil: $^1$H NMR (CDCl$_3$) □ 7.54 (m, 1H), 7.51 (d, j=9.1 Hz, 2H), 7.44–7.33 (m, 3H), 7.26–7.18 (m, 4H), 6.95 (d, j=9.2 Hz, 2H), 4.59 (s, 2H), 4.13 (m, 2H), 3.82 (s, 3H), 3.23 (t, j=6.6 Hz, 2H).

Part C. 1-[4-Methoxyphenyl]-3-trifluoromethyl-6-[2'-(3-(R)-hydroxy-N-pyrrolidinyl)methyl-3-fluoro-[1,1']-biphen-4-yl[-1,4,5,6-tetrahydropyrazolo-[3,4-c]-pyridin-7-one trifluoroacetic acid salt.

To a solution of 1-[4-methoxyphenyl]-3-trifluoromethyl-6-[2'-hydroxymethyl-3-fluoro-[1,1']-biphen-4-yl]-1,4,5,6-tetrahydropyrazolo-[3,4-c]-pyridin-7-one (0.1 g, 0.19 mmol) in CH$_2$Cl$_2$ (20 mL) was added PBr$_3$ (0.026 mL, 0.27 mmol) and the reaction was stirred 2 h. After quenching with ice water, the bromide was extracted with CH$_2$Cl$_2$, washed with brine and dried (Na$_2$SO$_4$). Acetonitrile (20 mL) and R-(3)-pyrrolidinol (85 mg, 0.97 mmol) were added to the crude bromide and the reaction was stirred 72 h. The reaction was concentrated and purification by HPLC (C18 reverse phase column, elution with a H$_2$O/CH$_3$CN gradient with 0.5% TFA) and freeze-drying afforded 90 mg (66%) of the title compound of Example 66 as a white solid: HRMS (M+H)$^+$ for C$_{31}$H$_{29}$F$_4$N$_4$O$_3$: 581.2191; $^1$H NMR (DMSO-d6) □ 7.78 (m,1H), 7.58(m, 3H), 7.53 (d, j=8.7 Hz, 2H), 7.41 (m, 2H), 7.27 (dd, j=8.1, 1.9 Hz, 1H), 7.05 (d, j=9.2 Hz, 2H), 4.49 (d, j=5.5 Hz, 1H), 4.38 (m, 2H), 4.13 t, j=5.5 Hz, 2H), 3.81 (s, 3H), 3.74–3.38 (m, 3H), 3.18 (t, j=6.2 Hz, 2H), 2.94 (m, 2H), 2.1–1.75 (m, 2H).

Example 67

1-[3-Aminomethylphenyl]-3-trifluoromethyl-6-[2'-methylsulfonyl-3-fluoro-[1,1']-biphen-4-yl]-1,4,5,6-tetrahydropyrazolo-[3,4-c]-pyridin-7-one trifluoroacetic acid salt

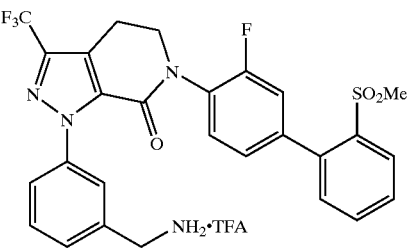

Part A. 1-[3-Cyanophenyl]-3-trifluoromethyl-6-[4-bromo-2-fluorophenyl]-1,4,5,6-tetrahydropyrazolo-[3,4-c]-pyridin-7-one.

The trione intermediate from Example 53, Part B (1.8 g, 4.7 mmol) and 3-cyanophenylhydrazine HCl (1 g, 6.1 mmol) were heated to reflux in MeOH (60 mL) and AcOH (15 mL) for 18 h. The solvents were removed and CH$_2$Cl$_2$/water added. The product was extracted with CH$_2$Cl$_2$, washed with brine and dried (Na$_2$SO$_4$). Purification by chromatography on silica with (2:1) hexanes/EtOAc as eluent afforded 1.26 g (56%) of the title compound. LRMS (ES–): 476.9–478 (M–H)$^-$.

Part B. 1-[3-Cyanophenyl]-3-trifluoromethyl-6-[2'-methylsulfonyl-3-fluoro-[1,1]-biphen-4-yl]-1,4,5,6-tetrahydropyrazolo-[3,4-c]-pyridin-7-one.

1-[3-Cyanophenyl]-3-trifluoromethyl-6-[4-bromo-2-fluorophenyl]-1,4,5,6-tetrahydropyrazolo-[3,4-c]-pyridin-7-one (1.2 g, 2.5 mmol) was coupled with 2-thiomethylphenyl boronic acid (1 g, 5.9 mmol) via Suzuki procedure. Purification by chromatography on silica with (2:1) hexanes/EtOAc as eluent afforded 1 g of a yellow foam. The thiomethyl intermediate was dissolved in CH$_2$Cl$_2$, cooled to 0° C. and oxidized with m-chloroperbenzoic acid (1.4 g, 4.6 mmol). After stirring for 24 h the reaction mixture was washed successively with sat'd sodium bisulfate, brine and dried (MgSO$_4$) to afford 0.73 g (52%) of the title compound as a yellow foam.

Part C. 1-[3-Aminomethylphenyl]-3-trifluoromethyl-6-[2'-methylsulfonyl-3-fluoro-[1,1']-biphen-4-yl]-1,4,5,6-tetrahydropyrazolo-[3,4-c]-pyridin-7-one trifluoroacetic acid salt.

1-[3-Cyanophenyl]-3-trifluoromethyl-6-[2'-methylsulfonyl-3-fluoro-[1,1']-biphen-4-yl]-1,4,5,6-tetrahydropyrazolo-[3,4-c]-pyridin-7-one (0.7 g, 1.3 mmol) was hydrogenated on the Parr at 45 psi in EtOH (30 mL) and TFA (2 mL) for 24 h. The reaction was filtered through Celite®, concentrated and purification by HPLC (C18 reverse phase column, elution with a H$_2$O/CH$_3$CN gradient with 0.5% TFA) and freeze-drying afforded 225 mg (26%) of the title compound of Example 67 as a white solid: HRMS (M+H)[30] for $C_{27}H_{23}F_4N_4O_3S$: 559.1449; $^1$H NMR (CDCl$_3$) ☐ 8.23 (s, 2H), 8.13 (dd, j=1.1, 7.7 Hz), 7.79–7.67 (m, 3H), 7.66–7.65 (m, 1H), 7.58 (s, 1H,+m, 2H), 7.44 (m, 2H), 7.33 (dd, j=1.8, 8 Hz, 1H), 4.17 (m, 4H), 3.18 (t, j=6.2 Hz, 2H), 2.94 (s, 3H).

Example 68

1-[4-Methoxyphenyl]-3-[(imidazol-1-yl)methyl]-5-methyl-6-[(2'-N-pyrrolidinylmethyl-[1,1']-biphen-4-yl)]-1,6-dihydropyrazolo-[4,3-d]-pyrimidin-7-one, bis-trifluoroacetic acid salt

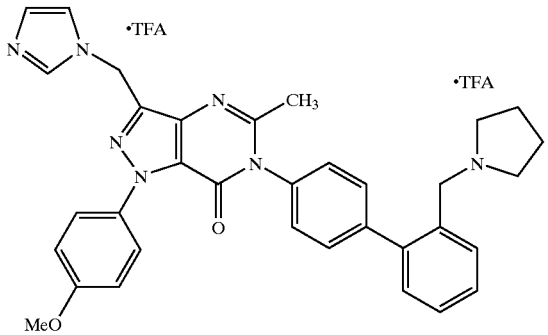

Part A. 1-(4-Methoxyphenyl)-3-(ethoxycarbonyl)-5-methyl-6-[(4-bromophenyl)]-1,6-dihydropyrazolo-[4,3-d]-pyrimidin-7-one.

To a solution of 1-(4-Methoxyphenyl)-3-(ethoxycarbonyl)-4-azido-5-[(4-bromophenyl) aminocarbonyl]pyrazole from Example 11, Part A (2.00 g, 4:12 mmol) in ethanol was added tin (II) chloride dihydrate (3.7 g, 16.5 mmol) and the solution was stirred at reflux for 1 h. The solution was filtered through a pad of silica gel and the silica rinsed with EtOAc. The volatiles were removed under reduced pressure and the residue was taken up in ethyl acetate, washed with 1N sodium hydroxide and brine, dried (MgSO$_4$) and concentrated. The residue was refluxed for 2 hours in 10 mL of N,N-dimethylacetamide dimethyl acetal. The volatiles were removed under reduced pressure and the solid residue was taken up in 20 mL of glacial acetic acid and stirred at reflux for 2 h. The reaction was cooled and concentrated, and the residue was taken up in ethyl acetate, washed with saturated sodium bicarbonate and brine, dried (MgSO$_4$) and concentrated to afford 1.5 g (75%) of the title compound as a solid. LRMS (ES+): 483.0/485.0 (M+H)+.

Part B. 1-(4-Methoxyphenyl)-3-(hydroxymethyl)-5-methyl-6-[(4-bromophenyl)]-1,6-dihydropyrazolo-[4,3-d]-pyrimidin-7-one.

To a solution of 1-(4-Methoxyphenyl)-3-(ethoxycarbonyl)-5-methyl-6-[(4-bromophenyl)]-1,6-dihydropyrazolo-[4,3-d]-pyrimidin-7-one (0.74 g, 1.53 mmol) in 20 mL of 1:1:1 methanol/THF/water was added potassium hydroxide (94 mg, 1.68 mmol) and the reaction was stirred at reflux for 2 h. The reaction was cooled to ambient temperature, diluted with water and extracted with hexanes/ethyl acetate (1:1). The aqueous layer was acidified with 1N HCl and extracted with ethyl acetate. This extract was washed with brine, dried (MgSO$_4$) and concentrated to afford 0.57 g (81%) of the carboxylic acid. This acid (0.57 g, 1.25 mmol) was taken up in THF at 0° C. and then there was added N-methylmorpholine (0.19 mL, 1.38 mmol) and isobutyl chloroformate (0.18 mL, 1.38 mmol). After stirring for 20 min there was added sodium borohydride (95 mg, 2.5 mmol) and the reaction was allowed to stir for 2 h. The reaction was quenched with excess 1N HCl and diluted with ethyl acetate. The organics were washed with brine, dried (MgSO$_4$) and concentrated. The residue was purified by flash chromatography (elution with 2:1 hexanes/ethyl acetate) to afford 0.40 g (73%) of the title compound.

Part C. 1-(4-Methoxyphenyl)-3-[(imidazol-1-yl)methyl]-5-methyl-6-[(4-bromophenyl)]-1,6-dihydropyrazolo-[4,3-d]-pyrimidin-7-one.

To a solution of 1-(4-Methoxyphenyl)-3-(hydroxymethyl)-5-methyl-6-[(4-bromophenyl)1-1,6-dihydropyrazolo-[4,3-d]-pyrimidin-7-one (0.19 g, 0.43 mmol) in 10 mL of methylene chloride was added phosphorous tribromide (0.23 g, 0.86 mmol) and the solution was allowed to stir at ambient temperature for 3 h. The reaction was quenched with water, diluted with ethyl acetate, washed with brine, dried (MgSO$_4$) and concentrated to afford a crude bromide, which was used without purification. This residue (0.17 g, 0.34 mmol) was taken up in 5 mL of DMF and then there was added imidazole (0.046 g, 0.67 mmol). The reaction was allowed to stir at ambient temperature for 16 h. The reaction was diluted with ethyl acetate, washed with brine, dried (MgSO$_4$) and concentrated to afford 160 mg (76%) of the title compound, which was sufficiently pure to be used without purification. LRMS (ES+): 491.1/493.1 (M+H)+.

Part D. 1-[4-Methoxyphenyl]-3-[(imidazol-1-yl)methyl]-5-methyl-6-[(2'-formyl-[1,1']-biphen-4-yl)]-1,6-dihydropyrazolo-(4,3-d]-pyrimidin-7-one.

To a solution of 1-(4-Methoxyphenyl)-3-[(imidazol-1-yl)methyl]-5-methyl-6-[(4-bromophenyl)]-1,6-dihydropyrazolo-[4,3-d]-pyrimidin-7-one (0.16 g, 0.33 mmol) in 10 mL of 1,$_4$-dioxane was added 2-formylphenylboronic acid (0.073 g, 0.49 mmol) and potassium phosphate tribasic (0.24 g, 1.15 mmol). This mixture was degassed with a stream of nitrogen for 15 minutes. Following the purge, tetrakis(triphenylphosphine) palladium (0) (0.038 g) was added and the solution was stirred at 100° C. for 4 h. The solution was cooled, diluted with EtOAc, washed twice with brine and the organics were dried over MgSO$_4$, filtered through a pad of silica gel and concentrated. The residue was purified by flash chromatography (elution with 2:1 hexanes/ethyl acetate) to afford 0.08 g (47%) of the title compound. LRMS (ES+): 517.2 (M+H)+.

Part E. 1-[4-Methoxyphenyl]-3-[(imidazol-1-yl)methyl]-5-methyl-6-[(2'-N-pyrrolidinylmethyl-[1,1']-biphen-4-yl)]-1,6-dihydropyrazolo-[4,3-d]-pyrimidin-7-one, bis-trifluoroacetic acid salt.

To a solution of 1-[4-Methoxyphenyl]-3-[(imidazol-1-yl) methyl]-5-methyl-6-[(2'-formyl-[1,1']-biphen-4-yl)]-1,6-dihydropyrazolo-[4,3-d]-pyrimidin-7-one (80 mg, 0.15 mmol) in 5 mL of THF was added pyrrolidine (0.05 mL, 0.60 mmol) and then sodium triacetoxyborohydride (64 mg, 0.3 mmol) and 2 drops of glacial acetic acid. The reaction was allowed to stir at ambient temperature for 3 h. The reaction was quenched with water and diluted with ethyl acetate and saturated aqueous NaHCO$_3$. The organics were washed with brine, dried (MgSO$_4$) and concentrated. The residue was purified by prep HPLC (C18 reverse phase column, elution with a H$_2$O/CH$_3$CN gradient with 0.5% TFA) and lyophilized to afford 28 mg (24%) of the title compound of Example 68. LRMS (ES+): 572.4 (M+H)+.

Examples 69 and 70

1-[4-Methoxyphenyl]-3-[(tetrazol-1-yl)methyl]-5-methyl-6-[(2'-N-pyrrolidinylmethyl-[1,1']-biphen-4-yl)]-1,6-dihydropyrazolo-[4,3-d]-pyrimidin-7-one, trifluoroacetic acid salt (Example 69) and 1-[4-Methoxyphenyl]-3-[(tetrazol-2-yl)methyl]-5-methyl-6-[(2'-N-pyrrolidinylmethyl-[1,1']-biphen-4-yl)]-1,6-dihydropyrazolo-[4,3-d]-pyrimidin-7-one, trifluoroacetic acid salt (Example 70)

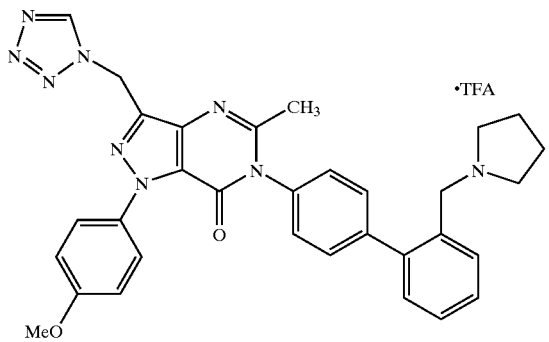

Example 69

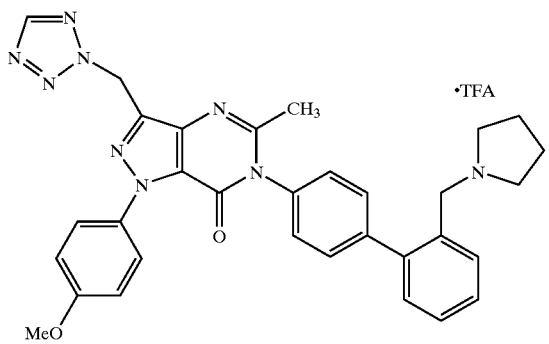

Example 70

Part A. 1-(4-Methoxyphenyl)-3-[(tetrazol-1-yl)methyl]-5-methyl-6-[(4-bromophenyl)-1,6-dihydropyrazolo-[4,3-d]-pyrimidin-7-one and 1-(4-Methoxyphenyl)-3-[(tetrazol-2-yl)methyl]-5-methyl-6-[(4-bromophenyl)]-1,6-dihydropyrazolo-[4,3-d]-pyrimidin-7-one To a solution of 1-(4-Methoxyphenyl)-3-(hydroxymethyl)-5-methyl-6-[(4-bromophenyl)]-1,6-dihydropyrazolo-[4,3-d]-pyrimidin-7-one (0.20 g, 0.45 mmol) in 10 mL of methylene chloride was added phosphorous tribromide (0.25 g, 0.90 mmol) and the solution was allowed to stir at ambient temperature for 3 h. The reaction was quenched with water, diluted with ethyl acetate, washed with brine, dried (MgSO$_4$) and concentrated to afford a crude bromide, which was used without purification. This residue was taken up in 5 mL of DMF and then there was added tetrazole (0.032 g, 0.45 mmol) and potassium carbonate (0.12 g, 0.90 mmol). The reaction was allowed to stir at ambient temperature for 16 h. The reaction was diluted with ethyl acetate, washed with water and brine, dried (MgSO$_4$) and concentrated to afford 180 mg (81%) of an approximately 1:1 mixture of the title compounds, which was sufficiently pure to be used without purification.

Part B. 1-[4-Methoxyphenyl]-3-[(tetrazol-1-yl)methyl]-5-methyl-6-[(2'-N-pyrrolidinylmethyl-[1,1']-biphen-4-yl)]-1,6-dihydropyrazolo-[4,3-d]-pyrimidin-7-one, trifluoroacetic acid salt (Example 69) and 1-[4-Methoxyphenyl]-3-[(tetrazol-2-yl)methyl]-5-methyl-6-[(2'-N-pyrrolidinylmethyl-[1,1']-biphen-4-yl)]-1,6-dihydropyrazolo-[4,3-d]-pyrimidin-7-one, trifluoroacetic acid salt (Example 70).

Following the procedures described in Example 68, Parts D and E, 1-(4-Methoxyphenyl)-3-[(tetrazol-1-yl)methyl]-5-methyl-6-[(4-bromophenyl)]-1,6-dihydropyrazolo-[4,3-d]-pyrimidin-7-one and 1-(4-Methoxyphenyl)-3-[(tetrazol-2-yl)methyl]-5-methyl-6-[(4-bromophenyl)]-1,6-dihydropyrazolo-[4,3-d]-pyrimidin-7-one were converted into the title compounds of Examples 69 and 70. The final products were separated by prep HPLC (C18 reverse phase column, elution with a H$_2$O/CH$_3$CN gradient with 0.5% TFA) and lyophilized to afford 11 mg of the title compound of Example 69 and 5 mg of the title compound of Example 70. Example 69: LRMS (ES+): 574.3 (M+H)$^+$. Example 70: LRMS (ES+): 574.3 (M+H)$^+$.

Example 71

1-[3-Aminobenzisoxazol-5'-yl]-3,5-dimethyl-6-[2'-N-dimethylaminomethyl-[1,1']-biphen-4-yl]-1,6-dihydropyrazolo-[4,3-d]-pyrimidin-7-one, trifluoroacetic acid salt

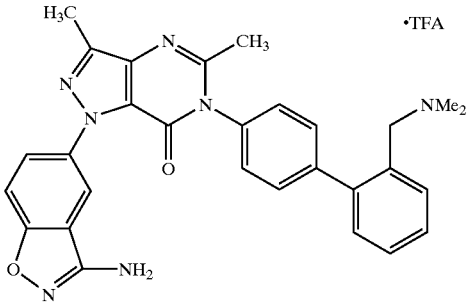

Part A. Ethyl[1-(3-cyano-4-fluoro)phenyl]-3-methyl-4-nitro pyrazole-5-carboxylate.

Ethyl [1-(3-cyano-4-fluoro)phenyl]-3-methylpyrazole-5-carboxylate (32.3 g, 118.21 mmol) was dissolved in 200 ml of trifluoroacetic acid followed by the addition of trifluoroacetic acid anhydride (116.9 ml, 827.48 mmol) and the resulting solution was cooled to 0° C. Ammonium nitrate (18.92, 236.42 mmol) was added slowly in 4 portions and allowed to stir overnight with warming to ambient temperature. The solution was neutralized with aq K$_2$CO$_3$ and the product was extracted with EtOAc. The organics were dried over MgSO$_4$, filtered through a plug of silica gel and the volatiles removed in vacuo to afford 35.0 g (93%) of the title compound. LRMS (NH$_3$-DCI): 336.2 (M+NH$_4$)$^+$.

Part B. [1-(3-cyano-4-fluoro)phenyl]-3-methyl-4-nitropyrazole-5-carboxylic acid.

Ethyl 1-(3-cyano-4-fluoro)phenyl-3-methyl-4-nitropyrazole-5-carboxylate (17.5 g, 54.99 mmol) was dissolved in 250 ml of methanol and cooled to 0° C. followed by the addition of lithium hydroxide (1.31 g, 54.99 mmol) that was pre-dissolved in a minimum amount of water. The solution was allowed to warm to RT. The reaction was followed by TLC and was complete within 2 hrs. The product was extracted with water and acidified with dilute HCl. The product was extracted with EtOAc and dried over MgSO$_4$, and the volatiles were removed in vacuo to afford 12.5 g (78%) of the title compound. LRMS (ES-): 579.2 (2M-H)$^-$.

Part C. [1-(3-cyano-4-fluoro)phenyl]-3-methyl-4-nitro-5-[(4-bromophenyl)aminocarbonyl]pyrazole.

[1-(3-Cyano-4-fluoro)phenyl]-3-methyl-4-nitropyrazole-5-carboxylic acid (11.5 g, 39.63 mmol) was dissolved in 300 ml of a 1:1 mixture of CH$_2$Cl$_2$/THF followed by the addition of 5.18 ml (59.44 mmol) of oxalyl chloride and 1 drop of DMF. This mixture was stirred at ambient temperature for 2 h. The volatiles were removed and the crude acid chloride was dried under high vacuum for 1 h. The acid chloride was then dissolved in 200 ml of CH₂Cl₂ followed by the addition of 4-bromoaniline (6.13 g, 35.66 mmol) and DMAP (14.52 g, 118.89 mmol) and the resulting mixture was stirred at ambient temperature for 16 h. The solution was filtered through a plug of silica gel and the volatiles were removed. The crude product was dissolved in a minimal amount of EtOAc and triturated with ethyl ether to afford 8.98 g (78%) of the title compound. LRMS (ES⁻): 414.1 (M−H)⁻.

Part D. [1-(3-cyano-4-fluoro)phenyl]-3-methyl-4-amino-5-[(4-bromophenyl) aminocarbonyl]pyrazole.

[1-(3-Cyano-4-fluoro)phenyl]-3-methyl-4-nitro-5-[(4-bromophenyl)aminocarbonyl]pyrazole (7.98 g, 17.96 mmol) was dissolved in 300 ml of methanol and cooled in an ice/water bath followed by the addition of CuCl (21.34 g, 215.59 mmol) and the slow addition of NaBH₄ (13.56 g, 251.52 mmol) and stirred with warming to ambient temperature over 2 h. The solution was poured through a pad of silica gel and the volatiles removed to yield 7.11 g (95%) of the title compound that was sufficiently pure to be used without purification.

Part E. [E-(3-cyano-4-fluoro)phenyl]-3,5-dimethyl-6-(4-bromophenyl)-1,6-dihydropyrazolo-[4,3-d]-pyrimidin-7-one.

[1-(3-Cyano-4-fluoro)phenyl]-3-methyl-4-amino-5-[(4-bromophenyl)aminocarbonyl]pyrazole (4.00 g, 9.65 mmol) was refluxed in a neat solution of N,N-dimethylacetamide dimethyl acetal (50 ml) for 1 h. The volatiles were removed in vacuo and the crude intermediate was then refluxed in 100 ml of glacial acetic acid for 1 h. The volatiles were removed in vacuo and the residue was washed with ethyl ether and dried to afford 2.2 g (53%) of the title compound.

Part F. 1-[3-Aminobenzisoxazol-5'-yl]-3,5-dimethyl-6-[2'-formyl-[1,1']-biphen-4-yl]-1,6-dihydropyrazolo-[4,3-d]-pyrimidin-7-one.

Following the procedures described in Example 47, Part C, [1-(3-cyano-4-fluoro)phenyl]-3,5-dimethyl-6-(4-bromophenyl)-1,6-dihydropyrazolo-[4,3-d]-pyrimidin-7-one was converted into the title compound.

Part G. 1-[3-Aminobenzisoxazol-5'-yl]-3,5-dimethyl-6-[2'-N-dimethylaminomethyl-[1,1']-biphen-4-yl]-1,6-dihydropyrazolo-[4,3-d]-pyrimidin-7-one, trifluoroacetic acid salt.

1-(3-Aminobenzisoxazol-5'-yl]-3,5-dimethyl-6-[2'-formyl-[1,1']-biphen-4-yl]-1,6-dihydropyrazolo-[4,3-d]-pyrimidin-7-one (0.80 g, 1.67 mmol) was dissolved in 100 ml of 1:1 CHCl₃/THF followed by the addition of a 2.0M solution of dimethyl amine in methanol (3.3 ml, 6.71 mmol) and 1 ml of HOAc. The solution was stirred at ambient temperature for 10 min followed by the addition of sodium triacetoxyborohydride (0.71 g, 3.35 mmol) and the solution was stirred at ambient temperature overnight. After 18 h at ambient temperature more CHCl₃ was added (100 mL) and the organics washed with water, dried (MgSO₄) and evaporated. The residue was purified by prep HPLC (C18 reverse phase column, elution with a H₂O/CH₃CN gradient with 0.5% TFA) and lyophilized to afford the title compound of Example 71 as a white solid. LRMS (ES⁺): 506.2 (M+H)⁺.

Example 72

1-[3-Aminobenzisoxazol-5'-yl]-3-methyl-6-[2'-N,N-dimethylaminomethyl-[1,1']-biphen-4-yl]-1,6-dihydropyrazolo-[4,3-d]-pyrimidin-7-one, trifluoroacetic acid salt

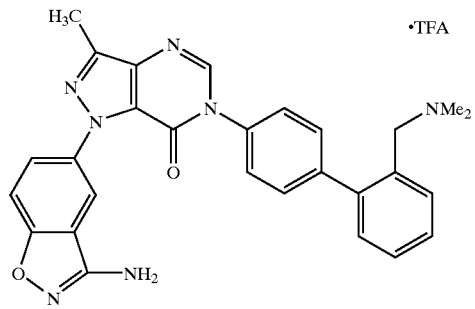

Part A. [1-(3-cyano-4-fluoro)phenyl]-3-methyl-6-(4-bromophenyl)-1,6-dihydropyrazolo-[4,3-d]-pyrimidin-7-one.

[1-(3-Cyano-4-fluoro)phenyl]-3-methyl-4-amino-5-[(4-bromophenyl)aminocarbonyl]pyrazole from Example 71, Part D (2.48 g, 5.58 mmol) was refluxed in 100 ml of 96% formic acid for 2 h. The volatiles were removed under vacuum, the crude product was washed with a small amount of methanol and the product was filtered and dried to afford 2.04 g (86%) of the title compound.

Part B. 1-[3-Aminobenzisoxazol-5'-yl]-3-methyl-6-[2'-formyl-[1,1']-biphen-4-yl]-1,6-dihydropyrazolo-[4,3-d]-pyrimidin-7-one.

Following the procedures described in Example 47, Part C, [1-(3-cyano-4-fluoro)phenyl]-3-methyl-6-(4-bromophenyl)-1,6-dihydropyrazolo-[4,3-d]-pyrimidin-7-one was converted into the title compound.

Part G. 1-[3-Aminobenzisoxazol-5'-yl]-3-methyl-6-[2'-N,N-dimethylaminomethyl-[1,1']-biphen-4-yl]-1,6-dihydropyrazolo-[4,3-d]-pyrimidin-7-one, trifluoroacetic acid salt.

Following the procedure described in Example 71, Part G, 1-[3-Aminobenzisoxazol-5'-yl]-3-methyl-6-[2'-formyl-[1,1']-biphen-4-yl]-1,6-dihydropyrazolo-[4,3-d]-pyrimidin-7-one was converted into the title compound of Example 72 as a white solid. LRMS (ES⁺): 492.2 (M+H)⁺.

Example 73

1-[3-Aminobenzisoxazol-5'-yl]-3-methyl-6-[2'-N-isopropylaminomethyl-[1,1']-biphen-4-yl]-1,6-dihydropyrazolo-[4,3-d]-pyrimidin-7-one, trifluoroacetic acid salt

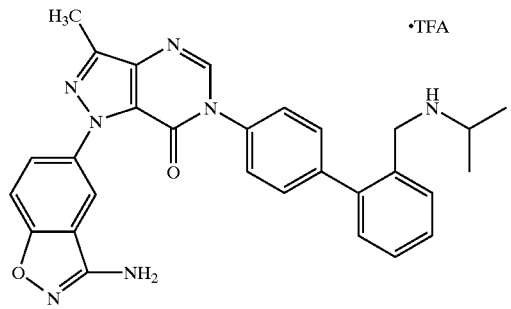

To a solution of 1-[(3-aminobenzisoxazol-5'-yl]-3-methyl-6-[2'-(hydroxymethyl)-[1,1']-biphen-4-yl]-1,6- dihydropyrazolo-[4,3-d]-pyrimidin-7-one, an intermediate from Example 72, Part B, (0.70 g, 1.57 mmol) in 200 mL of methylene chloride was added phosphorous tribromide (2.85 ml, 4.71 mmol) and the solution was stirred at ambient temperature for 2 h. The reaction was quenched by the addition of saturated $K_2CO_3$ solution and the product extracted using EtOAc. The bromide was dried using $MgSO_4$, filtered and dried under vacuum. A portion of the crude bromide (0.14 g, 0.26 mmol) was dissolved in 100 ml of $CH_3CN$ followed by the addition of isopropyl amine (0.22 mL, 2.5 mmol) and the resulting mixture was stirred overnight. The volatiles were removed in vacuum and the product purified by prep HPLC (C18 reverse phase column, elution with a $H_2O/CH_3CN$ gradient with 0.5% TFA) and lyophilized to afford the title compound of Example 73 as a white solid. LRMS (ES+): 506.2 (M+H)+.

Example 74

1-[3-Aminobenzisoxazol-5'-yl]-3-methyl-6-[2'-(3-(R)-hydroxy-N-pyrrolidinyl)methyl-[1,1']-biphen-4-yl]-1,6-dihydropyrazolo-[4,3-d]-pyrimidin-7-one, trifluoroacetic acid salt

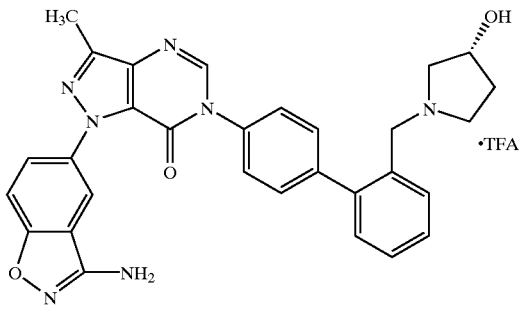

To a portion of the crude bromide from Example 73 (0.14 g, 0.26 mmol) in 100 ml of $CH_3CN$ was added (R)-3-hydroxypyrrolidine hydrochloride (0.32 g, 2.6 mmol) and potassium carbonate (0.88 g, 6.40 mmol) and the reaction stirred at ambient temperature overnight. The volatiles were removed in vacuo and the product purified by prep HPLC (C18 reverse phase column, elution with a $H_2O/CH_3CN$ gradient with 0.5% TFA) and lyophilized to afford the title compound of Example 74 as a white solid. LRMS (ES+): 534.2 (M+H)+.

Example 75

1-[3-Aminobenzisoxazol-5'-yl]-3-methyl-6-[4-(4,5-dihydroimidazol-1'-yl)phenyl]-1,6-dihydropyrazolo-[4,3-d]-pyrimidin-7-one, trifluoroacetic acid salt

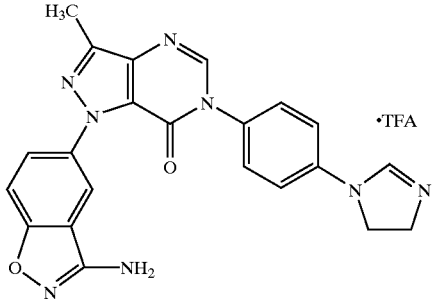

Part A. [N-(4-nitrophenyl)-N'-tert-butyloxycarbonyl]ethylene diamine.

To a solution of 4-fluoro-nitrobenzene (3.31 ml, 31.21 mmol) in 200 mL of THF was added 2-N-BOC ethylene diamine (5.0 g, 31.21 ml) and DMAP (5.72 g, 46.81 mmol) and the reaction was allowed to stir at ambient temperature overnight. The volatiles were removed and the residue was purified by flash column chromatography (elution with 1:1 hexane/EtOAc) to afford 4.17 g (47%) of the title compound.

Part B. [N-(4-aminophenyl)-N'-tert-butyloxycarbonyl]ethylene diamine.

[N-(4-nitrophenyl)-N'-tert-butyloxycarbonyl]ethylene diamine (4.17 g, 14.82 mmol) was dissolved in 100 ml of MeOH followed by the addition of 10% Pd/C (0.42 g) and placed on a Parr shaker under 55 psi of $H_2$ for 1 h. The solution was filtered through a pad of Celite and the volatiles were removed to afford 3.35 g (90%) of the title compound. LRMS (ES+): 252.4 (M+H)+.

Part C. [1-(3-cyano-4-fluoro)phenyl]-3-methyl-4-nitro-5-[[4-(2-N-(tert-butoxycarbonyl)aminoethylamino)phenyl]aminocarbonyl]pyrazole

[1-(3-Cyano-4-fluoro)phenyl]-3-methyl-4-nitropyrazole-5-carboxylic acid from Example 71, Part B (1.00 g, 3.44 mmol) was dissolved in 100 ml of 1:1 $CH_2Cl_2$/THF followed by the addition of oxalyl chloride (0.45 ml, 5.16 mmol) and 1 ml of DMF and the reaction was stirred at ambient temperature for 2 h. The volatiles were removed under vacuum and the crude acid chloride was dried under high vacuum for 1 hr. The residue was then dissolved in 100 ml of $CH_2Cl_2$ followed by the addition [N-(4-aminophenyl)-N'-tert-butyloxycarbonyl]ethylene diamine (0.87 g, 3.44 mmol) and DMAP (1.26 g, 10.33 mmol). The solution was allowed to stir overnight. The volatiles were removed under reduced pressure and the residue was purified by flash column chromatography (eluting with 1:1 hexane/EtOAc) to afford 1.15 g (64%) of the title compound. LRMS (ES+): 524.2 (M+H)+.

Part D. 1-[3-Aminobenzisoxazol-5'-yl]-3-methyl-6-[4-(4,5-dihydroimidazol-1'-yl)phenyl]-1,6-dihydropyrazolo-[4,3-d]-pyrimidin-7-one, trifluoroacetic acid salt.

To a solution of the product of Part C (1.15 g, 2.19 mol) in 100 ml of methanol was added CuCl (2.60 g, 26.63 mmol) and $KBH_4$ (1.66 g, 30.75 mmol). The reaction was stirred at rt for 2 h and the solution filtered through a pad of silica gel and the volatiles removed. The residue was dissolved in 100 ml of 96% formic acid and refluxed for 6 h. The volatiles were removed and the residue washed with a small amount of methanol and filtered. The residue was dissolved in 50 ml of DMF and 2 ml of $H_2O$ and then there was added acetohydroxamic acid (0.14 g, 1.88 mmol) and potassium carbonate (0.35 g, 2.51 mmol) the reaction was stirred at rt overnight. Ethyl ether was added to the reaction and the product washed twice with brine and the product dried over $MgSO_4$ and the volatiles removed under vacuum. The product was purified using prep HPLC (C18 reverse phase column, elution with a $H_2O/CH_3CN$ gradient with 0.5% TFA) and lyophilized to afford the title compound of Example 75 as a white solid. LRMS (ES+): 427.1 (M+H)+.

Example 76

1-[3-Aminobenzisoxazol-5'-yl]-3-methyl-6-[2'-N-(cyclopropylmethyl)aminomethyl-[1,1']-biphen-4-yl]-1,6-dihydropyrazolo-[4,3-d]-pyrimidin-7-one, trifluoroacetic acid salt

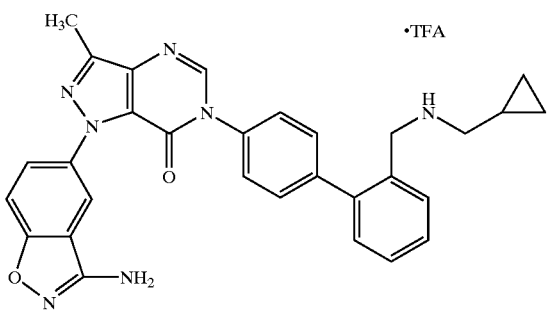

To the crude bromide from Example 73 (0.03 g, 0.056 mmol) in 100 ml of $CH_3CN$ was added (aminomethyl) cyclopropane (0.005 mL, 0.056 mmol) and the reaction stirred at ambient temperature overnight. The volatiles were removed in vacuo and the product purified by prep HPLC (C18 reverse phase column, elution with a $H_2O/CH_3CN$ gradient with 0.5% TFA) and lyophilized to afford the title compound of Example 76 as a white solid. LRMS (ES+): 518.2 (M+H)+.

Example 77

1-[3-Aminobenzisoxazol-5'-yl]-3-methyl-6-[2'-N-pyrrolidinylmethyl-[1,1']-biphen-4-yl]-1,6-dihydropyrazolo-(4,3-d]-pyrimidin-7-one, trifluoroacetic acid salt

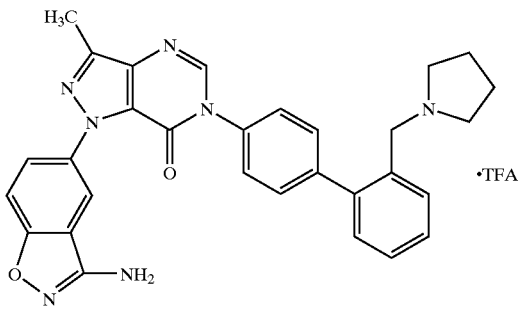

Following the procedure described in Example 47, Part D, 1-[3-Aminobenzisoxazol-5'-yl]-3-methyl-6-[2'-formyl-[1,1']-biphen-4-yl]-1,6-dihydropyrazolo-[4,3-d]-pyrimidin-7-one from Example 72, Part B was converted into the title compound of Example 77. LRMS (ES+): 518.2 (M+H)+.

Example 78

1-[3-Aminobenzisoxazol-5'-yl]-3-methyl-6-[2'-(N-methyl-N-isopropyl)aminomethyl-[1,1']-biphen-4-yl]-1,6-dihydropyrazolo-[4,3-d]-pyrimidin-7-one, trifluoroacetic acid salt

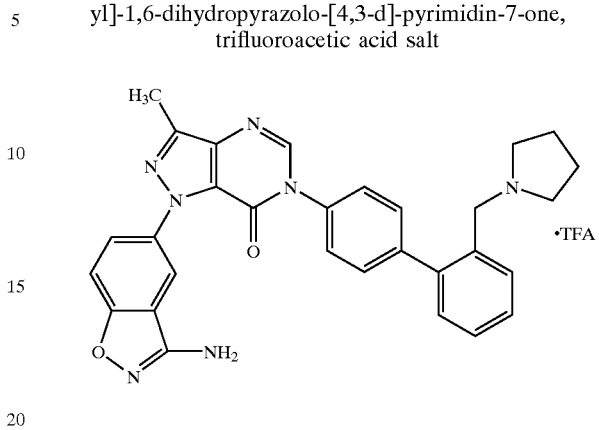

To a solution of 1-[(3-aminobenzisoxazol-5'-yl]-3-methyl-6-[2'-formyl-[1,1']-biphen-4-yl]-1,6-dihydropyrazolo-[4,3-d]-pyrimidin-7-one from Example 72, Part B (0.21 g, 0.44 mmol) in 100 ml of 1:1 $CHCl_3/THF$ was added N-methyl-N-isopropyl amine (0.18 ml, 1.76 mmol) and 1 ml of HOAc. The solution was stirred at rt for 10 min followed by the addition of sodium triacetoxyborohydride (0.18 g, 0.88 mmol) and the solution was stirred at rt overnight. The reaction was quenched with water, extracted with ethyl acetate, and the extracts were washed with brine, dried ($MgSO_4$) and concentrated in vacuo. The residue was purified by prep HPLC (C18 reverse phase column, elution with a $H_2O/CH_3CN$ gradient with 0.5% TFA) and lyophilized to afford the title compound of Example 78 as a white solid. LRMS (ES+): 534.1 (M+H)+.

Example 79

1-[3-Aminobenzisoxazol-5'-yl]-3,5-dimethyl-6-[2'-(3-(R)-hydroxy-N-pyrrolidinyl)methyl-[1,1']-biphen-4-yl]-1,6-dihydropyrazolo-[4,3-d]-pyrimidin-7-one, trifluoroacetic acid salt

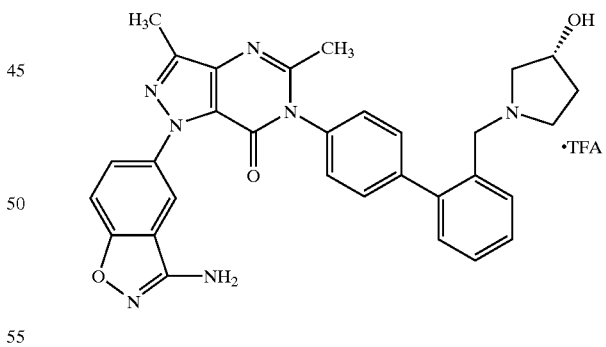

To a solution of 1-[(3-aminobenzisoxazol-5'-yl]-3,5-dimethyl-6-[2'-formyl-[1,1']-biphen-4-yl]-1,6-dihydropyrazolo-[4,3-d]-pyrimidin-7-one from Example 71, Part F (0.30 g, 0.63 mmol) in 100 ml of 50 mL of THF was added (R)-3-hydroxypyrrolidine (0.22 g, 2.52 mmol) and 1 ml of HOAc. The solution was stirred at rt for 10 min followed by the addition of sodium triacetoxyborohydride (0.27 g, 1.26 mmol) and the solution was stirred at rt overnight. The reaction was quenched with water, extracted with ethyl acetate, and the extracts were washed with brine, dried ($MgSO_4$) and concentrated in vacuo. The residue was purified by prep HPLC (C18 reverse phase column, elution

Example 80

1-[3-Aminobenzisoxazol-5'-yl]-3-trifluoromethyl-6-[2'-N,N-dimethylaminomethyl-[1,1']-biphen-4-yl]-1,6-dihydropyrazolo-[4,3-d]-pyrimidin-7-one, trifluoroacetic acid salt

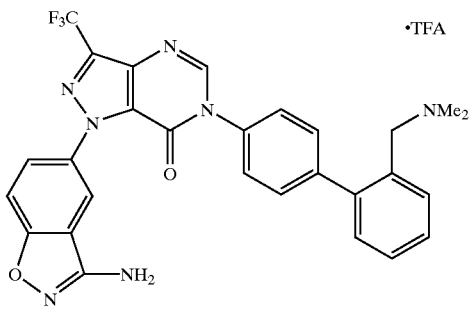

Part A. 1-(3-Cyano-4-fluorophenyl)]-3-trifluoromethyl-4-nitro-pyrazole-5-carboxylic acid.

To a solution of ammonium nitrate (2.4 g, 0.03 mol) in 100 mL of trifluoroacetic acid at 0° C. was added 1-(4-fluoro-3-cyano)phenyl-3-trifluoromethyl-pyrazole-5-carboxylic acid (6.0 g, 0.02 mol). This mixture was stirred for 15 min to dissolve the acid and then there was added trifluoroacetic anhydride (14.1 mL, 0.10 mol). The resulting mixture was allowed to stir with warming to ambient temperature for 72 h. The reaction mixture was poured into water, extracted with ethyl acetate, washed with brine, dried (MgSO$_4$) and concentrated to afford an approximately 2:1 mixture of product and starting material, which were separated in the following way. The residue was stirred in 400 mL of water for several hours and the solids were filtered and dried, yielding a mixture of product and recovered starting material. The filtrate was extracted with ethyl acetate, washed with brine, dried (MgSO$_4$) and concentrated to afford 1.5 g (22%) of pure title compound. The solids were resubjected to the purification procedure to afford an additional 2.0 g (29%) of the title compound. $^1$H NMR (CD$_3$OD): □ 8.13 (dd, 1H), 8.02 (m, 1H), 7.58 (t, 1H).

Part B. [1-(3-cyano-4-fluorophenyl)]-3-trifluoromethyl-6-[2'-formyl-[1,1']-biphen-4-yl]-1,6-dihydropyrazolo-[4,3-d]-pyrimidin-7-one.

Following procedures described in Example 71, Part D, Example 72, Part A and Example 47, Part C, [1-(3-cyano-4-fluorophenyl)]-3-trifluoromethyl-4-nitro-pyrazole-5-carboxylic acid was converted into the title compound.

Part C. [1-(3-cyano-4-fluorophenyl)]-3-trifluoromethyl-6-[2'-hydroxymethyl-[1,1']-biphen-4-yl]-1,6-dihydropyrazolo-[4,3-d]-pyrimidin-7-one and [1-(3-cyano-4-fluorophenyl)]-3-trifluoromethyl-6-[2'-hydroxymethyl-[1,1']-biphen-4-yl]-1,4,5,6-tetrahydropyrazolo-[4,3-d]-pyrimidin-7-one.

To a solution of [1-(3-cyano-4-fluorophenyl)]-3-trifluoromethyl-6-[2'-formyl-[1,1']-biphen-4-yl]-1,6-dihydropyrazolo-[4,3-d]-pyrimidin-7-one (0.59 g, 1.17 mmol) in 100 mL of THF was added sodium borohydride (0.04 g, 1.17 mmol). The reaction was stirred at ambient temperature for 3 h and then was filtered through Celite, diluted with ethyl acetate, washed with water and brine, dried (MgSO$_4$) and concentrated. Purification by flash chromatography (elution with 2:1 hexanes/ethyl acetate) afforded 0.13 g of [1-(3-cyano-4-fluorophenyl)]-3-trifluoromethyl-6-[2'-hydroxymethyl-[1,1']-biphen-4-yl]-1,6-dihydropyrazolo-[4,3-d]-pyrimidin-7-one and 0.12 g of the over reduction product, [1-(3-cyano-4-fluorophenyl)]-3-trifluoromethyl-6-[2'-hydroxymethyl-[1,1']-biphen-4-yl]-1,4,5,6-tetrahydropyrazolo-[4,3-d]-pyrimidin-7-one.

Part D. 1-[3-Aminobenzisoxazol-5'-yl]-3-trifluoromethyl-6-[2'-N,N-dimethylaminomethyl-[1,1']-biphen-4-yl]-1,6-dihydropyrazolo-[4,3-d]-pyrimidin-7-one, trifluoroacetic acid salt.

Following procedures described in Example 47, Part C and Example 71, Part G. [1-(3-cyano-4-fluorophenyl)]-3-trifluoromethyl-6-[2'-hydroxymethyl-[1,1']-biphen-4-yl]-1,6-dihydropyrazolo-[4,3-d]-pyrimidin-7-one was converted into the title compound of Example 80. LRMS (ES$^+$): 546.3 (M+H)$^+$.

Example 81

1-[3-Aminobenzisoxazol-5'-yl]-3-trifluoromethyl-6-[2'-N,N-dimethylaminomethyl-[1,1']-biphen-4-yl]-1,4,5,6-tetrahydropyrazolo-[4,3-d]-pyrimidin-7-one, trifluoroacetic acid salt

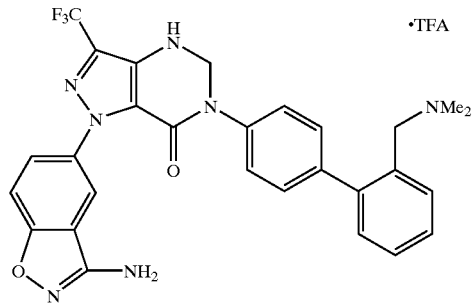

Following procedures described in Example 47, Part C and Example 71, Part G, the over reduction product [1-(3-cyano-4-fluorophenyl)]-3-trifluoromethyl-6-[2'-hydroxymethyl-[1,1']-biphen-4-yl]-1,4,5,6-tetrahydropyrazolo-[4,3-d]-pyrimidin-7-one from Example 80, Part C was converted into the title compound of Example 81.

LRMS (ES$^+$): 548.2 (M+H)$^+$.

Example 82

1-[3-Aminobenzisoxazol-5'-yl]-3-trifluoromethyl-6-[2'-(3-(R)-hydroxy-N-pyrrolidinyl)methyl-[1,1']-biphen-4-yl]-1,4,5,6-tetrahydropyrazolo-[4,3-d]-pyrimidin-7-one, trifluoroacetic acid salt

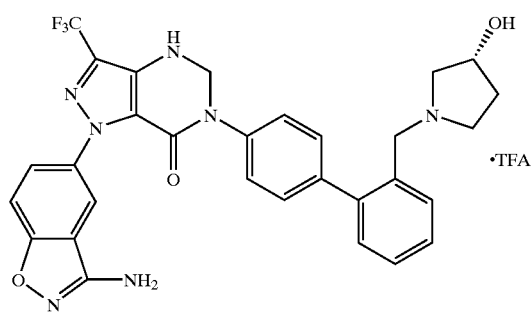

Following procedures described in Example 47, Part C and Example 79, the over reduction product [1-(3-cyano-4-fluorophenyl)]-3-trifluoromethyl-6-[2'-hydroxymethyl-[1,1']-biphen-4-yl]-1,4,5,6-tetrahydropyrazolo-[4,3-d]- pyrimidin-7-one from Example 80, Part C was converted into the title compound of Example 82. LRMS (ES⁻): 590.2 (M+H)⁺.

Example 83

1-[3-Aminobenzisoxazol-5'-yl]-3-trifluoromethyl-6-[2'-(3-(S)-hydroxy-N-pyrrolidinyl)methyl-[1,1']-biphen-4-yl]-1,4,5,6-tetrahydropyrazolo-[3,4-c]-pyridin-7-one, trifluoroacetic acid salt

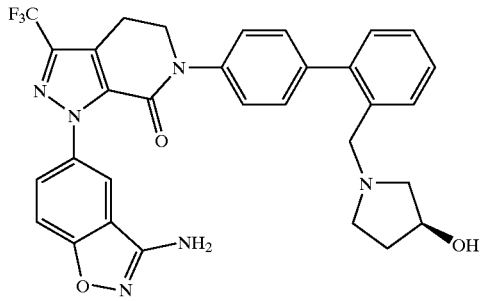

Following the procedure described in Example 60, except that (S)-3-pyrrolidinol was used, the title compound of Example 83 was prepared. Purification by HPLC and freeze-drying afforded 37 mg (15%): ¹H NMR (DMSO-d6) □ 8.11 (d, j=1.9 Hz, 1H), 7.81 (d, j=9.9 Hz, 1H), 7.72 (m, 1H), 7.58 (d, j=9.2 Hz, 2H), 7.54 (m, 2H), 7.51 (d, j=8.4 Hz, 2H), 7.40 (d, j=8.4 Hz, 2H), 7.34 (m, 1H), 6.58 (brd s, 2H), 4.48 (d, j=5.5 Hz, 1H), 4.37–4.29 (m, 2H), 4.23 (t, j=5.9 Hz, 2H), 3.50 (m, 2H), 3.18 (t, j=5.9 Hz, 2H), 2.95–2.85 (m, 2H,), 2.15–1.75 (m, 3H). LRMS (ES⁺): 589.2 (M+H)⁺.

Example 84

1-[3-Aminobenzisoxazol-5'-yl]-3-trifluoromethyl-6-[2'-N-(pyrrolindinyl)methyl-[1,1']-biphen-4-yl]-1,4,5,6-tetrahydropyrazolo-[3,4-c]-pyridin-7-one, trifluoroacetic acid salt

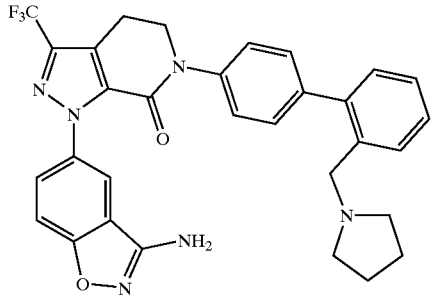

Following the procedure described in Example 60, except that pyrrolidine was used, the title compound of Example 84 was prepared. Purification by HPLC and freeze-drying afforded 25 mg (11%): ¹H NMR (DMSO-d6).□ 8.11 (d, j=2.2 Hz, 1H), 7.81 (dd, j=2.2, 9.2 Hz, 1H), 7.73 (m, 1H), 7.58 (d, j=9.2 Hz, 2H), 7.54 (m, 2H), 7.51 (d, j=8.4 Hz, 2H), 7.41 (d, j=8.5 Hz, 2H), 7.35 (m, 1H), 6.57 (brd s, 2H), 4.38 (d, t j=5.1 Hz, 2H), 4.23 (t, j=6.6, 2H), 3.34 (m, 2H), 3.19 (t, j=6.2 Hz, 2H), 2.81 (m, 2H,), 1.78 (m, 4H) ppm. LRMS (ES⁺): 573.2 (M+H)⁺.

Example 85

1-[3-Aminobenzisoxazol-5'-yl]-3-trifluoromethyl-6-[2'-N-(morpholino)methyl-[1,1']-biphen-4-yl]-1,4,5,6-tetrahydropyrazolo-[3,4-c]-pyridin-7-one, trifluoroacetic acid salt

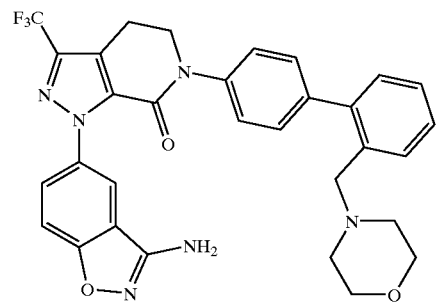

Following the procedure described in Example 60, except that morpholine was used, the title compound of Example 85 was prepared. Purification by HPLC and freeze-drying afforded 110 mg (45.8%): ¹H NMR (DMSO-d6) □ 8.11 (d, j=1.9 Hz, 1H), 7.81 (dd, j=2.2, 8.8 Hz, 1H), 7.76 (m, 1H), 7.58 (d, j=8.8 Hz, 2H), 7.54 (m, 1H), 7.51 (d, j=8.4 Hz, 2H), 7.40 (d, j=8.4 Hz, 2H), 7.34 (m, 1H), 6.60 (brd s, 2H), 4.36 (brd s, 2H), 4.24 (t, j=6.6, 2H), 3.77 (m, 2H), 3.59 (m, 2H), 3.21 (t, j=5.8 Hz, 2H), 3.17 (m, 2H,), 2.78 (m, 2H) ppm. LRMS (ES⁺): 589.2 (M+H)⁺.

Example 86

1-[3-Aminobenzisoxazol-5'-yl]-3-trifluoromethyl-6-[2'-N,N-dimethylaminomethyl-[1,1']-biphen-4-yl]-1,4,5,6-tetrahydropyrazolo-[3,4-c]-pyridin-7-one, trifluoroacetic acid salt

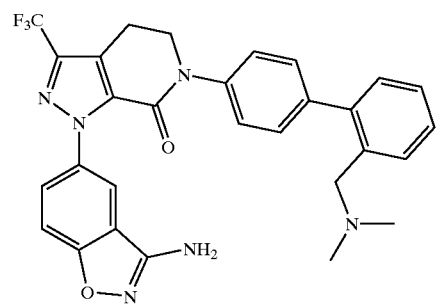

Following the procedure described in Example 60, except that dimethylamine in methanol was used, the title compound of Example 86 was prepared. Purification by HPLC and freeze-drying afforded 180 mg (79%): ¹H NMR (DMSO-d6) □ 9.55 (s, 1H), 8.11 (d, j=2.2 Hz, 1H), 7.81 (dd, j=2.2, 8.7 Hz, 1H), 7.72 (dd, j=3.7, 5.5 Hz, 1H), 7.57 (d, j=8.8 Hz, 2H), 7.54 (dd, j=2.5, 5.8 Hz, 1H), 7.51 (d, j=8.8 Hz, 2H), 7.39 (d, j=8.5 Hz, 2H), 7.36 (dd, j=1.8, 5.4 Hz, 1H), 6.57 (s, 1H), 4.32 (d, j=4.8 Hz, 2H), 4.23 (t, j=6.6, 2H), 3.21 (t, j=6.2 Hz, 2H), 2.57 (s, 3H,), 2.55 (s, 3H) ppm. LRMS (ES⁺): 547.2 (M+H)⁺.

Example 87

1-[3-Aminobenzisoxazol-5'-yl]-3-trifluoromethyl-7-[(3'-N-dimethylaminomethyl)-3-fluoro-[1,1']-biphen-4-yl]-4,5,6,7-tetrahydropyrazolo-[3,4-c]azepin-8-one trifluoroacetic acid salt

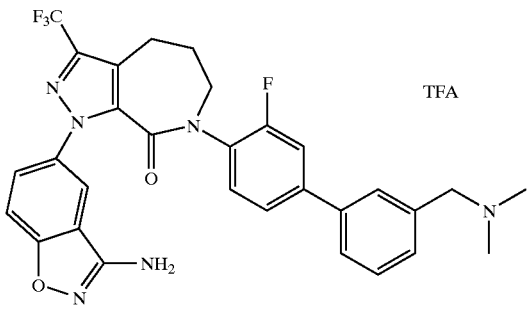

The title compound of Example 87 was prepared by the same methods described in Example 40. LRMS (ES$^+$): 579.3, (M+H). $^1$H NMR (CD$_3$OD) δ 7.98 (t, 1H), 7.81 (d, 1H), 7.79 (s, 1H), 7.67 (t, 1H), 7.59 (m, 1H), 7.55 (m, 2H), 7.51 (m, 2H), 7.47 (t, 1H), 4.39 (s, 2H), 4.01 (t, 2H), 3.15 (t, 2H), 2.89 (s, 6H), 2.31 (m, 2H).

Example 88

1-[3-Aminobenzisoxazol-5'-yl]-3-trifluoromethyl-7-[(3'-N-pyrrolidinylmethyl)-3-fluoro-[1,1']-biphen-4-yl]-4,5,6,7-tetrahydropyrazolo-[3,4-c]azepin-8-one trifluoroacetic acid salt

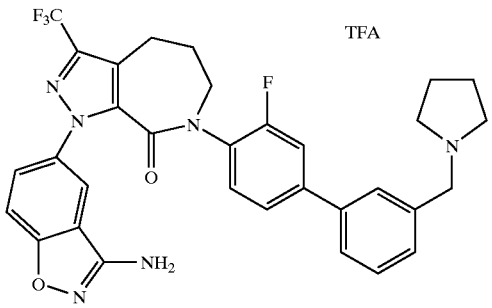

The title compound was prepared by the same methods described in Example 40. LRMS (ES$^{30}$): 605.3, (M+H)$^+$. $^1$H NMR (DMSO-d6) δ 8.10 (d, 1H), 7.89 (s, 1H), 7.81 (d, 1H), 7.65 (m, 2H), 7.59 (m, 2H), 7.51 (m, 3H), 6.58 (bs, 2H), 4.41 (d, 2H), 3.97 (t, 2H), 3.39 (m, 2H), 3.11 (m, 2H), 3.01 (t, 2H), 2.19 (m, 2H), 2.03 (m, 2H), 1.85 (m, 2H).

Example 89

1-[4-Methoxyphenyl]-3-trifluoromethyl-7-[(3'-N-pyrrolidinylmethyl)-[1,1']-biphen-4-yl]-4,5,6,7-tetrahydropyrazolo-[3,4-c]azepin-B-one trifluoroacetic acid salt

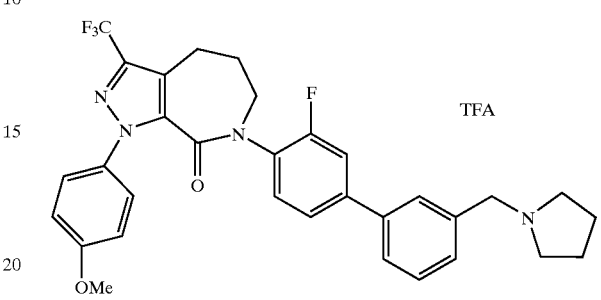

The title compound was prepared by the same methods described in Example 35. LRMS (ES$^+$): 579.3, (M+H)$^+$. $^1$H NMR (CDCl$_3$) δ 7.66 (s, 1H), 7.58 (d, 1H), 7.48 (t, 1H), 7.45–7.31 (m, 6H), 6.93 (d, 2H), 4.27 (d, 2H), 4.10 (bs, 2H), 3.91 (t, 2H), 3.80 (s, 3H), 3.72 (m, 2H), 3.10 (t, 2H), 2.90 (m, 2H), 2.24 (m, 2H), 2.10 (m, 4H).

Example 90

1-[4-Methoxyphenyl]-3-trifluoromethyl-7-[(3'-N-dimethylaminomethyl)-[1,1']-biphen-4-yl]-4,5,6,7-tetrahydropyrazolo-[3,4-c]azepin-9-one trifluoroacetic acid salt

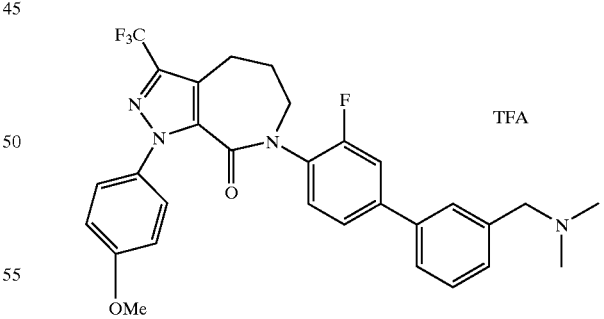

The title compound was prepared by the same methods described in Example 35. LRMS (ES$^-$): 553.3, (M+H)$^+$. $^1$H NMR (CDCl$_3$) δ 7.68 (s, 1H), 7.62 (d, 1H), 7.53 (t, 1H), 7.48–7.31 (m, 6H), 6.93 (d, 2H), 4.22 (s, 2H), 3.90 (m, 2H), 3.81 (s, 3H), 3.12 (t, 2H), 2.92 (bs, 2H), 2.81 (s, 62H), 2.25 (m, 2H).

Example 91

1-[4-Methoxyphenyl]-3-trifluoromethyl-7-[4-benzimidazol-1'-yl-3-fluorophenyl]-4,5,6,7-tetrahydropyrazolo-[3,4-c]azepin-8-one trifluoroacetic acid salt

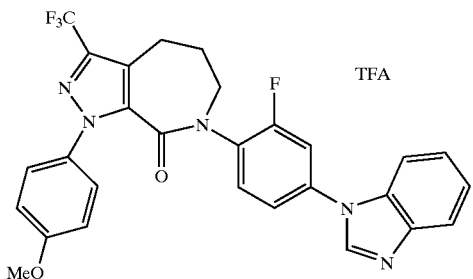

The title compound was prepared by the same methods described in Example 44. LRMS (ES+): 536.3, (M+H)+. $^1$H NMR (CDCl$_3$) δ 8.87 (bs, 1H), 8.02 (d, 1H), 7.59 (m, 4H), 7.45 (m, 4H), 6.95 (d, 2H), 3.87 (m, 2H), 3.82 (s, 3H), 3.12 (t, 2H), A 2.30 (m, 2H).

Example 92

1-[3-Aminobenzisoxazo-5'-yl]-3-trifluoromethyl-7-[(2'-N-pyrrolidinylmethyl)-3-fluoro-[1,1']-biphen-4-yl]-6,7-dihydropyrazolo-[3,4-c]azepin-8-one trifluoroacetic acid salt

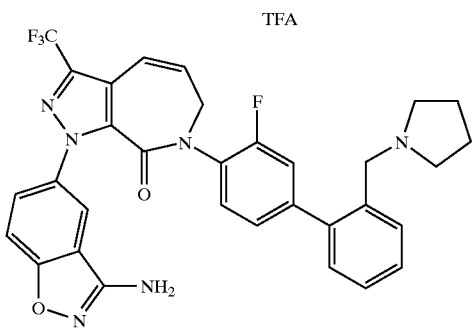

1-(3-Cyano-4-fluorophenyl)-3-trifluoromethyl-7-(2-fluoro-4-iodophenyl)-4,5,6,7-tetrahydropyrazolo-[3,4-c]azepin-8-one prepared by the same methods as shown in Example 40 (0.50 g, 0.90 mmol), N-bromosuccinimide (0.19 g, 1.08 mmol), and AIBN (9.0 mg) were refluxed with 50 mL of CCl$_4$ under N$_2$ for 2 h. The reaction mixture was cooled and filtered through Celite. The filtrate was concentrated to a brown solid. It was then dissolved in 20 mL of THF and 1, 8-diazabicyclo[5, 4, 0]unden-7-ene (DBU, 0.14 mL) was added. The mixture was refluxed for 12 h. The solvent was removed. It was dissolved in EtOAc and washed with water and brine, dried over MgSO$_4$ and concentrated. Flash chromatography on silica gel with 15% EtOAc in hexane gave 0.21 g of 1-(3-Cyano-4-fluorophenyl)-3-trifluoromethyl-7-(2-fluoro-4-iodophenyl)-6,7-dihydropyrazolo-[3,4-c]azepin-8-one. The title compound was then prepared from 1-(3-Cyano-4-fluorophenyl)-3-trifluoromethyl-7-(2-fluoro-4-iodophenyl)-6,7-dihydropyrazolo-[3,4-c]azepin-8-one by the same methods shown in Example 40. LRMS (ES+): 603.2, (M+H)+. $^1$H NMR (CDCl$_3$) 7.82 (d, 1H), 7.73 (m, 2H), 7.54–7.35 (m, 4H), 7.09 (dd, 4H), 6.46 (m, 1H), 4.34 (s, 2H), 4.32 (d, 2H), 3.86 (bs, 2H), 3.59 (m, 2H), 2.58 (m, 2H), 2.01 (m, 2H), 1.85 (m, 2H).

Example 93

1-[3-Aminobenzisoxazo-5'-yl-3-trifluoromethyl-7-[(2'-N-dimethylaminomethyl)-3-fluoro-[1,1']-biphen-4-yl]-6,7-dihydropyrazolo-[3,4-c]azepin-8-one trifluoroacetic acid salt

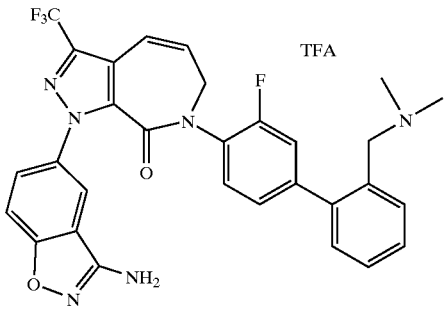

The title compound was prepared by the same methods described in Example 92. LRMS (ES+): 577.2, (M+H)+. $^1$H NMR (CDCl$_3$) 7.82 (d, 1H), 7.73 (m, 2H), 7.54–7.35 (m, 4H), 7.09 (dd, 4H), 6.46 (m, 1H), 4.33 (d, 2H), 4.29 (s, 2H), 3.89 (bs, 2H), 2.58 (s, 6H).

Example 94

1-[3-Aminobenzisoxazo-5'-yl]-3-trifluoromethyl-7-[(2'-N-(R)-3-hydroxypyrrolidinylmethyl)-3-fluoro-[1,1']-biphen-4-yl]-6,7-dihydropyrazolo-[3,4-c-]azepin-8-one

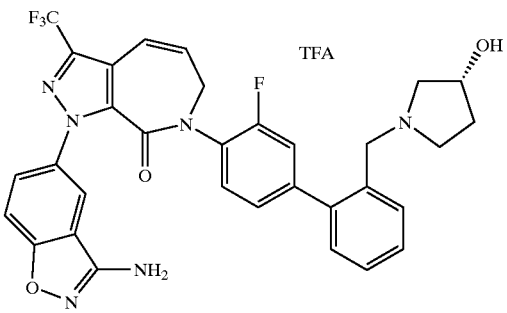

The title compound was prepared by the same methods described in Example 92. LRMS (ES+): 619.3, (M+H)+. $^1$H NMR (CDCl$_3$) 7.78–7.59 (m, 4H), 7.50–7.28 (m, 4H), 7.17–7.03 (m, 3H), 6.44 (m, 1H), 4.64 (s, 2H), 4.42–4.15 (m, 3H), 3.63–3.25 (m, 2H), 2.95–2.50 (m, 2H), 1.97–1.62 (m, 2H).

Example 95

1-[3-Aminobenzisoxazo-5'-yl]-3-trifluoromethyl-7-[(2'-N-(R)-3-hydroxypyrrolidinylmethyl)-[1,1']-biphen-4-yl]-6,7-dihydropyrazolo-[3,4-c]azepin-8-one trifluoroacetic acid salt

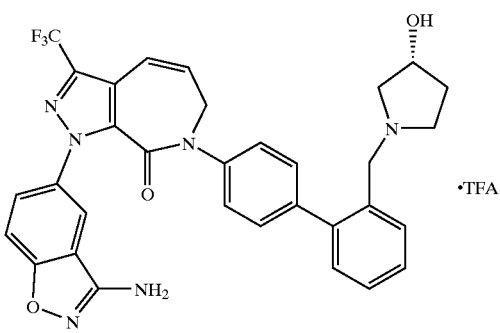

The title compound was prepared by the same methods described in Example 92. LRMS (ES+): 601.0, (M+H)+. $^1$H NMR (CDCl$_3$) 7.79 (s, 1H), 7.68 (m, 2H), 7.50–7.22 (m, 8H), 7.14 (d, 1H), 6.49 (m, 1H), 4.64 (s, 2H), 4.42–4.15 (m, 3H), 3.63–3.25 (m, 2H), 2.95–2.50 (m, 2H), 1.97–1.62 (m, 2H).

Example 96

1-[3-Aminobenzisoxazo-5'-yl]-3-trifluoromethyl-7-[(2'-N-dimethylaminomethyl)-[1,1']-biphen-4-yl]-6,7-dihydropyrazolo-[3,4-c]azepin-8-one trifluoroacetic acid salt

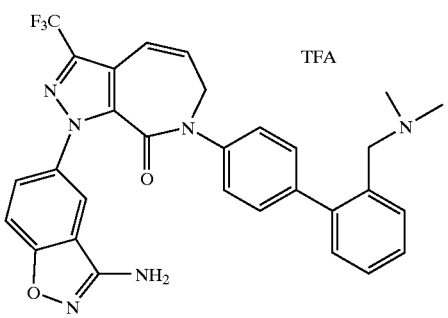

The title compound was prepared by the same methods described in Example 92. LRMS (ES+): 559.2, (M+H)+. $^1$H NMR (CDCl$_3$) 7.82 (d, 1H), 7.70 (m, 2H), 7.53–7.38 (m, 5H), 7.28 (m, 2H), 7.14 (d, 1H), 6.50 (m, 1H), 4.39 (d, 2H), 4.28 (s, 2H), 2.55 (s, 6H).

Example 97

1-[4-Methoxyphenyl]-3-trifluoromethyl-7-[(2'-N-pyrrolidinylmethyl)-[1,1']-biphen-4-yl]-6,7-dihydropyrazolo-[3,4-c]azepin-8-one trifluoroacetic acid salt

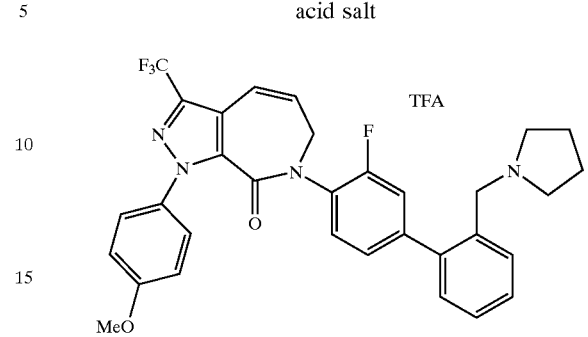

The title compound was prepared by the same methods described in Example 92. LRMS (ES+): 577.4, (M+H)+. $^1$H NMR (CDCl$_3$) 7.77 (d, 1H), 7.55–7.35 (m, 5H), 7.28 (m, 1H), 7.15–6.95 (m, 5H), 6.42 (m, 1H), 4.34 (s, 2H), 4.28 (d, 2H), 3.85 (s, 3H), 3.60 (m, 2H), 2.58 (m, 2H), 2.03 (m, 2H), 1.89 (m, 2H).

Example 98

1-[4-Methoxyphenyl]-3-trifluoromethyl-7-[(2'-N,N-dimethylaminomethyl)-[1,1']-biphen-4-yl]-6,7-dihydropyrazolo-[3,4-c]azepin-8-one trifluoroacetic acid salt

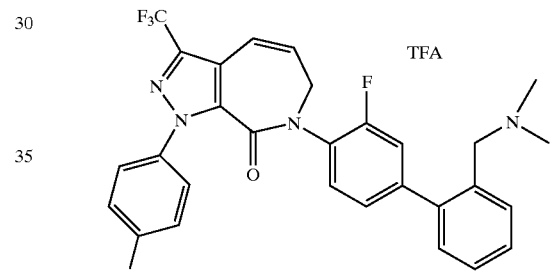

The title compound was prepared by the same methods described in Example 92. LRMS (ES+): 551.3, (M+H)+. $^1$H NMR (CDCl$_3$) 7.77 (d, 1H), 7.55–7.35 (m, 5H), 7.28 (m, 1H), 7.15–6.95 (m, 5H), 6.42 (m, 1H), 4.29 (d, 2H), 4.27 (s, 2H), 3.84 (s, 3H), 2.60 (s, 6H).

Example 99

1[4-Methoxyphenyl]-3-trifluoromethyl-6-[(4-aminomethyl)phenyl]-1,4,5,6-tetrahydropyrazolo-[3,4-c]pyridin-7-one trifluoroacetic acid salt

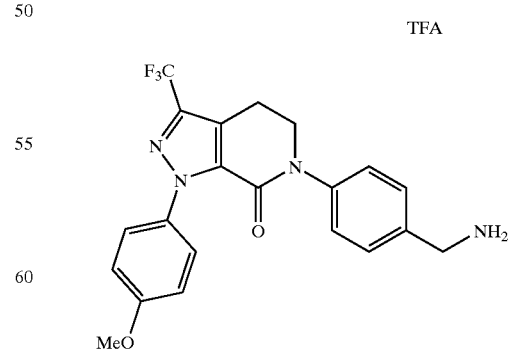

1[-Methoxyphenyl]-3-trifluoromethyl-6-[(4-carbomethyoxy)phenyl]-1,4,5,6-tetrahydropyrazolo-[3,4-c]

pyridin-7-one prepared by the same method as described in Park A of Example 66 (0.17 g, 0.38 mmol) was dissolved in 20 mL of THF. Aqueous LiOH (0.5 mL of 1M solution) was added. The mixture was stirred at room temperature under $N_2$ for 2 h. It was diluted with $Et_2O$ and washed with water and brine. It was then dried over $MgSO_4$ and concentrated to give 0.16 g of the acid. It was then dissolve din 15 mL of THF and cooled at 0° C. under $N_2$. To it was added $Et_3N$ (0.057 mL) and isobutylchloroformate (0.056 mL). The reaction mixture was stirred at 0° C. for 20 minutes. The precipitate was filtered off and washed with 15 mL of THF. The filtrate was transferred to another flask and to it was added $NaBH_4$ (28 mg) and a few drops of water. The mixture was stirred at 0° C. for 15 minute and then at room temperature for 1 h. The reaction was quenched with aqueous HCl and the solvent was removed. The residue was dissolved in EtOAc and washed with water and brine. It was dried over $MgSO_4$, concentrated, and chromatographed with 1:1 EtOAc to hexane to give 70 mg of the benzyl alcohol. LRMS ($ES^+$): 418.1, $(M+H)^+$.

The benzyl alcohol was dissolved in 7 mL of $CH_2Cl_2$ and $PBr_3$ (0.02 mL) was added. The mixture was stirred at room temperature for 30 minute. It was diluted with $CH_2Cl_2$ and washed with brine. After dried over $MgSO_4$, it was concentrated to a white solid. It was dissolved in 7 mL of DMF and $NaN_3$ (24 mg) was added. The mixture was stirred at 50° C. under $N_2$ for 2.5 h. It was poured into water and extracted with EtOAc. The EtOAc extract was washed with brine, dried over $MgSO_4$, concentrated to give the benzyl azide. The azide was dissolved in 10 mL of MeOH and refluxed with $SnCl_2 \cdot H_2O$ (0.31 mg) for 45 minutes. The solvent was removed. The residue was dissolved in EtOAc and saturated $NaHCO_3$ (4 mL) was added. It was filtered through Celite, concentrated, and purified by reverse phase HPLC (C18 reverse phase column, eluted with a $H_2O/CH_3CN$ gradient with 0.05% TFA) and lyophilized to afford 40 mg the title compound as the TFA salt (24%). LRMS ($ES^+$): 417.2, $(M+H)^+$. $^1H$ NMR ($CDCl_3$) δ 7.37 (d, 2H), 7.12 (s, 4H), 6.84 (d, 2H), 4.01 (t, 2H), 3.67 (s, 3H), 3.58 (bs, 2H), 3.11 (t, 2H).

Example 100

1-[3-Aminomethylphenyl]-3-methyl-6-E[(2'-N-((3-(S)-hydroxy)pyrrolidinyl) methyl-[1,1']-biphen-4-yl)]-1,4,5,6-tetrahydro-7H-pyrazolo-[3,4-c]-pyridin-7-one bis-trifluoroacetic acid salt

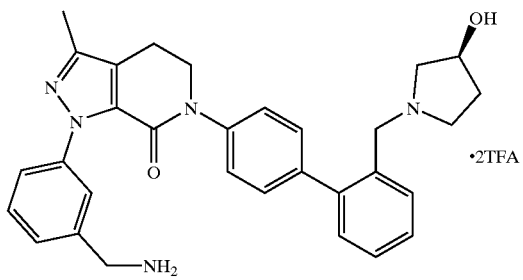

Part A. 1-(3-Cyanophenyl)-3-methyl-6-(4-bromophenyl)-1,4,5,6-tetrahydro-7H-pyrazolo[3,4-c]pyridin-7-one.

A mixture of 1-(4-bromophenyl)-3-hydroxy-4-acetyl-5,6-dihydropyridin-2-one (3.2 mmol, 1.0 g, Example 47, Part A) and 3-cyanophenylhydrazine (3.5 mmol, 0.60 g) in acetic acid (glacial, 40 mL) was heated at reflux for 3 h. The reaction was evaporated, applied to a column of flash silica gel (ca. 250 g) and eluted with gradient of 2:1 to 1:1 hexane:EtOAc. There was obtained 0.4 g of the title compound, 1-(3-cyanophenyl)-3-methyl-6-(4-bromophenyl)1,4,5,6-tetrahydro-7H-pyrazolo[3,4-c]pyridin-7-one. LRMS ($ES^+$): 409/411 $(M+H)^+$.

Part B. 1-(3-Cyanophenyl)-3-methyl-6-[(2'-N-((3-(S)-hydroxy)pyrrolidinyl)methyl-[1,1']-biphen-4-yl)]-1,4,5,6-tetrahydro-7H-pyrazolo[3,4-c]pyridin-7-one.

1-(3-Cyanophenyl)-3-methyl-6-(4-bromophenyl)1,4,5,6-tetrahydro-7H-pyrazolo[3,4-c]pyridin-7-one (0.49 mmol, 0.20 g), 2-formylphenylboronic acid (0.69 mmol, 0.10 g), and tetrabutylammonium bromide (0.024 mmol, 0.008 mmol) in benzene (12 mL) and 2N $Na_2CO_3$ (4 mL) was purged with $N_2$ gas for 15 min, then tetrakis (triphenylphosphine) palladium (0.031 mmol, 0.035 g) was added. This mixture was heated at reflux for 18 h. To this mixture was added brine and it was then extracted with EtOAc. The extract was dried ($MgSO_4$) and evaporated. The residue was purified further by flash chromatography using a gradient of 5:1 to 1:1 hexane:EtOAc as an eluant. There was obtained 0.12 g of the desired coupling product. LRMS ($ES^+$): 431 $(M-H)^-$.

This product (0.28 mmol, 0.12 g), 3 (S)-hydroxypyrrolidine (1.11 mmol, 0.097 g), acetic acid (glacial, 0.03 g) and sodium triacetoxyborohydride (0.56 mmol, 0.12 g) in $CHCl_3$ (5 mL) was stirred at ambient temperature for 18 h. The reaction was evaporated, dissolved in $CH_2Cl_2$, washed with water, dried ($MgSO_4$) and evaporated. There was obtained 0.13 g of the title compound. LRMS ($ES^+$): 504 $(M+H)^+$.

Part C. 1-(3-Methylaminophenyl)-3-methyl-6-[(2'-N-((3-(S)-hydroxy)pyrrolidinyl)methyl-[1,1']-biphen-4-yl)]-1,4,5,6-tetrahydro-7H-pyrazolo[3,4-c]pyridin-7-one bis-trifluoroacetic acid salt.

1-(3-Cyanophenyl)-3-methyl-6-[(2'-N-((3-(S)-hydroxy)pyrrolidinyl) methyl-[1,1']-biphen-4-yl)]-1,4,5,6-tetrahydro-7H-pyrazolo[3,4-c]pyridin-7-one (0.26 mmol, 0.13 g) in MeOH (20 mL) with TFA (1 mL) was shaken under an atmosphere of H2 gas (50 psi) in the presence of 10% Pd-C catalyst (50 mg) for 18 h. The reaction was purged with N2 gas, filtered through a pad of Celite then evaporated. The residue was purified by HPLC on a $Cl_8$ column by elution with a gradient of water (0.05% TFA, solvent A) and acetonitrile (0.05% TFA, solvent B). There was obtained 0.072 g of 1-[3-aminomethylphenyl]-3-methyl-6-[(2'-N-((3-(S)hydroxy)pyrrolidinyl) methyl-[1,1']-biphenyl-4-yl)]-1,4,5,6-tetrahydro-7H-pyrazolo[3,4-c]pyridin-7-one bis-trifluoroacetic acid salt with a purity of >90%; mp 79.2° C., HRMS $(C_{31}H_{34}O_2N_5)^+$: 508.2773 m/z.

Example 101

1-[3-Aminomethylphenyl]-3-methyl-6-[(2'-methylsulfonyl-[1,1']-biphen-4-yl)]-1,4,5,6-tetrahydro-7H-pyrazolo[3,4-c]pyridin-7-one, trifluoroacetic acid salt

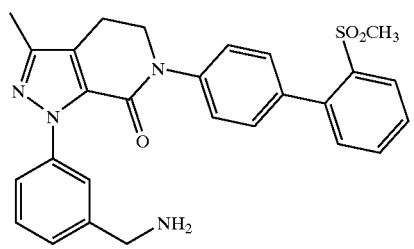

Part A. 1-(3-cyanophenyl)-3-methyl-6-[(2'-methylsulfonyl-[1,1']-biphen-4-yl)]-1,4,5,6-tetrahydro-7H-pyrazolo[3,4-c]pyridin-7-one.

1-(3-Cyanophenyl)-3-methyl-6-(4-bromophenyl)1,4,5,6-tetrahydro-7H-pyrazolo[3,4-c]pyridin-7-one (Example 100, Part A; 0.17 g, 0.42 mmol), 2-thiomethylphenylboronic acid (0.098 g, 0.58 mmol) and Bu₄NBr (0.008 g) in C₆H₆ (20 mL) and 2N Na₂CO₃ (4 mL) was purged with a stream of N₂ gas. Palladium tetrakis (triphenyl) phosphine (0.02 g, 0.02 mmol) was added and the mixture heated at reflux for 18 h. To the cooled reaction mixture, brine and EtOAc was added and the layers separated. The organic layer was dried (MgSO₄) and evaporated then the residue was purified by silica gel chromatography (100 g of SiO₂, eluted with 1:1 hexane:EtOAc) to give 0.12 g (3.2 mmol) of 1-(3-cyanophenyl)-3-methyl-6-[(21-thiomethyl-[1,1']-biphen-4-yl)]-1,4,5,6-tetrahydro-7H-pyrazolo[3,4-c]pyridin-7-one. LRMS (ES⁺): 451 (M+H)⁺.

A mixture of this product (0.12 g, 0.27 mmol) and m-chloroperbenzoic acid (0.14 g, 0.81 mmol) in CH2Cl12 were stirred for 18 h. Saturated NaHCO3 was added and the layers separated. The basic layer was extracted into CH2Cl12, then the organic layers were combined, dried (MgSO4) and evaporated to yield 0.14 g of the title compound. LRMS (ES⁺): 505 (M+Na)⁺.

Part B. 1-[3-Aminomethylphenyl]-3-methyl-6-[(2'-methylsulfonyl-[1,1']-biphen-4-yl)]-1,4,5,6-tetrahydro-7H-pyrazolo[3,4-c]pyridin-7-one, trifluoroacetic acid salt.

The product from above was treated as in Example 100, Part C and the residue was purified by HPLC on a C₁₈ column by elution with a gradient of water (0.05% TFA, solvent A) and acetonitrile (0.05% TFA, solvent B). There was obtained 0.066 g of the title compound of Example 101, 1-[3-aminomethylphenyl]-3-methyl-6-[(2'-methylsulfonyl-[1,1']-biphen-4-yl)]-1,4,5,6-tetrahydro-7H-pyrazolo[3,4-c]pyridin-7-one, trifluoroacetic acid salt with a purity of >94%. mp 131° C., HRMS (C₂₇H₂₇O₃N₄S)⁺: 487.1819 m/z.

Example 102

1-[3-Aminobenzisoxazol-51-yl]-3-methyl-6-[(3-fluoro-2'-N-(3 (S)-hydroxy)pyrrolidinylmethyl-[1,1']-biphen-4-yl)]-1,4,5,6-tetrahydro-7H-pyrazolo[3,4-c]pyridin-7-one, trifluoroacetic acid salt

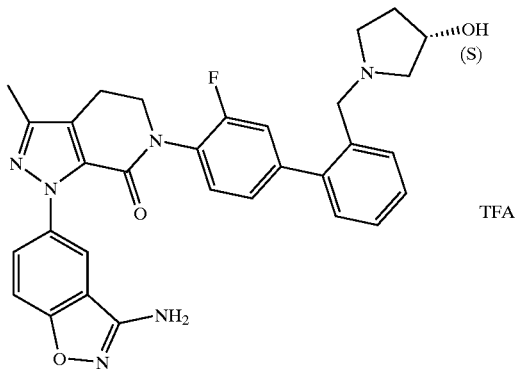

This compound was prepared and purified by the same procedure outlined in Example 47, Part D from a mixture of 1-[(3-aminobenzisoxazol-5'-yl]-3-methyl-6-[(3-fluoro-2'-formyl-[1,1']-biphen-4-yl)]-1,4,5,6-tetrahydro-7H-pyrazolo[3,4-c]pyridin-7-one and 3 (S)-hydroxypyrrolidine. There was obtained 0.030 g of the title product with a purity >98%. mp 207.7° C.; HRMS (C₃₁H₃₀N₆O₃F)⁺: 553.2377 m/z.

Example 103

1-[3-Aminobenzisoxazol-5'-yl]-3-methyl-6-[(3-fluoro-2'-N-pyrrolidinylmethyl-[1,1']-biphen-4-yl)]-1,4,5,6-tetrahydro-7H-pyrazolo [3,4-c]pyridin-7-one, trifluoroacetic acid salt

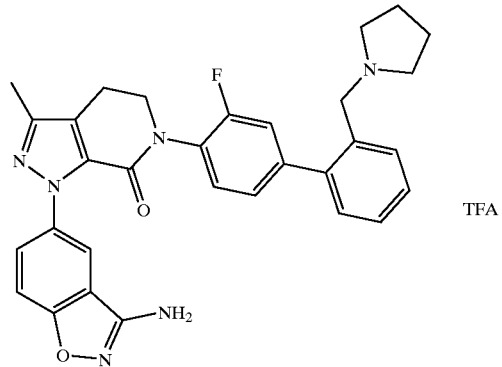

This compound was prepared and purified by the same procedure outlined in Example 47, Part D from a mixture of 1-[(3-aminobenzisoxazol-5l-yl]-3-methyl-6-[(3-fluoro-2'-formyl-[1,1']-biphen-4-yl)]-1,4,5,6-tetrahydro-7H-pyrazolo [3,4-c]pyridin-7-one and pyrrolidine. There was obtained 0.029 g of the title product with a purity >97%. HRMS (C₃₁H₃₀N₆O₂F)⁺: 537.2421 m/z.

Example 104

1-[1-Aminoisoquinolin-7'-yl]-3-trifluoromethyl-6-[4-(2-methylimidazol-1'-yl)phenyl]-1,4,5,6-tetrahydropyrazolo-[3,4-c]-pyridin-7-one bis-trifluoroacetic acid salt

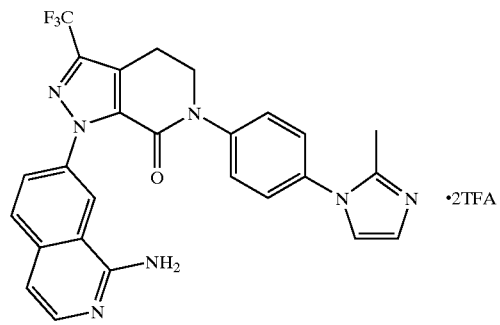

Part A. 1-(Isoquinolin-7'-yl)-3-trifluoromethyl-6-[4-bromophenyl]-1,4,5,6-tetrahydropyrazolo-[3,4-c]-pyridin-7-one 1, 5, 6-Trihydro-1-(4-bromophenyl)-4-trifluoroacetyl-pyridin-2,3-dione (0.84 g, 1.87 mmol) and 7-hydrazinoisoquinoline (tin salt from SnCl₂ reduction of diazonium salt) (0.72 g, 1.87 mmol) were heated to reflux in acetic acid (30 ml) for 4 h. The solvents were removed and ethyl acetate/sodium bicarbonate (sat) was added. The product was extracted with ethyl acetate, washed with brine and dried on sodium sulfate. Purification by chromatography on silica with (1:1) hexane/ethyl acetate as eluant afforded 0.60 g (64%) of the title compound. LRMS (ES+): 505/507.0 (Br pattern) (M+H)⁺.

Part B. 1-(1-Aminoisoquinolin-7'-yl)-3-trifluoromethyl-6-[4-bromophenyl]-1,4,5,6-tetrahydropyrazolo-[3,4-c]-pyridine-7-one 1-(Isoquinolin-7'-yl)-3-trifluoromethyl-6-[4-bromophenyl]-1,4,5,6-tetrahydropyrazolo-[3,4-c]-pyridin-7-one (0.50 g, 1 mmol) was mixed with MCPBA (65%) (0.45 g, 1.2 mmol) in methylene chloride. The mixture was stirred at RT overnight. The solvents were removed and ethyl acetate/sodium bicarbonate (sat) added. Organic layer was separated and washed with brine and dried on sodium sulfate. Filtered and concentrated to give isoquinoline N-oxide (0.51 g, 98%). LRMS (ES+): 521.2/523 (Br pattern) (M+H)+. The N-oxide was mixed with p-TsCl (229 mg, 1.2 mmol) in pyridine (10 ml). The mixture was stirred at RT overnight. Pyridine was removed under reduced pressure and ethanolamine (8 ml) was added. The resulting mixture was stirred at RT 1 h. Cold water was added and product was extracted with ethyl acetate, washed with brine and dried over sodium sulfate. Purification by chromatography on silica with (2:3) hexane/ethyl acetate as eluent afforded 0.26 g (50%) of the title compound. LRMS (ES+): 520.2/522.2 (Br pattern) (M+H)+.

Part C. 1-[1-Aminoisoquinolin-7'-yl]-3-trifluoromethyl-6-[4-(2-methylimidazol-1']-yl)phenyl]-1,4,5,6-tetrahydropyrazolo-[3,4-c]-pyridin-7-one bio-trifluoroacetic acid salt.

1-(1-aminoisoquinolin-7'-yl)-3-trifluoromethyl-6-[4-bromophenyl]-1,4,5,6-tetrahydropyrazolo-[3,4-c]-pyridine-7-one (0.25 g, 0.48 mmol) was mixed with 2-methylimidazole (59 mg, 0.72 mmol), potassium carbonate (133 mg, 0.96 mmol) and CuI (14 mg, 0.072) in DMSO. The mixture was degassed under argon for 15 min. The mixture was stirred at 125° C. for 10 h. The mixture was cooled to RT and partitioned between ethyl acetate and water, washed with water, brine and dried over sodium sulfate. Purification by HPLC (RP) gradient to give 29 mg (14%) of the title compound of Example 104. LRMS (ES+): 504.4 (M+H)+

Example 105

1-[3-Aminobenzisoxazol-5'-yl]-3-methyl-6-[4-(2-methylimidazol-1'-yl)phenyl]-1,6-dihydropyrazolo-[4,3-d]-pyrimidin-7-one bis-trifluoroacetic acid salt

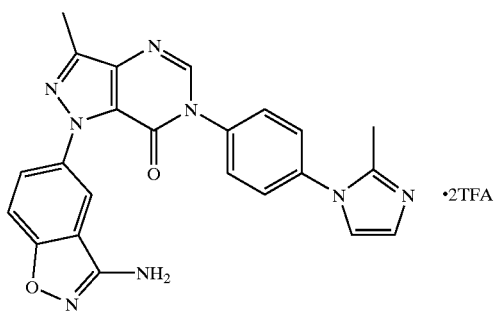

The title compound of Example 105 was prepared following procedures described previously. LRMS (ES+): 439.4 (M+H)+

Example 106

1-[3-Aminobenzisoxazol-5'-yl]-3-methyl-6-[4-(2-(dimethylaminomethyl)imidazol-1'-yl)-2-fluorophenyl]-1,6-dihydropyrazolo-[4,3-d]-pyrimidin-7-one bis-trifluoroacetic acid salt

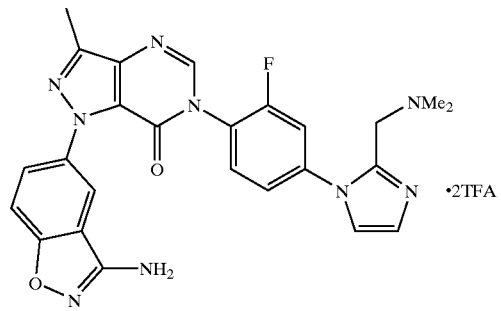

The title compound of Example 106 was prepared following procedures described previously. LRMS (ES+): 500.5 (M+H)+

Example 107

1-[3-Aminobenzisoxazol-5'-yl]-3-trifluoromethyl-6-[4-(2-(dimethylaminomethyl)imidazol-1'-yl)phenyl]-1,6-dihydropyrazolo-[4,3-d]-pyrimidin-7-one bis-trifluoroacetic acid salt

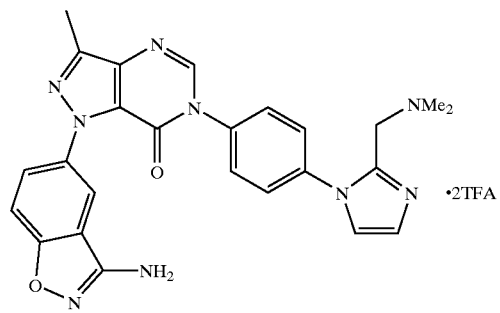

The title compound of Example 107 was prepared following procedures described previously. LRMS (ES+): 536.4 (M+H)+

Example 108

1-[3-Aminobenzisoxazol-5'-yl]-3-methyl-6-[4-(2-(dimethylaminomethyl)imidazol-1'-yl)-2-fluorophenyl]-1,4,5,6-tetrahydropyrazolo-[3,4-c]-pyridin-7-one bis-trifluoroacetic acid salt

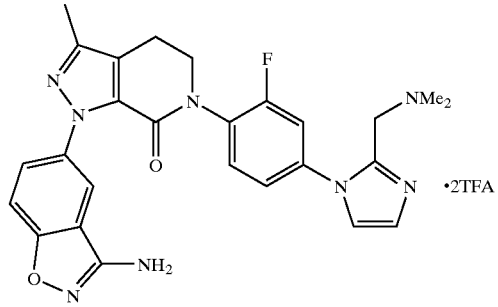

The title compound of Example 108 was prepared following procedures described previously. LRMS (ES+): 501.5 (M+H)+.

Example 109

1-[3-Aminobenzisoxazol-5'-yl]-3-methyl-6-(4-bromophenyl)-1,4,5,6-tetrahydropyrazolo-[3,4-c]-pyridin-7-one, trifluoroacetic acid salt

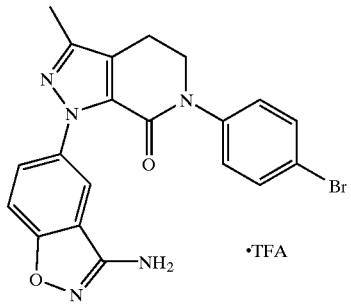

The title compound of Example 109 was prepared following procedures described previously. HRMS $(C_{20}H_{17}N_5O_2Br)^+$: 438.0557 m/z.

The following tables contain representative examples of the present invention. Each entry in each table is intended to be paired with each formulae at the start of the table. For example, in Tables 1 and 2, example 1 is intended to be paired with each of the formulae.

The following nomenclature is intended for group A in the following tables.

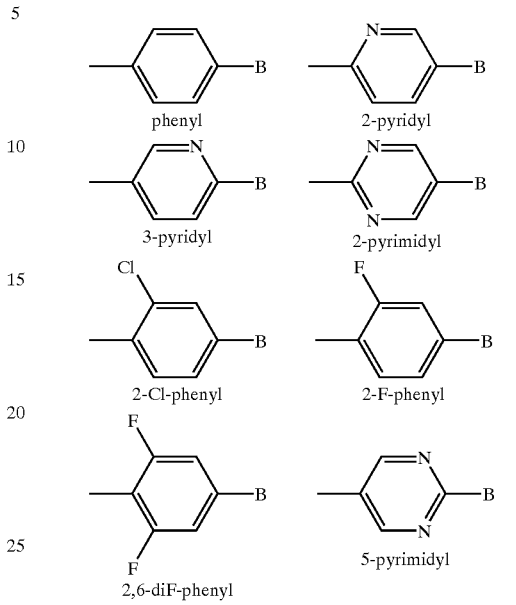

phenyl — 2-pyridyl — 3-pyridyl — 2-pyrimidyl — 2-Cl-phenyl — 2-F-phenyl — 2,6-diF-phenyl — 5-pyrimidyl

TABLE 1

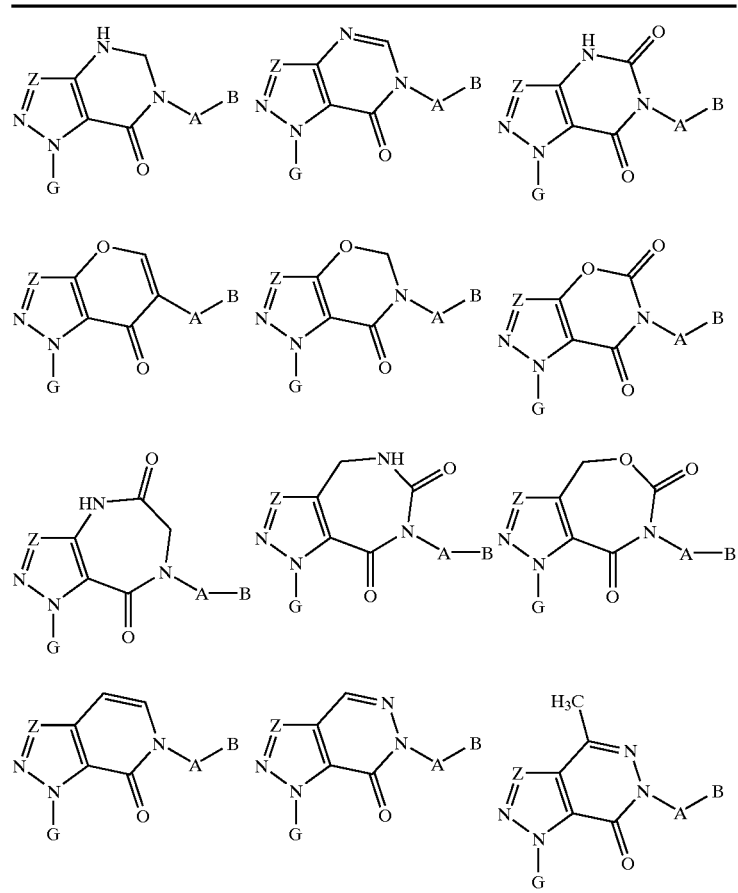

TABLE 1-continued

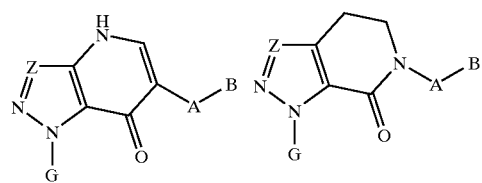

Z is CR$^{1a}$;
G is selected from:
- 4-(methoxy)phenyl;
- 2-(aminomethyl)phenyl;
- 3-(aminomethyl)phenyl;
- 2-(aminomethyl)-3-fluorophenyl;
- 2-(aminomethyl)-4-fluorophenyl;
- 2-(aminomethyl)-5-fluorophenyl;
- 2-(aminomethyl)-6-fluorophenyl;
- 3-amino-phthalazin-5-yl;
- 3-amino-phthalazin-6-yl;
- 1-aminoisoquinolin-6-yl;
- 1-aminoisoquinolin-7-yl;
- 4-aminoquinazol-6-yl;
- 4-aminoquinazol-7-yl;
- 3-aminobenzisoxazol-5-yl;
- 3-aminobenzisoxazol-6-yl;
- 3-aminoisobenzazol-5-yl; and,
- 3-aminoisobenzazaol-6-yl;

| Ex# | R$^{1a}$ | A | B |
|---|---|---|---|
| 1 | CH3 | phenyl | 2-(aminosulfonyl)phenyl |
| 2 | CH3 | phenyl | 2-(methylaminosulfonyl)phenyl |
| 3 | CH3 | phenyl | 1-pyrrolidinocarbonyl |
| 4 | CH3 | phenyl | 2-(methylsulfonyl)phenyl |
| 5 | CH3 | phenyl | 2-(N,N-dimethylaminomethyl)phenyl |
| 6 | CH3 | phenyl | 2-(N-pyrrolidinylmethyl)phenyl |
| 7 | CH3 | phenyl | 1-methyl-2-imidazolyl |
| 8 | CH3 | phenyl | 2-methyl-1-imidazolyl |
| 9 | CH3 | phenyl | 2-(dimethylaminomethyl)-1-imidazolyl |
| 10 | CH3 | phenyl | 2-(N-(cyclopropyl-methyl)aminomethyl)phenyl |
| 11 | CH3 | phenyl | 2-(N-(cyclobutyl)-aminomethyl)phenyl |
| 12 | CH3 | phenyl | 2-(N-(cyclopentyl)-aminomethyl)phenyl |
| 13 | CH3 | phenyl | 2-(N-(3-hydroxypyrrolidinyl)-methyl)phenyl |
| 14 | CH3 | 2-pyridyl | 2-(aminosulfonyl)phenyl |
| 15 | CH3 | 2-pyridyl | 2-(methylaminosulfonyl)phenyl |
| 16 | CH3 | 2-pyridyl | 1-pyrrolidinocarbonyl |
| 17 | CH3 | 2-pyridyl | 2-(methylsulfonyl)phenyl |
| 18 | CH3 | 2-pyridyl | 2-(N,N-dimethylaminomethyl)phenyl |
| 19 | CH3 | 2-pyridyl | 2-(N-pyrrolidinylmethyl)phenyl |
| 20 | CH3 | 2-pyridyl | 1-methyl-2-imidazolyl |
| 21 | CH3 | 2-pyridyl | 2-methyl-1-imidazolyl |
| 22 | CH3 | 2-pyridyl | 2-(dimethylaminomethyl)-1-imidazolyl |
| 23 | CH3 | 2-pyridyl | 2-(N-(cyclopropyl-methyl)aminomethyl)phenyl |
| 24 | CH3 | 2-pyridyl | 2-(N-(cyclobutyl)-aminomethyl)phenyl |
| 25 | CH3 | 2-pyridyl | 2-(N-(cyclopentyl)-aminomethyl)phenyl |
| 26 | CH3 | 2-pyridyl | 2-(N-(3-hydroxypyrrolidinyl)-methyl)phenyl |
| 27 | CH3 | 3-pyridyl | 2-(aminosulfonyl)phenyl |
| 28 | CH3 | 3-pyridyl | 2-(methylaminosulfonyl)phenyl |
| 29 | CH3 | 3-pyridyl | 1-pyrrolidinocarbonyl |
| 30 | CH3 | 3-pyridyl | 2-(methylsulfonyl)phenyl |
| 31 | CH3 | 3-pyridyl | 2-(N,N-dimethylaminomethyl)phenyl |
| 32 | CH3 | 3-pyridyl | 2-(N-pyrrolidinylmethyl)phenyl |
| 33 | CH3 | 3-pyridyl | 1-methyl-2-imidazolyl |
| 34 | CH3 | 3-pyridyl | 2-methyl-1-imidazolyl |
| 35 | CH3 | 3-pyridyl | 2-(dimethylaminomethyl)-1-imidazolyl |
| 36 | CH3 | 3-pyridyl | 2-(N-(cyclopropyl-methyl)aminomethyl)phenyl |
| 37 | CH3 | 3-pyridyl | 2-(N-(cyclobutyl)-aminomethyl)phenyl |
| 38 | CH3 | 3-pyridyl | 2-(N-(cyclopentyl)-aminomethyl)phenyl |
| 39 | CH3 | 3-pyridyl | 2-(N-(3-hydroxypyrrolidinyl)-methyl)phenyl |
| 40 | CH3 | 2-pyrimidyl | 2-(aminosulfonyl)phenyl |
| 41 | CH3 | 2-pyrimidyl | 2-(methylaminosulfonyl)phenyl |
| 42 | CH3 | 2-pyrimidyl | 1-pyrrolidinocarbonyl |
| 43 | CH3 | 2-pyrimidyl | 2-(methylsulfonyl)phenyl |
| 44 | CH3 | 2-pyrimidyl | 2-(N,N-dimethylaminomethyl)phenyl |
| 45 | CH3 | 2-pyrimidyl | 2-(N-pyrrolidinylmethyl)phenyl |
| 46 | CH3 | 2-pyrimidyl | 1-methyl-2-imidazolyl |
| 47 | CH3 | 2-pyrimidyl | 2-methyl-1-imidazolyl |
| 48 | CH3 | 2-pyrimidyl | 2-(dimethylaminomethyl)-1-imidazolyl |
| 49 | CH3 | 2-pyrimidyl | 2-(N-(cyclopropyl-methyl)aminomethyl)phenyl |
| 50 | CH3 | 2-pyrimidyl | 2-(N-(cyclobutyl)-aminomethyl)phenyl |
| 51 | CH3 | 2-pyrimidyl | 2-(N-(cyclopentyl)-aminomethyl)phenyl |
| 52 | CH3 | 2-pyrimidyl | 2-(N-(3-hydroxypyrrolidinyl)-methyl)phenyl |
| 53 | CH3 | 5-pyrimidyl | 2-(aminosulfonyl)phenyl |
| 54 | CH3 | 5-pyrimidyl | 2-(methylaminosulfonyl)phenyl |
| 55 | CH3 | 5-pyrimidyl | 1-pyrrolidinocarbonyl |
| 56 | CH3 | 5-pyrimidyl | 2-(methylsulfonyl)phenyl |
| 57 | CH3 | 5-pyrimidyl | 2-(N,N-dimethylaminomethyl)phenyl |
| 58 | CH3 | 5-pyrimidyl | 2-(N-pyrrolidinylmethyl)phenyl |
| 59 | CH3 | 5-pyrimidyl | 1-methyl-2-imidazolyl |
| 60 | CH3 | 5-pyrimidyl | 2-methyl-1-imidazolyl |
| 61 | CH3 | 5-pyrimidyl | 2-(dimethylaminomethyl)-1-imidazolyl |
| 62 | CH3 | 5-pyrimidyl | 2-(N-(cyclopropyl-methyl)aminomethyl)phenyl |
| 63 | CH3 | 5-pyrimidyl | 2-(N-(cyclobutyl)-aminomethyl)phenyl |
| 64 | CH3 | 5-pyrimidyl | 2-(N-(cyclopentyl)-aminomethyl)phenyl |
| 65 | CH3 | 5-pyrimidyl | 2-(N-(3-hydroxypyrrolidinyl)-methyl)phenyl |
| 66 | CH3 | 2-Cl-phenyl | 2-(aminosulfonyl)phenyl |

-continued

| Ex# | R¹ᵃ | A | B |
|---|---|---|---|
| 67 | CH3 | 2-Cl-phenyl | 2-(methylaminosulfonyl)phenyl |
| 68 | CH3 | 2-Cl-phenyl | 1-pyrrolidinocarbonyl |
| 69 | CH3 | 2-Cl-phenyl | 2-(methylsulfonyl)phenyl |
| 70 | CH3 | 2-Cl-phenyl | 2-(N,N-dimethylaminomethyl)phenyl |
| 71 | CH3 | 2-Cl-phenyl | 2-(N-pyrrolidinylmethyl)phenyl |
| 72 | CH3 | 2-Cl-phenyl | 1-methyl-2-imidazolyl |
| 73 | CH3 | 2-Cl-phenyl | 2-methyl-1-imidazolyl |
| 74 | CH3 | 2-Cl-phenyl | 2-(dimethylaminomethyl)-1-imidazolyl |
| 75 | CH3 | 2-Cl-phenyl | 2-(N-(cyclopropyl-methyl)aminomethyl)phenyl |
| 76 | CH3 | 2-Cl-phenyl | 2-(N-(cyclobutyl)-aminomethyl)phenyl |
| 77 | CH3 | 2-Cl-phenyl | 2-(N-(cyclopentyl)-aminomethyl)phenyl |
| 78 | CH3 | 2-Cl-phenyl | 2-(N-(3-hydroxypyrrolidinyl)-methyl)phenyl |
| 79 | CH3 | 2-F-phenyl | 2-(aminosulfonyl)phenyl |
| 80 | CH3 | 2-F-phenyl | 2-(methylaminosulfonyl)phenyl |
| 81 | CH3 | 2-F-phenyl | 1-pyrrolidinocarbonyl |
| 82 | CH3 | 2-F-phenyl | 2-(methylsulfonyl)phenyl |
| 83 | CH3 | 2-F-phenyl | 2-(N,N-dimethylaminomethyl)phenyl |
| 84 | CH3 | 2-F-phenyl | 2-(N-pyrrolidinylmethyl)phenyl |
| 85 | CH3 | 2-F-phenyl | 1-methyl-2-imidazolyl |
| 86 | CH3 | 2-F-phenyl | 2-methyl-1-imidazolyl |
| 87 | CH3 | 2-F-phenyl | 2-(dimethylaminomethyl)-1-imidazolyl |
| 88 | CH3 | 2-F-phenyl | 2-(N-(cyclopropyl-methyl)aminomethyl)phenyl |
| 89 | CH3 | 2-F-phenyl | 2-(N-(cyclobutyl)-aminomethyl)phenyl |
| 90 | CH3 | 2-F-phenyl | 2-(N-(cyclopentyl)-aminomethyl)phenyl |
| 91 | CH3 | 2-F-phenyl | 2-(N-(3-hydroxypyrrolidinyl)-methyl)phenyl |
| 92 | CH3 | 2,6-diF-phenyl | 2-(aminosulfonyl)phenyl |
| 93 | CH3 | 2,6-diF-phenyl | 2-(methylaminosulfonyl)phenyl |
| 94 | CH3 | 2,6-diF-phenyl | 1-pyrrolidinocarbonyl |
| 95 | CH3 | 2,6-diF-phenyl | 2-(methylsulfonyl)phenyl |
| 96 | CH3 | 2,6-diF-phenyl | 2-(N,N-dimethylaminomethyl)phenyl |
| 97 | CH3 | 2,6-diF-phenyl | 2-(N-pyrrolidinylmethyl)phenyl |
| 98 | CH3 | 2,6-diF-phenyl | 1-methyl-2-imidazolyl |
| 99 | CH3 | 2,6-diF-phenyl | 2-methyl-1-imidazolyl |
| 100 | CH3 | 2,6-diF-phenyl | 2-(dimethylaminomethyl)-1-imidazolyl |
| 101 | CH3 | 2,6-diF-phenyl | 2-(N-(cyclopropyl-methyl)aminomethyl)phenyl |
| 102 | CH3 | 2,6-diF-phenyl | 2-(N-(cyclobutyl)-aminomethyl)phenyl |
| 103 | CH3 | 2,6-diF-phenyl | 2-(N-(cyclopentyl)-aminomethyl)phenyl |
| 104 | CH3 | 2,6-diF-phenyl | 2-(N-(3-hydroxypyrrolidinyl)-methyl)phenyl |
| 105 | CH2CH3 | phenyl | 2-(aminosulfonyl)phenyl |
| 106 | CH2CH3 | phenyl | 2-(methylaminosulfonyl)phenyl |
| 107 | CH2CH3 | phenyl | 1-pyrrolidinocarbonyl |
| 108 | CH2CH3 | phenyl | 2-(methylsulfonyl)phenyl |
| 109 | CH2CH3 | phenyl | 2-(N,N-dimethylaminomethyl)phenyl |
| 110 | CH2CH3 | phenyl | 2-(N-pyrrolidinylmethyl)phenyl |
| 111 | CH2CH3 | phenyl | 1-methyl-2-imidazolyl |
| 112 | CH2CH3 | phenyl | 2-methyl-1-imidazolyl |
| 113 | CH2CH3 | phenyl | 2-(dimethylaminomethyl)-1-imidazolyl |
| 114 | CH2CH3 | phenyl | 2-(N-(cyclopropyl-methyl)aminomethyl)phenyl |
| 115 | CH2CH3 | phenyl | 2-(N-(cyclobutyl)-aminomethyl)phenyl |
| 116 | CH2CH3 | phenyl | 2-(N-(cyclopentyl)-aminomethyl)phenyl |
| 117 | CH2CH3 | phenyl | 2-(N-(3-hydroxypyrrolidinyl)-methyl)phenyl |
| 118 | CH2CH3 | 2-pyridyl | 2-(aminosulfonyl)phenyl |
| 119 | CH2CH3 | 2-pyridyl | 2-(methylaminosulfonyl)phenyl |
| 120 | CH2CH3 | 2-pyridyl | 1-pyrrolidinocarbonyl |
| 121 | CH2CH3 | 2-pyridyl | 2-(methylsulfonyl)phenyl |
| 122 | CH2CH3 | 2-pyridyl | 2-(N,N-dimethylaminomethyl)phenyl |
| 123 | CH2CH3 | 2-pyridyl | 2-(N-pyrrolidinylmethyl)phenyl |
| 124 | CH2CH3 | 2-pyridyl | 1-methyl-2-imidazolyl |
| 125 | CH2CH3 | 2-pyridyl | 2-methyl-1-imidazolyl |
| 126 | CH2CH3 | 2-pyridyl | 2-(dimethylaminomethyl)-1-imidazolyl |
| 127 | CH2CH3 | 2-pyridyl | 2-(N-(cyclopropyl-methyl)aminomethyl)phenyl |
| 128 | CH2CH3 | 2-pyridyl | 2-(N-(cyclobutyl)-aminomethyl)phenyl |
| 129 | CH2CH3 | 2-pyridyl | 2-(N-(cyclopentyl)-aminomethyl)phenyl |
| 130 | CH2CH3 | 2-pyridyl | 2-(N-(3-hydroxypyrrolidinyl)-methyl)phenyl |
| 131 | CH2CH3 | 3-pyridyl | 2-(aminosulfonyl)phenyl |
| 132 | CH2CH3 | 3-pyridyl | 2-(methylaminosulfonyl)phenyl |
| 133 | CH2CH3 | 3-pyridyl | 1-pyrrolidinocarbonyl |
| 134 | CH2CH3 | 3-pyridyl | 2-(methylsulfonyl)phenyl |
| 135 | CH2CH3 | 3-pyridyl | 2-(N,N-dimethylaminomethyl)phenyl |
| 136 | CH2CH3 | 3-pyridyl | 2-(N-pyrrolidinylmethyl)phenyl |
| 137 | CH2CH3 | 3-pyridyl | 1-methyl-2-imidazolyl |
| 138 | CH2CH3 | 3-pyridyl | 2-methyl-1-imidazolyl |
| 139 | CH2CH3 | 3-pyridyl | 2-(dimethylaminomethyl)-1-imidazolyl |
| 140 | CH2CH3 | 3-pyridyl | 2-(N-(cyclopropyl-methyl)aminomethyl)phenyl |
| 141 | CH2CH3 | 3-pyridyl | 2-(N-(cyclobutyl)-aminomethyl)phenyl |
| 142 | CH2CH3 | 3-pyridyl | 2-(N-(cyclopentyl)-aminomethyl)phenyl |
| 143 | CH2CH3 | 3-pyridyl | 2-(N-(3-hydroxypyrrolidinyl)-methyl)phenyl |
| 144 | CH2CH3 | 2-pyrimidyl | 2-(aminosulfonyl)phenyl |
| 145 | CH2CH3 | 2-pyrimidyl | 2-(methylaminosulfonyl)phenyl |
| 146 | CH2CH3 | 2-pyrimidyl | 1-pyrrolidinocarbonyl |
| 147 | CH2CH3 | 2-pyrimidyl | 2-(methylsulfonyl)phenyl |
| 148 | CH2CH3 | 2-pyrimidyl | 2-(N,N-dimethylaminomethyl)phenyl |
| 149 | CH2CH3 | 2-pyrimidyl | 2-(N-pyrrolidinylmethyl)phenyl |
| 150 | CH2CH3 | 2-pyrimidyl | 1-methyl-2-imidazolyl |
| 151 | CH2CH3 | 2-pyrimidyl | 2-methyl-1-imidazolyl |
| 152 | CH2CH3 | 2-pyrimidyl | 2-(dimethylaminomethyl)-1-imidazolyl |
| 153 | CH2CH3 | 2-pyrimidyl | 2-(N-(cyclopropyl-methyl)aminomethyl)phenyl |
| 154 | CH2CH3 | 2-pyrimidyl | 2-(N-(cyclobutyl)-aminomethyl)phenyl |
| 155 | CH2CH3 | 2-pyrimidyl | 2-(N-(cyclopentyl)-aminomethyl)phenyl |
| 156 | CH2CH3 | 2-pyrimidyl | 2-(N-(3-hydroxypyrrolidinyl)-methyl)phenyl |
| 157 | CH2CH3 | 5-pyrimidyl | 2-(aminosulfonyl)phenyl |
| 158 | CH2CH3 | 5-pyrimidyl | 2-(methylaminosulfonyl)phenyl |
| 159 | CH2CH3 | 5-pyrimidyl | 1-pyrrolidinocarbonyl |
| 160 | CH2CH3 | 5-pyrimidyl | 2-(methylsulfonyl)phenyl |
| 161 | CH2CH3 | 5-pyrimidyl | 2-(N,N-dimethylaminomethyl)phenyl |
| 162 | CH2CH3 | 5-pyrimidyl | 2-(N-pyrrolidinylmethyl)phenyl |
| 163 | CH2CH3 | 5-pyrimidyl | 1-methyl-2-imidazolyl |
| 164 | CH2CH3 | 5-pyrimidyl | 2-methyl-1-imidazolyl |
| 165 | CH2CH3 | 5-pyrimidyl | 2-(dimethylaminomethyl)-1-imidazolyl |
| 166 | CH2CH3 | 5-pyrimidyl | 2-(N-(cyclopropyl-methyl)aminomethyl)phenyl |
| 167 | CH2CH3 | 5-pyrimidyl | 2-(N-(cyclobutyl)-aminomethyl)phenyl |
| 168 | CH2CH3 | 5-pyrimidyl | 2-(N-(cyclopentyl)-aminomethyl)phenyl |
| 169 | CH2CH3 | 5-pyrimidyl | 2-(N-(3-hydroxypyrrolidinyl)-methyl)phenyl |
| 170 | CH2CH3 | 2-Cl-phenyl | 2-(aminosulfonyl)phenyl |
| 171 | CH2CH3 | 2-Cl-phenyl | 2-(methylaminosulfonyl)phenyl |
| 172 | CH2CH3 | 2-Cl-phenyl | 1-pyrrolidinocarbonyl |

-continued

| Ex# | R1a | A | B |
|---|---|---|---|
| 173 | CH2CH3 | 2-Cl-phenyl | 2-(methylsulfonyl)phenyl |
| 174 | CH2CH3 | 2-Cl-phenyl | 2-(N,N-dimethylaminomethyl)phenyl |
| 175 | CH2CH3 | 2-Cl-phenyl | 2-(N-pyrrolidinylmethyl)phenyl |
| 176 | CH2CH3 | 2-Cl-phenyl | 1-methyl-2-imidazolyl |
| 177 | CH2CH3 | 2-Cl-phenyl | 2-methyl-1-imidazolyl |
| 178 | CH2CH3 | 2-Cl-phenyl | 2-(dimethylaminomethyl)-1-imidazolyl |
| 179 | CH2CH3 | 2-Cl-phenyl | 2-(N-(cyclopropyl-methyl)aminomethyl)phenyl |
| 180 | CH2CH3 | 2-Cl-phenyl | 2-(N-(cyclobutyl)-aminomethyl)phenyl |
| 181 | CH2CH3 | 2-Cl-phenyl | 2-(N-(cyclopentyl)-aminomethyl)phenyl |
| 182 | CH2CH3 | 2-Cl-phenyl | 2-(N-(3-hydroxypyrrolidinyl)-methyl)phenyl |
| 183 | CH2CH3 | 2-F-phenyl | 2-(aminosulfonyl)phenyl |
| 184 | CH2CH3 | 2-F-phenyl | 2-(methylaminosulfonyl)phenyl |
| 185 | CH2CH3 | 2-F-phenyl | 1-pyrrolidinocarbonyl |
| 186 | CH2CH3 | 2-F-phenyl | 2-(methylsulfonyl)phenyl |
| 187 | CH2CH3 | 2-F-phenyl | 2-(N,N-dimethylaminomethyl)phenyl |
| 188 | CH2CH3 | 2-F-phenyl | 2-(N-pyrrolidinylmethyl)phenyl |
| 189 | CH2CH3 | 2-F-phenyl | 1-methyl-2-imidazolyl |
| 190 | CH2CH3 | 2-F-phenyl | 2-methyl-1-imidazolyl |
| 191 | CH2CH3 | 2-F-phenyl | 2-(dimethylaminomethyl)-1-imidazolyl |
| 192 | CH2CH3 | 2-F-phenyl | 2-(N-(cyclopropyl-methyl)aminomethyl)phenyl |
| 193 | CH2CH3 | 2-F-phenyl | 2-(N-(cyclobutyl)-aminomethyl)phenyl |
| 194 | CH2CH3 | 2-F-phenyl | 2-(N-(cyclopentyl)-aminomethyl)phenyl |
| 195 | CH2CH3 | 2-F-phenyl | 2-(N-(3-hydroxypyrrolidinyl)-methyl)phenyl |
| 196 | CH2CH3 | 2,6-diF-phenyl | 2-(aminosulfonyl)phenyl |
| 197 | CH2CH3 | 2,6-diF-phenyl | 2-(methylaminosulfonyl)phenyl |
| 198 | CH2CH3 | 2,6-diF-phenyl | 1-pyrrolidinocarbonyl |
| 199 | CH2CH3 | 2,6-diF-phenyl | 2-(methylsulfonyl)phenyl |
| 200 | CH2CH3 | 2,6-diF-phenyl | 2-(N,N-dimethylaminomethyl)phenyl |
| 201 | CH2CH3 | 2,6-diF-phenyl | 2-(N-pyrrolidinylmethyl)phenyl |
| 202 | CH2CH3 | 2,6-diF-phenyl | 1-methyl-2-imidazolyl |
| 203 | CH2CH3 | 2,6-diF-phenyl | 2-methyl-1-imidazolyl |
| 204 | CH2CH3 | 2,6-diF-phenyl | 2-(dimethylaminomethyl)-1-imidazolyl |
| 205 | CH2CH3 | 2,6-diF-phenyl | 2-(N-(cyclopropyl-methyl)aminomethyl)phenyl |
| 206 | CH2CH3 | 2,6-diF-phenyl | 2-(N-(cyclobutyl)-aminomethyl)phenyl |
| 207 | CH2CH3 | 2,6-diF-phenyl | 2-(N-(cyclopentyl)-aminomethyl)phenyl |
| 208 | CH2CH3 | 2,6-diF-phenyl | 2-(N-(3-hydroxypyrrolidinyl)-methyl)phenyl |
| 209 | CF3 | phenyl | 2-(aminosulfonyl)phenyl |
| 210 | CF3 | phenyl | 2-(methylaminosulfonyl)phenyl |
| 211 | CF3 | phenyl | 1-pyrrolidinocarbonyl |
| 212 | CF3 | phenyl | 2-(methylsulfonyl)phenyl |
| 213 | CF3 | phenyl | 2-(N,N-dimethylaminomethyl)phenyl |
| 214 | CF3 | phenyl | 2-(N-pyrrolidinylmethyl)phenyl |
| 215 | CF3 | phenyl | 1-methyl-2-imidazolyl |
| 216 | CF3 | phenyl | 2-methyl-1-imidazolyl |
| 217 | CF3 | phenyl | 2-(dimethylaminomethyl)-1-imidazolyl |
| 218 | CF3 | phenyl | 2-(N-(cyclopropyl-methyl)aminomethyl)phenyl |
| 219 | CF3 | phenyl | 2-(N-(cyclobutyl)-aminomethyl)phenyl |
| 220 | CF3 | phenyl | 2-(N-(cyclopentyl)-aminomethyl)phenyl |
| 221 | CF3 | phenyl | 2-(N-(3-hydroxypyrrolidinyl)-methyl)phenyl |
| 222 | CF3 | 2-pyridyl | 2-(aminosulfonyl)phenyl |
| 223 | CF3 | 2-pyridyl | 2-(methylaminosulfonyl)phenyl |
| 224 | CF3 | 2-pyridyl | 1-pyrrolidinocarbonyl |
| 225 | CF3 | 2-pyridyl | 2-(methylsulfonyl)phenyl |
| 226 | CF3 | 2-pyridyl | 2-(N,N-dimethylaminomethyl)phenyl |
| 227 | CF3 | 2-pyridyl | 2-(N-pyrrolidinylmethyl)phenyl |
| 228 | CF3 | 2-pyridyl | 1-methyl-2-imidazolyl |
| 229 | CF3 | 2-pyridyl | 2-methyl-1-imidazolyl |
| 230 | CF3 | 2-pyridyl | 2-(dimethylaminomethyl)-1-imidazolyl |
| 231 | CF3 | 2-pyridyl | 2-(N-(cyclopropyl-methyl)aminomethyl)phenyl |
| 232 | CF3 | 2-pyridyl | 2-(N-(cyclobutyl)-aminomethyl)phenyl |
| 233 | CF3 | 2-pyridyl | 2-(N-(cyclopentyl)-aminomethyl)phenyl |
| 234 | CF3 | 2-pyridyl | 2-(N-(3-hydroxypyrrolidinyl)-methyl)phenyl |
| 235 | CF3 | 3-pyridyl | 2-(aminosulfonyl)phenyl |
| 236 | CF3 | 3-pyridyl | 2-(methylaminosulfonyl)phenyl |
| 237 | CF3 | 3-pyridyl | 1-pyrrolidinocarbonyl |
| 238 | CF3 | 3-pyridyl | 2-(methylsulfonyl)phenyl |
| 239 | CF3 | 3-pyridyl | 2-(N,N-dimethylaminomethyl)phenyl |
| 240 | CF3 | 3-pyridyl | 2-(N-pyrrolidinylmethyl)phenyl |
| 241 | CF3 | 3-pyridyl | 1-methyl-2-imidazolyl |
| 242 | CF3 | 3-pyridyl | 2-methyl-1-imidazolyl |
| 243 | CF3 | 3-pyridyl | 2-(dimethylaminomethyl)-1-imidazolyl |
| 244 | CF3 | 3-pyridyl | 2-(N-(cyclopropyl-methyl)aminomethyl)phenyl |
| 245 | CF3 | 3-pyridyl | 2-(N-(cyclobutyl)-aminomethyl)phenyl |
| 246 | CF3 | 3-pyridyl | 2-(N-(cyclopentyl)-aminomethyl)phenyl |
| 247 | CF3 | 3-pyridyl | 2-(N-(3-hydroxypyrrolidinyl)-methyl)phenyl |
| 248 | CF3 | 2-pyrimidyl | 2-(aminosulfonyl)phenyl |
| 249 | CF3 | 2-pyrimidyl | 2-(methylaminosulfonyl)phenyl |
| 250 | CF3 | 2-pyrimidyl | 1-pyrrolidinocarbonyl |
| 251 | CF3 | 2-pyrimidyl | 2-(methylsulfonyl)phenyl |
| 252 | CF3 | 2-pyrimidyl | 2-(N,N-dimethylaminomethyl)phenyl |
| 253 | CF3 | 2-pyrimidyl | 2-(N-pyrrolidinylmethyl)phenyl |
| 254 | CF3 | 2-pyrimidyl | 1-methyl-2-imidazolyl |
| 255 | CF3 | 2-pyrimidyl | 2-methyl-1-imidazolyl |
| 256 | CF3 | 2-pyrimidyl | 2-(dimethylaminomethyl)-1-imidazolyl |
| 257 | CF3 | 2-pyrimidyl | 2-(N-(cyclopropyl-methyl)aminomethyl)phenyl |
| 258 | CF3 | 2-pyrimidyl | 2-(N-(cyclobutyl)-aminomethyl)phenyl |
| 259 | CF3 | 2-pyrimidyl | 2-(N-(cyclopentyl)-aminomethyl)phenyl |
| 260 | CF3 | 2-pyrimidyl | 2-(N-(3-hydroxypyrrolidinyl)-methyl)phenyl |
| 261 | CF3 | 5-pyrimidyl | 2-(aminosulfonyl)phenyl |
| 262 | CF3 | 5-pyrimidyl | 2-(methylaminosulfonyl)phenyl |
| 263 | CF3 | 5-pyrimidyl | 1-pyrrolidinocarbonyl |
| 264 | CF3 | 5-pyrimidyl | 2-(methylsulfonyl)phenyl |
| 265 | CF3 | 5-pyrimidyl | 2-(N,N-dimethylaminomethyl)phenyl |
| 266 | CF3 | 5-pyrimidyl | 2-(N-pyrrolidinylmethyl)phenyl |
| 267 | CF3 | 5-pyrimidyl | 1-methyl-2-imidazolyl |
| 268 | CF3 | 5-pyrimidyl | 2-methyl-1-imidazolyl |
| 269 | CF3 | 5-pyrimidyl | 2-(dimethylaminomethyl)-1-imidazolyl |
| 270 | CF3 | 5-pyrimidyl | 2-(N-(cyclopropyl-methyl)aminomethyl)phenyl |
| 271 | CF3 | 5-pyrimidyl | 2-(N-(cyclobutyl)-aminomethyl)phenyl |
| 272 | CF3 | 5-pyrimidyl | 2-(N-(cyclopentyl)-aminomethyl)phenyl |
| 273 | CF3 | 5-pyrimidyl | 2-(N-(3-hydroxypyrrolidinyl)-methyl)phenyl |
| 274 | CF3 | 2-Cl-phenyl | 2-(aminosulfonyl)phenyl |
| 275 | CF3 | 2-Cl-phenyl | 2-(methylaminosulfonyl)phenyl |
| 276 | CF3 | 2-Cl-phenyl | 1-pyrrolidinocarbonyl |
| 277 | CF3 | 2-Cl-phenyl | 2-(methylsulfonyl)phenyl |

-continued

| Ex# | R¹ᵃ | A | B |
|---|---|---|---|
| 278 | CF3 | 2-Cl-phenyl | 2-(N,N-dimethylaminomethyl)phenyl |
| 279 | CF3 | 2-Cl-phenyl | 2-(N-pyrrolidinylmethyl)phenyl |
| 280 | CF3 | 2-Cl-phenyl | 1-methyl-2-imidazolyl |
| 281 | CF3 | 2-Cl-phenyl | 2-methyl-1-imidazolyl |
| 282 | CF3 | 2-Cl-phenyl | 2-(dimethylaminomethyl)-1-imidazolyl |
| 283 | CF3 | 2-Cl-phenyl | 2-(N-(cyclopropyl-methyl)aminomethyl)phenyl |
| 284 | CF3 | 2-Cl-phenyl | 2-(N-(cyclobutyl)-aminomethyl)phenyl |
| 285 | CF3 | 2-Cl-phenyl | 2-(N-(cyclopentyl)-aminomethyl)phenyl |
| 286 | CF3 | 2-Cl-phenyl | 2-(N-(3-hydroxypyrrolidinyl)-methyl)phenyl |
| 287 | CF3 | 2-F-phenyl | 2-(aminosulfonyl)phenyl |
| 288 | CF3 | 2-F-phenyl | 2-(methylaminosulfonyl)phenyl |
| 289 | CF3 | 2-F-phenyl | 1-pyrrolidinocarbonyl |
| 290 | CF3 | 2-F-phenyl | 2-(methylsulfonyl)phenyl |
| 291 | CF3 | 2-F-phenyl | 2-(N,N-dimethylaminomethyl)phenyl |
| 292 | CF3 | 2-F-phenyl | 2-(N-pyrrolidinylmethyl)phenyl |
| 293 | CF3 | 2-F-phenyl | 1-methyl-2-imidazolyl |
| 294 | CF3 | 2-F-phenyl | 2-methyl-1-imidazolyl |
| 295 | CF3 | 2-F-phenyl | 2-(dimethylaminomethyl)-1-imidazolyl |
| 296 | CF3 | 2-F-phenyl | 2-(N-(cyclopropyl-methyl)aminomethyl)phenyl |
| 297 | CF3 | 2-F-phenyl | 2-(N-(cyclobutyl)-aminomethyl)phenyl |
| 298 | CF3 | 2-F-phenyl | 2-(N-(cyclopentyl)-aminomethyl)phenyl |
| 299 | CF3 | 2-F-phenyl | 2-(N-(3-hydroxypyrrolidinyl)-methyl)phenyl |
| 300 | CF3 | 2,6-diF-phenyl | 2-(aminosulfonyl)phenyl |
| 301 | CF3 | 2,6-diF-phenyl | 2-(methylaminosulfonyl)phenyl |
| 302 | CF3 | 2,6-diF-phenyl | 1-pyrrolidinocarbonyl |
| 303 | CF3 | 2,6-diF-phenyl | 2-(methylsulfonyl)phenyl |
| 304 | CF3 | 2,6-diF-phenyl | 2-(N,N-dimethylaminomethyl)phenyl |
| 305 | CF3 | 2,6-diF-phenyl | 2-(N-pyrrolidinylmethyl)phenyl |
| 306 | CF3 | 2,6-diF-phenyl | 1-methyl-2-imidazolyl |
| 307 | CF3 | 2,6-diF-phenyl | 2-methyl-1-imidazolyl |
| 308 | CF3 | 2,6-diF-phenyl | 2-(dimethylaminomethyl)-1-imidazolyl |
| 309 | CF3 | 2,6-diF-phenyl | 2-(N-(cyclopropyl-methyl)aminomethyl)phenyl |
| 310 | CF3 | 2,6-diF-phenyl | 2-(N-(cyclobutyl)-aminomethyl)phenyl |
| 311 | CF3 | 2,6-diF-phenyl | 2-(N-(cyclopentyl)-aminomethyl)phenyl |
| 312 | CF3 | 2,6-diF-phenyl | 2-(N-(3-hydroxypyrrolidinyl)-methyl)phenyl |
| 313 | SCH3 | phenyl | 2-(aminosulfonyl)phenyl |
| 314 | SCH3 | phenyl | 2-(methylaminosulfonyl)phenyl |
| 315 | SCH3 | phenyl | 1-pyrrolidinocarbonyl |
| 316 | SCH3 | phenyl | 2-(methylsulfonyl)phenyl |
| 317 | SCH3 | phenyl | 2-(N,N-dimethylaminomethyl)phenyl |
| 318 | SCH3 | phenyl | 2-(N-pyrrolidinylmethyl)phenyl |
| 319 | SCH3 | phenyl | 1-methyl-2-imidazolyl |
| 320 | SCH3 | phenyl | 2-methyl-1-imidazolyl |
| 321 | SCH3 | phenyl | 2-(dimethylaminomethyl)-1-imidazolyl |
| 322 | SCH3 | phenyl | 2-(N-(cyclopropyl-methyl)aminomethyl)phenyl |
| 323 | SCH3 | phenyl | 2-(N-(cyclobutyl)-aminomethyl)phenyl |
| 324 | SCH3 | phenyl | 2-(N-(cyclopentyl)-aminomethyl)phenyl |
| 325 | SCH3 | phenyl | 2-(N-(3-hydroxypyrrolidinyl)-methyl)phenyl |
| 326 | SCH3 | 2-pyridyl | 2-(aminosulfonyl)phenyl |
| 327 | SCH3 | 2-pyridyl | 2-(methylaminosulfonyl)phenyl |
| 328 | SCH3 | 2-pyridyl | 1-pyrrolidinocarbonyl |
| 329 | SCH3 | 2-pyridyl | 2-(methylsulfonyl)phenyl |
| 330 | SCH3 | 2-pyridyl | 2-(N,N-dimethylaminomethyl)phenyl |
| 331 | SCH3 | 2-pyridyl | 2-(N-pyrrolidinylmethyl)phenyl |
| 332 | SCH3 | 2-pyridyl | 1-methyl-2-imidazolyl |
| 333 | SCH3 | 2-pyridyl | 2-methyl-1-imidazolyl |
| 334 | SCH3 | 2-pyridyl | 2-(dimethylaminomethyl)-1-imidazolyl |
| 335 | SCH3 | 2-pyridyl | 2-(N-(cyclopropyl-methyl)aminomethyl)phenyl |
| 336 | SCH3 | 2-pyridyl | 2-(N-(cyclobutyl)-aminomethyl)phenyl |
| 337 | SCH3 | 2-pyridyl | 2-(N-(cyclopentyl)-aminomethyl)phenyl |
| 338 | SCH3 | 2-pyridyl | 2-(N-(3-hydroxypyrrolidinyl)-methyl)phenyl |
| 339 | SCH3 | 3-pyridyl | 2-(aminosulfonyl)phenyl |
| 340 | SCH3 | 3-pyridyl | 2-(methylaminosulfonyl)phenyl |
| 341 | SCH3 | 3-pyridyl | 1-pyrrolidinocarbonyl |
| 342 | SCH3 | 3-pyridyl | 2-(methylsulfonyl)phenyl |
| 343 | SCH3 | 3-pyridyl | 2-(N,N-dimethylaminomethyl)phenyl |
| 344 | SCH3 | 3-pyridyl | 2-(N-pyrrolidinylmethyl)phenyl |
| 345 | SCH3 | 3-pyridyl | 1-methyl-2-imidazolyl |
| 346 | SCH3 | 3-pyridyl | 2-methyl-1-imidazolyl |
| 347 | SCH3 | 3-pyridyl | 2-(dimethylaminomethyl)-1-imidazolyl |
| 348 | SCH3 | 3-pyridyl | 2-(N-(cyclopropyl-methyl)aminomethyl)phenyl |
| 349 | SCH3 | 3-pyridyl | 2-(N-(cyclobutyl)-aminomethyl)phenyl |
| 350 | SCH3 | 3-pyridyl | 2-(N-(cyclopentyl)-aminomethyl)phenyl |
| 351 | SCH3 | 3-pyridyl | 2-(N-(3-hydroxypyrrolidinyl)-methyl)phenyl |
| 352 | SCH3 | 2-pyrimidyl | 2-(aminosulfonyl)phenyl |
| 353 | SCH3 | 2-pyrimidyl | 2-(methylaminosulfonyl)phenyl |
| 354 | SCH3 | 2-pyrimidyl | 1-pyrrolidinocarbonyl |
| 355 | SCH3 | 2-pyrimidyl | 2-(methylsulfonyl)phenyl |
| 356 | SCH3 | 2-pyrimidyl | 2-(N,N-dimethylaminomethyl)phenyl |
| 357 | SCH3 | 2-pyrimidyl | 2-(N-pyrrolidinylmethyl)phenyl |
| 358 | SCH3 | 2-pyrimidyl | 1-methyl-2-imidazolyl |
| 359 | SCH3 | 2-pyrimidyl | 2-methyl-1-imidazolyl |
| 360 | SCH3 | 2-pyrimidyl | 2-(dimethylaminomethyl)-1-imidazolyl |
| 361 | SCH3 | 2-pyrimidyl | 2-(N-(cyclopropyl-methyl)aminomethyl)phenyl |
| 362 | SCH3 | 2-pyrimidyl | 2-(N-(cyclobutyl)-aminomethyl)phenyl |
| 363 | SCH3 | 2-pyrimidyl | 2-(N-(cyclopentyl)-aminomethyl)phenyl |
| 364 | SCH3 | 2-pyrimidyl | 2-(N-(3-hydroxypyrrolidinyl)-methyl)phenyl |
| 365 | SCH3 | 5-pyrimidyl | 2-(aminosulfonyl)phenyl |
| 366 | SCH3 | 5-pyrimidyl | 2-(methylaminosulfonyl)phenyl |
| 367 | SCH3 | 5-pyrimidyl | 1-pyrrolidinocarbonyl |
| 368 | SCH3 | 5-pyrimidyl | 2-(methylsulfonyl)phenyl |
| 369 | SCH3 | 5-pyrimidyl | 2-(N,N-dimethylaminomethyl)phenyl |
| 370 | SCH3 | 5-pyrimidyl | 2-(N-pyrrolidinylmethyl)phenyl |
| 371 | SCH3 | 5-pyrimidyl | 1-methyl-2-imidazolyl |
| 372 | SCH3 | 5-pyrimidyl | 2-methyl-1-imidazolyl |
| 373 | SCH3 | 5-pyrimidyl | 2-(dimethylaminomethyl)-1-imidazolyl |
| 374 | SCH3 | 5-pyrimidyl | 2-(N-(cyclopropyl-methyl)aminomethyl)phenyl |
| 375 | SCH3 | 5-pyrimidyl | 2-(N-(cyclobutyl)-aminomethyl)phenyl |
| 376 | SCH3 | 5-pyrimidyl | 2-(N-(cyclopentyl)-aminomethyl)phenyl |
| 377 | SCH3 | 5-pyrimidyl | 2-(N-(3-hydroxypyrrolidinyl)-methyl)phenyl |
| 378 | SCH3 | 2-Cl-phenyl | 2-(aminosulfonyl)phenyl |
| 379 | SCH3 | 2-Cl-phenyl | 2-(methylaminosulfonyl)phenyl |
| 380 | SCH3 | 2-Cl-phenyl | 1-pyrrolidinocarbonyl |
| 381 | SCH3 | 2-Cl-phenyl | 2-(methylsulfonyl)phenyl |
| 382 | SCH3 | 2-Cl-phenyl | 2-(N,N-dimethylaminomethyl)phenyl |

-continued

| Ex# | R1a | A | B |
|---|---|---|---|
| 383 | SCH3 | 2-Cl-phenyl | 2-(N-pyrrolidinylmethyl)phenyl |
| 384 | SCH3 | 2-Cl-phenyl | 1-methyl-2-imidazolyl |
| 385 | SCH3 | 2-Cl-phenyl | 2-methyl-1-imidazolyl |
| 386 | SCH3 | 2-Cl-phenyl | 2-(dimethylaminomethyl)-1-imidazolyl |
| 387 | SCH3 | 2-Cl-phenyl | 2-(N-(cyclopropyl-methyl)aminomethyl)phenyl |
| 388 | SCH3 | 2-Cl-phenyl | 2-(N-(cyclobutyl)-aminomethyl)phenyl |
| 389 | SCH3 | 2-Cl-phenyl | 2-(N-(cyclopentyl)-aminomethyl)phenyl |
| 390 | SCH3 | 2-Cl-phenyl | 2-(N-(3-hydroxypyrrolidinyl)-methyl)phenyl |
| 391 | SCH3 | 2-F-phenyl | 2-(aminosulfonyl)phenyl |
| 392 | SCH3 | 2-F-phenyl | 2-(methylaminosulfonyl)phenyl |
| 393 | SCH3 | 2-F-phenyl | 1-pyrrolidinocarbonyl |
| 394 | SCH3 | 2-F-phenyl | 2-(methylsulfonyl)phenyl |
| 395 | SCH3 | 2-F-phenyl | 2-(N,N-dimethylaminomethyl)phenyl |
| 396 | SCH3 | 2-F-phenyl | 2-(N-pyrrolidinylmethyl)phenyl |
| 397 | SCH3 | 2-F-phenyl | 1-methyl-2-imidazolyl |
| 398 | SCH3 | 2-F-phenyl | 2-methyl-1-imidazolyl |
| 399 | SCH3 | 2-F-phenyl | 2-(dimethylaminomethyl)-1-imidazolyl |
| 400 | SCH3 | 2-F-phenyl | 2-(N-(cyclopropyl-methyl)aminomethyl)phenyl |
| 401 | SCH3 | 2-F-phenyl | 2-(N-(cyclobutyl)-aminomethyl)phenyl |
| 402 | SCH3 | 2-F-phenyl | 2-(N-(cyclopentyl)-aminomethyl)phenyl |
| 403 | SCH3 | 2-F-phenyl | 2-(N-(3-hydroxypyrrolidinyl)-methyl)phenyl |
| 404 | SCH3 | 2,6-diF-phenyl | 2-(aminosulfonyl)phenyl |
| 405 | SCH3 | 2,6-diF-phenyl | 2-(methylaminosulfonyl)phenyl |
| 406 | SCH3 | 2,6-diF-phenyl | 1-pyrrolidinocarbonyl |
| 407 | SCH3 | 2,6-diF-phenyl | 2-(methylsulfonyl)phenyl |
| 408 | SCH3 | 2,6-diF-phenyl | 2-(N,N-dimethylaminomethyl)phenyl |
| 409 | SCH3 | 2,6-diF-phenyl | 2-(N-pyrrolidinylmethyl)phenyl |
| 410 | SCH3 | 2,6-diF-phenyl | 1-methyl-2-imidazolyl |
| 411 | SCH3 | 2,6-diF-phenyl | 2-methyl-1-imidazolyl |
| 412 | SCH3 | 2,6-diF-phenyl | 2-(dimethylaminomethyl)-1-imidazolyl |
| 413 | SCH3 | 2,6-diF-phenyl | 2-(N-(cyclopropyl-methyl)aminomethyl)phenyl |
| 414 | SCH3 | 2,6-diF-phenyl | 2-(N-(cyclobutyl)-aminomethyl)phenyl |
| 415 | SCH3 | 2,6-diF-phenyl | 2-(N-(cyclopentyl)-aminomethyl)phenyl |
| 416 | SCH3 | 2,6-diF-phenyl | 2-(N-(3-hydroxypyrrolidinyl)-methyl)phenyl |
| 417 | SOCH3 | phenyl | 2-(aminosulfonyl)phenyl |
| 418 | SOCH3 | phenyl | 2-(methylaminosulfonyl)phenyl |
| 419 | SOCH3 | phenyl | 1-pyrrolidinocarbonyl |
| 420 | SOCH3 | phenyl | 2-(methylsulfonyl)phenyl |
| 421 | SOCH3 | phenyl | 2-(N,N-dimethylaminomethyl)phenyl |
| 422 | SOCH3 | phenyl | 2-(N-pyrrolidinylmethyl)phenyl |
| 423 | SOCH3 | phenyl | 1-methyl-2-imidazolyl |
| 424 | SOCH3 | phenyl | 2-methyl-1-imidazolyl |
| 425 | SOCH3 | phenyl | 2-(dimethylaminomethyl)-1-imidazolyl |
| 426 | SOCH3 | phenyl | 2-(N-(cyclopropyl-methyl)aminomethyl)phenyl |
| 427 | SOCH3 | phenyl | 2-(N-(cyclobutyl)-aminomethyl)phenyl |
| 428 | SOCH3 | phenyl | 2-(N-(cyclopentyl)-aminomethyl)phenyl |
| 429 | SOCH3 | phenyl | 2-(N-(3-hydroxypyrrolidinyl)-methyl)phenyl |
| 430 | SOCH3 | 2-pyridyl | 2-(aminosulfonyl)phenyl |
| 431 | SOCH3 | 2-pyridyl | 2-(methylaminosulfonyl)phenyl |
| 432 | SOCH3 | 2-pyridyl | 1-pyrrolidinocarbonyl |
| 433 | SOCH3 | 2-pyridyl | 2-(methylsulfonyl)phenyl |
| 434 | SOCH3 | 2-pyridyl | 2-(N,N-dimethylaminomethyl)phenyl |
| 435 | SOCH3 | 2-pyridyl | 2-(N-pyrrolidinylmethyl)phenyl |
| 436 | SOCH3 | 2-pyridyl | 1-methyl-2-imidazolyl |
| 437 | SOCH3 | 2-pyridyl | 2-methyl-1-imidazolyl |
| 438 | SOCH3 | 2-pyridyl | 2-(dimethylaminomethyl)-1-imidazolyl |
| 439 | SOCH3 | 2-pyridyl | 2-(N-(cyclopropyl-methyl)aminomethyl)phenyl |
| 440 | SOCH3 | 2-pyridyl | 2-(N-(cyclobutyl)-aminomethyl)phenyl |
| 441 | SOCH3 | 2-pyridyl | 2-(N-(cyclopentyl)-aminomethyl)phenyl |
| 442 | SOCH3 | 2-pyridyl | 2-(N-(3-hydroxypyrrolidinyl)-methyl)phenyl |
| 443 | SOCH3 | 3-pyridyl | 2-(aminosulfonyl)phenyl |
| 444 | SOCH3 | 3-pyridyl | 2-(methylaminosulfonyl)phenyl |
| 445 | SOCH3 | 3-pyridyl | 1-pyrrolidinocarbonyl |
| 446 | SOCH3 | 3-pyridyl | 2-(methylsulfonyl)phenyl |
| 447 | SOCH3 | 3-pyridyl | 2-(N,N-dimethylaminomethyl)phenyl |
| 448 | SOCH3 | 3-pyridyl | 2-(N-pyrrolidinylmethyl)phenyl |
| 449 | SOCH3 | 3-pyridyl | 1-methyl-2-imidazolyl |
| 450 | SOCH3 | 3-pyridyl | 2-methyl-1-imidazolyl |
| 451 | SOCH3 | 3-pyridyl | 2-(dimethylaminomethyl)-1-imidazolyl |
| 452 | SOCH3 | 3-pyridyl | 2-(N-(cyclopropyl-methyl)aminomethyl)phenyl |
| 453 | SOCH3 | 3-pyridyl | 2-(N-(cyclobutyl)-aminomethyl)phenyl |
| 454 | SOCH3 | 3-pyridyl | 2-(N-(cyclopentyl)-aminomethyl)phenyl |
| 455 | SOCH3 | 3-pyridyl | 2-(N-(3-hydroxypyrrolidinyl)-methyl)phenyl |
| 456 | SOCH3 | 2-pyrimidyl | 2-(aminosulfonyl)phenyl |
| 457 | SOCH3 | 2-pyrimidyl | 2-(methylaminosulfonyl)phenyl |
| 458 | SOCH3 | 2-pyrimidyl | 1-pyrrolidinocarbonyl |
| 459 | SOCH3 | 2-pyrimidyl | 2-(methylsulfonyl)phenyl |
| 460 | SOCH3 | 2-pyrimidyl | 2-(N,N-dimethylaminomethyl)phenyl |
| 461 | SOCH3 | 2-pyrimidyl | 2-(N-pyrrolidinylmethyl)phenyl |
| 462 | SOCH3 | 2-pyrimidyl | 1-methyl-2-imidazolyl |
| 463 | SOCH3 | 2-pyrimidyl | 2-methyl-1-imidazolyl |
| 464 | SOCH3 | 2-pyrimidyl | 2-(dimethylaminomethyl)-1-imidazolyl |
| 465 | SOCH3 | 2-pyrimidyl | 2-(N-(cyclopropyl-methyl)aminomethyl)phenyl |
| 466 | SOCH3 | 2-pyrimidyl | 2-(N-(cyclobutyl)-aminomethyl)phenyl |
| 467 | SOCH3 | 2-pyrimidyl | 2-(N-(cyclopentyl)-aminomethyl)phenyl |
| 468 | SOCH3 | 2-pyrimidyl | 2-(N-(3-hydroxypyrrolidinyl)-methyl)phenyl |
| 469 | SOCH3 | 5-pyrimidyl | 2-(aminosulfonyl)phenyl |
| 470 | SOCH3 | 5-pyrimidyl | 2-(methylaminosulfonyl)phenyl |
| 471 | SOCH3 | 5-pyrimidyl | 1-pyrrolidinocarbonyl |
| 472 | SOCH3 | 5-pyrimidyl | 2-(methylsulfonyl)phenyl |
| 473 | SOCH3 | 5-pyrimidyl | 2-(N,N-dimethylaminomethyl)phenyl |
| 474 | SOCH3 | 5-pyrimidyl | 2-(N-pyrrolidinylmethyl)phenyl |
| 475 | SOCH3 | 5-pyrimidyl | 1-methyl-2-imidazolyl |
| 476 | SOCH3 | 5-pyrimidyl | 2-methyl-1-imidazolyl |
| 477 | SOCH3 | 5-pyrimidyl | 2-(dimethylaminomethyl)-1-imidazolyl |
| 478 | SOCH3 | 5-pyrimidyl | 2-(N-(cyclopropyl-methyl)aminomethyl)phenyl |
| 479 | SOCH3 | 5-pyrimidyl | 2-(N-(cyclobutyl)-aminomethyl)phenyl |
| 480 | SOCH3 | 5-pyrimidyl | 2-(N-(cyclopentyl)-aminomethyl)phenyl |
| 481 | SOCH3 | 5-pyrimidyl | 2-(N-(3-hydroxypyrrolidinyl)-methyl)phenyl |
| 482 | SOCH3 | 2-Cl-phenyl | 2-(aminosulfonyl)phenyl |
| 483 | SOCH3 | 2-Cl-phenyl | 2-(methylaminosulfonyl)phenyl |
| 484 | SOCH3 | 2-Cl-phenyl | 1-pyrrolidinocarbonyl |
| 485 | SOCH3 | 2-Cl-phenyl | 2-(methylsulfonyl)phenyl |
| 486 | SOCH3 | 2-Cl-phenyl | 2-(N,N-dimethylaminomethyl)phenyl |
| 487 | SOCH3 | 2-Cl-phenyl | 2-(N-pyrrolidinylmethyl)phenyl |
| 488 | SOCH3 | 2-Cl-phenyl | 1-methyl-2-imidazolyl |

-continued

| Ex# | R$^{1a}$ | A | B |
|---|---|---|---|
| 489 | SOCH3 | 2-Cl-phenyl | 2-methyl-1-imidazolyl |
| 490 | SOCH3 | 2-Cl-phenyl | 2-(dimethylaminomethyl)-1-imidazolyl |
| 491 | SOCH3 | 2-Cl-phenyl | 2-(N-(cyclopropyl-methyl)aminomethyl)phenyl |
| 492 | SOCH3 | 2-Cl-phenyl | 2-(N-(cyclobutyl)-aminomethyl)phenyl |
| 493 | SOCH3 | 2-Cl-phenyl | 2-(N-(cyclopentyl)-aminomethyl)phenyl |
| 494 | SOCH3 | 2-Cl-phenyl | 2-(N-(3-hydroxypyrrolidinyl)-methyl)phenyl |
| 495 | SOCH3 | 2-F-phenyl | 2-(aminosulfonyl)phenyl |
| 496 | SOCH3 | 2-F-phenyl | 2-(methylaminosulfonyl)phenyl |
| 497 | SOCH3 | 2-F-phenyl | 1-pyrrolidinocarbonyl |
| 498 | SOCH3 | 2-F-phenyl | 2-(methylsulfonyl)phenyl |
| 499 | SOCH3 | 2-F-phenyl | 2-(N,N-dimethylaminomethyl)phenyl |
| 500 | SOCH3 | 2-F-phenyl | 2-(N-pyrrolidinylmethyl)phenyl |
| 501 | SOCH3 | 2-F-phenyl | 1-methyl-2-imidazolyl |
| 502 | SOCH3 | 2-F-phenyl | 2-methyl-1-imidazolyl |
| 503 | SOCH3 | 2-F-phenyl | 2-(dimethylaminomethyl)-1-imidazolyl |
| 504 | SOCH3 | 2-F-phenyl | 2-(N-(cyclopropyl-methyl)aminomethyl)phenyl |
| 505 | SOCH3 | 2-F-phenyl | 2-(N-(cyclobutyl)-aminomethyl)phenyl |
| 506 | SOCH3 | 2-F-phenyl | 2-(N-(cyclopentyl)-aminomethyl)phenyl |
| 507 | SOCH3 | 2-F-phenyl | 2-(N-(3-hydroxypyrrolidinyl)-methyl)phenyl |
| 508 | SOCH3 | 2,6-diF-phenyl | 2-(aminosulfonyl)phenyl |
| 509 | SOCH3 | 2,6-diF-phenyl | 2-(methylaminosulfonyl)phenyl |
| 510 | SOCH3 | 2,6-diF-phenyl | 1-pyrrolidinocarbonyl |
| 511 | SOCH3 | 2,6-diF-phenyl | 2-(methylsulfonyl)phenyl |
| 512 | SOCH3 | 2,6-diF-phenyl | 2-(N,N-dimethylaminomethyl)phenyl |
| 513 | SOCH3 | 2,6-diF-phenyl | 2-(N-pyrrolidinylmethyl)phenyl |
| 514 | SOCH3 | 2,6-diF-phenyl | 1-methyl-2-imidazolyl |
| 515 | SOCH3 | 2,6-diF-phenyl | 2-methyl-1-imidazolyl |
| 516 | SOCH3 | 2,6-diF-phenyl | 2-(dimethylaminomethyl)-1-imidazolyl |
| 517 | SOCH3 | 2,6-diF-phenyl | 2-(N-(cyclopropyl-methyl)aminomethyl)phenyl |
| 518 | SOCH3 | 2,6-diF-phenyl | 2-(N-(cyclobutyl)-aminomethyl)phenyl |
| 519 | SOCH3 | 2,6-diF-phenyl | 2-(N-(cyclopentyl)-aminomethyl)phenyl |
| 520 | SOCH3 | 2,6-diF-phenyl | 2-(N-(3-hydroxypyrrolidinyl)-methyl)phenyl |
| 521 | SO2CH3 | phenyl | 2-(aminosulfonyl)phenyl |
| 522 | SO2CH3 | phenyl | 2-(methylaminosulfonyl)phenyl |
| 523 | SO2CH3 | phenyl | 1-pyrrolidinocarbonyl |
| 524 | SO2CH3 | phenyl | 2-(methylsulfonyl)phenyl |
| 525 | SO2CH3 | phenyl | 2-(N,N-dimethylaminomethyl)phenyl |
| 526 | SO2CH3 | phenyl | 2-(N-pyrrolidinylmethyl)phenyl |
| 527 | SO2CH3 | phenyl | 1-methyl-2-imidazolyl |
| 528 | SO2CH3 | phenyl | 2-methyl-1-imidazolyl |
| 529 | SO2CH3 | phenyl | 2-(dimethylaminomethyl)-1-imidazolyl |
| 530 | SO2CH3 | phenyl | 2-(N-(cyclopropyl-methyl)aminomethyl)phenyl |
| 531 | SO2CH3 | phenyl | 2-(N-(cyclobutyl)-aminomethyl)phenyl |
| 532 | SO2CH3 | phenyl | 2-(N-(cyclopentyl)-aminomethyl)phenyl |
| 533 | SO2CH3 | phenyl | 2-(N-(3-hydroxypyrrolidinyl)-methyl)phenyl |
| 534 | SO2CH3 | 2-pyridyl | 2-(aminosulfonyl)phenyl |
| 535 | SO2CH3 | 2-pyridyl | 2-(methylaminosulfonyl)phenyl |
| 536 | SO2CH3 | 2-pyridyl | 1-pyrrolidinocarbonyl |
| 537 | SO2CH3 | 2-pyridyl | 2-(methylsulfonyl)phenyl |
| 538 | SO2CH3 | 2-pyridyl | 2-(N,N-dimethylaminomethyl)phenyl |
| 539 | SO2CH3 | 2-pyridyl | 2-(N-pyrrolidinylmethyl)phenyl |
| 540 | SO2CH3 | 2-pyridyl | 1-methyl-2-imidazolyl |
| 541 | SO2CH3 | 2-pyridyl | 2-methyl-1-imidazolyl |

-continued

| Ex# | R$^{1a}$ | A | B |
|---|---|---|---|
| 542 | SO2CH3 | 2-pyridyl | 2-(dimethylaminomethyl)-1-imidazolyl |
| 543 | SO2CH3 | 2-pyridyl | 2-(N-(cyclopropyl-methyl)aminomethyl)phenyl |
| 544 | SO2CH3 | 2-pyridyl | 2-(N-(cyclobutyl)-aminomethyl)phenyl |
| 545 | SO2CH3 | 2-pyridyl | 2-(N-(cyclopentyl)-aminomethyl)phenyl |
| 546 | SO2CH3 | 2-pyridyl | 2-(N-(3-hydroxypyrrolidinyl)-methyl)phenyl |
| 547 | SO2CH3 | 3-pyridyl | 2-(aminosulfonyl)phenyl |
| 548 | SO2CH3 | 3-pyridyl | 2-(methylaminosulfonyl)phenyl |
| 549 | SO2CH3 | 3-pyridyl | 1-pyrrolidinocarbonyl |
| 550 | SO2CH3 | 3-pyridyl | 2-(methylsulfonyl)phenyl |
| 551 | SO2CH3 | 3-pyridyl | 2-(N,N-dimethylaminomethyl)phenyl |
| 552 | SO2CH3 | 3-pyridyl | 2-(N-pyrrolidinylmethyl)phenyl |
| 553 | SO2CH3 | 3-pyridyl | 1-methyl-2-imidazolyl |
| 554 | SO2CH3 | 3-pyridyl | 2-methyl-1-imidazolyl |
| 555 | SO2CH3 | 3-pyridyl | 2-(dimethylaminomethyl)-1-imidazolyl |
| 556 | SO2CH3 | 3-pyridyl | 2-(N-(cyclopropyl-methyl)aminomethyl)phenyl |
| 557 | SO2CH3 | 3-pyridyl | 2-(N-(cyclobutyl)-aminomethyl)phenyl |
| 558 | SO2CH3 | 3-pyridyl | 2-(N-(cyclopentyl)-aminomethyl)phenyl |
| 559 | SO2CH3 | 3-pyridyl | 2-(N-(3-hydroxypyrrolidinyl)-methyl)phenyl |
| 560 | SO2CH3 | 2-pyrimidyl | 2-(aminosulfonyl)phenyl |
| 561 | SO2CH3 | 2-pyrimidyl | 2-(methylaminosulfonyl)phenyl |
| 562 | SO2CH3 | 2-pyrimidyl | 1-pyrrolidinocarbonyl |
| 563 | SO2CH3 | 2-pyrimidyl | 2-(methylsulfonyl)phenyl |
| 564 | SO2CH3 | 2-pyrimidyl | 2-(N,N-dimethylaminomethyl)phenyl |
| 565 | SO2CH3 | 2-pyrimidyl | 2-(N-pyrrolidinylmethyl)phenyl |
| 566 | SO2CH3 | 2-pyrimidyl | 1-methyl-2-imidazolyl |
| 567 | SO2CH3 | 2-pyrimidyl | 2-methyl-1-imidazolyl |
| 568 | SO2CH3 | 2-pyrimidyl | 2-(dimethylaminomethyl)-1-imidazolyl |
| 569 | SO2CH3 | 2-pyrimidyl | 2-(N-(cyclopropyl-methyl)aminomethyl)phenyl |
| 570 | SO2CH3 | 2-pyrimidyl | 2-(N-(cyclobutyl)-aminomethyl)phenyl |
| 571 | SO2CH3 | 2-pyrimidyl | 2-(N-(cyclopentyl)-aminomethyl)phenyl |
| 572 | SO2CH3 | 2-pyrimidyl | 2-(N-(3-hydroxypyrrolidinyl)-methyl)phenyl |
| 573 | SO2CH3 | 5-pyrimidyl | 2-(aminosulfonyl)phenyl |
| 574 | SO2CH3 | 5-pyrimidyl | 2-(methylaminosulfonyl)phenyl |
| 575 | SO2CH3 | 5-pyrimidyl | 1-pyrrolidinocarbonyl |
| 576 | SO2CH3 | 5-pyrimidyl | 2-(methylsulfonyl)phenyl |
| 577 | SO2CH3 | 5-pyrimidyl | 2-(N,N-dimethylaminomethyl)phenyl |
| 578 | SO2CH3 | 5-pyrimidyl | 2-(N-pyrrolidinylmethyl)phenyl |
| 579 | SO2CH3 | 5-pyrimidyl | 1-methyl-2-imidazolyl |
| 580 | SO2CH3 | 5-pyrimidyl | 2-methyl-1-imidazolyl |
| 581 | SO2CH3 | 5-pyrimidyl | 2-(dimethylaminomethyl)-1-imidazolyl |
| 582 | SO2CH3 | 5-pyrimidyl | 2-(N-(cyclopropyl-methyl)aminomethyl)phenyl |
| 583 | SO2CH3 | 5-pyrimidyl | 2-(N-(cyclobutyl)-aminomethyl)phenyl |
| 584 | SO2CH3 | 5-pyrimidyl | 2-(N-(cyclopentyl)-aminomethyl)phenyl |
| 585 | SO2CH3 | 5-pyrimidyl | 2-(N-(3-hydroxypyrrolidinyl)-methyl)phenyl |
| 586 | SO2CH3 | 2-Cl-phenyl | 2-(aminosulfonyl)phenyl |
| 587 | SO2CH3 | 2-Cl-phenyl | 2-(methylaminosulfonyl)phenyl |
| 588 | SO2CH3 | 2-Cl-phenyl | 1-pyrrolidinocarbonyl |
| 589 | SO2CH3 | 2-Cl-phenyl | 2-(methylsulfonyl)phenyl |
| 590 | SO2CH3 | 2-Cl-phenyl | 2-(N,N-dimethylaminomethyl)phenyl |
| 591 | SO2CH3 | 2-Cl-phenyl | 2-(N-pyrrolidinylmethyl)phenyl |
| 592 | SO2CH3 | 2-Cl-phenyl | 1-methyl-2-imidazolyl |
| 593 | SO2CH3 | 2-Cl-phenyl | 2-methyl-1-imidazolyl |

-continued

| Ex# | R1a | A | B |
|---|---|---|---|
| 594 | SO2CH3 | 2-Cl-phenyl | 2-(dimethylaminomethyl)-1-imidazolyl |
| 595 | SO2CH3 | 2-Cl-phenyl | 2-(N-(cyclopropyl-methyl)aminomethyl)phenyl |
| 596 | SO2CH3 | 2-Cl-phenyl | 2-(N-(cyclobutyl)-aminomethyl)phenyl |
| 597 | SO2CH3 | 2-Cl-phenyl | 2-(N-(cyclopentyl)-aminomethyl)phenyl |
| 598 | SO2CH3 | 2-Cl-phenyl | 2-(N-(3-hydroxypyrrolidinyl)-methyl)phenyl |
| 599 | SO2CH3 | 2-F-phenyl | 2-(aminosulfonyl)phenyl |
| 600 | SO2CH3 | 2-F-phenyl | 2-(methylaminosulfonyl)phenyl |
| 601 | SO2CH3 | 2-F-phenyl | 1-pyrrolidinocarbonyl |
| 602 | SO2CH3 | 2-F-phenyl | 2-(methylsulfonyl)phenyl |
| 603 | SO2CH3 | 2-F-phenyl | 2-(N,N-dimethylaminomethyl)phenyl |
| 604 | SO2CH3 | 2-F-phenyl | 2-(N-pyrrolidinylmethyl)phenyl |
| 605 | SO2CH3 | 2-F-phenyl | 1-methyl-2-imidazolyl |
| 606 | SO2CH3 | 2-F-phenyl | 2-methyl-1-imidazolyl |
| 607 | SO2CH3 | 2-F-phenyl | 2-(dimethylaminomethyl)-1-imidazolyl |
| 608 | SO2CH3 | 2-F-phenyl | 2-(N-(cyclopropyl-methyl)aminomethyl)phenyl |
| 609 | SO2CH3 | 2-F-phenyl | 2-(N-(cyclobutyl)-aminomethyl)phenyl |
| 610 | SO2CH3 | 2-F-phenyl | 2-(N-(cyclopentyl)-aminomethyl)phenyl |
| 611 | SO2CH3 | 2-F-phenyl | 2-(N-(3-hydroxypyrrolidinyl)-methyl)phenyl |
| 612 | SO2CH3 | 2,6-diF-phenyl | 2-(aminosulfonyl)phenyl |
| 613 | SO2CH3 | 2,6-diF-phenyl | 2-(methylaminosulfonyl)phenyl |
| 614 | SO2CH3 | 2,6-diF-phenyl | 1-pyrrolidinocarbonyl |
| 615 | SO2CH3 | 2,6-diF-phenyl | 2-(methylsulfonyl)phenyl |
| 616 | SO2CH3 | 2,6-diF-phenyl | 2-(N,N-dimethylaminomethyl)phenyl |
| 617 | SO2CH3 | 2,6-diF-phenyl | 2-(N-pyrrolidinylmethyl)phenyl |
| 618 | SO2CH3 | 2,6-diF-phenyl | 1-methyl-2-imidazolyl |
| 619 | SO2CH3 | 2,6-diF-phenyl | 2-methyl-1-imidazolyl |
| 620 | SO2CH3 | 2,6-diF-phenyl | 2-(dimethylaminomethyl)-1-imidazolyl |
| 621 | SO2CH3 | 2,6-diF-phenyl | 2-(N-(cyclopropyl-methyl)aminomethyl)phenyl |
| 622 | SO2CH3 | 2,6-diF-phenyl | 2-(N-(cyclobutyl)-aminomethyl)phenyl |
| 623 | SO2CH3 | 2,6-diF-phenyl | 2-(N-(cyclopentyl)-aminomethyl)phenyl |
| 624 | SO2CH3 | 2,6-diF-phenyl | 2-(N-(3-hydroxypyrrolidinyl)-methyl)phenyl |
| 625 | Cl | phenyl | 2-(aminosulfonyl)phenyl |
| 626 | Cl | phenyl | 2-(methylaminosulfonyl)phenyl |
| 627 | Cl | phenyl | 1-pyrrolidinocarbonyl |
| 628 | Cl | phenyl | 2-(methylsulfonyl)phenyl |
| 629 | Cl | phenyl | 2-(N,N-dimethylaminomethyl)phenyl |
| 630 | Cl | phenyl | 2-(N-pyrrolidinylmethyl)phenyl |
| 631 | Cl | phenyl | 1-methyl-2-imidazolyl |
| 632 | Cl | phenyl | 2-methyl-1-imidazolyl |
| 633 | Cl | phenyl | 2-(dimethylaminomethyl)-1-imidazolyl |
| 634 | Cl | phenyl | 2-(N-(cyclopropyl-methyl)aminomethyl)phenyl |
| 635 | Cl | phenyl | 2-(N-(cyclobutyl)-aminomethyl)phenyl |
| 636 | Cl | phenyl | 2-(N-(cyclopentyl)-aminomethyl)phenyl |
| 637 | Cl | phenyl | 2-(N-(3-hydroxypyrrolidinyl)-methyl)phenyl |
| 638 | Cl | 2-pyridyl | 2-(aminosulfonyl)phenyl |
| 639 | Cl | 2-pyridyl | 2-(methylaminosulfonyl)phenyl |
| 640 | Cl | 2-pyridyl | 1-pyrrolidinocarbonyl |
| 641 | Cl | 2-pyridyl | 2-(methylsulfonyl)phenyl |
| 642 | Cl | 2-pyridyl | 2-(N,N-dimethylaminomethyl)phenyl |
| 643 | Cl | 2-pyridyl | 2-(N-pyrrolidinylmethyl)phenyl |
| 644 | Cl | 2-pyridyl | 1-methyl-2-imidazolyl |
| 645 | Cl | 2-pyridyl | 2-methyl-1-imidazolyl |
| 646 | Cl | 2-pyridyl | 2-(dimethylaminomethyl)-1-imidazolyl |
| 647 | Cl | 2-pyridyl | 2-(N-(cyclopropyl-methyl)aminomethyl)phenyl |
| 648 | Cl | 2-pyridyl | 2-(N-(cyclobutyl)-aminomethyl)phenyl |
| 649 | Cl | 2-pyridyl | 2-(N-(cyclopentyl)-aminomethyl)phenyl |
| 650 | Cl | 2-pyridyl | 2-(N-(3-hydroxypyrrolidinyl)-methyl)phenyl |
| 651 | Cl | 3-pyridyl | 2-(aminosulfonyl)phenyl |
| 652 | Cl | 3-pyridyl | 2-(methylaminosulfonyl)phenyl |
| 653 | Cl | 3-pyridyl | 1-pyrrolidinocarbonyl |
| 654 | Cl | 3-pyridyl | 2-(methylsulfonyl)phenyl |
| 655 | Cl | 3-pyridyl | 2-(N,N-dimethylaminomethyl)phenyl |
| 656 | Cl | 3-pyridyl | 2-(N-pyrrolidinylmethyl)phenyl |
| 657 | Cl | 3-pyridyl | 1-methyl-2-imidazolyl |
| 658 | Cl | 3-pyridyl | 2-methyl-1-imidazolyl |
| 659 | Cl | 3-pyridyl | 2-(dimethylaminomethyl)-1-imidazolyl |
| 660 | Cl | 3-pyridyl | 2-(N-(cyclopropyl-methyl)aminomethyl)phenyl |
| 661 | Cl | 3-pyridyl | 2-(N-(cyclobutyl)-aminomethyl)phenyl |
| 662 | Cl | 3-pyridyl | 2-(N-(cyclopentyl)-aminomethyl)phenyl |
| 663 | Cl | 3-pyridyl | 2-(N-(3-hydroxypyrrolidinyl)-methyl)phenyl |
| 664 | Cl | 2-pyrimidyl | 2-(aminosulfonyl)phenyl |
| 665 | Cl | 2-pyrimidyl | 2-(methylaminosulfonyl)phenyl |
| 666 | Cl | 2-pyrimidyl | 1-pyrrolidinocarbonyl |
| 667 | Cl | 2-pyrimidyl | 2-(methylsulfonyl)phenyl |
| 668 | Cl | 2-pyrimidyl | 2-(N,N-dimethylaminomethyl)phenyl |
| 669 | Cl | 2-pyrimidyl | 2-(N-pyrrolidinylmethyl)phenyl |
| 670 | Cl | 2-pyrimidyl | 1-methyl-2-imidazolyl |
| 671 | Cl | 2-pyrimidyl | 2-methyl-1-imidazolyl |
| 672 | Cl | 2-pyrimidyl | 2-(dimethylaminomethyl)-1-imidazolyl |
| 673 | Cl | 2-pyrimidyl | 2-(N-(cyclopropyl-methyl)aminomethyl)phenyl |
| 674 | Cl | 2-pyrimidyl | 2-(N-(cyclobutyl)-aminomethyl)phenyl |
| 675 | Cl | 2-pyrimidyl | 2-(N-(cyclopentyl)-aminomethyl)phenyl |
| 676 | Cl | 2-pyrimidyl | 2-(N-(3-hydroxypyrrolidinyl)-methyl)phenyl |
| 677 | Cl | 5-pyrimidyl | 2-(aminosulfonyl)phenyl |
| 678 | Cl | 5-pyrimidyl | 2-(methylaminosulfonyl)phenyl |
| 679 | Cl | 5-pyrimidyl | 1-pyrrolidinocarbonyl |
| 680 | Cl | 5-pyrimidyl | 2-(methylsulfonyl)phenyl |
| 681 | Cl | 5-pyrimidyl | 2-(N,N-dimethylaminomethyl)phenyl |
| 682 | Cl | 5-pyrimidyl | 2-(N-pyrrolidinylmethyl)phenyl |
| 683 | Cl | 5-pyrimidyl | 1-methyl-2-imidazolyl |
| 684 | Cl | 5-pyrimidyl | 2-methyl-1-imidazolyl |
| 685 | Cl | 5-pyrimidyl | 2-(dimethylaminomethyl)-1-imidazolyl |
| 686 | Cl | 5-pyrimidyl | 2-(N-(cyclopropyl-methyl)aminomethyl)phenyl |
| 687 | Cl | 5-pyrimidyl | 2-(N-(cyclobutyl)-aminomethyl)phenyl |
| 688 | Cl | 5-pyrimidyl | 2-(N-(cyclopentyl)-aminomethyl)phenyl |
| 689 | Cl | 5-pyrimidyl | 2-(N-(3-hydroxypyrrolidinyl)-methyl)phenyl |
| 690 | Cl | 2-Cl-phenyl | 2-(aminosulfonyl)phenyl |
| 691 | Cl | 2-Cl-phenyl | 2-(methylaminosulfonyl)phenyl |
| 692 | Cl | 2-Cl-phenyl | 1-pyrrolidinocarbonyl |
| 693 | Cl | 2-Cl-phenyl | 2-(methylsulfonyl)phenyl |
| 694 | Cl | 2-Cl-phenyl | 2-(N,N-dimethylaminomethyl)phenyl |
| 695 | Cl | 2-Cl-phenyl | 2-(N-pyrrolidinylmethyl)phenyl |
| 696 | Cl | 2-Cl-phenyl | 1-methyl-2-imidazolyl |
| 697 | Cl | 2-Cl-phenyl | 2-methyl-1-imidazolyl |

-continued

| Ex# | R<sup>1a</sup> | A | B |
|---|---|---|---|
| 698 | Cl | 2-Cl-phenyl | 2-(dimethylaminomethyl)-1-imidazolyl |
| 699 | Cl | 2-Cl-phenyl | 2-(N-(cyclopropyl-methyl)aminomethyl)phenyl |
| 700 | Cl | 2-Cl-phenyl | 2-(N-(cyclobutyl)-aminomethyl)phenyl |
| 701 | Cl | 2-Cl-phenyl | 2-(N-(cyclopentyl)-aminomethyl)phenyl |
| 702 | Cl | 2-Cl-phenyl | 2-(N-(3-hydroxypyrrolidinyl)-methyl)phenyl |
| 703 | Cl | 2-F-phenyl | 2-(aminosulfonyl)phenyl |
| 704 | Cl | 2-F-phenyl | 2-(methylaminosulfonyl)phenyl |
| 705 | Cl | 2-F-phenyl | 1-pyrrolidinocarbonyl |
| 706 | Cl | 2-F-phenyl | 2-(methylsulfonyl)phenyl |
| 707 | Cl | 2-F-phenyl | 2-(N,N-dimethylaminomethyl)phenyl |
| 708 | Cl | 2-F-phenyl | 2-(N-pyrrolidinylmethyl)phenyl |
| 709 | Cl | 2-F-phenyl | 1-methyl-2-imidazolyl |
| 710 | Cl | 2-F-phenyl | 2-methyl-1-imidazolyl |
| 711 | Cl | 2-F-phenyl | 2-(dimethylaminomethyl)-1-imidazolyl |
| 712 | Cl | 2-F-phenyl | 2-(N-(cyclopropyl-methyl)aminomethyl)phenyl |
| 713 | Cl | 2-F-phenyl | 2-(N-(cyclobutyl)-aminomethyl)phenyl |
| 714 | Cl | 2-F-phenyl | 2-(N-(cyclopentyl)-aminomethyl)phenyl |
| 715 | Cl | 2-F-phenyl | 2-(N-(3-hydroxypyrrolidinyl)-methyl)phenyl |
| 716 | Cl | 2,6-diF-phenyl | 2-(aminosulfonyl)phenyl |
| 717 | Cl | 2,6-diF-phenyl | 2-(methylaminosulfonyl)phenyl |
| 718 | Cl | 2,6-diF-phenyl | 1-pyrrolidinocarbonyl |
| 719 | Cl | 2,6-diF-phenyl | 2-(methylsulfonyl)phenyl |
| 720 | Cl | 2,6-diF-phenyl | 2-(N,N-dimethylaminomethyl)phenyl |
| 721 | Cl | 2,6-diF-phenyl | 2-(N-pyrrolidinylmethyl)phenyl |
| 722 | Cl | 2,6-diF-phenyl | 1-methyl-2-imidazolyl |
| 723 | Cl | 2,6-diF-phenyl | 2-methyl-1-imidazolyl |
| 724 | Cl | 2,6-diF-phenyl | 2-(dimethylaminomethyl)-1-imidazolyl |
| 725 | Cl | 2,6-diF-phenyl | 2-(N-(cyclopropyl-methyl)aminomethyl)phenyl |
| 726 | Cl | 2,6-diF-phenyl | 2-(N-(cyclobutyl)-aminomethyl)phenyl |
| 727 | Cl | 2,6-diF-phenyl | 2-(N-(cyclopentyl)-aminomethyl)phenyl |
| 728 | Cl | 2,6-diF-phenyl | 2-(N-(3-hydroxypyrrolidinyl)-methyl)phenyl |
| 729 | F | phenyl | 2-(aminosulfonyl)phenyl |
| 730 | F | phenyl | 2-(methylaminosulfonyl)phenyl |
| 731 | F | phenyl | 1-pyrrolidinocarbonyl |
| 732 | F | phenyl | 2-(methylsulfonyl)phenyl |
| 733 | F | phenyl | 2-(N,N-dimethylaminomethyl)phenyl |
| 734 | F | phenyl | 2-(N-pyrrolidinylmethyl)phenyl |
| 735 | F | phenyl | 1-methyl-2-imidazolyl |
| 736 | F | phenyl | 2-methyl-1-imidazolyl |
| 737 | F | phenyl | 2-(dimethylaminomethyl)-1-imidazolyl |
| 738 | F | phenyl | 2-(N-(cyclopropyl-methyl)aminomethyl)phenyl |
| 739 | F | phenyl | 2-(N-(cyclobutyl)-aminomethyl)phenyl |
| 740 | F | phenyl | 2-(N-(cyclopentyl)-aminomethyl)phenyl |
| 741 | F | phenyl | 2-(N-(3-hydroxypyrrolidinyl)-methyl)phenyl |
| 742 | F | 2-pyridyl | 2-(aminosulfonyl)phenyl |
| 743 | F | 2-pyridyl | 2-(methylaminosulfonyl)phenyl |
| 744 | F | 2-pyridyl | 1-pyrrolidinocarbonyl |
| 745 | F | 2-pyridyl | 2-(methylsulfonyl)phenyl |
| 746 | F | 2-pyridyl | 2-(N,N-dimethylaminomethyl)phenyl |
| 747 | F | 2-pyridyl | 2-(N-pyrrolidinylmethyl)phenyl |
| 748 | F | 2-pyridyl | 1-methyl-2-imidazolyl |
| 749 | F | 2-pyridyl | 2-methyl-1-imidazolyl |
| 750 | F | 2-pyridyl | 2-(dimethylaminomethyl)-1-imidazolyl |
| 751 | F | 2-pyridyl | 2-(N-(cyclopropyl-methyl)aminomethyl)phenyl |
| 752 | F | 2-pyridyl | 2-(N-(cyclobutyl)-aminomethyl)phenyl |
| 753 | F | 2-pyridyl | 2-(N-(cyclopentyl)-aminomethyl)phenyl |
| 754 | F | 2-pyridyl | 2-(N-(3-hydroxypyrrolidinyl)-methyl)phenyl |
| 755 | F | 3-pyridyl | 2-(aminosulfonyl)phenyl |
| 756 | F | 3-pyridyl | 2-(methylaminosulfonyl)phenyl |
| 757 | F | 3-pyridyl | 1-pyrrolidinocarbonyl |
| 758 | F | 3-pyridyl | 2-(methylsulfonyl)phenyl |
| 759 | F | 3-pyridyl | 2-(N,N-dimethylaminomethyl)phenyl |
| 760 | F | 3-pyridyl | 2-(N-pyrrolidinylmethyl)phenyl |
| 761 | F | 3-pyridyl | 1-methyl-2-imidazolyl |
| 762 | F | 3-pyridyl | 2-methyl-1-imidazolyl |
| 763 | F | 3-pyridyl | 2-(dimethylaminomethyl)-1-imidazolyl |
| 764 | F | 3-pyridyl | 2-(N-(cyclopropyl-methyl)aminomethyl)phenyl |
| 765 | F | 3-pyridyl | 2-(N-(cyclobutyl)-aminomethyl)phenyl |
| 766 | F | 3-pyridyl | 2-(N-(cyclopentyl)-aminomethyl)phenyl |
| 767 | F | 3-pyridyl | 2-(N-(3-hydroxypyrrolidinyl)-methyl)phenyl |
| 768 | F | 2-pyrimidyl | 2-(aminosulfonyl)phenyl |
| 769 | F | 2-pyrimidyl | 2-(methylaminosulfonyl)phenyl |
| 770 | F | 2-pyrimidyl | 1-pyrrolidinocarbonyl |
| 771 | F | 2-pyrimidyl | 2-(methylsulfonyl)phenyl |
| 772 | F | 2-pyrimidyl | 2-(N,N-dimethylaminomethyl)phenyl |
| 773 | F | 2-pyrimidyl | 2-(N-pyrrolidinylmethyl)phenyl |
| 774 | F | 2-pyrimidyl | 1-methyl-2-imidazolyl |
| 775 | F | 2-pyrimidyl | 2-methyl-1-imidazolyl |
| 776 | F | 2-pyrimidyl | 2-(dimethylaminomethyl)-1-imidazolyl |
| 777 | F | 2-pyrimidyl | 2-(N-(cyclopropyl-methyl)aminomethyl)phenyl |
| 778 | F | 2-pyrimidyl | 2-(N-(cyclobutyl)-aminomethyl)phenyl |
| 779 | F | 2-pyrimidyl | 2-(N-(cyclopentyl)-aminomethyl)phenyl |
| 780 | F | 2-pyrimidyl | 2-(N-(3-hydroxypyrrolidinyl)-methyl)phenyl |
| 781 | F | 5-pyrimidyl | 2-(aminosulfonyl)phenyl |
| 782 | F | 5-pyrimidyl | 2-(methylaminosulfonyl)phenyl |
| 783 | F | 5-pyrimidyl | 1-pyrrolidinocarbonyl |
| 784 | F | 5-pyrimidyl | 2-(methylsulfonyl)phenyl |
| 785 | F | 5-pyrimidyl | 2-(N,N-dimethylaminomethyl)phenyl |
| 786 | F | 5-pyrimidyl | 2-(N-pyrrolidinylmethyl)phenyl |
| 787 | F | 5-pyrimidyl | 1-methyl-2-imidazolyl |
| 788 | F | 5-pyrimidyl | 2-methyl-1-imidazolyl |
| 789 | F | 5-pyrimidyl | 2-(dimethylaminomethyl)-1-imidazolyl |
| 790 | F | 5-pyrimidyl | 2-(N-(cyclopropyl-methyl)aminomethyl)phenyl |
| 791 | F | 5-pyrimidyl | 2-(N-(cyclobutyl)-aminomethyl)phenyl |
| 792 | F | 5-pyrimidyl | 2-(N-(cyclopentyl)-aminomethyl)phenyl |
| 793 | F | 5-pyrimidyl | 2-(N-(3-hydroxypyrrolidinyl)-methyl)phenyl |
| 794 | F | 2-F-phenyl | 2-(aminosulfonyl)phenyl |
| 795 | F | 2-F-phenyl | 2-(methylaminosulfonyl)phenyl |
| 796 | F | 2-F-phenyl | 1-pyrrolidinocarbonyl |
| 797 | F | 2-F-phenyl | 2-(methylsulfonyl)phenyl |
| 798 | F | 2-F-phenyl | 2-(N,N-dimethylaminomethyl)phenyl |
| 799 | F | 2-F-phenyl | 2-(N-pyrrolidinylmethyl)phenyl |
| 800 | F | 2-F-phenyl | 1-methyl-2-imidazolyl |
| 801 | F | 2-F-phenyl | 2-methyl-1-imidazolyl |

-continued

| Ex# | R1a | A | B |
|---|---|---|---|
| 802 | F | 2-F-phenyl | 2-(dimethylaminomethyl)-1-imidazolyl |
| 803 | F | 2-F-phenyl | 2-(N-(cyclopropyl-methyl)aminomethyl)phenyl |
| 804 | F | 2-F-phenyl | 2-(N-(cyclobutyl)-aminomethyl)phenyl |
| 805 | F | 2-F-phenyl | 2-(N-(cyclopentyl)-aminomethyl)phenyl |
| 806 | F | 2-F-phenyl | 2-(N-(3-hydroxypyrrolidinyl)-methyl)phenyl |
| 807 | F | 2-F-phenyl | 2-(aminosulfonyl)phenyl |
| 808 | F | 2-F-phenyl | 2-(methylaminosulfonyl)phenyl |
| 809 | F | 2-F-phenyl | 1-pyrrolidinocarbonyl |
| 810 | F | 2-F-phenyl | 2-(methylsulfonyl)phenyl |
| 811 | F | 2-F-phenyl | 2-(N,N-dimethylaminomethyl)phenyl |
| 812 | F | 2-F-phenyl | 2-(N-pyrrolidinylmethyl)phenyl |
| 813 | F | 2-F-phenyl | 1-methyl-2-imidazolyl |
| 814 | F | 2-F-phenyl | 2-methyl-1-imidazolyl |
| 815 | F | 2-F-phenyl | 2-(dimethylaminomethyl)-1-imidazolyl |
| 816 | F | 2-F-phenyl | 2-(N-(cyclopropyl-methyl)aminomethyl)phenyl |
| 817 | F | 2-F-phenyl | 2-(N-(cyclobutyl)-aminomethyl)phenyl |
| 818 | F | 2-F-phenyl | 2-(N-(cyclopentyl)-aminomethyl)phenyl |
| 819 | F | 2-F-phenyl | 2-(N-(3-hydroxypyrrolidinyl)-methyl)phenyl |
| 820 | F | 2,6-diF-phenyl | 2-(aminosulfonyl)phenyl |
| 821 | F | 2,6-diF-phenyl | 2-(methylaminosulfonyl)phenyl |
| 822 | F | 2,6-diF-phenyl | 1-pyrrolidinocarbonyl |
| 823 | F | 2,6-diF-phenyl | 2-(methylsulfonyl)phenyl |
| 824 | F | 2,6-diF-phenyl | 2-(N,N-dimethylaminomethyl)phenyl |
| 825 | F | 2,6-diF-phenyl | 2-(N-pyrrolidinylmethyl)phenyl |
| 826 | F | 2,6-diF-phenyl | 1-methyl-2-imidazolyl |
| 827 | F | 2,6-diF-phenyl | 2-methyl-1-imidazolyl |
| 828 | F | 2,6-diF-phenyl | 2-(dimethylaminomethyl)-1-imidazolyl |
| 829 | F | 2,6-diF-phenyl | 2-(N-(cyclopropyl-methyl)aminomethyl)phenyl |
| 830 | F | 2,6-diF-phenyl | 2-(N-(cyclobutyl)-aminomethyl)phenyl |
| 831 | F | 2,6-diF-phenyl | 2-(N-(cyclopentyl)-aminomethyl)phenyl |
| 832 | F | 2,6-diF-phenyl | 2-(N-(3-hydroxypyrrolidinyl)-methyl)phenyl |
| 833 | CO2CH3 | phenyl | 2-(aminosulfonyl)phenyl |
| 834 | CO2CH3 | phenyl | 2-(methylaminosulfonyl)phenyl |
| 835 | CO2CH3 | phenyl | 1-pyrrolidinocarbonyl |
| 836 | CO2CH3 | phenyl | 2-(methylsulfonyl)phenyl |
| 837 | CO2CH3 | phenyl | 2-(N,N-dimethylaminomethyl)phenyl |
| 838 | CO2CH3 | phenyl | 2-(N-pyrrolidinylmethyl)phenyl |
| 839 | CO2CH3 | phenyl | 1-methyl-2-imidazolyl |
| 840 | CO2CH3 | phenyl | 2-methyl-1-imidazolyl |
| 841 | CO2CH3 | phenyl | 2-(dimethylaminomethyl)-1-imidazolyl |
| 842 | CO2CH3 | phenyl | 2-(N-(cyclopropyl-methyl)aminomethyl)phenyl |
| 843 | CO2CH3 | phenyl | 2-(N-(cyclobutyl)-aminomethyl)phenyl |
| 844 | CO2CH3 | phenyl | 2-(N-(cyclopentyl)-aminomethyl)phenyl |
| 845 | CO2CH3 | phenyl | 2-(N-(3-hydroxypyrrolidinyl)-methyl)phenyl |
| 846 | CO2CH3 | 2-pyridyl | 2-(aminosulfonyl)phenyl |
| 847 | CO2CH3 | 2-pyridyl | 2-(methylaminosulfonyl)phenyl |
| 848 | CO2CH3 | 2-pyridyl | 1-pyrrolidinocarbonyl |
| 849 | CO2CH3 | 2-pyridyl | 2-(methylsulfonyl)phenyl |
| 850 | CO2CH3 | 2-pyridyl | 2-(N,N-dimethylaminomethyl)phenyl |
| 851 | CO2CH3 | 2-pyridyl | 2-(N-pyrrolidinylmethyl)phenyl |
| 852 | CO2CH3 | 2-pyridyl | 1-methyl-2-imidazolyl |
| 853 | CO2CH3 | 2-pyridyl | 2-methyl-1-imidazolyl |
| 854 | CO2CH3 | 2-pyridyl | 2-(dimethylaminomethyl)-1-imidazolyl |
| 855 | CO2CH3 | 2-pyridyl | 2-(N-(cyclopropyl-methyl)aminomethyl)phenyl |
| 856 | CO2CH3 | 2-pyridyl | 2-(N-(cyclobutyl)-aminomethyl)phenyl |
| 857 | CO2CH3 | 2-pyridyl | 2-(N-(cyclopentyl)-aminomethyl)phenyl |
| 858 | CO2CH3 | 2-pyridyl | 2-(N-(3-hydroxypyrrolidinyl)-methyl)phenyl |
| 859 | CO2CH3 | 3-pyridyl | 2-(aminosulfonyl)phenyl |
| 860 | CO2CH3 | 3-pyridyl | 2-(methylaminosulfonyl)phenyl |
| 861 | CO2CH3 | 3-pyridyl | 1-pyrrolidinocarbonyl |
| 862 | CO2CH3 | 3-pyridyl | 2-(methylsulfonyl)phenyl |
| 863 | CO2CH3 | 3-pyridyl | 2-(N,N-dimethylaminomethyl)phenyl |
| 864 | CO2CH3 | 3-pyridyl | 2-(N-pyrrolidinylmethyl)phenyl |
| 865 | CO2CH3 | 3-pyridyl | 1-methyl-2-imidazolyl |
| 866 | CO2CH3 | 3-pyridyl | 2-methyl-1-imidazolyl |
| 867 | CO2CH3 | 3-pyridyl | 2-(dimethylaminomethyl)-1-imidazolyl |
| 868 | CO2CH3 | 3-pyridyl | 2-(N-(cyclopropyl-methyl)aminomethyl)phenyl |
| 869 | CO2CH3 | 3-pyridyl | 2-(N-(cyclobutyl)-aminomethyl)phenyl |
| 870 | CO2CH3 | 3-pyridyl | 2-(N-(cyclopentyl)-aminomethyl)phenyl |
| 871 | CO2CH3 | 3-pyridyl | 2-(N-(3-hydroxypyrrolidinyl)-methyl)phenyl |
| 872 | CO2CH3 | 2-pyrimidyl | 2-(aminosulfonyl)phenyl |
| 873 | CO2CH3 | 2-pyrimidyl | 2-(methylaminosulfonyl)phenyl |
| 874 | CO2CH3 | 2-pyrimidyl | 1-pyrrolidinocarbonyl |
| 875 | CO2CH3 | 2-pyrimidyl | 2-(methylsulfonyl)phenyl |
| 876 | CO2CH3 | 2-pyrimidyl | 2-(N,N-dimethylaminomethyl)phenyl |
| 877 | CO2CH3 | 2-pyrimidyl | 2-(N-pyrrolidinylmethyl)phenyl |
| 878 | CO2CH3 | 2-pyrimidyl | 1-methyl-2-imidazolyl |
| 879 | CO2CH3 | 2-pyrimidyl | 2-methyl-1-imidazolyl |
| 880 | CO2CH3 | 2-pyrimidyl | 2-(dimethylaminomethyl)-1-imidazolyl |
| 881 | CO2CH3 | 2-pyrimidyl | 2-(N-(cyclopropyl-methyl)aminomethyl)phenyl |
| 882 | CO2CH3 | 2-pyrimidyl | 2-(N-(cyclobutyl)-aminomethyl)phenyl |
| 883 | CO2CH3 | 2-pyrimidyl | 2-(N-(cyclopentyl)-aminomethyl)phenyl |
| 884 | CO2CH3 | 2-pyrimidyl | 2-(N-(3-hydroxypyrrolidinyl)-methyl)phenyl |
| 885 | CO2CH3 | 5-pyrimidyl | 2-(aminosulfonyl)phenyl |
| 886 | CO2CH3 | 5-pyrimidyl | 2-(methylaminosulfonyl)phenyl |
| 887 | CO2CH3 | 5-pyrimidyl | 1-pyrrolidinocarbonyl |
| 888 | CO2CH3 | 5-pyrimidyl | 2-(methylsulfonyl)phenyl |
| 889 | CO2CH3 | 5-pyrimidyl | 2-(N,N-dimethylaminomethyl)phenyl |
| 890 | CO2CH3 | 5-pyrimidyl | 2-(N-pyrrolidinylmethyl)phenyl |
| 891 | CO2CH3 | 5-pyrimidyl | 1-methyl-2-imidazolyl |
| 892 | CO2CH3 | 5-pyrimidyl | 2-methyl-1-imidazolyl |
| 893 | CO2CH3 | 5-pyrimidyl | 2-(dimethylaminomethyl)-1-imidazolyl |
| 894 | CO2CH3 | 5-pyrimidyl | 2-(N-(cyclopropyl-methyl)aminomethyl)phenyl |
| 895 | CO2CH3 | 5-pyrimidyl | 2-(N-(cyclobutyl)-aminomethyl)phenyl |
| 896 | CO2CH3 | 5-pyrimidyl | 2-(N-(cyclopentyl)-aminomethyl)phenyl |
| 897 | CO2CH3 | 5-pyrimidyl | 2-(N-(3-hydroxypyrrolidinyl)-methyl)phenyl |
| 898 | CO2CH3 | 2-F-phenyl | 2-(aminosulfonyl)phenyl |
| 899 | CO2CH3 | 2-F-phenyl | 2-(methylaminosulfonyl)phenyl |
| 900 | CO2CH3 | 2-F-phenyl | 1-pyrrolidinocarbonyl |
| 901 | CO2CH3 | 2-F-phenyl | 2-(methylsulfonyl)phenyl |
| 902 | CO2CH3 | 2-F-phenyl | 2-(N,N-dimethylaminomethyl)phenyl |
| 903 | CO2CH3 | 2-F-phenyl | 2-(N-pyrrolidinylmethyl)phenyl |
| 904 | CO2CH3 | 2-F-phenyl | 1-methyl-2-imidazolyl |
| 905 | CO2CH3 | 2-F-phenyl | 2-methyl-1-imidazolyl |

-continued

| Ex# | R1a | A | B |
|---|---|---|---|
| 906 | CO2CH3 | 2-F-phenyl | 2-(dimethylaminomethyl)-1-imidazolyl |
| 907 | CO2CH3 | 2-F-phenyl | 2-(N-(cyclopropyl-methyl)aminomethyl)phenyl |
| 908 | CO2CH3 | 2-F-phenyl | 2-(N-(cyclobutyl)-aminomethyl)phenyl |
| 909 | CO2CH3 | 2-F-phenyl | 2-(N-(cyclopentyl)-aminomethyl)phenyl |
| 910 | CO2CH3 | 2-F-phenyl | 2-(N-(3-hydroxypyrrolidinyl)-methyl)phenyl |
| 911 | CO2CH3 | 2-F-phenyl | 2-(aminosulfonyl)phenyl |
| 912 | CO2CH3 | 2-F-phenyl | 2-(methylaminosulfonyl)phenyl |
| 913 | CO2CH3 | 2-F-phenyl | 1-pyrrolidinocarbonyl |
| 914 | CO2CH3 | 2-F-phenyl | 2-(methylsulfonyl)phenyl |
| 915 | CO2CH3 | 2-F-phenyl | 2-(N,N-dimethylaminomethyl)phenyl |
| 916 | CO2CH3 | 2-F-phenyl | 2-(N-pyrrolidinylmethyl)phenyl |
| 917 | CO2CH3 | 2-F-phenyl | 1-methyl-2-imidazolyl |
| 918 | CO2CH3 | 2-F-phenyl | 2-methyl-1-imidazolyl |
| 919 | CO2CH3 | 2-F-phenyl | 2-(dimethylaminomethyl)-1-imidazolyl |
| 920 | CO2CH3 | 2-F-phenyl | 2-(N-(cyclopropyl-methyl)aminomethyl)phenyl |
| 921 | CO2CH3 | 2-F-phenyl | 2-(N-(cyclobutyl)-aminomethyl)phenyl |
| 922 | CO2CH3 | 2-F-phenyl | 2-(N-(cyclopentyl)-aminomethyl)phenyl |
| 923 | CO2CH3 | 2-F-phenyl | 2-(N-(3-hydroxypyrrolidinyl)-methyl)phenyl |
| 924 | CO2CH3 | 2,6-diF-phenyl | 2-(aminosulfonyl)phenyl |
| 925 | CO2CH3 | 2,6-diF-phenyl | 2-(methylaminosulfonyl)phenyl |
| 926 | CO2CH3 | 2,6-diF-phenyl | 1-pyrrolidinocarbonyl |
| 927 | CO2CH3 | 2,6-diF-phenyl | 2-(methylsulfonyl)phenyl |
| 928 | CO2CH3 | 2,6-diF-phenyl | 2-(N,N-dimethylaminomethyl)phenyl |
| 929 | CO2CH3 | 2,6-diF-phenyl | 2-(N-pyrrolidinylmethyl)phenyl |
| 930 | CO2CH3 | 2,6-diF-phenyl | 1-methyl-2-imidazolyl |
| 931 | CO2CH3 | 2,6-diF-phenyl | 2-methyl-1-imidazolyl |
| 932 | CO2CH3 | 2,6-diF-phenyl | 2-(dimethylaminomethyl)-1-imidazolyl |
| 933 | CO2CH3 | 2,6-diF-phenyl | 2-(N-(cyclopropyl-methyl)aminomethyl)phenyl |
| 934 | CO2CH3 | 2,6-diF-phenyl | 2-(N-(cyclobutyl)-aminomethyl)phenyl |
| 935 | CO2CH3 | 2,6-diF-phenyl | 2-(N-(cyclopentyl)-aminomethyl)phenyl |
| 936 | CO2CH3 | 2,6-diF-phenyl | 2-(N-(3-hydroxypyrrolidinyl)-methyl)phenyl |
| 937 | CH2OCH3 | phenyl | 2-(aminosulfonyl)phenyl |
| 938 | CH2OCH3 | phenyl | 2-(methylaminosulfonyl)phenyl |
| 939 | CH2OCH3 | phenyl | 1-pyrrolidinocarbonyl |
| 940 | CH2OCH3 | phenyl | 2-(methylsulfonyl)phenyl |
| 941 | CH2OCH3 | phenyl | 2-(N,N-dimethylaminomethyl)phenyl |
| 942 | CH2OCH3 | phenyl | 2-(N-pyrrolidinylmethyl)phenyl |
| 943 | CH2OCH3 | phenyl | 1-methyl-2-imidazolyl |
| 944 | CH2OCH3 | phenyl | 2-methyl-1-imidazolyl |
| 945 | CH2OCH3 | phenyl | 2-(dimethylaminomethyl)-1-imidazolyl |
| 946 | CH2OCH3 | phenyl | 2-(N-(cyclopropyl-methyl)aminomethyl)phenyl |
| 947 | CH2OCH3 | phenyl | 2-(N-(cyclobutyl)-aminomethyl)phenyl |
| 948 | CH2OCH3 | phenyl | 2-(N-(cyclopentyl)-aminomethyl)phenyl |
| 949 | CH2OCH3 | phenyl | 2-(N-(3-hydroxypyrrolidinyl)-methyl)phenyl |
| 950 | CH2OCH3 | 2-pyridyl | 2-(aminosulfonyl)phenyl |
| 951 | CH2OCH3 | 2-pyridyl | 2-(methylaminosulfonyl)phenyl |
| 952 | CH2OCH3 | 2-pyridyl | 1-pyrrolidinocarbonyl |
| 953 | CH2OCH3 | 2-pyridyl | 2-(methylsulfonyl)phenyl |
| 954 | CH2OCH3 | 2-pyridyl | 2-(N,N-dimethylaminomethyl)phenyl |
| 955 | CH2OCH3 | 2-pyridyl | 2-(N-pyrrolidinylmethyl)phenyl |
| 956 | CH2OCH3 | 2-pyridyl | 1-methyl-2-imidazolyl |
| 957 | CH2OCH3 | 2-pyridyl | 2-methyl-1-imidazolyl |
| 958 | CH2OCH3 | 2-pyridyl | 2-(dimethylaminomethyl)-1-imidazolyl |
| 959 | CH2OCH3 | 2-pyridyl | 2-(N-(cyclopropyl-methyl)aminomethyl)phenyl |
| 960 | CH2OCH3 | 2-pyridyl | 2-(N-(cyclobutyl)-aminomethyl)phenyl |
| 961 | CH2OCH3 | 2-pyridyl | 2-(N-(cyclopentyl)-aminomethyl)phenyl |
| 962 | CH2OCH3 | 2-pyridyl | 2-(N-(3-hydroxypyrrolidinyl)-methyl)phenyl |
| 963 | CH2OCH3 | 3-pyridyl | 2-(aminosulfonyl)phenyl |
| 964 | CH2OCH3 | 3-pyridyl | 2-(methylaminosulfonyl)phenyl |
| 965 | CH2OCH3 | 3-pyridyl | 1-pyrrolidinocarbonyl |
| 966 | CH2OCH3 | 3-pyridyl | 2-(methylsulfonyl)phenyl |
| 967 | CH2OCH3 | 3-pyridyl | 2-(N,N-dimethylaminomethyl)phenyl |
| 968 | CH2OCH3 | 3-pyridyl | 2-(N-pyrrolidinylmethyl)phenyl |
| 969 | CH2OCH3 | 3-pyridyl | 1-methyl-2-imidazolyl |
| 970 | CH2OCH3 | 3-pyridyl | 2-methyl-1-imidazolyl |
| 971 | CH2OCH3 | 3-pyridyl | 2-(dimethylaminomethyl)-1-imidazolyl |
| 972 | CH2OCH3 | 3-pyridyl | 2-(N-(cyclopropyl-methyl)aminomethyl)phenyl |
| 973 | CH2OCH3 | 3-pyridyl | 2-(N-(cyclobutyl)-aminomethyl)phenyl |
| 974 | CH2OCH3 | 3-pyridyl | 2-(N-(cyclopentyl)-aminomethyl)phenyl |
| 975 | CH2OCH3 | 3-pyridyl | 2-(N-(3-hydroxypyrrolidinyl)-methyl)phenyl |
| 976 | CH2OCH3 | 2-pyrimidyl | 2-(aminosulfonyl)phenyl |
| 977 | CH2OCH3 | 2-pyrimidyl | 2-(methylaminosulfonyl)phenyl |
| 978 | CH2OCH3 | 2-pyrimidyl | 1-pyrrolidinocarbonyl |
| 979 | CH2OCH3 | 2-pyrimidyl | 2-(methylsulfonyl)phenyl |
| 980 | CH2OCH3 | 2-pyrimidyl | 2-(N,N-dimethylaminomethyl)phenyl |
| 981 | CH2OCH3 | 2-pyrimidyl | 2-(N-pyrrolidinylmethyl)phenyl |
| 982 | CH2OCH3 | 2-pyrimidyl | 1-methyl-2-imidazolyl |
| 983 | CH2OCH3 | 2-pyrimidyl | 2-methyl-1-imidazolyl |
| 984 | CH2OCH3 | 2-pyrimidyl | 2-(dimethylaminomethyl)-1-imidazolyl |
| 985 | CH2OCH3 | 2-pyrimidyl | 2-(N-(cyclopropyl-methyl)aminomethyl)phenyl |
| 986 | CH2OCH3 | 2-pyrimidyl | 2-(N-(cyclobutyl)-aminomethyl)phenyl |
| 987 | CH2OCH3 | 2-pyrimidyl | 2-(N-(cyclopentyl)-aminomethyl)phenyl |
| 988 | CH2OCH3 | 2-pyrimidyl | 2-(N-(3-hydroxypyrrolidinyl)-methyl)phenyl |
| 989 | CH2OCH3 | 5-pyrimidyl | 2-(aminosulfonyl)phenyl |
| 990 | CH2OCH3 | 5-pyrimidyl | 2-(methylaminosulfonyl)phenyl |
| 991 | CH2OCH3 | 5-pyrimidyl | 1-pyrrolidinocarbonyl |
| 992 | CH2OCH3 | 5-pyrimidyl | 2-(methylsulfonyl)phenyl |
| 993 | CH2OCH3 | 5-pyrimidyl | 2-(N,N-dimethylaminomethyl)phenyl |
| 994 | CH2OCH3 | 5-pyrimidyl | 2-(N-pyrrolidinylmethyl)phenyl |
| 995 | CH2OCH3 | 5-pyrimidyl | 1-methyl-2-imidazolyl |
| 996 | CH2OCH3 | 5-pyrimidyl | 2-methyl-1-imidazolyl |
| 997 | CH2OCH3 | 5-pyrimidyl | 2-(dimethylaminomethyl)-1-imidazolyl |
| 998 | CH2OCH3 | 5-pyrimidyl | 2-(N-(cyclopropyl-methyl)aminomethyl)phenyl |
| 999 | CH2OCH3 | 5-pyrimidyl | 2-(N-(cyclobutyl)-aminomethyl)phenyl |
| 1000 | CH2OCH3 | 5-pyrimidyl | 2-(N-(cyclopentyl)-aminomethyl)phenyl |
| 1001 | CH2OCH3 | 5-pyrimidyl | 2-(N-(3-hydroxypyrrolidinyl)-methyl)phenyl |
| 1002 | CH2OCH3 | 2-F-phenyl | 2-(aminosulfonyl)phenyl |
| 1003 | CH2OCH3 | 2-F-phenyl | 2-(methylaminosulfonyl)phenyl |
| 1004 | CH2OCH3 | 2-F-phenyl | 1-pyrrolidinocarbonyl |
| 1005 | CH2OCH3 | 2-F-phenyl | 2-(methylsulfonyl)phenyl |
| 1006 | CH2OCH3 | 2-F-phenyl | 2-(N,N-dimethylaminomethyl)phenyl |
| 1007 | CH2OCH3 | 2-F-phenyl | 2-(N-pyrrolidinylmethyl)phenyl |
| 1008 | CH2OCH3 | 2-F-phenyl | 1-methyl-2-imidazolyl |
| 1009 | CH2OCH3 | 2-F-phenyl | 2-methyl-1-imidazolyl |

| Ex# | R1a | A | B |
|---|---|---|---|
| 1010 | CH2OCH3 | 2-F-phenyl | 2-(dimethylaminomethyl)-1-imidazolyl |
| 1011 | CH2OCH3 | 2-F-phenyl | 2-(N-(cyclopropyl-methyl)aminomethyl)phenyl |
| 1012 | CH2OCH3 | 2-F-phenyl | 2-(N-(cyclobutyl)-aminomethyl)phenyl |
| 1013 | CH2OCH3 | 2-F-phenyl | 2-(N-(cyclopentyl)-aminomethyl)phenyl |
| 1014 | CH2OCH3 | 2-F-phenyl | 2-(N-(3-hydroxypyrrolidinyl)-methyl)phenyl |
| 1015 | CH2OCH3 | 2-F-phenyl | 2-(aminosulfonyl)phenyl |
| 1016 | CH2OCH3 | 2-F-phenyl | 2-(methylaminosulfonyl)phenyl |
| 1017 | CH2OCH3 | 2-F-phenyl | 1-pyrrolidinocarbonyl |
| 1018 | CH2OCH3 | 2-F-phenyl | 2-(methylsulfonyl)phenyl |
| 1019 | CH2OCH3 | 2-F-phenyl | 2-(N,N-dimethylaminomethyl)phenyl |
| 1020 | CH2OCH3 | 2-F-phenyl | 2-(N-pyrrolidinylmethyl)phenyl |
| 1021 | CH2OCH3 | 2-F-phenyl | 1-methyl-2-imidazolyl |
| 1022 | CH2OCH3 | 2-F-phenyl | 2-methyl-1-imidazolyl |
| 1023 | CH2OCH3 | 2-F-phenyl | 2-(dimethylaminomethyl)-1-imidazolyl |
| 1024 | CH2OCH3 | 2-F-phenyl | 2-(N-(cyclopropyl-methyl)aminomethyl)phenyl |
| 1025 | CH2OCH3 | 2-F-phenyl | 2-(N-(cyclobutyl)-aminomethyl)phenyl |
| 1026 | CH2OCH3 | 2-F-phenyl | 2-(N-(cyclopentyl)-aminomethyl)phenyl |
| 1027 | CH2OCH3 | 2-F-phenyl | 2-(N-(3-hydroxypyrrolidinyl)-methyl)phenyl |
| 1028 | CH2OCH3 | 2,6-diF-phenyl | 2-(aminosulfonyl)phenyl |
| 1029 | CH2OCH3 | 2,6-diF-phenyl | 2-(methylaminosulfonyl)phenyl |
| 1030 | CH2OCH3 | 2,6-diF-phenyl | 1-pyrrolidinocarbonyl |
| 1031 | CH2OCH3 | 2,6-diF-phenyl | 2-(methylsulfonyl)phenyl |
| 1032 | CH2OCH3 | 2,6-diF-phenyl | 2-(N,N-dimethylaminomethyl)phenyl |
| 1033 | CH2OCH3 | 2,6-diF-phenyl | 2-(N-pyrrolidinylmethyl)phenyl |
| 1034 | CH2OCH3 | 2,6-diF-phenyl | 1-methyl-2-imidazolyl |
| 1035 | CH2OCH3 | 2,6-diF-phenyl | 2-methyl-1-imidazolyl |
| 1036 | CH2OCH3 | 2,6-diF-phenyl | 2-(dimethylaminomethyl)-1-imidazolyl |
| 1037 | CH2OCH3 | 2,6-diF-phenyl | 2-(N-(cyclopropyl-methyl)aminomethyl)phenyl |
| 1038 | CH2OCH3 | 2,6-diF-phenyl | 2-(N-(cyclobutyl)-aminomethyl)phenyl |
| 1039 | CH2OCH3 | 2,6-diF-phenyl | 2-(N-(cyclopentyl)-aminomethyl)phenyl |
| 1040 | CH2OCH3 | 2,6-diF-phenyl | 2-(N-(3-hydroxypyrrolidinyl)-methyl)phenyl |
| 1041 | CONH2 | phenyl | 2-(aminosulfonyl)phenyl |
| 1042 | CONH2 | phenyl | 2-(methylaminosulfonyl)phenyl |
| 1043 | CONH2 | phenyl | 1-pyrrolidinocarbonyl |
| 1044 | CONH2 | phenyl | 2-(methylsulfonyl)phenyl |
| 1045 | CONH2 | phenyl | 2-(N,N-dimethylaminomethyl)phenyl |
| 1046 | CONH2 | phenyl | 2-(N-pyrrolidinylmethyl)phenyl |
| 1047 | CONH2 | phenyl | 1-methyl-2-imidazolyl |
| 1048 | CONH2 | phenyl | 2-methyl-1-imidazolyl |
| 1049 | CONH2 | phenyl | 2-(dimethylaminomethyl)-1-imidazolyl |
| 1050 | CONH2 | phenyl | 2-(N-(cyclopropyl-methyl)aminomethyl)phenyl |
| 1051 | CONH2 | phenyl | 2-(N-(cyclobutyl)-aminomethyl)phenyl |
| 1052 | CONH2 | phenyl | 2-(N-(cyclopentyl)-aminomethyl)phenyl |
| 1053 | CONH2 | phenyl | 2-(N-(3-hydroxypyrrolidinyl)-methyl)phenyl |
| 1054 | CONH2 | 2-pyridyl | 2-(aminosulfonyl)phenyl |
| 1055 | CONH2 | 2-pyridyl | 2-(methylaminosulfonyl)phenyl |
| 1056 | CONH2 | 2-pyridyl | 1-pyrrolidinocarbonyl |
| 1057 | CONH2 | 2-pyridyl | 2-(methylsulfonyl)phenyl |
| 1058 | CONH2 | 2-pyridyl | 2-(N,N-dimethylaminomethyl)phenyl |
| 1059 | CONH2 | 2-pyridyl | 2-(N-pyrrolidinylmethyl)phenyl |
| 1060 | CONH2 | 2-pyridyl | 1-methyl-2-imidazolyl |
| 1061 | CONH2 | 2-pyridyl | 2-methyl-1-imidazolyl |
| 1062 | CONH2 | 2-pyridyl | 2-(dimethylaminomethyl)-1-imidazolyl |
| 1063 | CONH2 | 2-pyridyl | 2-(N-(cyclopropyl-methyl)aminomethyl)phenyl |
| 1064 | CONH2 | 2-pyridyl | 2-(N-(cyclobutyl)-aminomethyl)phenyl |
| 1065 | CONH2 | 2-pyridyl | 2-(N-(cyclopentyl)-aminomethyl)phenyl |
| 1066 | CONH2 | 2-pyridyl | 2-(N-(3-hydroxypyrrolidinyl)-methyl)phenyl |
| 1067 | CONH2 | 3-pyridyl | 2-(aminosulfonyl)phenyl |
| 1068 | CONH2 | 3-pyridyl | 2-(methylaminosulfonyl)phenyl |
| 1069 | CONH2 | 3-pyridyl | 1-pyrrolidinocarbonyl |
| 1070 | CONH2 | 3-pyridyl | 2-(methylsulfonyl)phenyl |
| 1071 | CONH2 | 3-pyridyl | 2-(N,N-dimethylaminomethyl)phenyl |
| 1072 | CONH2 | 3-pyridyl | 2-(N-pyrrolidinylmethyl)phenyl |
| 1073 | CONH2 | 3-pyridyl | 1-methyl-2-imidazolyl |
| 1074 | CONH2 | 3-pyridyl | 2-methyl-1-imidazolyl |
| 1075 | CONH2 | 3-pyridyl | 2-(dimethylaminomethyl)-1-imidazolyl |
| 1076 | CONH2 | 3-pyridyl | 2-(N-(cyclopropyl-methyl)aminomethyl)phenyl |
| 1077 | CONH2 | 3-pyridyl | 2-(N-(cyclobutyl)-aminomethyl)phenyl |
| 1078 | CONH2 | 3-pyridyl | 2-(N-(cyclopentyl)-aminomethyl)phenyl |
| 1079 | CONH2 | 3-pyridyl | 2-(N-(3-hydroxypyrrolidinyl)-methyl)phenyl |
| 1080 | CONH2 | 2-pyrimidyl | 2-(aminosulfonyl)phenyl |
| 1081 | CONH2 | 2-pyrimidyl | 2-(methylaminosulfonyl)phenyl |
| 1082 | CONH2 | 2-pyrimidyl | 1-pyrrolidinocarbonyl |
| 1083 | CONH2 | 2-pyrimidyl | 2-(methylsulfonyl)phenyl |
| 1084 | CONH2 | 2-pyrimidyl | 2-(N,N-dimethylaminomethyl)phenyl |
| 1085 | CONH2 | 2-pyrimidyl | 2-(N-pyrrolidinylmethyl)phenyl |
| 1086 | CONH2 | 2-pyrimidyl | 1-methyl-2-imidazolyl |
| 1087 | CONH2 | 2-pyrimidyl | 2-methyl-1-imidazolyl |
| 1088 | CONH2 | 2-pyrimidyl | 2-(dimethylaminomethyl)-1-imidazolyl |
| 1089 | CONH2 | 2-pyrimidyl | 2-(N-(cyclopropyl-methyl)aminomethyl)phenyl |
| 1090 | CONH2 | 2-pyrimidyl | 2-(N-(cyclobutyl)-aminomethyl)phenyl |
| 1091 | CONH2 | 2-pyrimidyl | 2-(N-(cyclopentyl)-aminomethyl)phenyl |
| 1092 | CONH2 | 2-pyrimidyl | 2-(N-(3-hydroxypyrrolidinyl)-methyl)phenyl |
| 1093 | CONH2 | 5-pyrimidyl | 2-(aminosulfonyl)phenyl |
| 1094 | CONH2 | 5-pyrimidyl | 2-(methylaminosulfonyl)phenyl |
| 1095 | CONH2 | 5-pyrimidyl | 1-pyrrolidinocarbonyl |
| 1096 | CONH2 | 5-pyrimidyl | 2-(methylsulfonyl)phenyl |
| 1097 | CONH2 | 5-pyrimidyl | 2-(N,N-dimethylaminomethyl)phenyl |
| 1098 | CONH2 | 5-pyrimidyl | 2-(N-pyrrolidinylmethyl)phenyl |
| 1099 | CONH2 | 5-pyrimidyl | 1-methyl-2-imidazolyl |
| 1100 | CONH2 | 5-pyrimidyl | 2-methyl-1-imidazolyl |
| 1101 | CONH2 | 5-pyrimidyl | 2-(dimethylaminomethyl)-1-imidazolyl |
| 1102 | CONH2 | 5-pyrimidyl | 2-(N-(cyclopropyl-methyl)aminomethyl)phenyl |
| 1103 | CONH2 | 5-pyrimidyl | 2-(N-(cyclobutyl)-aminomethyl)phenyl |
| 1104 | CONH2 | 5-pyrimidyl | 2-(N-(cyclopentyl)-aminomethyl)phenyl |
| 1105 | CONH2 | 5-pyrimidyl | 2-(N-(3-hydroxypyrrolidinyl)-methyl)phenyl |
| 1106 | CONH2 | 2-F-phenyl | 2-(aminosulfonyl)phenyl |
| 1107 | CONH2 | 2-F-phenyl | 2-(methylaminosulfonyl)phenyl |
| 1108 | CONH2 | 2-F-phenyl | 1-pyrrolidinocarbonyl |
| 1109 | CONH2 | 2-F-phenyl | 2-(methylsulfonyl)phenyl |
| 1110 | CONH2 | 2-F-phenyl | 2-(N,N-dimethylaminomethyl)phenyl |
| 1111 | CONH2 | 2-F-phenyl | 2-(N-pyrrolidinylmethyl)phenyl |
| 1112 | CONH2 | 2-F-phenyl | 1-methyl-2-imidazolyl |
| 1113 | CONH2 | 2-F-phenyl | 2-methyl-1-imidazolyl |

-continued

| Ex# | R1a | A | B |
|---|---|---|---|
| 1114 | CONH2 | 2-F-phenyl | 2-(dimethylaminomethyl)-1-imidazolyl |
| 1115 | CONH2 | 2-F-phenyl | 2-(N-(cyclopropyl-methyl)aminomethyl)phenyl |
| 1116 | CONH2 | 2-F-phenyl | 2-(N-(cyclobutyl)-aminomethyl)phenyl |
| 1117 | CONH2 | 2-F-phenyl | 2-(N-(cyclopentyl)-aminomethyl)phenyl |
| 1118 | CONH2 | 2-F-phenyl | 2-(N-(3-hydroxypyrrolidinyl)-methyl)phenyl |
| 1119 | CONH2 | 2-F-phenyl | 2-(aminosulfonyl)phenyl |
| 1120 | CONH2 | 2-F-phenyl | 2-(methylaminosulfonyl)phenyl |
| 1121 | CONH2 | 2-F-phenyl | 1-pyrrolidinocarbonyl |
| 1122 | CONH2 | 2-F-phenyl | 2-(methylsulfonyl)phenyl |
| 1123 | CONH2 | 2-F-phenyl | 2-(N,N-dimethylaminomethyl)phenyl |
| 1124 | CONH2 | 2-F-phenyl | 2-(N-pyrrolidinylmethyl)phenyl |
| 1125 | CONH2 | 2-F-phenyl | 1-methyl-2-imidazolyl |
| 1126 | CONH2 | 2-F-phenyl | 2-methyl-1-imidazolyl |
| 1127 | CONH2 | 2-F-phenyl | 2-(dimethylaminomethyl)-1-imidazolyl |
| 1128 | CONH2 | 2-F-phenyl | 2-(N-(cyclopropyl-methyl)aminomethyl)phenyl |
| 1129 | CONH2 | 2-F-phenyl | 2-(N-(cyclobutyl)-aminomethyl)phenyl |
| 1130 | CONH2 | 2-F-phenyl | 2-(N-(cyclopentyl)-aminomethyl)phenyl |
| 1131 | CONH2 | 2-F-phenyl | 2-(N-(3-hydroxypyrrolidinyl)-methyl)phenyl |
| 1132 | CONH2 | 2,6-diF-phenyl | 2-(aminosulfonyl)phenyl |
| 1133 | CONH2 | 2,6-diF-phenyl | 2-(methylaminosulfonyl)phenyl |
| 1134 | CONH2 | 2,6-diF-phenyl | 1-pyrrolidinocarbonyl |
| 1135 | CONH2 | 2,6-diF-phenyl | 2-(methylsulfonyl)phenyl |
| 1136 | CONH2 | 2,6-diF-phenyl | 2-(N,N-dimethylaminomethyl)phenyl |
| 1137 | CONH2 | 2,6-diF-phenyl | 2-(N-pyrrolidinylmethyl)phenyl |
| 1138 | CONH2 | 2,6-diF-phenyl | 1-methyl-2-imidazolyl |
| 1139 | CONH2 | 2,6-diF-phenyl | 2-methyl-1-imidazolyl |
| 1140 | CONH2 | 2,6-diF-phenyl | 2-(dimethylaminomethyl)-1-imidazolyl |
| 1141 | CONH2 | 2,6-diF-phenyl | 2-(N-(cyclopropyl-methyl)aminomethyl)phenyl |
| 1142 | CONH2 | 2,6-diF-phenyl | 2-(N-(cyclobutyl)-aminomethyl)phenyl |
| 1143 | CONH2 | 2,6-diF-phenyl | 2-(N-(cyclopentyl)-aminomethyl)phenyl |
| 1144 | CONH2 | 2,6-diF-phenyl | 2-(N-(3-hydroxypyrrolidinyl)-methyl)phenyl |
| 1145 | CN | phenyl | 2-(aminosulfonyl)phenyl |
| 1146 | CN | phenyl | 2-(methylaminosulfonyl)phenyl |
| 1147 | CN | phenyl | 1-pyrrolidinocarbonyl |
| 1148 | CN | phenyl | 2-(methylsulfonyl)phenyl |
| 1149 | CN | phenyl | 2-(N,N-dimethylaminomethyl)phenyl |
| 1150 | CN | phenyl | 2-(N-pyrrolidinylmethyl)phenyl |
| 1151 | CN | phenyl | 1-methyl-2-imidazolyl |
| 1152 | CN | phenyl | 2-methyl-1-imidazolyl |
| 1153 | CN | phenyl | 2-(dimethylaminomethyl)-1-imidazolyl |
| 1154 | CN | phenyl | 2-(N-(cyclopropyl-methyl)aminomethyl)phenyl |
| 1155 | CN | phenyl | 2-(N-(cyclobutyl)-aminomethyl)phenyl |
| 1156 | CN | phenyl | 2-(N-(cyclopentyl)-aminomethyl)phenyl |
| 1157 | CN | phenyl | 2-(N-(3-hydroxypyrrolidinyl)-methyl)phenyl |
| 1158 | CN | 2-pyridyl | 2-(aminosulfonyl)phenyl |
| 1159 | CN | 2-pyridyl | 2-(methylaminosulfonyl)phenyl |
| 1160 | CN | 2-pyridyl | 1-pyrrolidinocarbonyl |
| 1161 | CN | 2-pyridyl | 2-(methylsulfonyl)phenyl |
| 1162 | CN | 2-pyridyl | 2-(N,N-dimethylaminomethyl)phenyl |
| 1163 | CN | 2-pyridyl | 2-(N-pyrrolidinylmethyl)phenyl |
| 1164 | CN | 2-pyridyl | 1-methyl-2-imidazolyl |
| 1165 | CN | 2-pyridyl | 2-methyl-1-imidazolyl |
| 1166 | CN | 2-pyridyl | 2-(dimethylaminomethyl)-1-imidazolyl |
| 1167 | CN | 2-pyridyl | 2-(N-(cyclopropyl-methyl)aminomethyl)phenyl |
| 1168 | CN | 2-pyridyl | 2-(N-(cyclobutyl)-aminomethyl)phenyl |
| 1169 | CN | 2-pyridyl | 2-(N-(cyclopentyl)-aminomethyl)phenyl |
| 1170 | CN | 2-pyridyl | 2-(N-(3-hydroxypyrrolidinyl)-methyl)phenyl |
| 1171 | CN | 3-pyridyl | 2-(aminosulfonyl)phenyl |
| 1172 | CN | 3-pyridyl | 2-(methylaminosulfonyl)phenyl |
| 1173 | CN | 3-pyridyl | 1-pyrrolidinocarbonyl |
| 1174 | CN | 3-pyridyl | 2-(methylsulfonyl)phenyl |
| 1175 | CN | 3-pyridyl | 2-(N,N-dimethylaminomethyl)phenyl |
| 1176 | CN | 3-pyridyl | 2-(N-pyrrolidinylmethyl)phenyl |
| 1177 | CN | 3-pyridyl | 1-methyl-2-imidazolyl |
| 1178 | CN | 3-pyridyl | 2-methyl-1-imidazolyl |
| 1179 | CN | 3-pyridyl | 2-(dimethylaminomethyl)-1-imidazolyl |
| 1180 | CN | 3-pyridyl | 2-(N-(cyclopropyl-methyl)aminomethyl)phenyl |
| 1181 | CN | 3-pyridyl | 2-(N-(cyclobutyl)-aminomethyl)phenyl |
| 1182 | CN | 3-pyridyl | 2-(N-(cyclopentyl)-aminomethyl)phenyl |
| 1183 | CN | 3-pyridyl | 2-(N-(3-hydroxypyrrolidinyl)-methyl)phenyl |
| 1184 | CN | 2-pyrimidyl | 2-(aminosulfonyl)phenyl |
| 1185 | CN | 2-pyrimidyl | 2-(methylaminosulfonyl)phenyl |
| 1186 | CN | 2-pyrimidyl | 1-pyrrolidinocarbonyl |
| 1187 | CN | 2-pyrimidyl | 2-(methylsulfonyl)phenyl |
| 1188 | CN | 2-pyrimidyl | 2-(N,N-dimethylaminomethyl)phenyl |
| 1189 | CN | 2-pyrimidyl | 2-(N-pyrrolidinylmethyl)phenyl |
| 1190 | CN | 2-pyrimidyl | 1-methyl-2-imidazolyl |
| 1191 | CN | 2-pyrimidyl | 2-methyl-1-imidazolyl |
| 1192 | CN | 2-pyrimidyl | 2-(dimethylaminomethyl)-1-imidazolyl |
| 1193 | CN | 2-pyrimidyl | 2-(N-(cyclopropyl-methyl)aminomethyl)phenyl |
| 1194 | CN | 2-pyrimidyl | 2-(N-(cyclobutyl)-aminomethyl)phenyl |
| 1195 | CN | 2-pyrimidyl | 2-(N-(cyclopentyl)-aminomethyl)phenyl |
| 1196 | CN | 2-pyrimidyl | 2-(N-(3-hydroxypyrrolidinyl)-methyl)phenyl |
| 1197 | CN | 5-pyrimidyl | 2-(aminosulfonyl)phenyl |
| 1198 | CN | 5-pyrimidyl | 2-(methylaminosulfonyl)phenyl |
| 1199 | CN | 5-pyrimidyl | 1-pyrrolidinocarbonyl |
| 1200 | CN | 5-pyrimidyl | 2-(methylsulfonyl)phenyl |
| 1201 | CN | 5-pyrimidyl | 2-(N,N-dimethylaminomethyl)phenyl |
| 1202 | CN | 5-pyrimidyl | 2-(N-pyrrolidinylmethyl)phenyl |
| 1203 | CN | 5-pyrimidyl | 1-methyl-2-imidazolyl |
| 1204 | CN | 5-pyrimidyl | 2-methyl-1-imidazolyl |
| 1205 | CN | 5-pyrimidyl | 2-(dimethylaminomethyl)-1-imidazolyl |
| 1206 | CN | 5-pyrimidyl | 2-(N-(cyclopropyl-methyl)aminomethyl)phenyl |
| 1207 | CN | 5-pyrimidyl | 2-(N-(cyclobutyl)-aminomethyl)phenyl |
| 1208 | CN | 5-pyrimidyl | 2-(N-(cyclopentyl)-aminomethyl)phenyl |
| 1209 | CN | 5-pyrimidyl | 2-(N-(3-hydroxypyrrolidinyl)-methyl)phenyl |
| 1210 | CN | 2-F-phenyl | 2-(aminosulfonyl)phenyl |
| 1211 | CN | 2-F-phenyl | 2-(methylaminosulfonyl)phenyl |
| 1212 | CN | 2-F-phenyl | 1-pyrrolidinocarbonyl |
| 1213 | CN | 2-F-phenyl | 2-(methylsulfonyl)phenyl |
| 1214 | CN | 2-F-phenyl | 2-(N,N-dimethylaminomethyl)phenyl |
| 1215 | CN | 2-F-phenyl | 2-(N-pyrrolidinylmethyl)phenyl |
| 1216 | CN | 2-F-phenyl | 1-methyl-2-imidazolyl |
| 1217 | CN | 2-F-phenyl | 2-methyl-1-imidazolyl |

| Ex# | R¹ᵃ | A | B |
|---|---|---|---|
| 1218 | CN | 2-F-phenyl | 2-(dimethylaminomethyl)-1-imidazolyl |
| 1219 | CN | 2-F-phenyl | 2-(N-(cyclopropyl-methyl)aminomethyl)phenyl |
| 1220 | CN | 2-F-phenyl | 2-(N-(cyclobutyl)-aminomethyl)phenyl |
| 1221 | CN | 2-F-phenyl | 2-(N-(cyclopentyl)-aminomethyl)phenyl |
| 1222 | CN | 2-F-phenyl | 2-(N-(3-hydroxypyrrolidinyl)-methyl)phenyl |
| 1223 | CN | 2-F-phenyl | 2-(aminosulfonyl)phenyl |
| 1224 | CN | 2-F-phenyl | 2-(methylaminosulfonyl)phenyl |
| 1225 | CN | 2-F-phenyl | 1-pyrrolidinocarbonyl |
| 1226 | CN | 2-F-phenyl | 2-(methylsulfonyl)phenyl |
| 1227 | CN | 2-F-phenyl | 2-(N,N-dimethylaminomethyl)phenyl |
| 1228 | CN | 2-F-phenyl | 2-(N-pyrrolidinylmethyl)phenyl |
| 1229 | CN | 2-F-phenyl | 1-methyl-2-imidazolyl |
| 1230 | CN | 2-F-phenyl | 2-methyl-1-imidazolyl |
| 1231 | CN | 2-F-phenyl | 2-(dimethylaminomethyl)-1-imidazolyl |
| 1232 | CN | 2-F-phenyl | 2-(N-(cyclopropyl-methyl)aminomethyl)phenyl |
| 1233 | CN | 2-F-phenyl | 2-(N-(cyclobutyl)-aminomethyl)phenyl |
| 1234 | CN | 2-F-phenyl | 2-(N-(cyclopentyl)-aminomethyl)phenyl |
| 1235 | CN | 2-F-phenyl | 2-(N-(3-hydroxypyrrolidinyl)-methyl)phenyl |
| 1236 | CN | 2,6-diF-phenyl | 2-(aminosulfonyl)phenyl |
| 1237 | CN | 2,6-diF-phenyl | 2-(methylaminosulfonyl)phenyl |
| 1238 | CN | 2,6-diF-phenyl | 1-pyrrolidinocarbonyl |
| 1239 | CN | 2,6-diF-phenyl | 2-(methylsulfonyl)phenyl |
| 1240 | CN | 2,6-diF-phenyl | 2-(N,N-dimethylaminomethyl)phenyl |
| 1241 | CN | 2,6-diF-phenyl | 2-(N-pyrrolidinylmethyl)phenyl |
| 1242 | CN | 2,6-diF-phenyl | 1-methyl-2-imidazolyl |
| 1243 | CN | 2,6-diF-phenyl | 2-methyl-1-imidazolyl |
| 1244 | CN | 2,6-diF-phenyl | 2-(dimethylaminomethyl)-1-imidazolyl |
| 1245 | CN | 2,6-diF-phenyl | 2-(N-(cyclopropyl-methyl)aminomethyl)phenyl |
| 1246 | CN | 2,6-diF-phenyl | 2-(N-(cyclobutyl)-aminomethyl)phenyl |
| 1247 | CN | 2,6-diF-phenyl | 2-(N-(cyclopentyl)-aminomethyl)phenyl |
| 1248 | CN | 2,6-diF-phenyl | 2-(N-(3-hydroxypyrrolidinyl)-methyl)phenyl |
| 1249 | CH2NH2 | phenyl | 2-(aminosulfonyl)phenyl |
| 1250 | CH2NH2 | phenyl | 2-(methylaminosulfonyl)phenyl |
| 1251 | CH2NH2 | phenyl | 1-pyrrolidinocarbonyl |
| 1252 | CH2NH2 | phenyl | 2-(methylsulfonyl)phenyl |
| 1253 | CH2NH2 | phenyl | 2-(N,N-dimethylaminomethyl)phenyl |
| 1254 | CH2NH2 | phenyl | 2-(N-pyrrolidinylmethyl)phenyl |
| 1255 | CH2NH2 | phenyl | 1-methyl-2-imidazolyl |
| 1256 | CH2NH2 | phenyl | 2-methyl-1-imidazolyl |
| 1257 | CH2NH2 | phenyl | 2-(dimethylaminomethyl)-1-imidazolyl |
| 1258 | CH2NH2 | phenyl | 2-(N-(cyclopropyl-methyl)aminomethyl)phenyl |
| 1259 | CH2NH2 | phenyl | 2-(N-(cyclobutyl)-aminomethyl)phenyl |
| 1260 | CH2NH2 | phenyl | 2-(N-(cyclopentyl)-aminomethyl)phenyl |
| 1261 | CH2NH2 | phenyl | 2-(N-(3-hydroxypyrrolidinyl)-methyl)phenyl |
| 1262 | CH2NH2 | 2-pyridyl | 2-(aminosulfonyl)phenyl |
| 1263 | CH2NH2 | 2-pyridyl | 2-(methylaminosulfonyl)phenyl |
| 1264 | CH2NH2 | 2-pyridyl | 1-pyrrolidinocarbonyl |
| 1265 | CH2NH2 | 2-pyridyl | 2-(methylsulfonyl)phenyl |
| 1266 | CH2NH2 | 2-pyridyl | 2-(N,N-dimethylaminomethyl)phenyl |
| 1267 | CH2NH2 | 2-pyridyl | 2-(N-pyrrolidinylmethyl)phenyl |
| 1268 | CH2NH2 | 2-pyridyl | 1-methyl-2-imidazolyl |
| 1269 | CH2NH2 | 2-pyridyl | 2-methyl-1-imidazolyl |
| 1270 | CH2NH2 | 2-pyridyl | 2-(dimethylaminomethyl)-1-imidazolyl |
| 1271 | CH2NH2 | 2-pyridyl | 2-(N-(cyclopropyl-methyl)aminomethyl)phenyl |
| 1272 | CH2NH2 | 2-pyridyl | 2-(N-(cyclobutyl)-aminomethyl)phenyl |
| 1273 | CH2NH2 | 2-pyridyl | 2-(N-(cyclopentyl)-aminomethyl)phenyl |
| 1274 | CH2NH2 | 2-pyridyl | 2-(N-(3-hydroxypyrrolidinyl)-methyl)phenyl |
| 1275 | CH2NH2 | 3-pyridyl | 2-(aminosulfonyl)phenyl |
| 1276 | CH2NH2 | 3-pyridyl | 2-(methylaminosulfonyl)phenyl |
| 1277 | CH2NH2 | 3-pyridyl | 1-pyrrolidinocarbonyl |
| 1278 | CH2NH2 | 3-pyridyl | 2-(methylsulfonyl)phenyl |
| 1279 | CH2NH2 | 3-pyridyl | 2-(N,N-dimethylaminomethyl)phenyl |
| 1280 | CH2NH2 | 3-pyridyl | 2-(N-pyrrolidinylmethyl)phenyl |
| 1281 | CH2NH2 | 3-pyridyl | 1-methyl-2-imidazolyl |
| 1282 | CH2NH2 | 3-pyridyl | 2-methyl-1-imidazolyl |
| 1283 | CH2NH2 | 3-pyridyl | 2-(dimethylaminomethyl)-1-imidazolyl |
| 1284 | CH2NH2 | 3-pyridyl | 2-(N-(cyclopropyl-methyl)aminomethyl)phenyl |
| 1285 | CH2NH2 | 3-pyridyl | 2-(N-(cyclobutyl)-aminomethyl)phenyl |
| 1286 | CH2NH2 | 3-pyridyl | 2-(N-(cyclopentyl)-aminomethyl)phenyl |
| 1287 | CH2NH2 | 3-pyridyl | 2-(N-(3-hydroxypyrrolidinyl)-methyl)phenyl |
| 1288 | CH2NH2 | 2-pyrimidyl | 2-(aminosulfonyl)phenyl |
| 1289 | CH2NH2 | 2-pyrimidyl | 2-(methylaminosulfonyl)phenyl |
| 1290 | CH2NH2 | 2-pyrimidyl | 1-pyrrolidinocarbonyl |
| 1291 | CH2NH2 | 2-pyrimidyl | 2-(methylsulfonyl)phenyl |
| 1292 | CH2NH2 | 2-pyrimidyl | 2-(N,N-dimethylaminomethyl)phenyl |
| 1293 | CH2NH2 | 2-pyrimidyl | 2-(N-pyrrolidinylmethyl)phenyl |
| 1294 | CH2NH2 | 2-pyrimidyl | 1-methyl-2-imidazolyl |
| 1295 | CH2NH2 | 2-pyrimidyl | 2-methyl-1-imidazolyl |
| 1296 | CH2NH2 | 2-pyrimidyl | 2-(dimethylaminomethyl)-1-imidazolyl |
| 1297 | CH2NH2 | 2-pyrimidyl | 2-(N-(cyclopropyl-methyl)aminomethyl)phenyl |
| 1298 | CH2NH2 | 2-pyrimidyl | 2-(N-(cyclobutyl)-aminomethyl)phenyl |
| 1299 | CH2NH2 | 2-pyrimidyl | 2-(N-(cyclopentyl)-aminomethyl)phenyl |
| 1300 | CH2NH2 | 2-pyrimidyl | 2-(N-(3-hydroxypyrrolidinyl)-methyl)phenyl |
| 1301 | CH2NH2 | 5-pyrimidyl | 2-(aminosulfonyl)phenyl |
| 1302 | CH2NH2 | 5-pyrimidyl | 2-(methylaminosulfonyl)phenyl |
| 1303 | CH2NH2 | 5-pyrimidyl | 1-pyrrolidinocarbonyl |
| 1304 | CH2NH2 | 5-pyrimidyl | 2-(methylsulfonyl)phenyl |
| 1305 | CH2NH2 | 5-pyrimidyl | 2-(N,N-dimethylaminomethyl)phenyl |
| 1306 | CH2NH2 | 5-pyrimidyl | 2-(N-pyrrolidinylmethyl)phenyl |
| 1307 | CH2NH2 | 5-pyrimidyl | 1-methyl-2-imidazolyl |
| 1308 | CH2NH2 | 5-pyrimidyl | 2-methyl-1-imidazolyl |
| 1309 | CH2NH2 | 5-pyrimidyl | 2-(dimethylaminomethyl)-1-imidazolyl |
| 1310 | CH2NH2 | 5-pyrimidyl | 2-(N-(cyclopropyl-methyl)aminomethyl)phenyl |
| 1311 | CH2NH2 | 5-pyrimidyl | 2-(N-(cyclobutyl)-aminomethyl)phenyl |
| 1312 | CH2NH2 | 5-pyrimidyl | 2-(N-(cyclopentyl)-aminomethyl)phenyl |
| 1313 | CH2NH2 | 5-pyrimidyl | 2-(N-(3-hydroxypyrrolidinyl)-methyl)phenyl |
| 1314 | CH2NH2 | 2-F-phenyl | 2-(aminosulfonyl)phenyl |
| 1315 | CH2NH2 | 2-F-phenyl | 2-(methylaminosulfonyl)phenyl |
| 1316 | CH2NH2 | 2-F-phenyl | 1-pyrrolidinocarbonyl |
| 1317 | CH2NH2 | 2-F-phenyl | 2-(methylsulfonyl)phenyl |
| 1318 | CH2NH2 | 2-F-phenyl | 2-(N,N-dimethylaminomethyl)phenyl |
| 1319 | CH2NH2 | 2-F-phenyl | 2-(N-pyrrolidinylmethyl)phenyl |
| 1320 | CH2NH2 | 2-F-phenyl | 1-methyl-2-imidazolyl |
| 1321 | CH2NH2 | 2-F-phenyl | 2-methyl-1-imidazolyl |

-continued

| Ex# | R1a | A | B |
|---|---|---|---|
| 1322 | CH2NH2 | 2-F-phenyl | 2-(dimethylaminomethyl)-1-imidazolyl |
| 1323 | CH2NH2 | 2-F-phenyl | 2-(N-(cyclopropyl-methyl)aminomethyl)phenyl |
| 1324 | CH2NH2 | 2-F-phenyl | 2-(N-(cyclobutyl)-aminomethyl)phenyl |
| 1325 | CH2NH2 | 2-F-phenyl | 2-(N-(cyclopentyl)-aminomethyl)phenyl |
| 1326 | CH2NH2 | 2-F-phenyl | 2-(N-(3-hydroxypyrrolidinyl)-methyl)phenyl |
| 1327 | CH2NH2 | 2-F-phenyl | 2-(aminosulfonyl)phenyl |
| 1328 | CH2NH2 | 2-F-phenyl | 2-(methylaminosulfonyl)phenyl |
| 1329 | CH2NH2 | 2-F-phenyl | 1-pyrrolidinocarbonyl |
| 1330 | CH2NH2 | 2-F-phenyl | 2-(methylsulfonyl)phenyl |
| 1331 | CH2NH2 | 2-F-phenyl | 2-(N,N-dimethylaminomethyl)phenyl |
| 1332 | CH2NH2 | 2-F-phenyl | 2-(N-pyrrolidinylmethyl)phenyl |
| 1333 | CH2NH2 | 2-F-phenyl | 1-methyl-2-imidazolyl |
| 1334 | CH2NH2 | 2-F-phenyl | 2-methyl-1-imidazolyl |
| 1335 | CH2NH2 | 2-F-phenyl | 2-(dimethylaminomethyl)-1-imidazolyl |
| 1336 | CH2NH2 | 2-F-phenyl | 2-(N-(cyclopropyl-methyl)aminomethyl)phenyl |
| 1337 | CH2NH2 | 2-F-phenyl | 2-(N-(cyclobutyl)-aminomethyl)phenyl |
| 1338 | CH2NH2 | 2-F-phenyl | 2-(N-(cyclopentyl)-aminomethyl)phenyl |
| 1339 | CH2NH2 | 2-F-phenyl | 2-(N-(3-hydroxypyrrolidinyl)-methyl)phenyl |
| 1340 | CH2NH2 | 2,6-diF-phenyl | 2-(aminosulfonyl)phenyl |
| 1341 | CH2NH2 | 2,6-diF-phenyl | 2-(methylaminosulfonyl)phenyl |
| 1342 | CH2NH2 | 2,6-diF-phenyl | 1-pyrrolidinocarbonyl |
| 1343 | CH2NH2 | 2,6-diF-phenyl | 2-(methylsulfonyl)phenyl |
| 1344 | CH2NH2 | 2,6-diF-phenyl | 2-(N,N-dimethylaminomethyl)phenyl |
| 1345 | CH2NH2 | 2,6-diF-phenyl | 2-(N-pyrrolidinylmethyl)phenyl |
| 1346 | CH2NH2 | 2,6-diF-phenyl | 1-methyl-2-imidazolyl |
| 1347 | CH2NH2 | 2,6-diF-phenyl | 2-methyl-1-imidazolyl |
| 1348 | CH2NH2 | 2,6-diF-phenyl | 2-(dimethylaminomethyl)-1-imidazolyl |
| 1349 | CH2NH2 | 2,6-diF-phenyl | 2-(N-(cyclopropyl-methyl)aminomethyl)phenyl |
| 1350 | CH2NH2 | 2,6-diF-phenyl | 2-(N-(cyclobutyl)-aminomethyl)phenyl |
| 1351 | CH2NH2 | 2,6-diF-phenyl | 2-(N-(cyclopentyl)-aminomethyl)phenyl |
| 1352 | CH2NH2 | 2,6-diF-phenyl | 2-(N-(3-hydroxypyrrolidinyl)-methyl)phenyl |
| 1353 | CH2NH—SO2CH3 | phenyl | 2-(aminosulfonyl)phenyl |
| 1354 | CH2NH—SO2CH3 | phenyl | 2-(methylaminosulfonyl)phenyl |
| 1355 | CH2NH—SO2CH3 | phenyl | 1-pyrrolidinocarbonyl |
| 1356 | CH2NH—SO2CH3 | phenyl | 2-(methylsulfonyl)phenyl |
| 1357 | CH2NH—SO2CH3 | phenyl | 2-(N,N-dimethylaminomethyl)phenyl |
| 1358 | CH2NH—SO2CH3 | phenyl | 2-(N-pyrrolidinylmethyl)phenyl |
| 1359 | CH2NH—SO2CH3 | phenyl | 1-methyl-2-imidazolyl |
| 1360 | CH2NH—SO2CH3 | phenyl | 2-methyl-1-imidazolyl |
| 1361 | CH2NH—SO2CH3 | phenyl | 2-(dimethylaminomethyl)-1-imidazolyl |
| 1362 | CH2NH—SO2CH3 | phenyl | 2-(N-(cyclopropyl-methyl)aminomethyl)phenyl |
| 1363 | CH2NH—SO2CH3 | phenyl | 2-(N-(cyclobutyl)-aminomethyl)phenyl |
| 1364 | CH2NH—SO2CH3 | phenyl | 2-(N-(cyclopentyl)-aminomethyl)phenyl |
| 1365 | CH2NH—SO2CH3 | phenyl | 2-(N-(3-hydroxypyrrolidinyl)-methyl)phenyl |
| 1366 | CH2NH—SO2CH3 | 2-pyridyl | 2-(aminosulfonyl)phenyl |
| 1367 | CH2NH—SO2CH3 | 2-pyridyl | 2-(methylaminosulfonyl)phenyl |
| 1368 | CH2NH—SO2CH3 | 2-pyridyl | 1-pyrrolidinocarbonyl |
| 1369 | CH2NH—SO2CH3 | 2-pyridyl | 2-(methylsulfonyl)phenyl |
| 1370 | CH2NH—SO2CH3 | 2-pyridyl | 2-(N,N-dimethylaminomethyl)phenyl |
| 1371 | CH2NH—SO2CH3 | 2-pyridyl | 2-(N-pyrrolidinylmethyl)phenyl |
| 1372 | CH2NH—SO2CH3 | 2-pyridyl | 1-methyl-2-imidazolyl |
| 1373 | CH2NH—SO2CH3 | 2-pyridyl | 2-methyl-1-imidazolyl |
| 1374 | CH2NH—SO2CH3 | 2-pyridyl | 2-(dimethylaminomethyl)-1-imidazolyl |
| 1375 | CH2NH—SO2CH3 | 2-pyridyl | 2-(N-(cyclopropyl-methyl)aminomethyl)phenyl |
| 1376 | CH2NH—SO2CH3 | 2-pyridyl | 2-(N-(cyclobutyl)-aminomethyl)phenyl |
| 1377 | CH2NH—SO2CH3 | 2-pyridyl | 2-(N-(cyclopentyl)-aminomethyl)phenyl |
| 1378 | CH2NH—SO2CH3 | 2-pyridyl | 2-(N-(3-hydroxypyrrolidinyl)-methyl)phenyl |
| 1379 | CH2NH—SO2CH3 | 3-pyridyl | 2-(aminosulfonyl)phenyl |
| 1380 | CH2NH—SO2CH3 | 3-pyridyl | 2-(methylaminosulfonyl)phenyl |
| 1381 | CH2NH—SO2CH3 | 3-pyridyl | 1-pyrrolidinocarbonyl |
| 1382 | CH2NH—SO2CH3 | 3-pyridyl | 2-(methylsulfonyl)phenyl |
| 1383 | CH2NH—SO2CH3 | 3-pyridyl | 2-(N,N-dimethylaminomethyl)phenyl |
| 1384 | CH2NH—SO2CH3 | 3-pyridyl | 2-(N-pyrrolidinylmethyl)phenyl |
| 1385 | CH2NH—SO2CH3 | 3-pyridyl | 1-methyl-2-imidazolyl |
| 1386 | CH2NH—SO2CH3 | 3-pyridyl | 2-methyl-1-imidazolyl |
| 1387 | CH2NH—SO2CH3 | 3-pyridyl | 2-(dimethylaminomethyl)-1-imidazolyl |
| 1388 | CH2NH—SO2CH3 | 3-pyridyl | 2-(N-(cyclopropyl-methyl)aminomethyl)phenyl |
| 1389 | CH2NH—SO2CH3 | 3-pyridyl | 2-(N-(cyclobutyl)-aminomethyl)phenyl |
| 1390 | CH2NH—SO2CH3 | 3-pyridyl | 2-(N-(cyclopentyl)-aminomethyl)phenyl |
| 1391 | CH2NH—SO2CH3 | 3-pyridyl | 2-(N-(3-hydroxypyrrolidinyl)-methyl)phenyl |
| 1392 | CH2NH—SO2CH3 | 2-pyrimidyl | 2-(aminosulfonyl)phenyl |
| 1393 | CH2NH—SO2CH3 | 2-pyrimidyl | 2-(methylaminosulfonyl)phenyl |
| 1394 | CH2NH—SO2CH3 | 2-pyrimidyl | 1-pyrrolidinocarbonyl |
| 1395 | CH2NH—SO2CH3 | 2-pyrimidyl | 2-(methylsulfonyl)phenyl |
| 1396 | CH2NH—SO2CH3 | 2-pyrimidyl | 2-(N,N-dimethylaminomethyl)phenyl |
| 1397 | CH2NH—SO2CH3 | 2-pyrimidyl | 2-(N-pyrrolidinylmethyl)phenyl |
| 1398 | CH2NH—SO2CH3 | 2-pyrimidyl | 1-methyl-2-imidazolyl |
| 1399 | CH2NH—SO2CH3 | 2-pyrimidyl | 2-methyl-1-imidazolyl |
| 1400 | CH2NH—SO2CH3 | 2-pyrimidyl | 2-(dimethylaminomethyl)-1-imidazolyl |
| 1401 | CH2NH—SO2CH3 | 2-pyrimidyl | 2-(N-(cyclopropyl-methyl)aminomethyl)phenyl |
| 1402 | CH2NH—SO2CH3 | 2-pyrimidyl | 2-(N-(cyclobutyl)-aminomethyl)phenyl |
| 1403 | CH2NH—SO2CH3 | 2-pyrimidyl | 2-(N-(cyclopentyl)-aminomethyl)phenyl |
| 1404 | CH2NH—SO2CH3 | 2-pyrimidyl | 2-(N-(3-hydroxypyrrolidinyl)-methyl)phenyl |

-continued

| Ex# | R¹ᵃ | A | B |
|---|---|---|---|
| 1405 | CH2NH—SO2CH3 | 5-pyrimidyl | 2-(aminosulfonyl)phenyl |
| 1406 | CH2NH—SO2CH3 | 5-pyrimidyl | 2-(methylaminosulfonyl)phenyl |
| 1407 | CH2NH—SO2CH3 | 5-pyrimidyl | 1-pyrrolidinocarbonyl |
| 1408 | CH2NH—SO2CH3 | 5-pyrimidyl | 2-(methylsulfonyl)phenyl |
| 1409 | CH2NH—SO2CH3 | 5-pyrimidyl | 2-(N,N-dimethylaminomethyl)phenyl |
| 1410 | CH2NH—SO2CH3 | 5-pyrimidyl | 2-(N-pyrrolidinylmethyl)phenyl |
| 1411 | CH2NH—SO2CH3 | 5-pyrimidyl | 1-methyl-2-imidazolyl |
| 1412 | CH2NH—SO2CH3 | 5-pyrimidyl | 2-methyl-1-imidazolyl |
| 1413 | CH2NH—SO2CH3 | 5-pyrimidyl | 2-(dimethylaminomethyl)-1-imidazolyl |
| 1414 | CH2NH—SO2CH3 | 5-pyrimidyl | 2-(N-(cyclopropyl-methyl)aminomethyl)phenyl |
| 1415 | CH2NH—SO2CH3 | 5-pyrimidyl | 2-(N-(cyclobutyl)-aminomethyl)phenyl |
| 1416 | CH2NH—SO2CH3 | 5-pyrimidyl | 2-(N-(cyclopentyl)-aminomethyl)phenyl |
| 1417 | CH2NH—SO2CH3 | 5-pyrimidyl | 2-(N-(3-hydroxypyrrolidinyl)-methyl)phenyl |
| 1418 | CH2NH—SO2CH3 | 2-Cl-phenyl | 2-(aminosulfonyl)phenyl |
| 1419 | CH2NH—SO2CH3 | 2-Cl-phenyl | 2-(methylaminosulfonyl)phenyl |
| 1420 | CH2NH—SO2CH3 | 2-Cl-phenyl | 1-pyrrolidinocarbonyl |
| 1421 | CH2NH—SO2CH3 | 2-Cl-phenyl | 2-(methylsulfonyl)phenyl |
| 1422 | CH2NH—SO2CH3 | 2-Cl-phenyl | 2-(N,N-dimethylaminomethyl)phenyl |
| 1423 | CH2NH—SO2CH3 | 2-Cl-phenyl | 2-(N-pyrrolidinylmethyl)phenyl |
| 1424 | CH2NH—SO2CH3 | 2-Cl-phenyl | 1-methyl-2-imidazolyl |
| 1425 | CH2NH—SO2CH3 | 2-Cl-phenyl | 2-methyl-1-imidazolyl |
| 1426 | CH2NH—SO2CH3 | 2-Cl-phenyl | 2-(dimethylaminomethyl)-1-imidazolyl |
| 1427 | CH2NH—SO2CH3 | 2-Cl-phenyl | 2-(N-(cyclopropyl-methyl)aminomethyl)phenyl |
| 1428 | CH2NH—SO2CH3 | 2-Cl-phenyl | 2-(N-(cyclobutyl)-aminomethyl)phenyl |
| 1429 | CH2NH—SO2CH3 | 2-Cl-phenyl | 2-(N-(cyclopentyl)-aminomethyl)phenyl |
| 1430 | CH2NH—SO2CH3 | 2-Cl-phenyl | 2-(N-(3-hydroxypyrrolidinyl)-methyl)phenyl |
| 1431 | CH2NH—SO2CH3 | 2-F-phenyl | 2-(aminosulfonyl)phenyl |
| 1432 | CH2NH—SO2CH3 | 2-F-phenyl | 2-(methylaminosulfonyl)phenyl |
| 1433 | CH2NH—SO2CH3 | 2-F-phenyl | 1-pyrrolidinocarbonyl |
| 1434 | CH2NH—SO2CH3 | 2-F-phenyl | 2-(methylsulfonyl)phenyl |
| 1435 | CH2NH—SO2CH3 | 2-F-phenyl | 2-(N,N-dimethylaminomethyl)phenyl |
| 1436 | CH2NH—SO2CH3 | 2-F-phenyl | 2-(N-pyrrolidinylmethyl)phenyl |
| 1437 | CH2NH—SO2CH3 | 2-F-phenyl | 1-methyl-2-imidazolyl |
| 1438 | CH2NH—SO2CH3 | 2-F-phenyl | 2-methyl-1-imidazolyl |
| 1439 | CH2NH—SO2CH3 | 2-F-phenyl | 2-(dimethylaminomethyl)-1-imidazolyl |
| 1440 | CH2NH—SO2CH3 | 2-F-phenyl | 2-(N-(cyclopropyl-methyl)aminomethyl)phenyl |
| 1441 | CH2NH—SO2CH3 | 2-F-phenyl | 2-(N-(cyclobutyl)-aminomethyl)phenyl |
| 1442 | CH2NH—SO2CH3 | 2-F-phenyl | 2-(N-(cyclopentyl)-aminomethyl)phenyl |
| 1443 | CH2NH—SO2CH3 | 2-F-phenyl | 2-(N-(3-hydroxypyrrolidinyl)-methyl)phenyl |
| 1444 | CH2NH—SO2CH3 | 2,6-diF-phenyl | 2-(aminosulfonyl)phenyl |
| 1445 | CH2NH—SO2CH3 | 2,6-diF-phenyl | 2-(methylaminosulfonyl)phenyl |
| 1446 | CH2NH—SO2CH3 | 2,6-diF-phenyl | 1-pyrrolidinocarbonyl |
| 1447 | CH2NH—SO2CH3 | 2,6-diF-phenyl | 2-(methylsulfonyl)phenyl |
| 1448 | CH2NH—SO2CH3 | 2,6-diF-phenyl | 2-(N,N-dimethylaminomethyl)phenyl |
| 1449 | CH2NH—SO2CH3 | 2,6-diF-phenyl | 2-(N-pyrrolidinylmethyl)phenyl |
| 1450 | CH2NH—SO2CH3 | 2,6-diF-phenyl | 1-methyl-2-imidazolyl |
| 1451 | CH2NH—SO2CH3 | 2,6-diF-phenyl | 2-methyl-1-imidazolyl |
| 1452 | CH2NH—SO2CH3 | 2,6-diF-phenyl | 2-(dimethylaminomethyl)-1-imidazolyl |
| 1453 | CH2NH—SO2CH3 | 2,6-diF-phenyl | 2-(N-(cyclopropyl-methyl)aminomethyl)phenyl |
| 1454 | CH2NH—SO2CH3 | 2,6-diF-phenyl | 2-(N-(cyclobutyl)-aminomethyl)phenyl |
| 1455 | CH2NH—SO2CH3 | 2,6-diF-phenyl | 2-(N-(cyclopentyl)-aminomethyl)phenyl |
| 1456 | CH2NH—SO2CH3 | 2,6-diF-phenyl | 2-(N-(3-hydroxypyrrolidinyl)-methyl)phenyl |

TABLE 2
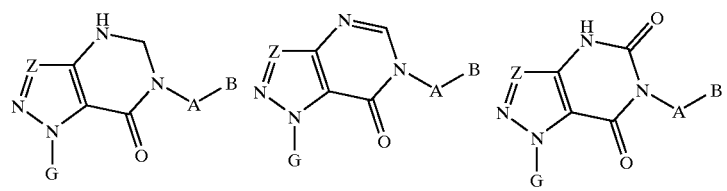
Z is N;
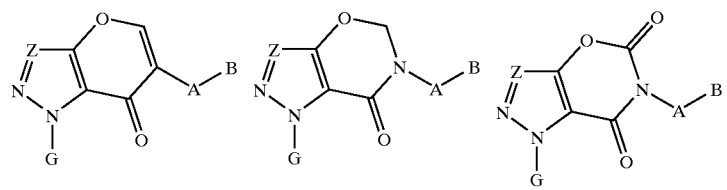
Z is N;
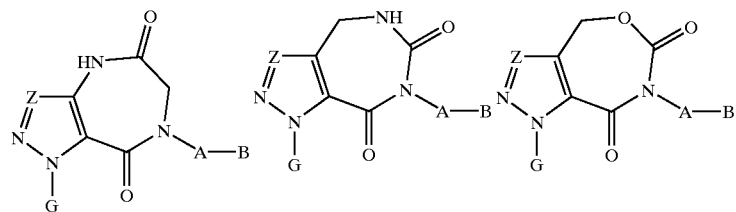
Z is N;
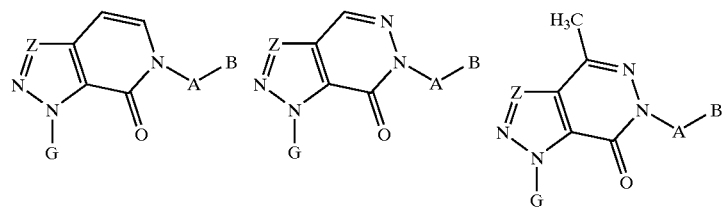
Z is N;
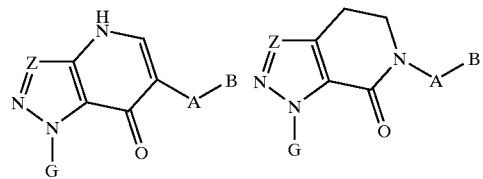
Z is N;
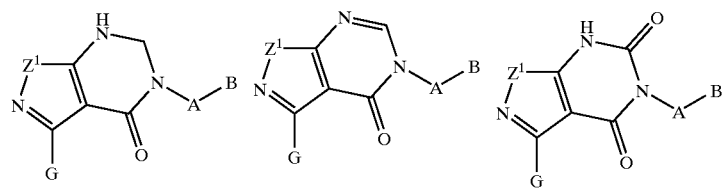

TABLE 2-continued
$Z^1$ is O;
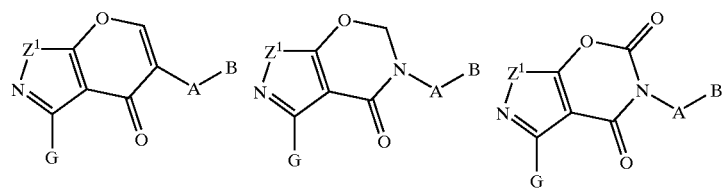
$Z^1$ is O;
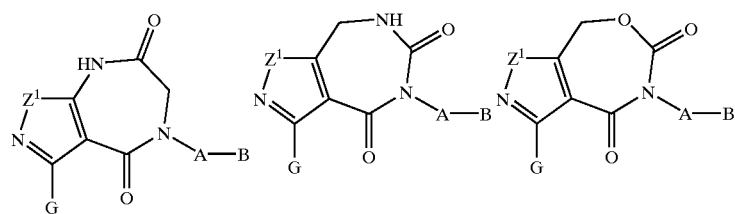
$Z^1$ is O;
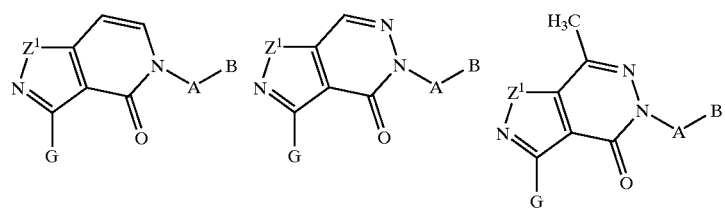
$Z^1$ is O;
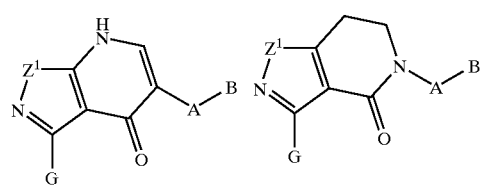
$Z^1$ is O;
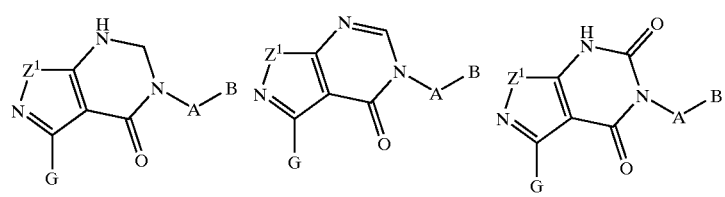
$Z^1$ is S;
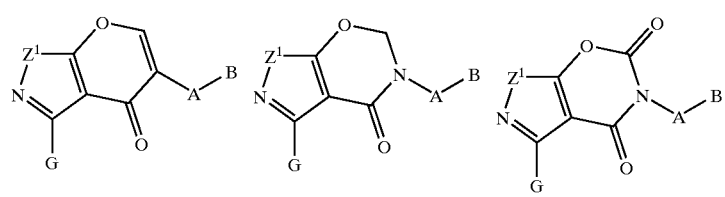

TABLE 2-continued
$Z^1$ is S;
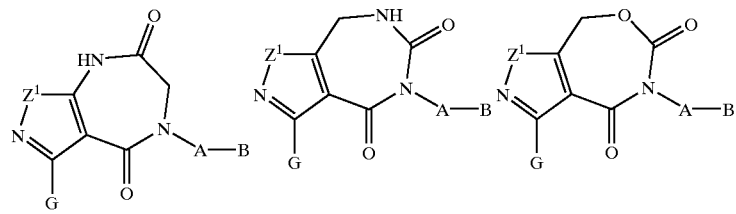
$Z^1$ is S;
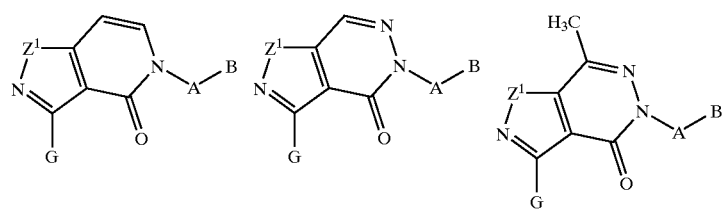
$Z^1$ is S;
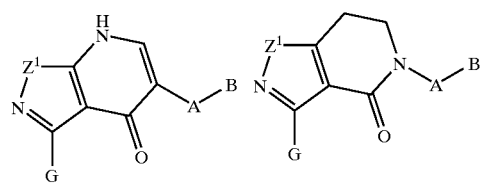
$Z^1$ is S;
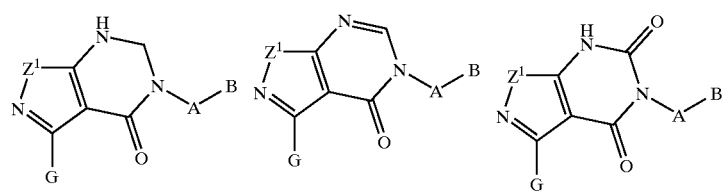
$Z^1$ is NH;
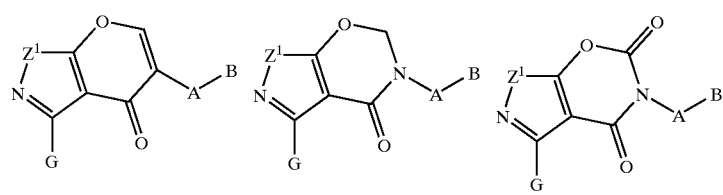
$Z^1$ is NH;
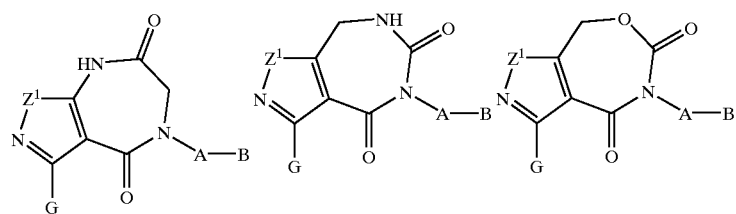

TABLE 2-continued
$Z^1$ is NH;
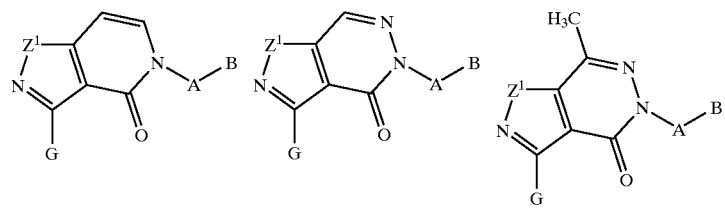
$Z^1$ is NH;
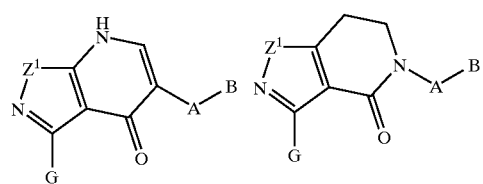
$Z^1$ is NH;
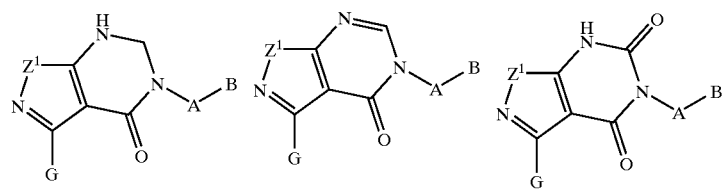
$Z^1$ is NCH$_3$;
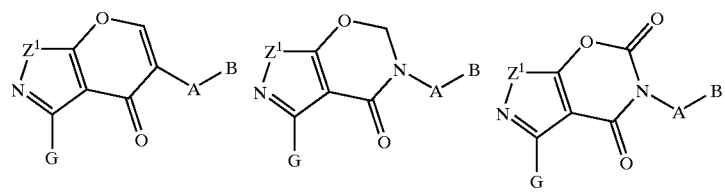
$Z^1$ is NCH$_3$;
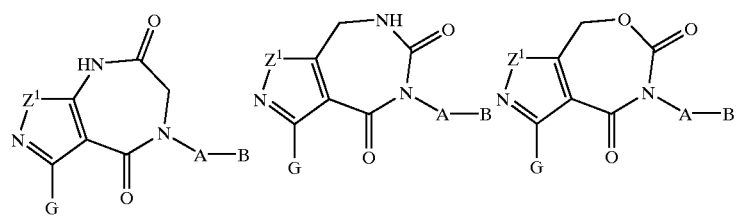
$Z^1$ is NCH$_3$;
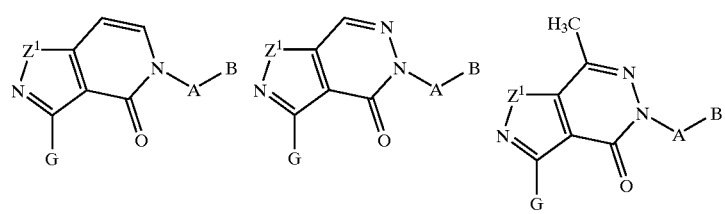

TABLE 2-continued $Z^1$ is $NCH_3$;

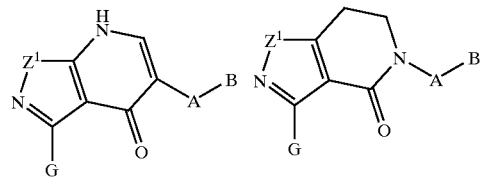

$Z^1$ is $NCH_3$;

G is selected from:
4-(methoxy)phenyl;
2-(aminomethyl)phenyl;
3-(aminomethyl)phenyl;
2-(aminomethyl)-3-fluorophenyl;
2-(aminomethyl)-4-fluorophenyl;
2-(aminomethyl)-5-fluorophenyl;
2-(aminomethyl)-6-fluorophenyl;
3-amino-phthalazin-5-yl;
3-amino-phthalazin-6-yl;
1-aminoisoquinolin-6-yl;
1-aminoisoquinolin-7-yl;
4-aminoquinazol-6-yl;
4-aminoquinazol-7-yl;
3-aminobenzisoxazol-5-yl;
3-aminobenzisoxazol-6-yl;
3-aminoisobenzazol-5-yl; and,
3-aminoisobenzazaol-6-yl;

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 2-(N,N-dimethylaminomethyl)phenyl |
| 6 | phenyl | 2-(N-pyrrolidinylmethyl)phenyl |
| 7 | phenyl | 1-methyl-2-imidazolyl |
| 8 | phenyl | 2-methyl-1-imidazolyl |
| 9 | phenyl | 2-(dimethylaminomethyl)-1-imidazolyl |
| 10 | phenyl | 2-(N-(cyclopropyl-methyl)aminomethyl)phenyl |
| 11 | phenyl | 2-(N-(cyclobutyl)-aminomethyl)phenyl |
| 12 | phenyl | 2-(N-(cyclopentyl)-aminomethyl)phenyl |
| 13 | phenyl | 2-(N-(3-hydroxypyrrolidinyl)-methyl)phenyl |
| 14 | 2-pyridyl | 2-(aminosulfonyl)phenyl |
| 15 | 2-pyridyl | 2-(methylaminosulfonyl)phenyl |
| 16 | 2-pyridyl | 1-pyrrolidinocarbonyl |
| 17 | 2-pyridyl | 2-(methylsulfonyl)phenyl |
| 18 | 2-pyridyl | 2-(N,N-dimethylaminomethyl)phenyl |
| 19 | 2-pyridyl | 2-(N-pyrrolidinylmethyl)phenyl |
| 20 | 2-pyridyl | 1-methyl-2-imidazolyl |
| 21 | 2-pyridyl | 2-methyl-1-imidazolyl |
| 22 | 2-pyridyl | 2-(dimethylaminomethyl)-1-imidazolyl |
| 23 | 2-pyridyl | 2-(N-(cyclopropyl-methyl)aminomethyl)phenyl |
| 24 | 2-pyridyl | 2-(N-(cyclobutyl)-aminomethyl)phenyl |
| 25 | 2-pyridyl | 2-(N-(cyclopentyl)-aminomethyl)phenyl |
| 26 | 2-pyridyl | 2-(N-(3-hydroxypyrrolidinyl)-methyl)phenyl |
| 27 | 3-pyridyl | 2-(aminosulfonyl)phenyl |
| 28 | 3-pyridyl | 2-(methylaminosulfonyl)phenyl |
| 29 | 3-pyridyl | 1-pyrrolidinocarbonyl |
| 30 | 3-pyridyl | 2-(methylsulfonyl)phenyl |
| 31 | 3-pyridyl | 2-(N,N-dimethylaminomethyl)phenyl |
| 32 | 3-pyridyl | 2-(N-pyrrolidinylmethyl)phenyl |
| 33 | 3-pyridyl | 1-methyl-2-imidazolyl |
| 34 | 3-pyridyl | 2-methyl-1-imidazolyl |
| 35 | 3-pyridyl | 2-(dimethylaminomethyl)-1-imidazolyl |
| 36 | 3-pyridyl | 2-(N-(cyclopropyl-methyl)aminomethyl)phenyl |
| 37 | 3-pyridyl | 2-(N-(cyclobutyl)-aminomethyl)phenyl |
| 38 | 3-pyridyl | 2-(N-(cyclopentyl)-aminomethyl)phenyl |
| 39 | 3-pyridyl | 2-(N-(3-hydroxypyrrolidinyl)-methyl)phenyl |
| 40 | 2-pyrimidyl | 2-(aminosulfonyl)phenyl |
| 41 | 2-pyrimidyl | 2-(methylaminosulfonyl)phenyl |
| 42 | 2-pyrimidyl | 1-pyrrolidinocarbonyl |
| 43 | 2-pyrimidyl | 2-(methylsulfonyl)phenyl |
| 44 | 2-pyrimidyl | 2-(N,N-dimethylaminomethyl)phenyl |
| 45 | 2-pyrimidyl | 2-(N-pyrrolidinylmethyl)phenyl |
| 46 | 2-pyrimidyl | 1-methyl-2-imidazolyl |
| 47 | 2-pyrimidyl | 2-methyl-1-imidazolyl |
| 48 | 2-pyrimidyl | 2-(dimethylaminomethyl)-1-imidazolyl |
| 49 | 2-pyrimidyl | 2-(N-(cyclopropyl-methyl)aminomethyl)phenyl |
| 50 | 2-pyrimidyl | 2-(N-(cyclobutyl)-aminomethyl)phenyl |
| 51 | 2-pyrimidyl | 2-(N-(cyclopentyl)-aminomethyl)phenyl |
| 52 | 2-pyrimidyl | 2-(N-(3-hydroxypyrrolidinyl)-methyl)phenyl |
| 53 | 5-pyrimidyl | 2-(aminosulfonyl)phenyl |
| 54 | 5-pyrimidyl | 2-(methylaminosulfonyl)phenyl |
| 55 | 5-pyrimidyl | 1-pyrrolidinocarbonyl |
| 56 | 5-pyrimidyl | 2-(methylsulfonyl)phenyl |
| 57 | 5-pyrimidyl | 2-(N,N-dimethylaminomethyl)phenyl |
| 58 | 5-pyrimidyl | 2-(N-pyrrolidinylmethyl)phenyl |
| 59 | 5-pyrimidyl | 1-methyl-2-imidazolyl |
| 60 | 5-pyrimidyl | 2-methyl-1-imidazolyl |
| 61 | 5-pyrimidyl | 2-(dimethylaminomethyl)-1-imidazolyl |
| 62 | 5-pyrimidyl | 2-(N-(cyclopropyl-methyl)aminomethyl)phenyl |
| 63 | 5-pyrimidyl | 2-(N-(cyclobutyl)-aminomethyl)phenyl |
| 64 | 5-pyrimidyl | 2-(N-(cyclopentyl)-aminomethyl)phenyl |
| 65 | 5-pyrimidyl | 2-(N-(3-hydroxypyrrolidinyl)-methyl)phenyl |
| 66 | 2-Cl-phenyl | 2-(aminosulfonyl)phenyl |
| 67 | 2-Cl-phenyl | 2-(methylaminosulfonyl)phenyl |
| 68 | 2-Cl-phenyl | 1-pyrrolidinocarbonyl |
| 69 | 2-Cl-phenyl | 2-(methylsulfonyl)phenyl |
| 70 | 2-Cl-phenyl | 2-(N,N-dimethylaminomethyl)phenyl |
| 71 | 2-Cl-phenyl | 2-(N-pyrrolidinylmethyl)phenyl |
| 72 | 2-Cl-phenyl | 1-methyl-2-imidazolyl |
| 73 | 2-Cl-phenyl | 2-methyl-1-imidazolyl |
| 74 | 2-Cl-phenyl | 2-(dimethylaminomethyl)-1-imidazolyl |
| 75 | 2-Cl-phenyl | 2-(N-(cyclopropyl-methyl)aminomethyl)phenyl |
| 76 | 2-Cl-phenyl | 2-(N-(cyclobutyl)-aminomethyl)phenyl |
| 77 | 2-Cl-phenyl | 2-(N-(cyclopentyl)-aminomethyl)phenyl |

-continued

| Ex # | A | B |
|---|---|---|
| 78 | 2-Cl-phenyl | 2-(N-(3-hydroxypyrrolidinyl)-methyl)phenyl |
| 79 | 2-F-phenyl | 2-(aminosulfonyl)phenyl |
| 80 | 2-F-phenyl | 2-(methylaminosulfonyl)phenyl |
| 81 | 2-F-phenyl | 1-pyrrolidinocarbonyl |
| 82 | 2-F-phenyl | 2-(methylsulfonyl)phenyl |
| 83 | 2-F-phenyl | 2-(N,N-dimethylaminomethyl)phenyl |
| 84 | 2-F-phenyl | 2-(N-pyrrolidinylmethyl)phenyl |
| 85 | 2-F-phenyl | 1-methyl-2-imidazolyl |
| 86 | 2-F-phenyl | 2-methyl-1-imidazolyl |
| 87 | 2-F-phenyl | 2-(dimethylaminomethyl)-1-imidazolyl |
| 88 | 2-F-phenyl | 2-(N-(cyclopropyl-methyl)aminomethyl)phenyl |
| 89 | 2-F-phenyl | 2-(N-(cyclobutyl)-aminomethyl)phenyl |
| 90 | 2-F-phenyl | 2-(N-(cyclopentyl)-aminomethyl)phenyl |
| 91 | 2-F-phenyl | 2-(N-(3-hydroxypyrrolidinyl)-methyl)phenyl |
| 92 | 2,6-diF-phenyl | 2-(aminosulfonyl)phenyl |
| 93 | 2,6-diF-phenyl | 2-(methylaminosulfonyl)phenyl |
| 94 | 2,6-diF-phenyl | 1-pyrrolidinocarbonyl |
| 95 | 2,6-diF-phenyl | 2-(methylsulfonyl)phenyl |
| 96 | 2,6-diF-phenyl | 2-(N,N-dimethylaminomethyl)phenyl |
| 97 | 2,6-diF-phenyl | 2-(N-pyrrolidinylmethyl)phenyl |
| 98 | 2,6-diF-phenyl | 1-methyl-2-imidazolyl |
| 99 | 2,6-diF-phenyl | 2-methyl-1-imidazolyl |
| 100 | 2,6-diF-phenyl | 2-(dimethylaminomethyl)-1-imidazolyl |
| 101 | 2,6-diF-phenyl | 2-(N-(cyclopropyl-methyl)aminomethyl)phenyl |
| 102 | 2,6-diF-phenyl | 2-(N-(cyclobutyl)-aminomethyl)phenyl |
| 103 | 2,6-diF-phenyl | 2-(N-(cyclopentyl)-aminomethyl)phenyl |
| 104 | 2,6-diF-phenyl | 2-(N-(3-hydroxypyrrolidinyl)-methyl)phenyl |

UTILITY

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, Km, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of $\leq 10$ μM, thereby confirming the utility of the compounds of the present invention as effective Xa inhibitors.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in J. Biol. Chem. 1990, 265, 18289–18297, herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component maybe administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/ or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent is Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound selected from the group:

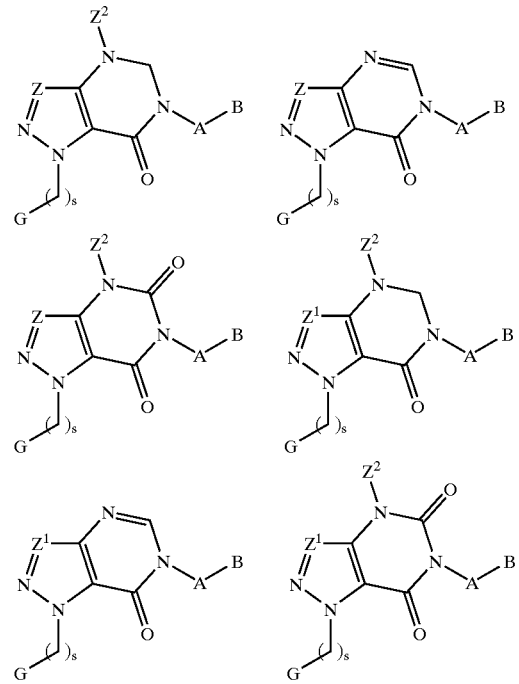

or a sterioisomer or pharmaceutically acceptable salt thereof, wherein compounds of the above formulas are substituted with 0–2 $R^3$;

G is a group of formula I or II:

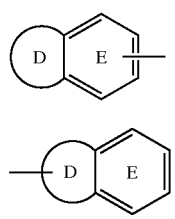

ring D is selected from —$(CH_2)_3$—, —$(CH_2)_4$—, —$CH_2N=CH$—, —$CH_2CH_2N=CH$—, and a 5–6 membered aromatic system containing from 0-2 heteroatoms selected from the group N, O, and S, provided that from 0–1 O and S atoms are present;

ring D, when present, is substituted with 0–2 R;

E is selected from phenyl, pyridyl, pyrimidyl, pyrazinyl, and pyridazinyl, substituted with 0–1 R;

R is selected from Cl, F, Br, 1, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

alternatively, ring D is absent;

when ring D is absent, ring E is selected from phenyl, pyridyl, pyrimidyl, pyrazinyl, and pyridazinyl, and ring E is substituted with R" and R';

R" is selected from F, Cl, Br, I, OH, $C_{1-3}$ alkoxy, CN, $C(=NR^8)NR^7R^9$, $NHC(=NR^8)NR^7R^9$, $NR^8CH(=NR^7)$, $C(O)NR^7RB$, $(CR^8R^9)_rNR^7R^8$, SH, $C_{1-3}$ alkyl-S, $S(O)R^{3b}$, $S(O)_2R^{3a}$, $S(O)_2NR^2R^{2a}$, and $OCF_3$;

R' is selected from H, F, Cl, Br, I, $SR^3$, $CO_2R^3$, $NO_2$, $(CH_2)_rOR^3$, $C_{1-4}$ alkyl, $OCF_3$, $CF_3$, $C(O)NR^7R^8$, and $(CR^8R^9)_rNR^7R^8$; alternatively, R" and R' combine to form methylenedioxy or ethylenedioxy;

Z is N or $CR^{1a}$;

$Z^1$ is S, O, or $NR^3$;

$Z^2$ is selected from H, $C_{1-4}$ alkyl, phenyl, benzyl, $C(O)R^3$, and $S(O)_pR^{3c}$;

$R^{1a}$ is selected from H, $-(CH_2)_r-R^{1'}$, $-CH=CH-R^{1'}$, $NHCH_2R^{1'}$, $OCH_2R^{1'}$, $SCH_2R^{1'}$, $NH(CH_2)_2(CH_2)_rR^{1'}$, $O(CH_2)_2(CH_2)_rR^{1'}$, and $S(CH_2)_2(CH_2)_rR^{1'}$;

$R^{1'}$ is selected from H, $C_{1-3}$ alkyl, F, Cl, Br, I, $-CN$, $-CHO$, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $C(=NR^2C)NR^2R^{2a}$, $NR^2C(O)R^{2b}$, $NR^2C(O)R^3$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

R" is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, a $C_{3-6}$ carbocyclic-$CH_2$— residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is selected from:
$C_{3-10}$ carbocyclic residue substituted with 0–2 $R^4$, and 5–10 membered heterocyclic system containing from 1–4 heteroatoms selected from the group consisting of N, O, and S substituted with 0–2 $R^4$;

B is selected from:
Y, X-Y, $C(=NR^2)NR^2R^{2a}$, and $NR^2C(=NR^2)NR^2R^{2a}$;

X is selected from $C_{1-4}$ alkylene, $-CR^2(CR^2R^{2b})(CH_2)_t-$, $-C(O)-$, $-C(=NR^{1''})-$, $-CR^2(NR^{1''}R^2)-$, $-CR^2(OR^2)-$, $-CR^2(SR^2)$, $-C(O)CR^2R^{2a}-$, $-CR^2R^{2a}C(O)$, $-S(O)_p-$, $-S(O)_pCR^2R^{2a}-$, $-CR^2R^{2a}S(O)_p-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2-$, $-NR^2CR^2R^{2a}$, $CR^2R^{2a}NR^2$, O, $-CR^2R^{2a}O-$, and $-OCR^2R^{2a}-$;

Y is selected from:
$CH_2NR^2R^{2a}$;
$CH_2CH_2NR^2R^{2a}$;
$C_{3-10}$ carbocyclic residue substituted with 0–2 $R^{4a}$, and 5–10 membered heterocyclic system containing from 1–4 heteroatoms selected from the group consisting of N, O, and S substituted with $O_2 R^{4a}$;

$R^4$, at each occurrence, is selected from H, $=O$, $(CH_2)_rOR^2$, F, Cl, Br, 1, $C_{1-4}$ alkyl, $-CN$, $NO_2$, $(CH_2)_rNR^2R^{2a}$, $(CH_2)_rC(O)R^{2c}NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2-C_{1-4}$ alkyl, $NR^2SO_2R^5$, $S(O)_pR^5$, $(CF_2)_rCF_3$, $NCH_2R^{1'}$, $OCH_2R^{1'}$, $SCH_2R^{1'}$, $N(CH_2)_2(CH_2)_rR^{1'}$, $O(CH_2)_2(CH_2)_rR^{1'}$, and $S(CH_2)_2(CH_2)_rR^{1'}$;

alternatively, one $R^4$ is a 5–6 membered aromatic heterocycle containing from 1–4 heteroatoms selected from the group consisting of N, O, and S;

$R^{4a}$, at each occurrence, is selected from H, $=O$, $(CH_2)_rOR^2$, $(CH_2)_r-F$, $(CH_2)_r-Br$, $(CH_2)_r-Cl$, Cl, Br, F, I, $C_4$ alkyl, $-CN$, $NO_2$, $(CH_2)_rNR^2R^{2a}$, $(CH_2)_rC(O)R^2C$, $NR^2C(O)R^{2b}$, $C(O)NR^2R^{2a}$, $(CH_2)_rN=CHOR^3$, $C(O)NH(CH_2)_2NR^2R^{2a}$, $NR^2C(O)NR^2R^{2a}$, $C(=NR^2)NR^2R^{2a}$, $SO_2NR^2R^{2a}$, $NR^2SO_2NR^2R^{2a}$, $NR^2SO_2-C_{1-4}$ alkyl, $C(O)NHSO_2-C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from H, $=O$, $(CH_2)_rOR^3$, F, Cl, Br, I, $C_{1-4}$ alkyl, $-CN$, $NO_2$, $(CH_2)_rNR^3R^{3a}$, $(CH_2)_rC(O)R^3$, $(CH_2)_rC(O)OR^{3c}$, $NR^3C(O)$ R$^{3a}$, C(O)NR$^3$R$^{3a}$, NR$^3$C(O)NR$^3$R$^{3a}$, C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$-C$_{1-4}$ alkyl, S(O)$_p$-phenyl, and (CF$_2$)$_r$CF$_3$;

R$^5$, at each occurrence, is selected from CF$_3$, C$_{1-6}$ alkyl, phenyl substituted with 0–2 R$^6$, and benzyl substituted with 0–2 R$^6$;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$ C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkylcarbonyl, C$_{1-6}$ alkoxy, C$_{1-4}$ alkoxycarbonyl, (CH$_2$)$_n$-phenyl, C$_{6-10}$ aryloxy, C$_{6-10}$ aryloxycarbonyl, C$_{6-10}$ arylmethylcarbonyl, C$_{1-4}$ alkylcarbonyloxy C$_{1-4}$ alkoxycarbonyl, C$_{6-10}$ arylcarbonyloxy C$_{1-4}$ alkoxycarbonyl, C$_{1-6}$ alkylanocarbonyl, phenylaminocarbonyl, and phenyl C$_{1-4}$ alkoxycarbonyl;

R$^8$, at each occurrence, is selected from H, C$_{1-6}$ alkyl and (CH$_2$)$_n$-phenyl;

alternatively, R$^7$ and R$^8$ combine to form a 5 or 6 membered saturated, ring which contains from 0–1 additional heteroatoms selected from the group consisting of N, O, and S;

R$^9$, at each occurrence, is selected from H, C$_{1-6}$ alkyl and (CH$_2$)$_n$-phenyl;

n, at each occurrence, is selected from 0, 1, 2, and 3;
m, at each occurrence, is selected from 0, 1, and 2;
p, at each occurrence, is selected from 0, 1, and 2;
r, at each occurrence, is selected from 0, 1, 2, and 3;
s, at each occurrence is selected from 0, 1, and 2; and,
t, at each occurrence is selected from 0, 1, 2, and 3.

2. A compound of claim 1, wherein the compound is selected from the group:

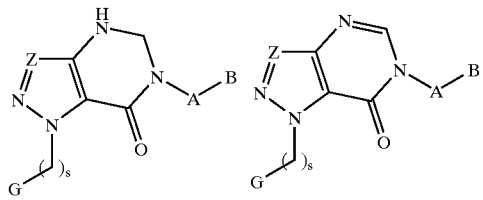

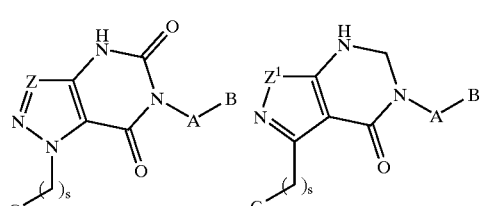

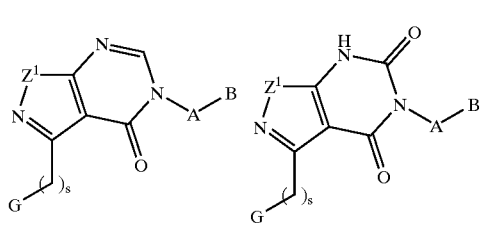

wherein compounds of the above formulas are substituted with 0–2 R$^3$;

G is selected from the group:

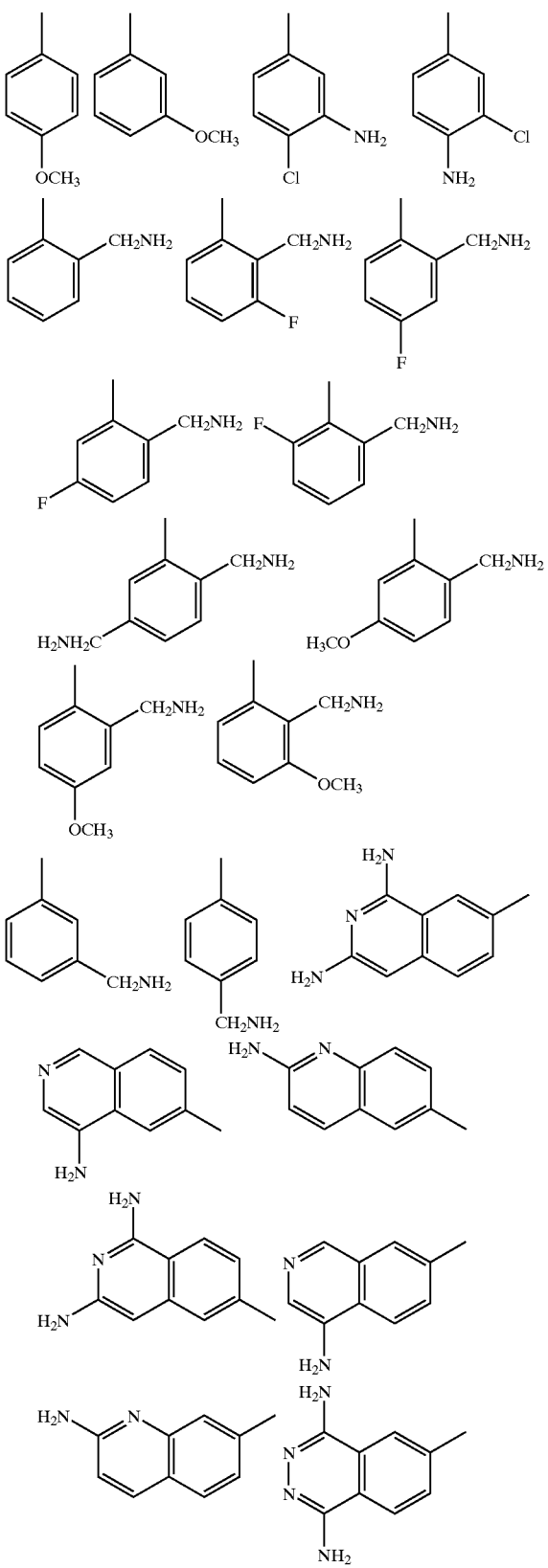

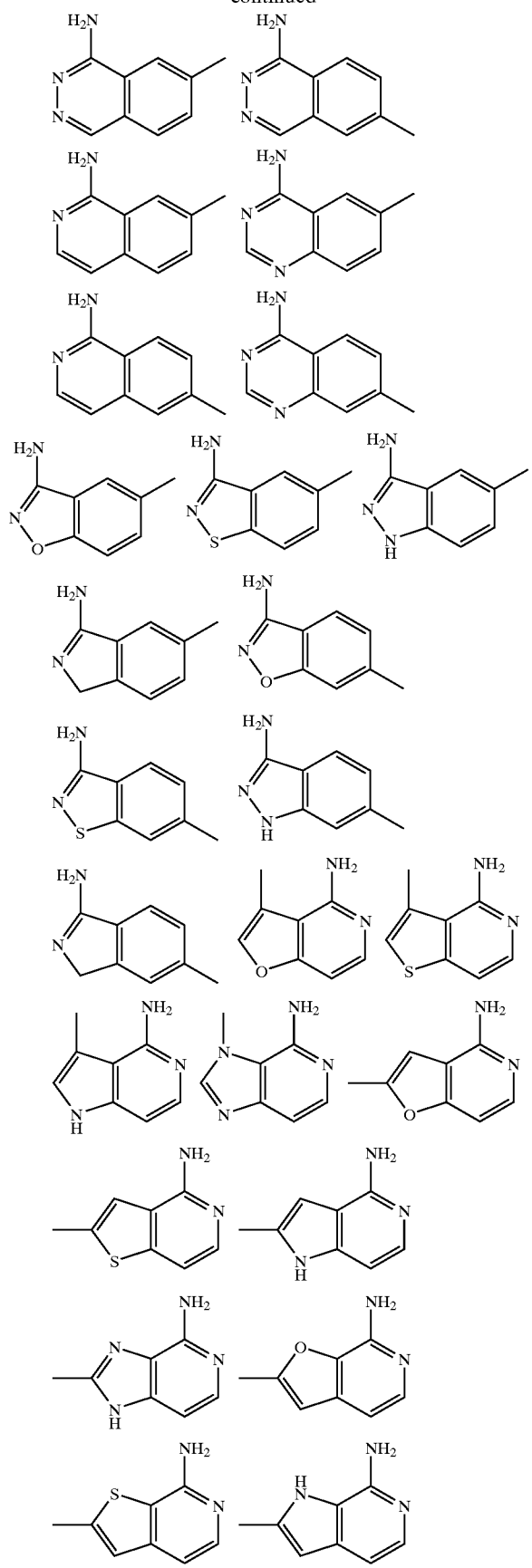

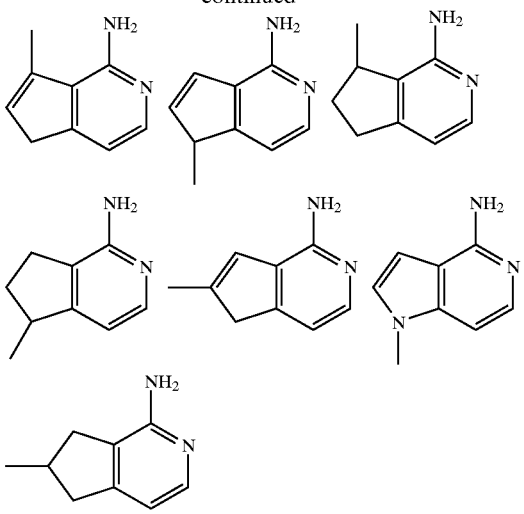

A is selected from one of the following carbocyclic and heterocyclic systems which are substituted with 0–2 $R^4$;

phenyl, piperidinyl, piperazinyl, pyridyl, pyrirnidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzioidazolyl, benzoxazolyl, benzthiazolyl, indazolyl, benzisoxazolyl, benzisothiazolyl, and isoindazolyl;

B is selected from: Y and X-Y;

X is selected from $C_{1-4}$ alkylene, —C(O)—, —C(=NR$^{1\prime\prime}$)—, —CR$^2$(NR$^{1\prime\prime}$R$^2$)—, —C(O)CR$^2$R$^{2a}$—, —CR$^2$R$^{2a}$C(O), —C(O)NR$^2$—, —NR$^2$C(O)—, C(O)NR$^2$CR$^2$R$^{2a}$, —NR$^2$C(O)CR$^2$R$^{2a}$, —CR$^2$R$^{2a}$C(O)NR$^2$—, CR$^2$R$^{2a}$NR$^2$C(O), —NR$^2$C(O)NR$^2$—, —NR$^2$—, —NR$^2$CR$^2$R$^{2a}$, CR$^2$R$^{2a}$NR$^2$, O, CR$^2$R$^{2a}$O—, and —OCR$^2$R$^{2a}$—;

Y is $C_2NR^2R^{2a}$ or $CH_2CH_2N^2R^{2a}$;

alternatively, Y is selected from one of the following carbocyclic and heterocyclic systems that are substituted with 0–2 $R^{4a}$;

cyclopropyl, cyclopentyl, cyclohexyl, phenyl, piperidinyl, piperazinyl, pyridyl, pyrimidyl, furanyl, morpholinyl, thiophenyl, pyrrolyl, pyffolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4 oxadiazolyl, 1,2,5 oxadiazolyl, 1,3,4-oxadiazolyl, 1,2,3-thliadiazolyl, 1,2,4-thiadiazolyl, 1,2,5-thiadiazolyl, 11,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

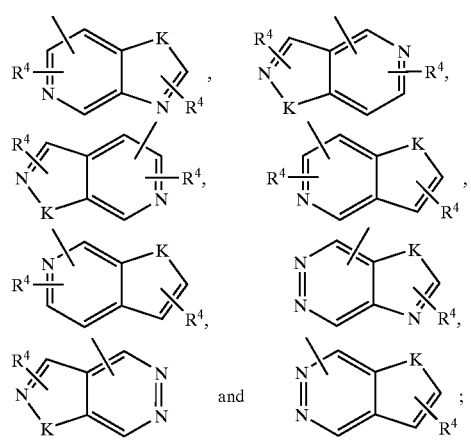
K is selected from O, S, NH, and N; and,
s is 0.
3. A compound of claim 2, wherein G is selected from the group:
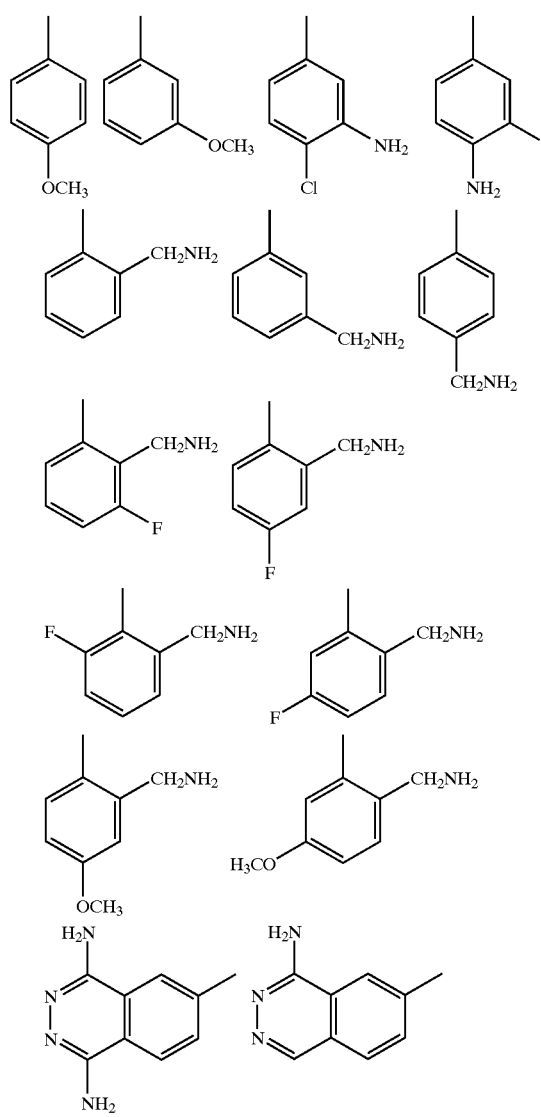
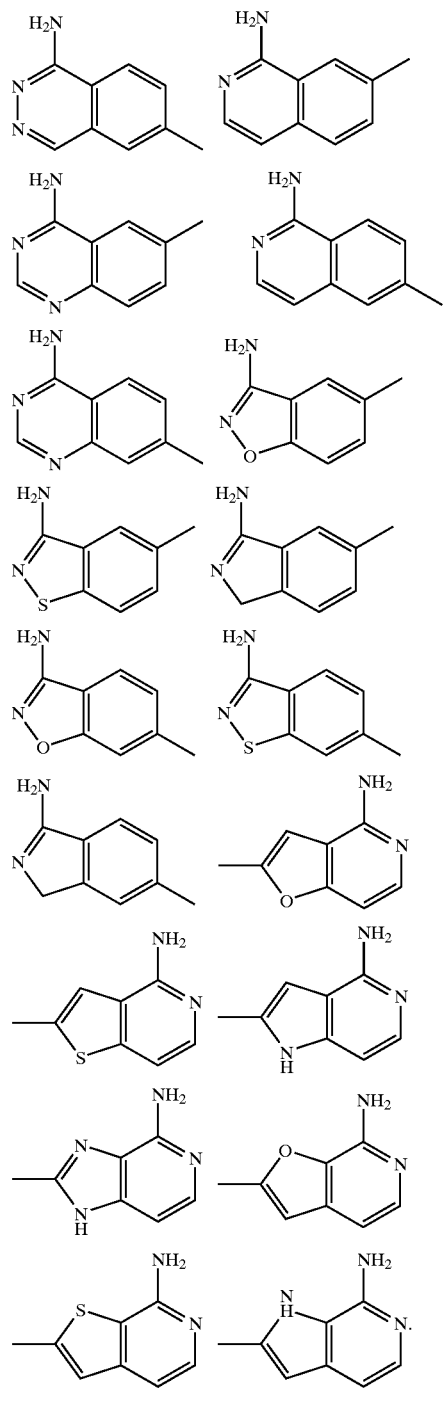
4. A compound of claim 3, wherein:
G is selected from:
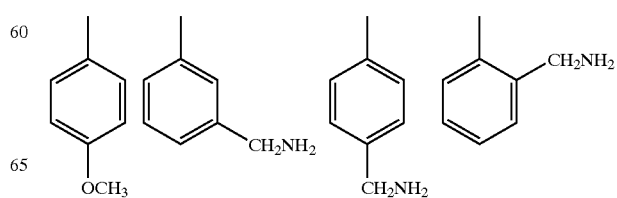

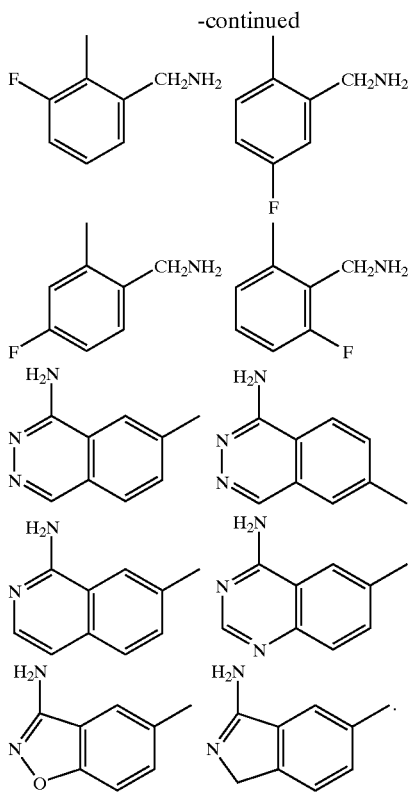

5. A compound of claim 4, wherein:

A is selected from phenyl, pyridyl, and pyrimidyl, and is substituted with 0–2 $R^4$; and, B is selected from X-Y, phenyl, pyrrolidino, morpholino, 1,2,3-triazolyl, and imidazolyl, and is substituted with 0–1 $R^{4a}$;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$; alternatively, $R^2$ and $R^{2a}$, together with the atom to which they are attached, combine to form pyrrolidine substituted with $O_2$ $R^{4b}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from ClA alkyl, $CF_3$, $(CH_2)_rOR^2$, $(CH_2)_r$ $NR^2R^{2a}$, $S(O)_pR^5$, $SO_2NR^2R^{2a}$, and 1-$CF_3$-tetrazol-2-yl;

$R^{4b}$, at each occurrence, is selected from H, $CH_3$, and OH;

$R^5$, at each occurrence, is selected from $CF_3$, $C_{1-6}$ alkyl, phenyl, and benzyl;

X is $CH_2$ or C(O);

Y is selected from pyrrolidino and morpholino; and, r, at each occurrence, is selected from 0, 1, and 2.

6. A compound of claim 5, wherein:

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(N-(cyclopropylmethyl)aminomethyl) phenyl, 2-(N-(cyclobutyl)aminomethyl)phenyl, 2-(N-(cyclopentyl)aminomethyl)phenyl, and 2-(N-(3-hydroxypyrrolidinyl)methyl)phenyl.

7. A compound of claim 1, wherein the compound is selected from:

1-[4-Methoxyphenyl]-3-cyano-6-[2'-methylsulfonyl-3-fluoro-[1,1']-biphen-4-yl]-1,4-dihydropyrazolo-[4,3-d]-pyrimidine-5,7-dione;

1-[4-Methoxyphenyl]-3-(methoxycarbonyl)-6-[2'-aminosulfonyl-3-fluoro-[1, 1']-biphen-4-yl]-1,6-dihydropyrazolo-[4,3-d]-pyrimidin-7-one;

1-[4-Methoxyphenyl]-3-(aminocarbonyl)-6-[2'-aminosulfonyl-3-fluoro-[1,1]-biphen-4-yl]-1,6-dihydropyrazolo-[4,3-d]-pyrimidin-7-one;

1-[4-Methoxyphenyl]-3-(methoxycarbonyl)-6-[2'-aminosulfonyl-[1,1']-biphen-4-yl]-1,6-dihydropyrazolo-[4,3-d]-pyrimidin-7-one;

1-[4-Methoxyphenyl]-6-[2'-aminosulfonyl-[1,1']-biphen-4-yl]-1,6-dihydropyrazolo-[4,3-d]-pyrimidin-7-one-3-carboxylic acid;

1-[4-Methoxyphenyl]-3-(aminocarbonyl)$_6$-[2'-aminosulfonyl-[1,1']-biphen-4-yl]-1,6-dihydropyrazolo-[4,3-d]-pyrimidin-7-one;

1-[4-Methoxyphenyl]-3-cyano-6-[2'-aminosulfonyl-[1, 1']-biphen-4-yl]-1,6-dihydropyrazolo-[4,3-d]-pyrimidin-7-one;

1-[4-Methoxyphenyl]-3-(aminomethyl)-6-[2'-aminosulfonyl-[1,1']-biphen-4-yl-1,6-dihydropyrazolo-[4,3-d]-pyrimidin-7-one;

1-[4-Methoxyphenyl]-3-(ethoxycarbonyl)-6[4-(2-methylimidazol-1'-yl)phenyl]-1,6-dihydropyrazolo-[4,3-d]-pyrimidin-7-one;

1-[4-Methoxyphenyl]-3-(aminocarbonyl)-6-[4-(2-methylimidazol-1'-yl)phenyl]-1,6-dihydropyrazolo-[4,3-d]-pyrimidin-7-one;

1-[4-Methoxyphenyl]-3-(ethoxycarbonyl)-6-[2'-N-pyrrolidinylmethyl-[1,1' ]-biphen-4-yl]-1,6-dihydropyrazolo-[4,3-d]-pyrimidin-7-one;

1-[4-Methoxyphenyl]-3-(ethoxycarbonyl)-6-[2'-N-pyrrolidinylmethyl-[1,1' ]-biphen-4-yl]-1,4,5,6-tetrahydropyrazolo-[4,3-d]-pyrimidin-7-one;

1-[4-Methoxyphenyl]-3-(aminocarbonyl)-6-12'-N-pyrrolidinylmethyl-[1,1']-biphen-4-yl]-1,6-dihydropyrazolo-[4,3-d]-pyrimidin-7-one;

1-[4-Methoxyphenyl]-3-cyano-6-[2'-N-pyrrolidinylmethyl-[1,1']-biphen-4-yl]-1,6-dihydropyrazolo-[4,3-d]-pyrimidin-7-one;

1-[4-Methoxyphenyl]-3-(ethoxycarbonyl)-6-[2-fluoro-4-(2-dimethylaminomethylimidazol-1'-yl)phenyl]-1,6-dihydropyrazolo-[4,3-d]-pyrimidin-7-one;

1-[2-Aminomethylphenyl]-3-(ethoxycarbonyl)-6-[2'-methylsulfonyl-[1,1']-biphen-4-yl]-1,6-dihydropyrazolo-[4,3-d]-pyrimidin-7-one;

1-[4-Methoxyphenyl] 3-cyano-6-[2'-N,N-dimethylaminomethyl-[1,1']-biphen-4-yl]-1,6-dihydropyrazolo-[4,3-d]-pyrimidin-7-one;

1-[4-Methoxyphenyl]-3-cyano-5-methyl-6-[2'-N,N-dimethylaminomethyl-[1,1']-biphen-4-yl]-1,6-dihydropyrazolo-[4,3-d]-pyrimidin-7-one;

1-[2-Aminomethylphenyl]-3-cyano-6-[2'-methylsulfonyl-3-fluoro-[1,1']-biphen-4-yl]-1,6-dihydropyrazolo-[4,3-d]-pyrimidin-7-one;

1-[3-Aminobenzisoxazol-5'-yl]-3-trifluoromethyl-6-[4-(1-methylimidazol-2'-yl)phenyl]-1,6-dihydropyrazolo-[4,3-d]-pyrimidin-7-one;

1-[4-Methoxyphenyl]-3-(ethoxycarbonyl)-6-[2'-hydroxymethyl-3-fluoro-[1,1' ]-biphen-4-yl]-1,6-dihydropyrazolo-[4,3-d]-pyrimidin-7-one;

1-[4-Methoxyphenyl]-3-(ethoxycarbonyl)-6-[2'-N-pyrrolidinylmethyl-3-fluoro-[1,1']-biphen-4-yl]-1,6-dihydropyrazolo-[4,3-d]-pyrimidin-7-one;

1-[4-Methoxyphenyl]-3-(aminocarbonyl)-6-[2'-N-pyrrolidinylmethyl-3-fluoro-[1,1']-biphen-4-yl]-1,6-dihydropyrazolo-[4,3-d]-pyrimidin-7-one;

1-[4-Methoxyphenyl]-3-(aminocarbonyl)-6-[2'-(3-(R)-hydroxy-N-pyrrolidinylmethyl)-3-fluoro-[1,1' ]-biphen-4-yl]-1,6-dihydropyrazolo-[4,3-d]-pyrimidin-7-one;

1-[4-Methoxyphenyl]-3-(N-formylaminomethyl)-6-[2'-methylsulfonyl-3-fluoro-[1,1']-biphen-4-yl]-1,6-dihydropyrazolo-[4,3-d]-pyrimidin-7-one;

1-[3-Aminobenzisoxazol-5'-yl]-3-(ethoxycarbonyl)-6-[2'-hydroxymethyl-[1,1']-biphen-4-yl]-1,6-dihydropyrazolo-[4,3-d]-pyrimidin-7-one;

1-[3-Aminobenzisoxazol-5'-yl]-3-(ethoxycarbonyl)-6-[2'-N-pyrrolidinylmethyl-[1,1']-biphen-4-yl]-1,6-dihydropyrazolo-[4,3-d]-pyrimidin-7-one;

1-[4-Methoxyphenyl]-3-[(imidazol-1-yl)methyl]-5-methyl-6-[(2'-N-pyrrolidinylmethyl-[1,1']-biphen-4-yl)]-1,6-dihydropyrazolo-[4,3-d]-pyrimidin-7-one;

1-[4-Methoxyphenyl]-3-[(tetrazol-1-yl)methyl]-5-methyl-6-[(2'-N-pyrrolidinylmethyl-[1,1' ]-biphen-4-yl)]-1,6-dihydropyrazolo-[4,3-d]-pyrimidin-7-one;

1-[4-Methoxyphenyl]-3-[(tetrazol-2-yl)methyl]-5-methyl-6-[(2'-N-pyrrolidinylmethyl-[1,1']-biphen-4-yl)]-1,6-dihydropyrazolo-[4,3-d]-pyrimidin-7-one;

1-[3-Aminobenzisoxazol-5'-yl]-3,5-dimethyl-6-[2'-N-dimethylaminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-N,N-dimethylaminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-N-isopropylaminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-(3-(R)-hydroxy-N-pyrrolidinyl)methyl-[1,1']-biphen-4-yl]-1,6-dihydropyrazolo-[4,3-d]-pyrimidin-7-one;

1-[3-Aminobenzisoxazol-5'-yl]-3-methyl-6-[4-(4,5-dihydroimidazol-1'-yl)phenyl]-1,6-dihydropyrazolo-[4,3-d]-pyrimidin-7-one;

1-[3-Aminobenzisoxazol-5'-yl]-3-methyl-6-[2'-N-(cyclopropylmethyl)aminomethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-N-pyrrolidinylmethyl-[1,1']-biphen-4-yl]-1,6-dihydropyrazolo-[4,3-d]-pyrimidin-7-one;

1-[3-Aminobenzisoxazol-5'-yl]-3-methyl-6-[2'-(N-methyl-N-isopropyl)aminomethyl-[1,1' ]-biphen-4-yl]-1,6-dihydropyrazolo-[4,3-d]-pyrimidin-7-one;

1-[3-Aminobenzisoxazol-5'-yl]-3,5-dimethyl-[2'-(3-(R)-hydroxy-N-pyrrolidinyl)methyl-[1,1']-biphen-4-yl]-1,6-dihydropyrazolo-[4,3-d]-pyrimidin-7-one;

1-[3-Aminobenzisoxazol-5'-yl]-3-trifluoromethyl-6-[2'-N,N-dimethylaminomethyl-[1,1']-biphen-4-yl]-1,6-dihydropyrazolo-[4,3-d]-pyrimidin-7-one;

1-[3-Aminobenzisoxazol-5'-yl]-3-trifluoromethyl-6-[2'-N,N-dimethylaminomethyl-[1,1' 1-biphen-4-yl]-1,4,5,6-tetrahydropyrazolo-[4,3-d]-pyrimidin-7-one;

1-3-Aminobenzisoxazol-5'-yl]-3-trifluoromethyl-6-[2'-(3-(R)-hydroxy-N-pyrrolidinyl)methyl-[1,1']-biphen-4-yl]-1,4,5,6-tetrahydropyrazolo-[4,3-d]-pyrimidin-7-one;

1-[3-Aminobenzisoxazol-5'-yl]-3-methyl6-[4(2-methylimidazol-1'-yl)phenyl]-1,6-dihydropyrazolo-[4,3-d]-pyrimidin-7-one;

1-[3-Aminobenzisoxazol-5'-yl]-3-methyl-6-[4-(2-(dimethylaminomethyl)imidazol-1'-yl)-2-fluorophenyl]-1,6-dihydropyrazolo-[4,3-d]-pyrimidin-7-one; and, 1-[3-Aminobenzisoxazol-5'-yl]-3-trifluoromethyl-6-[4-(2-(dimethylaminomethyl)imidazol-1'-yl)phenyl]-1,6-dihydropyrazolo-[4,3-d]-pyrimidin-7-one;

or a pharmaceutically acceptable salt form thereof.

8. A pharmaceutical compositions, comprising: a pharmaceutically acceptable carrier and a therapeutically effective amount of a compound of claim 1 or a pharmaceutically acceptable salt form thereof.

9. A pharmaceutical compositions, comprising: a pharmaceutically acceptable carrier and a therapeutically effective amount of a compound of claim 2 or a pharmaceutically acceptable salt form thereof.

10. A pharmaceutical compositions, comprising: a pharmaceutically acceptable carrier and a therapeutically effective amount of a compound of claim 3 or a pharmaceutically acceptable salt form thereof.

11. A pharmaceutical compositions, comprising: a pharmaceutically acceptable carrier and a therapeutically effective amount of a compound of claim 4 or a pharmaceutically acceptable salt form thereof.

12. A pharmaceutical compositions, comprising: a pharmaceutically acceptable carrier and a therapeutically effective amount of a compound of claim 5 or a pharmaceutically acceptable salt form thereof.

13. A pharmaceutical compositions, comprising: a pharmaceutically acceptable carrier and a therapeutically effective amount of a compound of claim 6 or a pharmaceutically acceptable salt form thereof.

14. A pharmaceutical compositions, comprising: a pharmaceutically acceptable carrier and a therapeutically effective amount of a compound of claim 7 or a pharmaceutically acceptable salt form thereof.

15. A method for treating a thromboembolic disorder, comprising: administering to a patient in need thereof a therapeutically effective amount of a compound of claim 1 or a pharmaceutically acceptable salt form thereof.

16. A method for treating a thromboembolic disorder, comprising:
administering to a patient in need thereof a therapeutically effective amount of a compound of claim 2 or a pharmaceutically acceptable salt form thereof.

17. A method for treating a thromboembolic disorder, comprising:
administering to a patient in need thereof a therapeutically effective amount of a compound of claim 3 or a pharmaceutically acceptable salt form thereof.

18. A method for treating a thromboembolic disorder, comprising:
   administering to a patient in need thereof a therapeutically effective amount of a compound of claim 4 or a pharmaceutically acceptable salt form thereof.

19. A method for treating a thromboembolic disorder, comprising:
   administering to a patient in need thereof a therapeutically effective amount of a compound of claim 5 or a pharmaceutically acceptable salt form thereof.

20. A method for treating a thromboembolic disorder, comprising:
   administering to a patient in need thereof a therapeutically effective amount of a compound of claim 6 or a pharmaceutically acceptable salt form thereof.

21. A method for treating a thromboembolic disorder, comprising:
   administering to a patient in need thereof a therapeutically effective amount of a compound of claim 7 or a pharmaceutically acceptable salt form thereof.

* * * * *

UNITED STATES PATENT AND TRADEMARK OFFICE
CERTIFICATE OF CORRECTION

PATENT NO. : 6,858,616 B2
DATED : February 22, 2005
INVENTOR(S) : Fevig et al.

It is certified that error appears in the above-identified patent and that said Letters Patent is hereby corrected as shown below:

<u>Title page,</u>
Item [62], Related U.S. Application Data, should read as follows:
-- [62] Division of application No. 09/898,279, filed on Jul. 3, 2001, now Pat. No. 6,673,810 which is a continuation-in-part of application No. 09/470,326, filed on Dec. 22, 1999, now Pat. No. 6,413,980. --.

<u>Column 211,</u>
Line 15, "$C(O)NR^7RB$" should read -- $C(O)NR^7R^8$ --

Signed and Sealed this

Seventh Day of June, 2005

JON W. DUDAS
*Director of the United States Patent and Trademark Office*